United States Patent
Or et al.

(10) Patent No.: US 7,064,110 B2
(45) Date of Patent: *Jun. 20, 2006

(54) 6-11 BICYCLE KETOLIDE DERIVATIVES

(75) Inventors: Yat Sun Or, Watertown, MA (US); Wang Guoqiang, Belmont, MA (US); Ly Tam Phan, Quincy, MA (US); Deqiang Niu, Lexington, MA (US); Nha Huu Vo, Southborough, MA (US); Yao-Ling Qiu, Andover, MA (US); Yanchun Wang, Somerville, MA (US); Marina Busuyek, Natick, MA (US); Ying Hou, Everett, MA (US); Yulin Peng, Belmont, MA (US); Heejin Kim, Allston, MA (US); Tongzhu Liu, Auburndale, MA (US); Jay Judson Farmer, New Haven, CT (US); Guoyou Xu, Auburndale, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 235 days.

This patent is subject to a terminal disclaimer.

(21) Appl. No.: 10/717,290

(22) Filed: Nov. 19, 2003

(65) Prior Publication Data

US 2004/0157787 A1    Aug. 12, 2004

Related U.S. Application Data

(63) Continuation-in-part of application No. 10/429,485, filed on May 5, 2003, now Pat. No. 6,878,691, which is a continuation-in-part of application No. 10/144,558, filed on May 13, 2002, now abandoned.

(51) Int. Cl.
*A61K 31/70* (2006.01)
*C07H 17/08* (2006.01)

(52) U.S. Cl. .................................. 514/29; 536/7.4
(58) Field of Classification Search ................ 536/7.4; 514/29
See application file for complete search history.

(56) References Cited

U.S. PATENT DOCUMENTS

| | | |
|---|---|---|
| 4,921,836 A | 5/1990 | Bigham et al. |
| 4,990,602 A | 2/1991 | Morimoto et al. ........... 536/7.4 |
| 5,202,434 A | 4/1993 | Wilkening |
| 5,403,923 A | 4/1995 | Kashimura et al. .......... 536/7.4 |
| 5,441,939 A | 8/1995 | Yang |
| 5,444,051 A | 8/1995 | Agouridas et al. ............ 514/29 |
| 5,527,780 A | 6/1996 | Agouridas et al. ............ 514/29 |
| 5,556,839 A | 9/1996 | Greene et al. |
| 5,631,355 A | 5/1997 | Asaka et al. .................. 536/7.4 |
| 5,866,549 A | 2/1999 | Or et al. ........................ 514/29 |
| 5,969,161 A | 10/1999 | Bonnet et al. ............... 549/271 |
| 6,046,171 A | 4/2000 | Or et al. ........................ 514/29 |
| 6,124,269 A | 9/2000 | Phan et al. .................... 514/29 |
| 6,399,582 B1 | 6/2002 | Hlasta et al. .................. 514/29 |
| 6,645,941 B1 | 11/2003 | Wang et al. ................... 514/29 |

OTHER PUBLICATIONS

8th International Antibacterial Drug Discovery and Development Summut, Strategic Research Institute, Mar. 25-25, 2003, Princeton, NJ.*

* cited by examiner

*Primary Examiner*—Elli Peselev
(74) *Attorney, Agent, or Firm*—Elmore, Craig & Vanstone, P.C.; Darlene A. Vanstone; Carolyn S. Elmore

(57) ABSTRACT

The present invention discloses compounds of formula I, or pharmaceutically acceptable salts, esters, or prodrugs thereof:

(I)

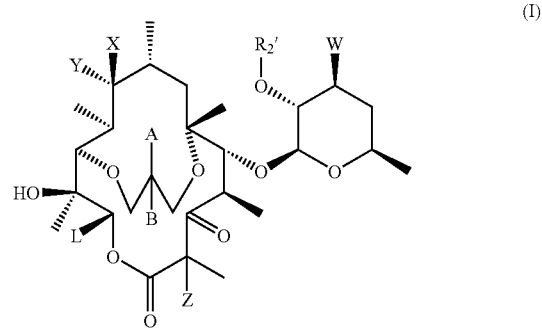

which exhibit antibacterial properties. The present invention further relates to pharmaceutical compositions comprising the aforementioned compounds for administration to a subject in need of antibiotic treatment. The invention also relates to methods of treating a bacterial infection in a subject by administering a pharmaceutical composition comprising the compounds of the present invention. The invention further includes process by which to make the compounds of the present invention.

22 Claims, No Drawings

6-11 BICYCLE KETOLIDE DERIVATIVES

This application is a continuation-in-part of application Ser. No. 10/429,485 (filed May 5, 2003), now U.S. Pat. No. 6,878,691, which is a continuation-in-part of application Ser. No. 10/144,558 (filed May 13, 2002), now abandoned.

TECHNICAL FIELD

The present invention relates to novel semisynthetic macrolides having antibacterial activity and useful in the treatment and prevention of bacterial infections. More particularly, the invention relates to 6–11 bicyclic ketolide derivatives, compositions containing such compounds and methods for using the same, as well as processes for making such compounds.

BACKGROUND OF THE INVENTION

Macrolide antibiotics play a therapeutically important role, particularly with the emergence of new pathogens. Structural differences are related to the size of the lactone ring and to the number and nature (neutral or basic) of the sugars. Macrolides are classified according to the size of the lactone ring (12, 14, 15 or 16 atoms). The macrolide antibiotic family (14-, 15- and 16-membered ring derivatives) shows a wide range of characteristics (antibacterial spectrum, side-effects and bioavailability). Among the commonly used macrolides are erythromycin, clarithromycin, and azithromycin. Macrolides possessing a 3-oxo moiety in place of the 3-cladinose sugar are known as ketolides and have shown enhanced activity towards gram-negative bacteria and macrolide resistant gram-positive bacteria. The search for macrolide compounds which are active against $MLS_B$-resistant strains ($MLS_B$=Macrolides-Lincosamides-type B Streptogramines) has become a major goal, together with retaining the overall profile of the macrolides in terms of stability, tolerance and pharmacokinetics.

SUMMARY OF THE INVENTION

The present invention provides a novel class of C6–C11 bridged erythromycin derivatives which possess antibacterial activity.

In one aspect of the present invention there are provided novel bridged ketolide compounds represented by formula I as illustrated below:

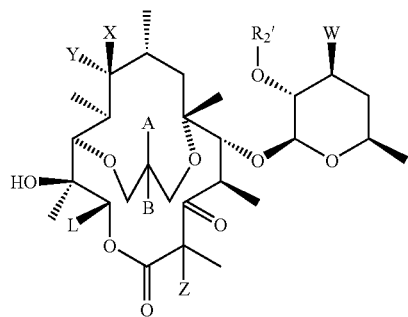

(I)

or a racemate, enantiomer, regioisomer, salt, ester or prodrug thereof, wherein

A and B are independently selected from the group consisting of hydrogen, deuterium, halogen, $R_1$, $OR_1$, $S(O)_nR_1$, $-NR_1C(O)R_1$, $-NR_1C(O)NR_3R_4$, $-NHS(O)_nR_1$, $-CONR_3R_4$, and $NR_3R_4$;

Each $R_1$ is independently selected from the group consisting of hydrogen, acyl, silane, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, saturated or unsaturated heterocyclic group;

$R_3$ and $R_4$ is independently selected from the group consisting of hydrogen, acyl, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, saturated or unsaturated heterocyclic group; or can be taken together with the nitrogen atom to which they are attached to form a substituted or unsubstituted heterocyclic or heteroaromatic ring;

or A and B, taken together with the carbon atom to which they are attached, form a substituted or unsubstituted alicyclic, aromatic, heterocyclic or heteroaromatic ring;

or A and B, taken together with the carbon atom to which they are attached, are selected from the group consisting of CO, C=CHR$_1$, C=NR$_1$, C=NOR$_1$, C=NO(CH$_2$)$_m$R$_1$, C=NNHR$_1$, C=NNHCOR$_1$, C=NNHCONR$_1$R$_2$, C=NNHS(O)$_n$R$_1$, or C=N—N=CHR$_1$;

X and Y are independently selected from the group consisting of hydrogen, deuterium, halogen, $R_1$, $OR_1$, $S(O)_nR_1$, $-NR_1C(O)R_1$, $-NR_1C(O)NR_3R_4$, $-NR_1S(O)_nR_1$, $-CONR_3R_4$, and $NR_3R_4$;

or X and Y, taken together with the carbon atom to which they are attached, are selected from the group consisting of CO, C=CHR$_1$, C=NR$_1$, C=NOR$_1$, C=NO(CH$_2$)$_m$R$_1$, C=NNHR$_1$, C=NNHCOR$_1$, C=NNHCONR$_1$R$_2$, C=NNHS(O)$_n$R$_1$, or C=N—N=CHR$_1$;

L is selected from the group consisting of hydrogen, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, saturated or unsaturated heterocyclic group;

W is $NR_3R_4$

Z is hydrogen, alkyl or halogen;

$R_2'$ is $R_1$;

m is an integer; and n is 0, 1, or 2.

Or a compound represented by formula I, or a racemate, enantiomer, regioisomer, salt, ester or prodrug thereof, wherein A is selected from:
a) —OH;
b) —OR$_p$, where R$_p$ is a hydroxy protecting group;
c) —R$_1$, where R$_1$ is independently selected from:
 (1) aryl;
 (2) substituted aryl;
 (3) heteroaryl;
 (4) substituted heteroaryl;
 (5) heterocycloalkyl; or
 (6) substituted heterocycloalkyl;
d) —OR$_1$, where R$_1$ is as previously defined;
e) —R$_2$, where R$_2$ is selected from:
 (1) hydrogen;
 (2) halogen;

(3) $C_1$–$C_{12}$ alkyl optionally containing 0, 1, 2, or 3 heteroatoms selected from O, $S(O)_n$, where n is 0, 1, or 2, or N, optionally substituted with one or more substituents selected from halogen, aryl, substituted aryl, heteroaryl, substituted heteroaryl, heterocycloalkyl, or substituted heterocycloalkyl;

(4) $C_2$–$C_{12}$ alkenyl optionally containing 0, 1, 2, or 3 heteroatoms selected from O, $S(O)_n$, where n is as previously defined, and N, optionally substituted with one or more substituents selected from halogen, aryl, substituted aryl, heteroaryl, substituted heteroaryl, heterocycloalkyl, or substituted heterocycloalkyl; and (5) $C_2$–$C_{12}$ alkynyl optionally containing 0, 1, 2, or 3 heteroatoms selected from O, $S(O)_n$, where n is as previously defined, and N, optionally substituted with one or more substituents selected from halogen, aryl, substituted aryl, heteroaryl, substituted heteroaryl, heterocycloalkyl, or substituted heterocycloalkyl;

f) —$OR_2$, where $R_2$ is independently previously defined;

g) —$S(O)_n R_{11}$, where n is as previously defined and $R_{11}$ is independently hydrogen, $R_1$ or $R_2$, where $R_1$ and $R_2$ are as previously defined;

h) —$NHC(O)R_{11}$, where $R_{11}$ is as previously defined;

i) —$NHC(O)NHR_{11}$, where $R_{11}$ is as previously defined;

j) —$NHS(O)R_{11}$, where n and $R_{11}$ are as previously defined;

k) —$NR_{14}R_{15}$, where $R_{14}$ and $R_{15}$ are each independently $R_{11}$, where $R_{11}$ is as previously defined; or l) —$NHR_3$, where $R_3$ is an amino protecting group;

B is selected from:
a) hydrogen;
b) deuterium;
c) halogen;
d) —OH;
e) $R_1$, where $R_1$ is as previously defined;
f) $R_2$, where $R_2$ is as previously defined; or
g) —$OR_p$, where $R_p$ is as previously defined,
h) provided that when B is halogen, —OH, or —$OR_p$, A is $R_1$ or $R_2$;

or alternatively, A and B taken together with the carbon atom to which they are attached are selected from:

a) $C(OR_{16})(OR_{17})$, where $R_{16}$ and $R_{17}$ taken together are —$(CH_2)_m$—, and where m is 2 or 3;

b) $C(SR_{16})(SR_{17})$, where $R_{16}$ and $R_{17}$ taken together are —$(CH_2)_m$ and, where m is as previously defined, c) C=$CHR_{11}$, where $R_{11}$ is as previously defined;

d) C=N—O—$Ar_1$—M—$Ar_2$, wherein (1) —$Ar_1$— is absent or selected from $R_{31}$, where $R_{31}$ is independently selected from:

(a) $R_1$, where $R_1$ is as previously defined;

(b) $C_1$–$C_{12}$ alkyl optionally containing 0, 1, 2, or 3 heteroatoms selected from O, $S(O)_n$, where n is as previously defined, and N, optionally substituted with one or more substituents selected from halogen, aryl, substituted aryl, heteroaryl, substituted heteroaryl, heterocycloalkyl, or substituted heterocycloalkyl;

(c) $C_2$–$C_{12}$ alkenyl optionally containing 0, 1, 2, or 3 heteroatoms selected from O, $S(O)_n$, where n is as previously defined, and N, optionally substituted with one or more substituents selected from halogen, aryl, substituted aryl, heteroaryl, substituted heteroaryl, heterocycloalkyl, or substituted heterocycloalkyl; or (d) $C_2$–$C_{12}$ alkynyl optionally containing 0, 1, 2, or 3 heteroatoms selected from O, $S(O)_n$, where n is as previously defined, and N, optionally substituted with one or more substituents selected from halogen, aryl, substituted aryl, heteroaryl, substituted heteroaryl, heterocycloalkyl, or substituted heterocycloalkyl;

(2) —M— is absent or selected from:

(a) —$C_1$–$C_{12}$ alkyl optionally containing:

(1) 0–3 heteroatoms selected from O, $S(O)_n$, where n is as previously defined, or N; and (2) 0–3 groups selected from —C=N—, —N=N, —C(O)—;

(b) —$C_2$–$C_{12}$ alkenyl optionally containing:

(1) 0–3 heteroatoms selected from O, $S(O)_n$, where n is as previously defined, or N; and (2) 0–3 groups selected from —C=N—, —N=N, —C(O)—;

(c) —$C_2$–$C_{12}$ alkynyl optionally containing;

(1) 0–3 heteroatoms selected from O, $S(O)_n$, where n is as previously defined, or N; and (2) 0–3 groups selected from —C=N—, —N=N, —C(O)—;

(d) substituted aryl;
(e) substituted heteroaryl;
(f) heterocycloalkyl; or
(g) substituted heterocycloalkyl; and (3) —$Ar_2$ is absent or selected from:
(a) aryl;
(b) substituted aryl;
(c) heteroaryl;
(d) substituted heteroaryl;
(e) heterocycloalkyl; or
(f) substituted heterocycloalkyl;

e) C=$NNHR_{11}$, where $R_{11}$ is as previously defined;

f) C=$NNHC(O)R_{11}$, where $R_{11}$ is as previously defined;

g) C=$NNHC(O)NHR_{11}$, where $R_{11}$ is as previously defined;

h) C=$NNHS(O)_n R_{11}$, where n and $R_{11}$ are as previously defined;

i) C=$NNHR_3$, where $R_3$ is as previously defined;

j) C=$NR_{11}$, where $R_{11}$ is as previously defined; or k) C=N—N=$CHR_{11}$, where $R_{11}$ is as previously defined;

one of X and Y is hydrogen and the other is selected from:
a) hydrogen;
b) deuterium;
c) —OH;
d) —$OR_p$, where $R_p$ is as previously defined;
e) —$NR_4R_5$, where $R_4$ and $R_5$ are each independently selected from:

(1) hydrogen;

(2) $C_1$–$C_{12}$ alkyl, optionally substituted with one or more substituents selected from halogen, aryl, substituted aryl, heteroaryl, substituted heteroaryl, heterocycloalkyl, or substituted heterocycloalkyl; or (3) $R_4$ and $R_5$, taken together with the nitrogen atom to which they are attached to form a heterocycloalkyl moiety;

alternatively, X and Y taken together with the carbon atom to which they are attached are selected from:

a) C═O;
b) C═N—Q, wherein Q is selected from:
  (1) —$R_{11}$, where $R_{11}$ is as previously defined;
  (2) amino protecting group;
  (3) —C(O)$R_{11}$, where $R_{11}$ is as previously defined;
  (4) —O$R_6$, where $R_6$ is independently selected from:
   a. hydrogen;
   b. —$CH_2O(CH_2)_2OCH_3$,
   c. —$CH_2O(CH_2)_nCH_3$ where n is as previously defined;
   d. —$C_1$–$C_{12}$ alkyl, optionally substituted with one or more substituents selected from aryl, substituted aryl, heteroaryl, substituted heteroaryl, heterocycloalkyl, or substituted heterocycloalkyl;
   e. —$C_3$–$C_{12}$ cycloalkyl;
   f. —C(O)—$C_1$–$C_{12}$ alkyl;
   g. —C(O)—$C_3$–$C_{12}$ cycloalkyl;
   h. —C(O)—$R_1$, where $R_1$ is as previously defined; or
   i. —Si($R_a$)($R_b$)($R_c$), wherein $R_a$, $R_b$ and $R_c$ are each independently selected from $C_1$–$C_{12}$ alkyl, aryl or substituted aryl; or
  (5) O—C($R_7$)($R_8$)—O—$R_6$, where $R_6$ is as previously defined, provided that $R_6$ is not C(O)—$C_1$–$C_{12}$ alkyl, C(O)—$C_3$–$C_{12}$ cycloalkyl, or C(O)—$R_1$, and $R_7$ and $R_8$ taken together with the carbon atom to which they are attached form a $C_3$–$C_{12}$ cycloalkyl group or each independently is selected from:
   a. hydrogen; or
   b. $C_1$–$C_{12}$ alkyl;
L is selected from:
 a) —$CH_3$;
 b) —$CH_2CH_3$;
 c) —CH(OH)$CH_3$;
 d) —$(CH_2)_n$NHC(O)—$R_{11}$, wherein n and $R_{11}$ are as previously defined;
 e) $C_1$–$C_6$ alkyl, optionally substituted with one or more substituents selected from aryl, substituted aryl, heteroaryl, substituted heteroaryl, heterocycloalkyl, or substituted heterocycloalkyl;
 f) $C_2$–$C_6$ alkenyl, optionally substituted with one or more substituents selected from aryl, substituted aryl, heteroaryl, substituted heteroaryl, heterocycloalkyl, or substituted heterocycloalkyl; or
 g) $C_2$–$C_6$ alkynyl, optionally substituted with one or more substituents selected from aryl, substituted aryl, heteroaryl, substituted heteroaryl, heterocycloalkyl, or substituted heterocycloalkyl;
W is —$NR_{20}R_{21}$, where $R_{20}$ and $R_{21}$ are each independently selected from:
 a) hydrogen;
 b) $C_1$–$C_{12}$ alkyl, optionally substituted with one or more substituents selected from halogen, aryl, substituted aryl, heteroaryl, substituted heteroaryl, heterocycloalkyl, or substituted heterocycloalkyl;
 c) $C_2$–$C_{12}$ alkenyl, optionally substituted with one or more substituents selected from halogen, aryl, substituted aryl, heteroaryl, substituted heteroaryl, heterocycloalkyl, or substituted heterocycloalkyl;
 d) $C_2$–$C_{12}$ alkynyl, optionally substituted with one or more substituents selected from halogen, aryl, substituted aryl, heteroaryl, substituted heteroaryl, heterocycloalkyl, or substituted heterocycloalkyl; or
 e) $R_{20}$ and $R_{21}$, taken together with the nitrogen atom to which they are attached form a heterocycloalkyl moiety; or Z is selected from:
 a) hydrogen;
 b) methyl; or
 c) halogen; and
$R_2'$ is hydrogen, or $R_p$, where $R_p$, is as previously defined.

In another embodiment of the present invention there are disclosed pharmaceutical compositions comprising a therapeutically effective amount of any compound of the present invention in combination with a pharmaceutically acceptable carrier or excipient. In yet another embodiment of the invention are methods of treating antibacterial infections in a subject with said pharmaceutical compositions. Suitable carriers and methods of formulation are also disclosed.

In a further aspect of the present invention there are provided processes for the preparation of 6,11-3C-bridged ketolide derivatives of formula (I) via any synthetic route delineated herein.

DETAILED DESCRIPTION OF THE INVENTION

A first embodiment of the present invention is a compound of formula I as defined herein, or its pharmaceutically acceptable salt, ester, or prodrug.

Representative subgenera of the present invention are:

A compound according to claim 1 which is represented by the formula

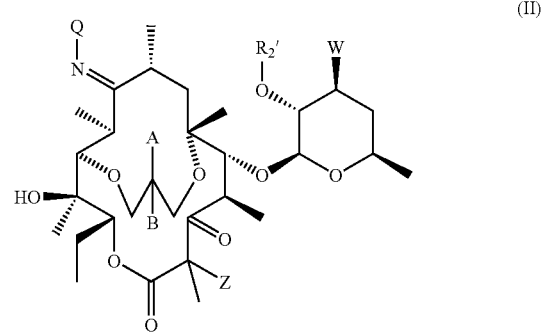

(II)

wherein A, B, $R_2'$, Q, W, and Z are as defined in claim;

A compound according to claim 1 which is represented by the formula

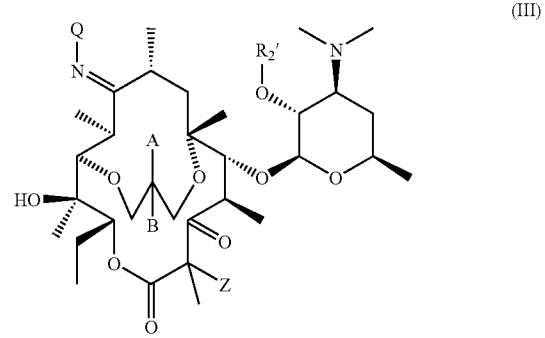

(III)

wherein A, B, $R_2'$, Q, and Z are as defined in claim 1;

A compound according to claim 1 which is represented by the formula

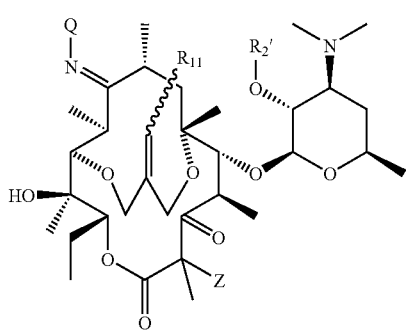
(IV)

wherein A, B, R$_2$', Q, and Z are as defined in claim 1;

A compound according to claim 1 which is represented by the formula

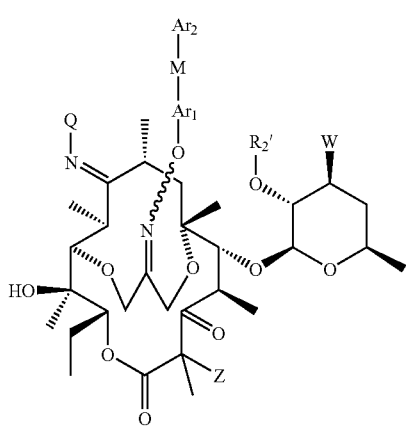
(V)

wherein Ar$_1$, Ar$_2$, R$_2$', M, Q, W, and Z are as defined in claim 1;

A compound according to claim 1 which is represented by the formula:

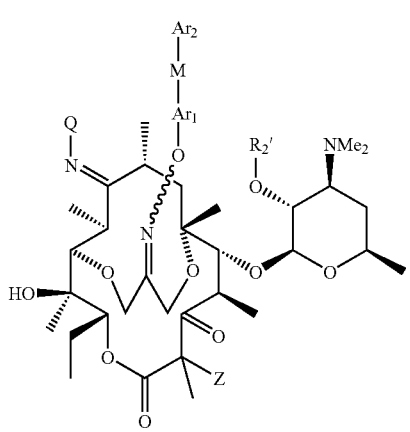
(VI)

wherein Ar$_1$, Ar$_2$, R$_2$', M, Q, and Z are as defined in claim 1;

A compound according to claim 1 which is represented by the formula:

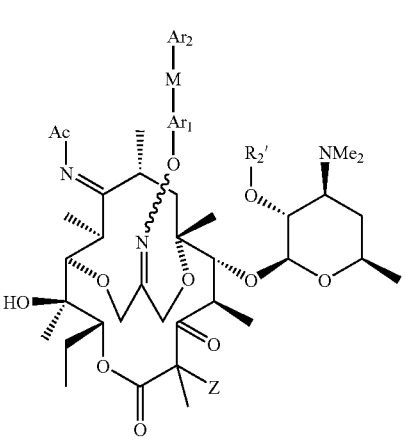
(VII)

wherein Ar$_1$, Ar$_2$, R$_2$', M, and Z are as defined in claim 1; or

A compound according to claim 1 which is represented by the formula:

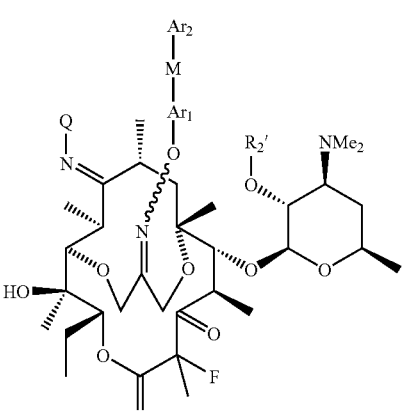
(VIII)

wherein Ar$_1$, Ar$_2$, R$_2$', M, and Q are as defined in claim 1.

Compound of formula I, wherein B is hydrogen or OH;

Compound of formula I, wherein A and B taken together with the carbon atom to which they are attached are C=CH—R$_{11}$;

Compound of formula I, wherein A and B taken together with the carbon atom to which they are attached are C=CH—R$_{11}$ and X and Y taken together with the carbon atom to which they are attached are C=N—Q;

Compound of formula I, wherein A and B taken together with the carbon atom to which they are attached are C=CH—R$_{11}$ and X and Y taken together with the carbon atom to which they are attached are C=N—Ac;

Compound of formula I, wherein X and Y taken together with the carbon atom to which they are attached are C=N—Q; or Compound of formula I, wherein A and B taken together with the carbon atom to which they are attached are selected from:

(a) C=N—NHR$_{11}$, where R$_{11}$ is as defined in claim 1;
(b) C=N—NHC(O)R$_{11}$, where R$_{11}$ is as previously defined;
(c) C=N—NHC(O)NHR$_{11}$, where R$_{11}$ is as previously defined;
(d) C=N—NHS(O)$_2$R$_{11}$, where R$_{11}$ is as previously defined;
(e) C=N—NHR$_3$, where R$_3$ is as defined in claim 1;
(f) C=N—R$_{11}$, where R$_{11}$ is as previously defined; or
(g) C=N—N=CHR$_{11}$, where R$_{11}$ is as previously defined.

Representative species of the present invention are:

Example 1. Compound of formula I: A and B taken together with the carbon atom to which they attached are C=CH$_2$, X and Y taken together with the carbon atom to which they are attached are C=N—Ac, L=CH$_2$CH$_3$, Z=H, and R$_2$'=Ac;

Example 2. Compound of formula I: A and B taken together with the carbon atom to which they are attached are C=CH$_2$, X and Y taken together with the carbon atom to which they are attached are C=N—Ac, L=CH$_2$CH$_3$, Z=H and R$_2$'=H;

Example 3. Compound of formula I: A and B taken together with the carbon atom to which they are attached are C=O, X and Y taken together with the carbon atom to which they attached are C=N—Ac, L=CH$_2$CH$_3$, Z=H and R$_2$'=H;

Example 4. Compound of formula I: A and B taken together with the carbon atom to which they are attached are C=N—O—CH$_2$-Ph, X and Y taken together with the carbon atom to which they are attached are C=N—Ac, L=CH$_2$CH$_3$, Z=H and R$_2$'=H;

Example 5. Compound of formula I: A and B taken together with the carbon atom to which they are attached are C=N—O—CH$_2$—(3-pyridyl), X and Y taken together with the carbon atom to which they are attached are C=N—Ac, L=CH$_2$CH$_3$, Z=H and R$_2$'=H;

Example 6. Compound of formula I: A and B taken together with the carbon atom to which they are attached are C=N—O—CH$_2$—(2-pyridyl), X and Y taken together with the carbon atom to which they are attached are C=N—Ac, L=CH$_2$CH$_3$, Z=H and R$_2$'=H;

Example 7. Compound of formula I: A and B taken together with the carbon atom to which they are attached are C=N—O—CH$_2$—(3-quinolyl), X and Y taken together with the carbon atom to which they are attached are C=N—Ac, L=CH$_2$CH$_3$, Z=H and R$_2$'=H;

Example 8. Compound of formula I: A and B taken together with the carbon atom to which they are attached are C=N—O—CH$_2$—(2-quinolyl), X and Y taken together with the carbon atom to which they are attached are C=N—Ac, L=CH$_2$CH$_3$, Z=H and R$_2$'=H;

Example 9. Compound of formula I: A and B taken together with the carbon atom to which they are attached are C=N—O—CH$_2$(5-pyridin-2-ylthiophen-2yl), X and Y taken together with the carbon atom to which they are attached are C=N—Ac, L=CH$_2$CH$_3$, Z=H and R$_2$'=H;

Example 10. Compound of formula I: A and B taken together with the carbon atom to which they are attached are C=N—O—[3-(pyrimidin-2-yl)prop-2-ynyl], X and Y taken together with the carbon atom to which they are attached are C=N—Ac, L=CH$_2$CH$_3$, Z=H and R$_2$'=H;

Example 11. Compound of formula I: A and B taken together with the carbon atom to which they are attached are C=N—O-Ph, X and Y taken together with the carbon atom to which they are attached are C=N—Ac, L=CH$_2$CH$_3$, Z=H and R$_2$'=H;

Example 12. Compound of formula I: A=NHCH$_2$-Ph, B=H, X and Y taken together with the carbon atom to which they are attached are C=N—Ac, L=CH$_2$CH$_3$, Z=H and R$_2$'=H;

Example 13. Compound of formula I: A=NHCH$_2$CH$_2$-Ph, B=H, X and Y taken together with the carbon atom to which they are attached are C=N—Ac, L=CH$_2$CH$_3$, Z=H and R$_2$'=H;

Example 14. Compound of formula I: A and B taken together with the carbon atom to which they are attached are C=CH$_2$, X and Y taken together with the carbon atom to which they are attached are C=N—O—CH$_2$—O—CH$_3$, L=CH$_2$CH$_3$, Z=H, and R$_2$'=Ac;

Example 15. Compound of formula I: A and B taken together with the carbon atom to which they are attached are C=CH$_2$, X and Y taken together with the carbon atom to which they are attached are C=N—O—CH$_2$—O—CH$_3$, L=CH$_2$CH$_3$, Z=H and R$_2$'=H;

Example 16. Compound of formula I: A and B taken together with the carbon atom to which they are attached are C=O, X and Y taken together with the carbon atom to which they are attached are C=N—O—CH$_2$—O—CH$_3$, L=CH$_2$CH$_3$, Z=H and R$_2$'=H;

Example 17. Compound of formula I: A and B taken together with the carbon atom to which they are attached are C=NOCH$_2$-Ph, X and Y taken together with the carbon atom to which they are attached are C=N—O—CH$_2$—O—CH$_3$, L=CH$_2$CH$_3$, Z=H and R$_2$'=H;

Example 18. Compound of formula I: A and B taken together with the carbon atom to which they are attached are C=O, X and Y taken together with the carbon atom to which they are attached are C=O, L=CH$_2$CH$_3$, Z=H, and R$_2$'=Ac;

Example 19. Compound of formula I: A and B taken together with the carbon atom to which they are attached are C=CH$_2$, X and Y taken together with the carbon atom to which they are attached are C=O, L=CH$_2$CH$_3$, Z=H, and R$_2$'=H;

Example 20. Compound of formula I: A and B taken together with the carbon atom to which they are attached are C=O, X and Y taken together with the carbon atom to which they are attached are C=O, L=CH$_2$CH$_3$, Z=H, and R$_2$'=H;

Example 21. Compound of formula I: A and B taken together with the carbon atom to which they are attached are C=N—O—CH$_2$-Ph, X and Y taken together with the carbon atom to which they are attached are C=O, L=CH$_2$CH$_3$, Z=H, and R$_2$'=H;

Example 22. Compound of formula I: A and B taken together with the carbon atom to which they are attached are C=CH$_2$, X and Y taken together with the carbon atom to which they are attached are C=NH, L=CH$_2$CH$_3$, Z=H, and R$_2$'=H;

Example 23. Compound of formula I: A and B taken together with the carbon atom to which they are attached are C=N—O—CH$_2$-p-NO$_2$-Ph, X and Y taken together with the carbon atom to which they are attached are C=N—Ac, L=CH$_2$CH$_3$, Z=H, and R$_2$'=H;

Example 24. Compound of formula I: A and B taken together with the carbon atom to which they are attached are C=N—O—(CH$_2$)$_2$-Ph, X and Y taken together with the carbon atom to which they are attached are C=N—Ac, L=CH$_2$CH$_3$, Z=H, and R$_2$'=H;

Example 25. Compound of formula I: A and B taken together with the carbon atom to which they are attached are C=N—O—(CH$_2$)$_3$-Ph, X and Y taken together with the carbon atom to which they are attached are C=N—Ac, L=CH$_2$CH$_3$, Z=H, and R$_2$'=H;

Example 26. Compound of formula I: A and B taken together with the carbon atom to which they are attached are C=N—O—CH$_2$—CH=CH-Ph, X and Y taken together with the carbon atom to which they are attached are C=N—Ac, L=CH$_2$CH$_3$, Z=H, and R$_2$'=H;

Example 27. Compound of formula I: A is NH—(CH$_2$)$_3$-Ph, B is H, X and Y taken together with the carbon atom to which they are attached are C=N—Ac, L=CH$_2$CH$_3$, Z=H, and R$_2$'=H;

Example 28. Compound of formula I: A is NH—(CH$_2$)$_4$-Ph, B is H, X and Y taken together with the carbon atom to which they are attached are C=N—Ac, L=CH$_2$CH$_3$, Z=H, and R$_2$'=H;

Example 29. Compound of formula I: A is CH$_2$—CH=CH$_2$, B is OH, X and Y taken together with the carbon atom to which they are attached are C=N—Ac, L=CH$_2$CH$_3$, Z=H, and R$_2$'=H;

Example 30. Compound of formula I: A is CH$_2$-Ph, B is OH, X and Y taken together with the carbon atom to which they are attached are C=N—Ac, L=CH$_2$CH$_3$, Z=H, and R$_2$'=H;

Example 31. Compound of formula I: A is Ph, B is OH, X and Y taken together with the carbon atom to which they are attached are C=N—Ac, L=CH$_2$CH$_3$, Z=H, and R$_2$'=H;

Example 32. Compound of formula I: A is Ph, B is OH, X and Y taken together with the carbon atom to which they are attached are C=N—Ac, L=CH$_2$CH$_3$, Z=H, and R$_2$'=H;

Example 33. Compound of formula I: A is CH$_2$—CH=CH-Ph, B is OH, X and Y taken together with the carbon atom to which they are attached are C=N—Ac, L=CH$_2$CH$_3$, Z=H, and R$_2$'=H;

Example 34. Compound of formula I: A is (CH$_2$)$_3$-Ph, B is OH, X and Y taken together with the carbon atom to which they are attached are C=N—Ac, L=CH$_2$CH$_3$, Z=H, and R$_2$'=H;

Example 35. Compound of formula I: A and B taken together with the carbon atom to which they are attached are C=CH—CH=CH-Ph, X and Y taken together with the carbon atom to which they are attached are C=N—Ac, L=CH$_2$CH$_3$, Z=H, and R$_2$'=H;

Example 36. Compound of formula I: A is (CH$_2$)$_3$-Ph, B is H, X and Y taken together with the carbon atom to which they are attached are C=N—Ac, L=CH$_2$CH$_3$, Z=H, and R$_2$'=H;

Example 37. Compound of formula I: A and B taken together with the carbon atom to which they are attached are C=CH—CH=CH-3-pyridyl, X and Y taken together with the carbon atom to which they are attached are C=N—Ac, L=CH$_2$CH$_3$, Z=H, and R$_2$'=H;

Example 38. Compound of formula I: A and B taken together with the carbon atom to which they are attached are C=CH—CH=CH-3-quinolyl, X and Y taken together with the carbon atom to which they are attached are C=N—Ac, L=CH$_2$CH$_3$, Z=H, and R$_2$'=H;

Example 39. Compound of formula I: A and B taken together with the carbon atom to which they are attached are C=CH-2-quinolyl, X and Y taken together with the carbon atom to which they are attached are C=N—Ac, L=CH$_2$CH$_3$, Z=H, and R$_2$'=H;

Example 40. Compound of formula I: A and B taken together with the carbon atom to which they are attached are C=CH-2-quinolyl, X and Y taken together with the carbon atom to which they are attached are C=N—H, L=CH$_2$CH$_3$, Z=H, and R$_2$'=H;

Example 41. Compound of formula I: A and B taken together with the carbon atom to which they are attached are C=CH-4-biphenyl, X and Y taken together with the carbon atom to which they are attached are C=N—Ac, L=CH$_2$CH$_3$, Z=H, and R$_2$'=H;

Example 42. Compound of formula I: A and B taken together with the carbon atom to which they are attached are C=CH-3-biphenyl, X and Y taken together with the carbon atom to which they are attached are C=N—Ac, L=CH$_2$CH$_3$, Z=H, and R$_2$'=H;

Example 43. Compound of formula I: A and B taken together with the carbon atom to which they are attached are C=CH-4-phenoxyphenyl, X and Y taken together with the carbon atom to which they are attached are C=N—Ac, L=CH$_2$CH$_3$, Z=H, and R$_2$'=H;

Example 44. Compound of formula I: A and B taken together with the carbon atom to which they are attached are C=CH-Ph, X and Y taken together with the carbon atom to which they are attached are C=N—Ac, L=CH$_2$CH$_3$, Z=H, and R$_2$'=H;

Example 45. Compound of formula I: A and B taken together with the carbon atom to which they are attached are C=CH-2-(2pyridyl)-thiophen-5-yl, X and Y taken together with the carbon atom to which they are attached are C=N—Ac, L=CH$_2$CH$_3$, Z=H, and R$_2$'=H; or Example 46. Compound of formula I: A and B taken together with the carbon atom to which they are attached are C=O, X and Y taken together with the carbon atom to which they are attached are C=N—Ac, L=CH$_2$CH$_3$, Z=F, and R$_2$'=Ac.

Further representative species of the present invention are:

Example compounds 47–114 of the formula A:

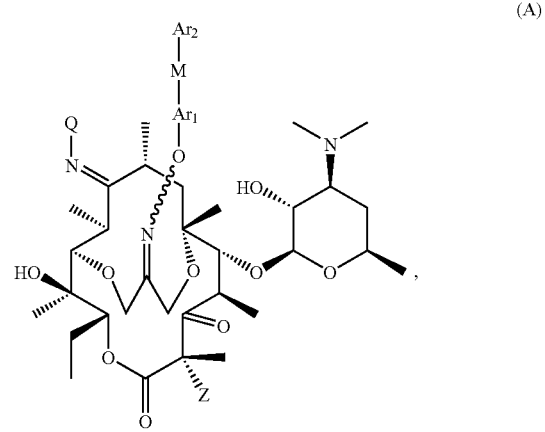

(A)

wherein Ar$_1$, Ar$_2$, M, Q, and Z are delineated for each example in Table A:

TABLE A
| Example | Q | —Ar₁—M—Ar₂ | Z |
|---------|-----|------------|---|
| Example 47. | Ac | 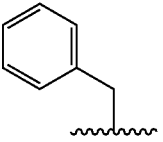 | H |
| Example 48. | Ac | 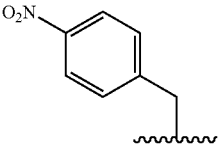 | H |
| Example 49. | Ac | 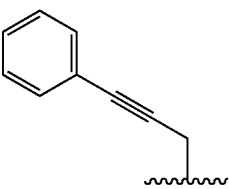 | H |
| Example 50. | Ac | 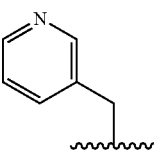 | H |
| Example 51. | Ac | 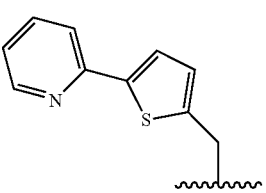 | H |
| Example 52. | Ac | 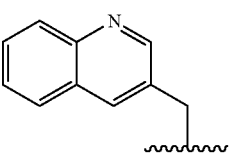 | H |
| Example 53. | Ac | 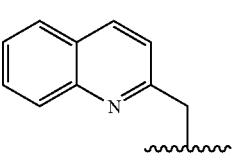 | H |
| Example 54. | Ac | 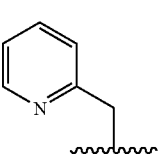 | H |
| Example 55. | MOM | 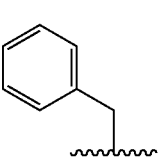 | H |

TABLE A-continued
| Example | Q | —Ar₁—M—Ar₂ | Z |
|---|---|---|---|
| Example 56. | Ac | 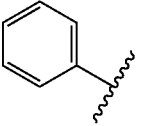 | H |
| Example 57. | Ac | 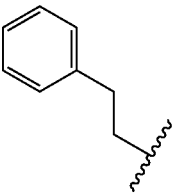 | H |
| Example 58. | Ac | 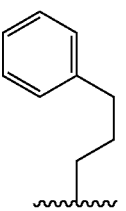 | H |
| Example 59. | Ac | 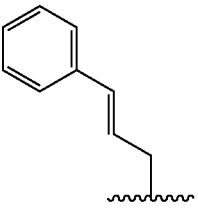 | H |
| Example 60. | Ac | 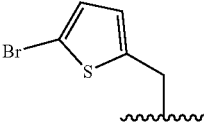 | H |
| Example 61. | Ac | 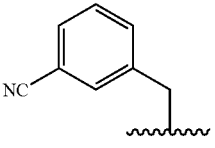 | H |
| Example 62. | Ac | 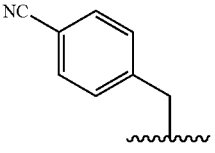 | H |
| Example 63. | Ac | 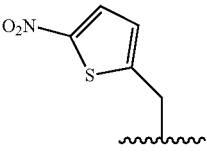 | H |
| Example 64. | Ac | 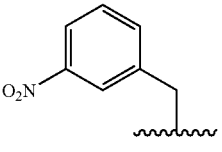 | H |

TABLE A-continued

| Example | Q | —Ar₁—M—Ar₂ | Z |
|---|---|---|---|
| Example 65. | Ac | 3,4-difluorobenzyl | H |
| Example 66. | Ac | 5-(pyridin-3-yl)thiophen-2-ylmethyl | H |
| Example 67. | Ac | (2-aminopyridin-4-yl)methyl | H |
| Example 68. | Ac | (2-acetamidopyridin-4-yl)methyl | H |
| Example 69. | Ac | 5-(pyridin-3-yl)isoxazol-3-ylmethyl | H |
| Example 70. | Ac | 5-(2-methyl-2H-tetrazol-5-yl)thiophen-2-ylmethyl | H |
| Example 71. | Ac | 4-(1H-pyrazol-1-yl)benzyl | H |
| Example 72. | Ac | 4-(1,2,3-thiadiazol-4-yl)benzyl | H |

TABLE A-continued
| Example | Q | —Ar₁—M—Ar₂ | Z |
| --- | --- | --- | --- |
| Example 73. | Ac | 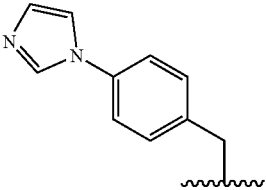 | H |
| Example 74. | Ac | 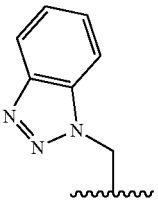 | H |
| Example 75. | Ac | 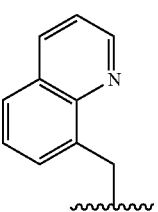 | H |
| Example 76. | Ac | 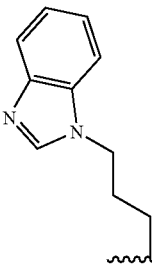 | H |
| Example 77. | Ac | 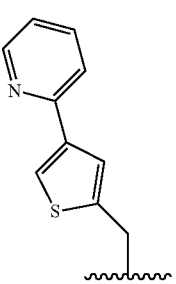 | H |
| Example 78. | Ac | 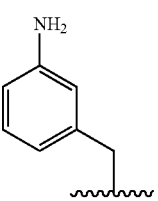 | H |

TABLE A-continued
| Example | Q | —Ar₁—M—Ar₂ | Z |
|---|---|---|---|
| Example 79. | Ac | 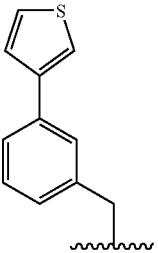 | H |
| Example 80. | Ac | 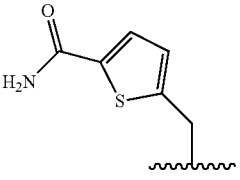 | F |
| Example 81. | H | 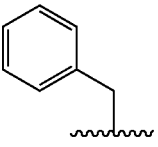 | H |
| Example 82. | Ac | 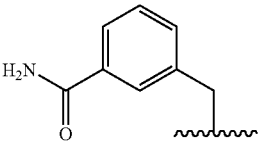 | H |
| Example 83. | Ac | 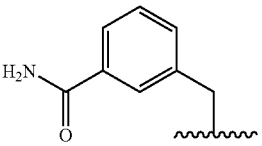 | F |
| Example 84. | Ac | 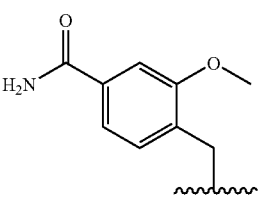 | H |
| Example 85. | Ac | 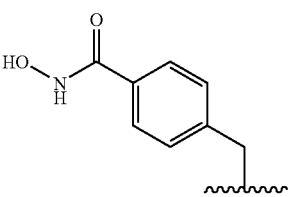 | H |
| Example 86. | Ac | 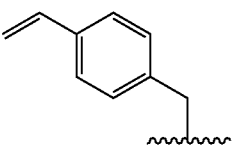 | H |

TABLE A-continued
| Example | Q | —Ar₁—M—Ar₂ | Z |
|---|---|---|---|
| Example 87. | Ac | 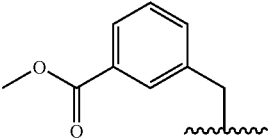 | H |
| Example 88. | Ac | 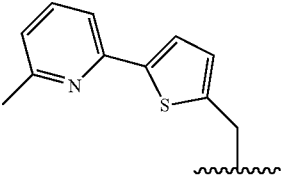 | H |
| Example 89. | Ac | 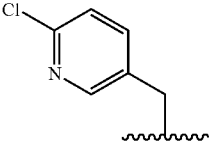 | H |
| Example 90. | H | 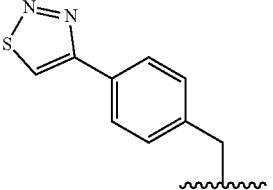 | H |
| Example 91. | H | 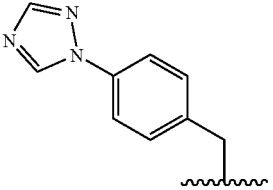 | H |
| Example 92. | OMe | 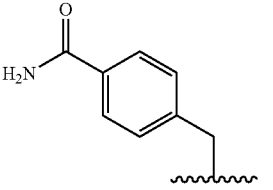 | H |
| Example 93. | —OMOM | 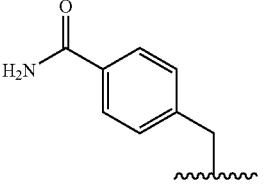 | H |
| Example 94. | —OCH₂CN | 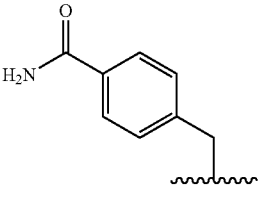 | H |

TABLE A-continued

| Example | Q | —Ar₁—M—Ar₂ | Z |
|---|---|---|---|
| Example 95. | —OCH₂CH₂OH | 4-(H₂N-C(=O))-phenyl-CH₂- | H |
| Example 96. | H | 4-(H₂N)-phenyl-CH₂- | H |
| Example 97. | Ac | 4-(H₂N)-phenyl-CH₂- | H |
| Example 98. | Ac | 2-pyridyl-thiophene-thiophene-CH₂- | H |
| Example 99. | Ac | pyrazolyl-pyridyl-CH₂- | H |
| Example 100. | Ac | HC≡C-CH₂- | H |
| Example 101. | Ac | 2-pyridyl-thiophene-C≡C-CH₂- | H |
| Example 102. | Ac | quinolin-3-yl-C≡C-CH₂- | H |

TABLE A-continued
| Example | Q | —Ar₁—M—Ar₂ | Z |
|---|---|---|---|
| Example 103. | Ac | 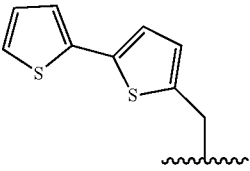 | H |
| Example 104. | Ac | 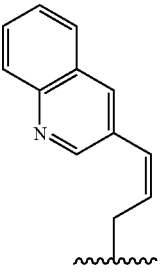 | H |
| Example 105. | Ac | 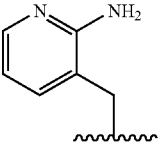 | H |
| Example 106. | Ac | 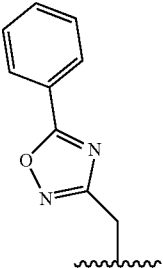 | H |
| Example 107. | Ac | 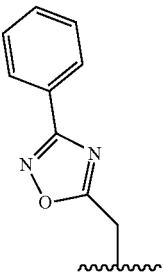 | H |
| Example 108. | Ac | 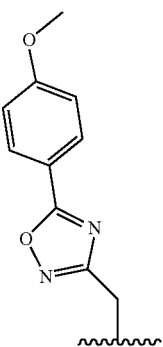 | H |

TABLE A-continued
| Example | Q | —Ar₁—M—Ar₂ | Z |
|---|---|---|---|
| Example 109. | Ac | 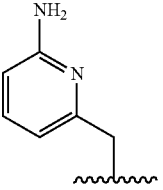 | H |
| Example 110. | Ac | 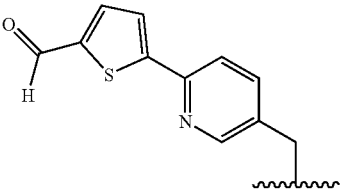 | H |
| Example 111. | Ac | 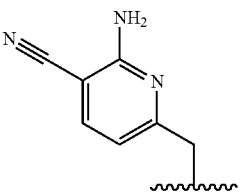 | H |
| Example 112. | Ac | 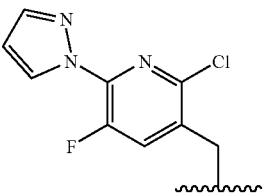 | H |
| Example 113. | Ac | 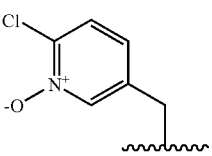 | H |
| Example 114. | Ac | 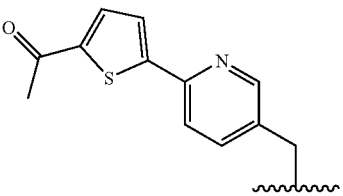 | H |

Example compounds 115–263 of formula A1:
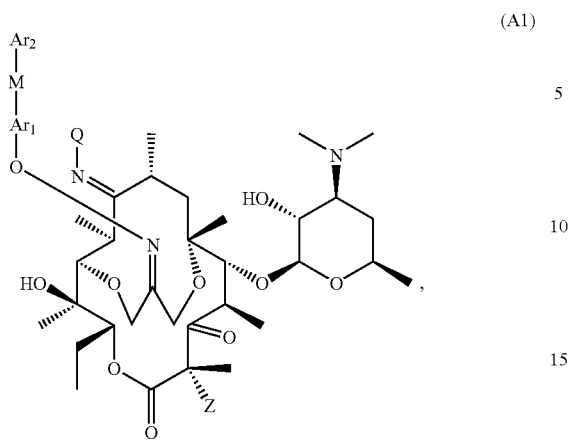
wherein Ar$_1$, Ar$_2$, M, Q, and Z are delineated for each example in Table A1:
TABLE A1
| Example | Q | —Ar$_1$—M—Ar$_2$ | Z |
| --- | --- | --- | --- |
| Example 115. | Ac | 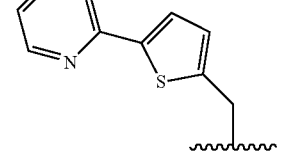 | H |
| Example 116. | Ac | 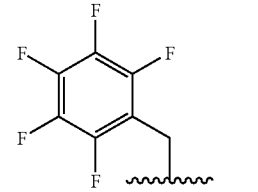 | H |
| Example 117. | Ac | 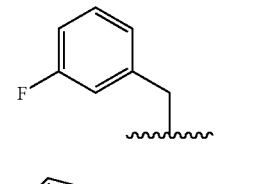 | H |
| Example 118. | Ac | 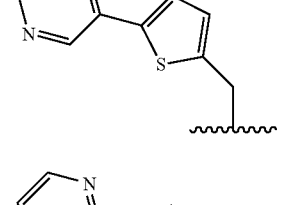 | H |
| Example 119. | Ac | 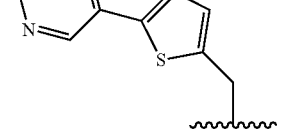 | H |

TABLE A1-continued
| Example | Q | —Ar₁—M—Ar₂ | Z |
|---|---|---|---|
| Example 120. | Ac | 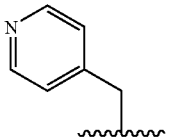 | H |
| Example 121. | Ac | 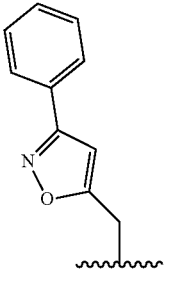 | H |
| Example 122. | Ac | 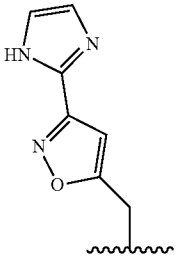 | H |
| Example 123. | Ac | 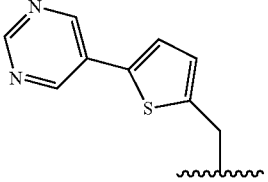 | H |
| Example 124. | Ac | 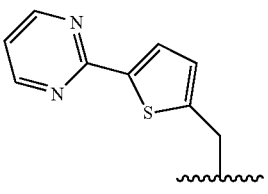 | H |
| Example 125. | Ac | 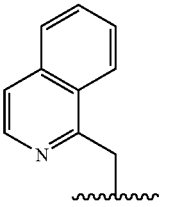 | H |
| Example 126. | Ac | 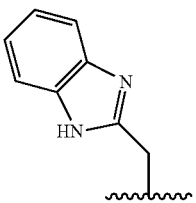 | H |

TABLE A1-continued
| Example | Q | —Ar₁—M—Ar₂ | Z |
|---|---|---|---|
| Example 127. | Ac | 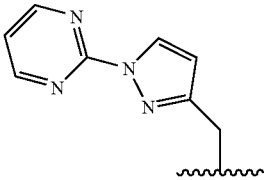 | H |
| Example 128. | Ac | 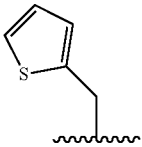 | H |
| Example 129. | Ac | 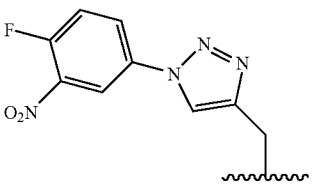 | H |
| Example 130. | Ac | 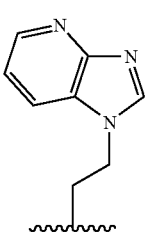 | H |
| Example 131. | Ac | 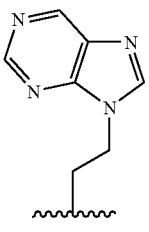 | H |
| Example 132. | Ac | 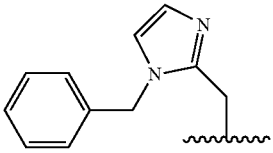 | H |
| Example 133. | Ac | 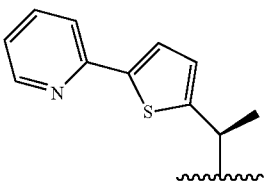 | H |
| Example 134. | Ac | 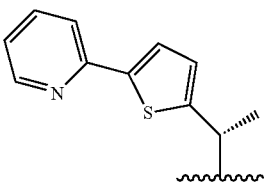 | H |

TABLE A1-continued
| Example | Q | —Ar₁—M—Ar₂ | Z |
|---------|---|------------|---|
| Example 135. | Ac | 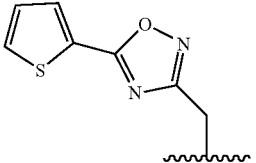 | H |
| Example 136. | Ac | 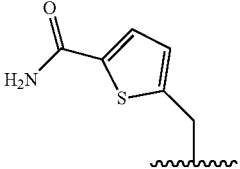 | H |
| Example 137. | Ac | 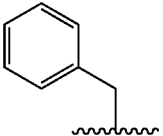 | H |
| Example 138. | Ac | 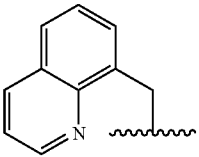 | F |
| Example 139. | Ac | 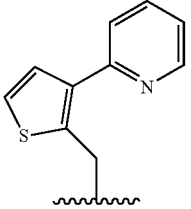 | H |
| Example 140. | Ac | 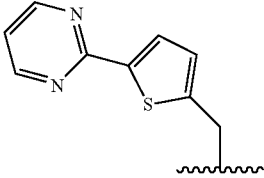 | F |
| Example 141. | Ac | 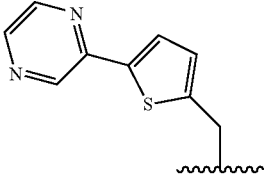 | F |
| Example 142. | Ac | 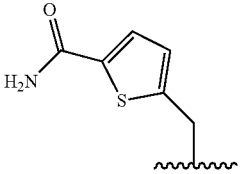 | F |

TABLE A1-continued
| Example | Q | —Ar₁—M—Ar₂ | Z |
|---|---|---|---|
| Example 143. | Ac | 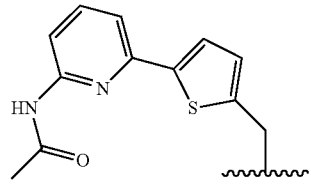 | H |
| Example 144. | Ac | 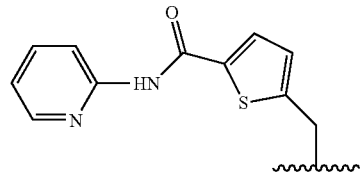 | H |
| Example 145. | Ac | 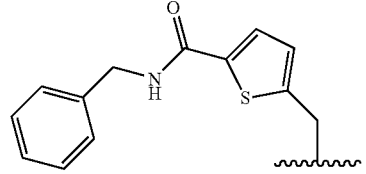 | H |
| Example 146. | Ac | 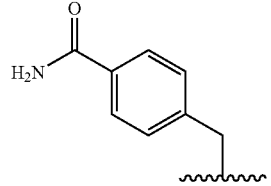 | H |
| Example 147. | Ac | 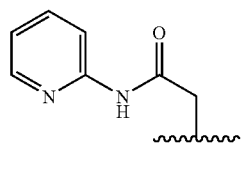 | H |
| Example 148. | Ac | 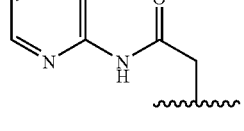 | F |
| Example 149. | Ac | 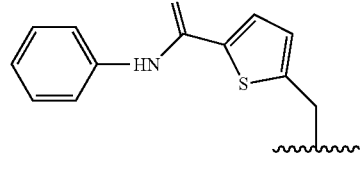 | H |
| Example 150. | Ac | 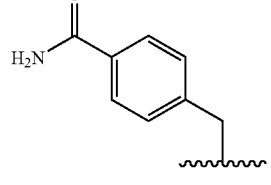 | F |

TABLE A1-continued

| Example | Q | —Ar₁—M—Ar₂ | Z |
|---|---|---|---|
| Example 151. | Ac | 5-carbamoyl-thiophen-2-yl-methylene | H |
| Example 152. | Ac | 5-(hydroxyimino-methyl)-thiophen-2-yl-methylene | H |
| Example 153. | Ac | 4-(phenylcarbamoyl)-benzyl | H |
| Example 154. | Ac | 4-(pyridin-2-ylcarbamoyl)-benzyl | H |
| Example 155. | Ac | 4-(N,N-dimethylcarbamoyl)-benzyl | H |
| Example 156. | Ac | 6-(2,4-dioxo-1,2,3,4-tetrahydropyrimidin-6-yl)-methylene | H |
| Example 157. | Ac | 4-(N-methylcarbamoyl)-benzyl | H |

TABLE A1-continued
| Example | Q | —Ar₁—M—Ar₂ | Z |
|---------|-----|------------|---|
| Example 158. | Ac | 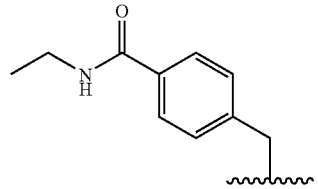 | H |
| Example 159. | Ac | 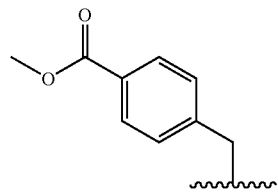 | H |
| Example 160. | Ac | 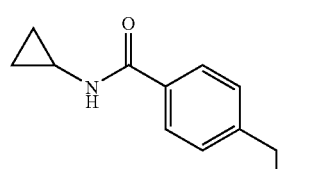 | H |
| Example 161. | Ac | 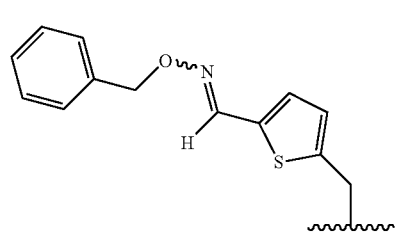 | H |
| Example 162. | Ac | 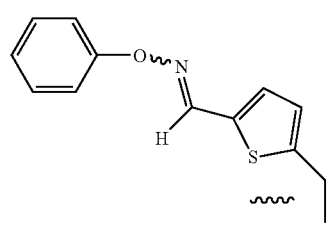 | H |
| Example 163. | Ac | 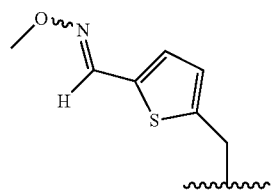 | H |
| Example 164. | Ac | 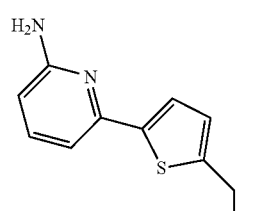 | H |

TABLE A1-continued

| Example | Q | —Ar₁—M—Ar₂ | Z |
|---|---|---|---|
| Example 165. | Ac | pyridin-2-yl-NH-C(O)-CH₂-CH₂- | H |
| Example 166. | Ac | 3,4-dimethoxyphenyl-thiophen-2-yl-CH₂- | H |
| Example 167. | Ac | methyl 3-methoxy-4-(CH₂-)benzoate | H |
| Example 168. | Ac | 4-carbamoyl-2-methoxyphenyl-CH₂- | H |
| Example 169. | Ac | 4-acetamidophenyl-CH₂- | H |
| Example 170. | Ac | 5-cyanothiophen-2-yl-CH₂- | H |
| Example 171. | Ac | 4-(hydrazinocarbonyl)phenyl-CH₂- | H |
| Example 172. | Ac | methyl 4-(CH₂-)phenylcarbamate | H |

TABLE A1-continued
| Example | Q | —Ar₁—M—Ar₂ | Z |
|---|---|---|---|
| Example 173. | Ac | 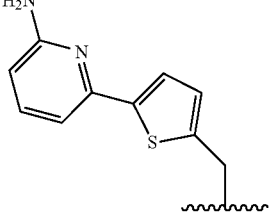 | F |
| Example 174. | Ac | 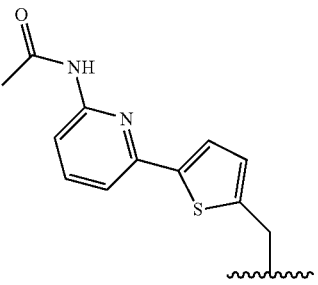 | F |
| Example 175. | Ac | 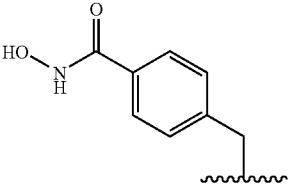 | H |
| Example 176. | Ac | 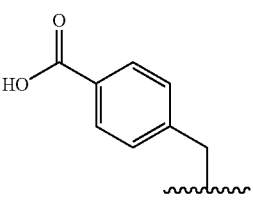 | H |
| Example 177. | Ac | 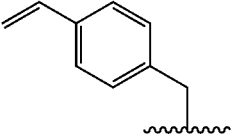 | H |
| Example 178. | Ac | 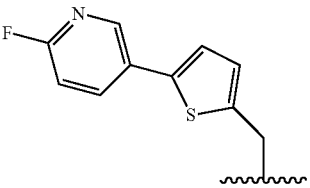 | H |
| Example 179. | Ac | 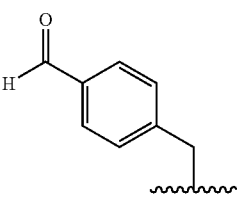 | H |

TABLE A1-continued
| Example | Q | —Ar₁—M—Ar₂ | Z |
|---|---|---|---|
| Example 180. | H | 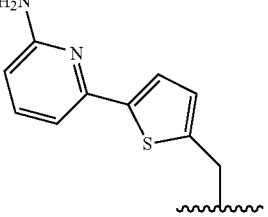 | H |
| Example 181. | Ac | 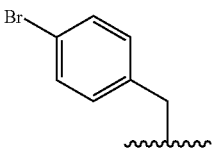 | H |
| Example 182. | Ac | 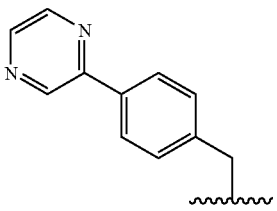 | H |
| Example 183. | Ac | 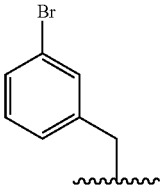 | H |
| Example 184. | Ac | 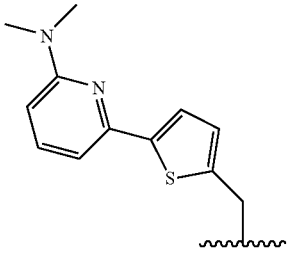 | F |
| Example 185. | Ac | 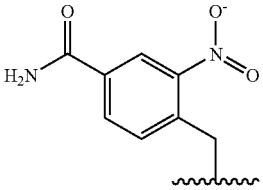 | H |
| Example 186. | Ac | 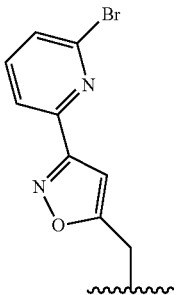 | H |

TABLE A1-continued
| Example | Q | —Ar₁—M—Ar₂ | Z |
| --- | --- | --- | --- |
| Example 187. | Ac | 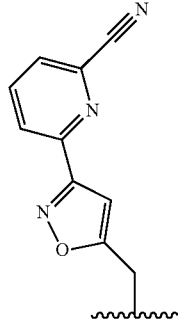 | H |
| Example 188. | Ac | 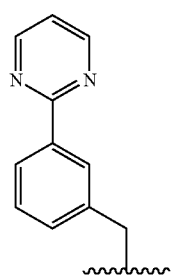 | H |
| Example 189. | Ac | 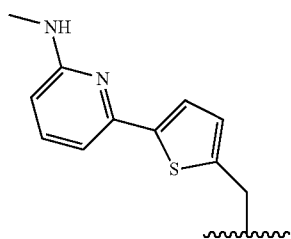 | F |
| Example 190. | Ac | 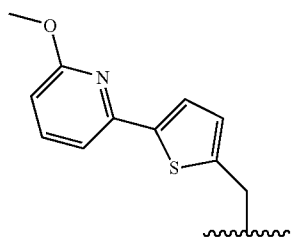 | H |
| Example 191. | H | 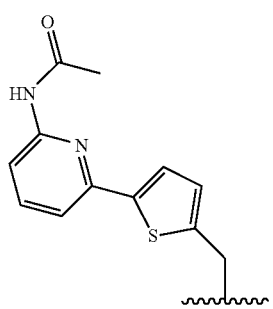 | H |

TABLE A1-continued
| Example | Q | —Ar₁—M—Ar₂ | Z |
| --- | --- | --- | --- |
| Example 192. | Ac | 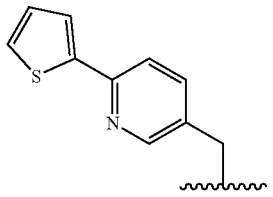 | H |
| Example 193. | Ac | 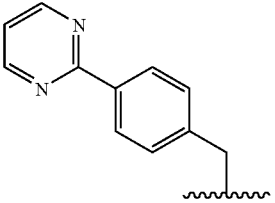 | H |
| Example 194. | H | 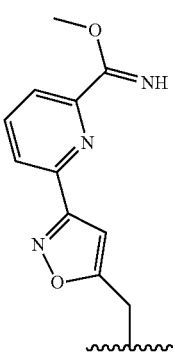 | H |
| Example 195. | Ac | 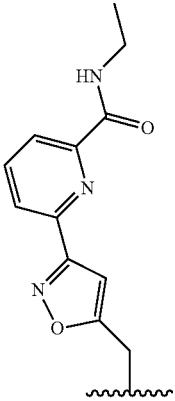 | H |
| Example 196. | H | 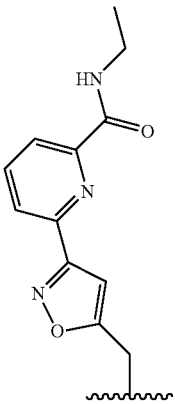 | H |

TABLE A1-continued
| Example | Q | —Ar$_1$—M—Ar$_2$ | Z |
|---|---|---|---|
| Example 197. | H | 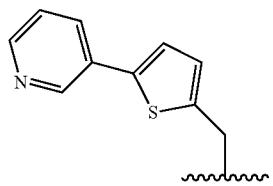 | H |
| Example 198. | H | 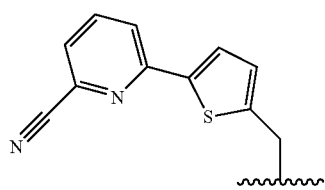 | H |
| Example 199. | Ac | 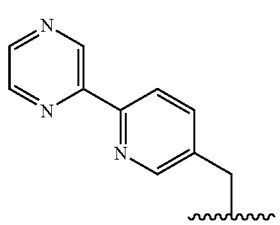 | H |
| Example 200. | Ac | 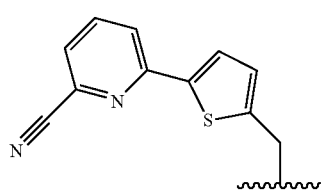 | H |
| Example 201. | Ac | 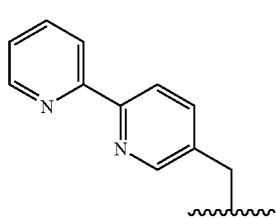 | H |
| Example 202. | H | 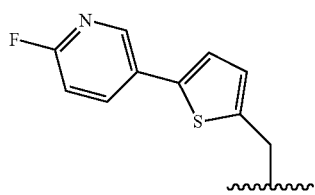 | H |
| Example 203. | H | 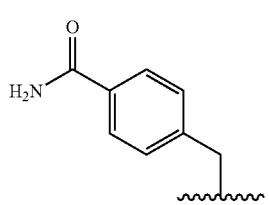 | H |

TABLE A1-continued
| Example | Q | —Ar₁—M—Ar₂ | Z |
|---|---|---|---|
| Example 204. | H | 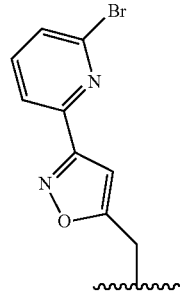 | H |
| Example 205. | Ac | 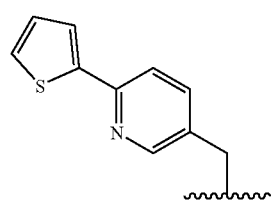 | H |
| Example 206. | H | 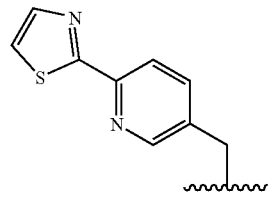 | H |
| Example 207. | Ac | 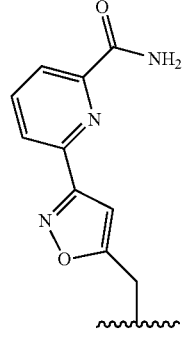 | H |
| Example 208. | Ac | 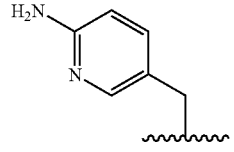 | H |
| Example 209. | Ac | 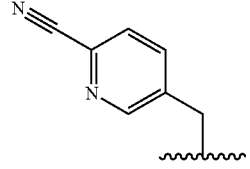 | H |
| Example 210. | Ac | 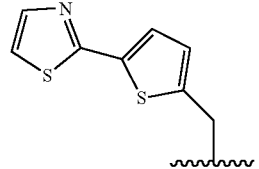 | H |

TABLE A1-continued
| Example | Q | —Ar₁—M—Ar₂ | Z |
|---|---|---|---|
| Example 211. | Ac | 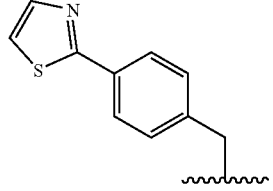 | F |
| Example 212. | H | 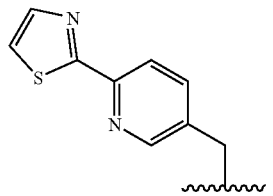 | F |
| Example 213. | H | 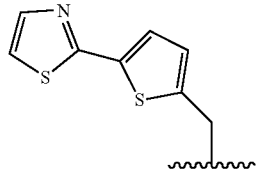 | H |
| Example 214. | Ac | 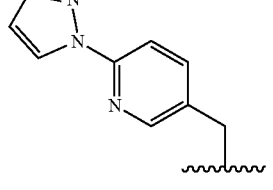 | F |
| Example 215. | Ac | 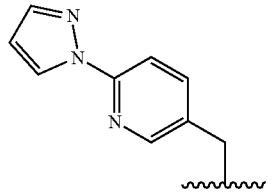 | H |
| Example 216. | Ac | 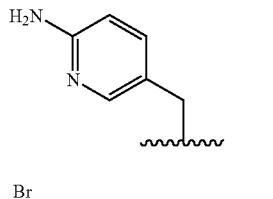 | F |
| Example 217. | Ac | 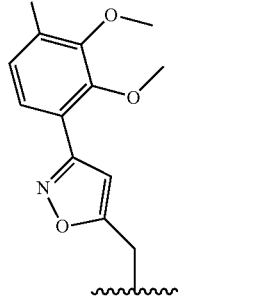 | H |

TABLE A1-continued

| Example | Q | —Ar₁—M—Ar₂ | Z |
|---------|---|------------|---|
| Example 218. | Ac | 2-nitrophenyl-isoxazole | H |
| Example 219. | Ac | 5-bromothiophene-isoxazole | H |
| Example 220. | Ac | thiadiazole-pyridine | F |
| Example 221. | Ac | 5-cyanothiophene-isoxazole | H |
| Example 222. | Ac | 2,3-dimethoxyphenyl-isoxazole | H |
| Example 223. | Ac | thiadiazole-phenyl | H |

TABLE A1-continued
| Example | Q | —Ar₁—M—Ar₂ | Z |
|---|---|---|---|
| Example 224. | Ac | 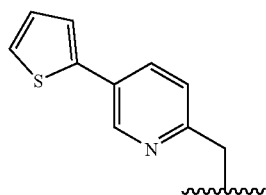 | H |
| Example 225. | Ac | 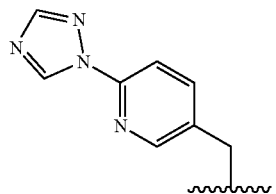 | H |
| Example 226. | Ac | 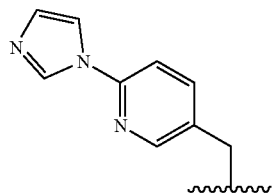 | H |
| Example 227. | Ac | 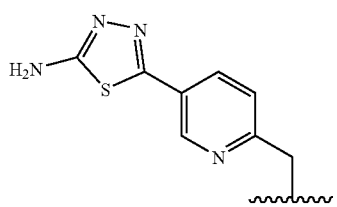 | H |
| Example 228. | Ac | 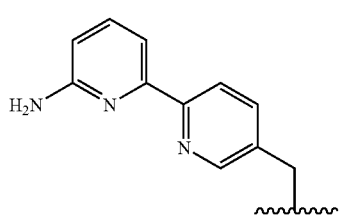 | H |
| Example 229. | Ac | 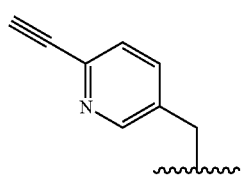 | H |
| Example 230. | H | 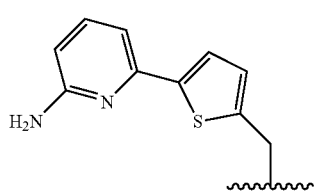 | F |

TABLE A1-continued
| Example | Q | —Ar₁—M—Ar₂ | Z |
|---|---|---|---|
| Example 231. | H | 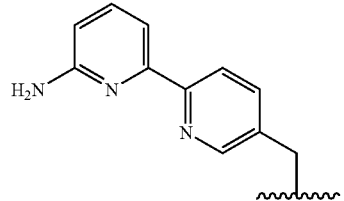 | H |
| Example 232. | Ac | 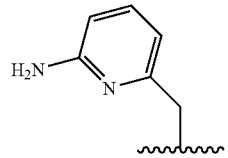 | H |
| Example 233. | Ac | 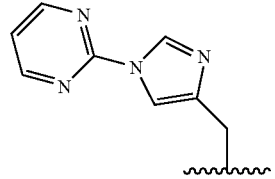 | H |
| Example 234. | Ac | 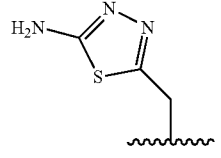 | H |
| Example 235. | Ac | 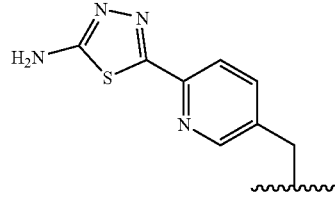 | H |
| Example 236. | Ac | 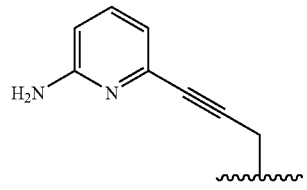 | H |
| Example 237. | Ac | 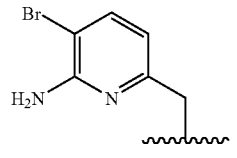 | H |
| Example 238. | Ac | 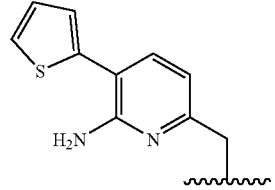 | H |

TABLE A1-continued

| Example | Q | —Ar₁—M—Ar₂ | Z |
| --- | --- | --- | --- |
| Example 239. | Ac | 2-amino-3-vinylpyridine linked at 6-position via CH₂ | H |
| Example 240. | Ac | 3-amino-pyridine linked at 6-position via cis-CH=CH-CH₂ | H |
| Example 241. | Ac | 7-azaindole (1H-pyrrolo[2,3-b]pyridine) linked at 6-position via CH₂ | H |
| Example 242. | Ac | 2-(4-methylpyrazol-1-yl)pyridine linked at 5-position via CH₂ | H |
| Example 243. | Ac | 2-amino-3-formylpyridine linked at 6-position via CH₂ | H |
| Example 244. | Ac | 2-(1,2,3-triazol-1-yl)pyridine linked at 5-position via CH₂ | H |
| Example 245. | Ac | 2-(5-hydroxy-1,3,4-thiadiazol-2-yl)pyridine linked at 5-position via CH₂ | H |

TABLE A1-continued
| Example | Q | —Ar₁—M—Ar₂ | Z |
|---|---|---|---|
| Example 246. | Ac | 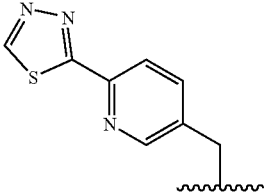 | H |
| Example 247. | Ac | 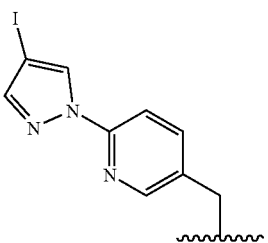 | H |
| Example 248. | Ac | 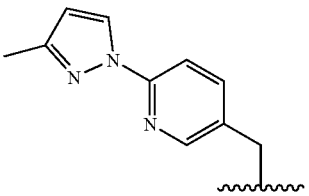 | H |
| Example 249. | Ac | 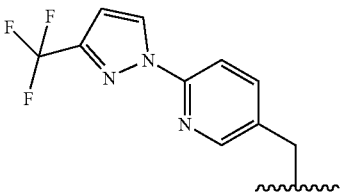 | H |
| Example 250. | Ac | 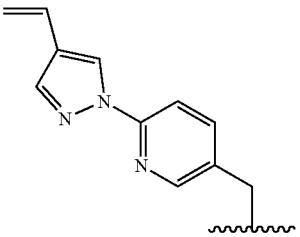 | H |
| Example 251. | Ac | 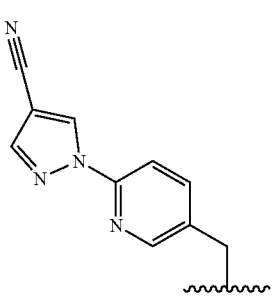 | H |

TABLE A1-continued

| Example | Q | —Ar₁—M—Ar₂ | Z |
|---|---|---|---|
| Example 252. | Ac | pyrazol-1-yl-pyrimidin-5-yl-CH₂- | H |
| Example 253. | Ac | (dimethylamino)methylene-amino-1,2,4-triazol-1-yl-pyridin-2-yl-5-CH₂- | H |
| Example 254. | Ac | 5-bromothiophen-2-yl-pyrazol-1-yl-pyridin-2-yl-5-CH₂- | H |
| Example 255. | Ac | thiophen-2-yl-pyrazol-1-yl-pyridin-2-yl-5-CH₂- | H |
| Example 256. | Ac | 2-amino-3-(pyrimidin-2-yl)pyridin-6-yl-CH₂- | H |
| Example 257. | H | 1H-indazol-6-yl-CH₂- | H |
| Example 258. | Ac | 1H-indazol-6-yl-CH₂- | H |
| Example 259. | Ac | pyrazol-1-yl-pyridine N-oxide-5-yl-CH₂- | H |

TABLE A1-continued
| Example | Q | —Ar₁—M—Ar₂ | Z |
|---|---|---|---|
| Example 260. | Ac | (pyrazolyl-fluoropyridinyl) | H |
| Example 261. | —COCH₂CH₃ | (pyrazolyl-pyridinyl) | H |
| Example 262. | Ac | (2-amino-benzothiazolyl) | H |
| Example 263. | Ac | (thiadiazolyl-pyridinyl) | H |
Example compounds 264–338 of formula A2:
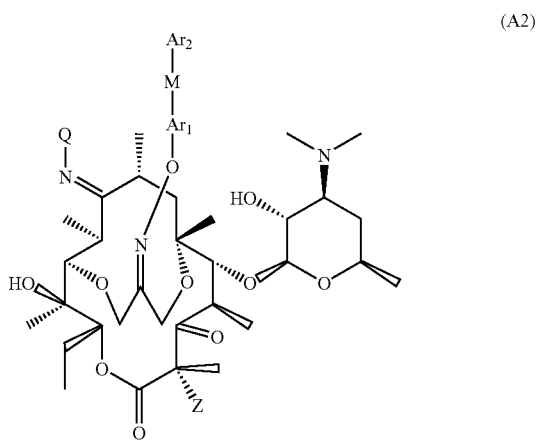
wherein Ar₁, Ar₂, M, Q, and Z are delineated for each example in Table A2:

TABLE A2
| Example | Q | -Ar₁-M-Ar₂ | Z |
|---|---|---|---|
| Example 264. | Ac | 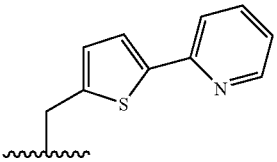 | H |
| Example 265. | Ac | 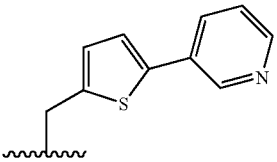 | H |
| Example 266. | Ac | 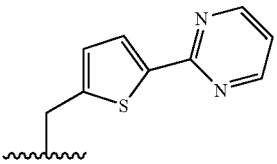 | H |
| Example 267. | Ac | 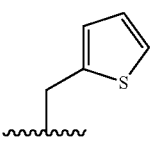 | H |
| Example 268. | Ac | 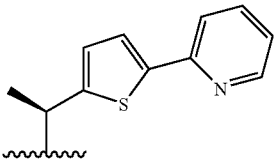 | H |
| Example 269. | Ac | 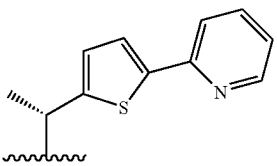 | H |
| Example 270. | Ac | 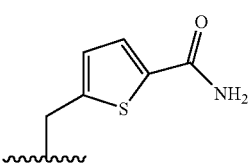 | H |
| Example 271. | Ac | 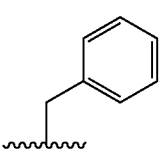 | H |
| Example 272. | Ac | 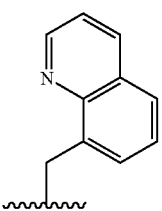 | F |

TABLE A2-continued
| Example | Q | -Ar₁-M-Ar₂ | Z |
|---|---|---|---|
| Example 273. | Ac | 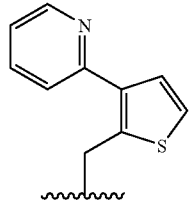 | H |
| Example 274. | Ac | 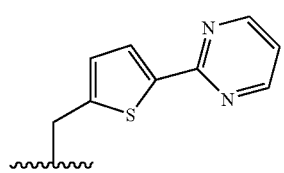 | F |
| Example 275. | Ac | 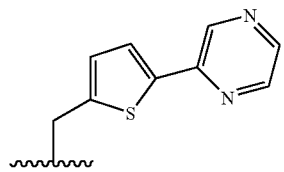 | F |
| Example 276. | Ac | 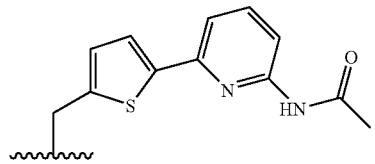 | H |
| Example 277. | Ac | 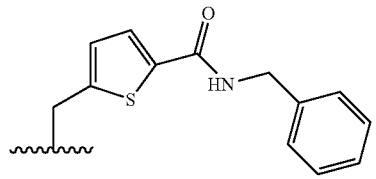 | H |
| Example 278. | Ac | 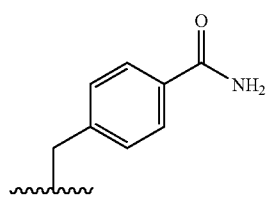 | H |
| Example 279. | Ac | 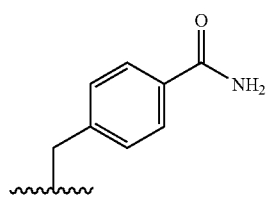 | F |
| Example 280. | Ac | 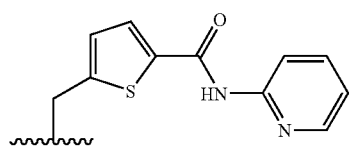 | H |

TABLE A2-continued
| Example | Q | -Ar₁-M-Ar₂ | Z |
|---|---|---|---|
| Example 281. | Ac | 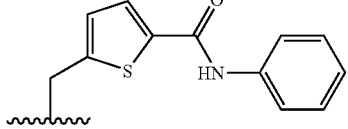 | H |
| Example 282. | Ac | 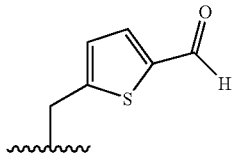 | H |
| Example 283. | Ac | 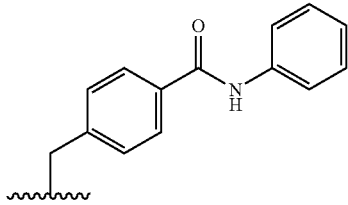 | H |
| Example 284. | Ac | 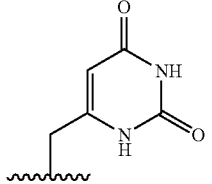 | H |
| Example 285. | Ac | 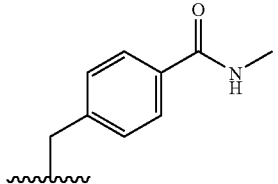 | H |
| Example 286. | Ac | 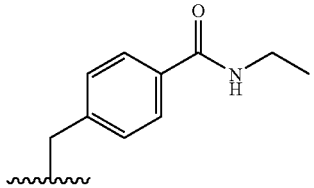 | H |
| Example 287. | Ac | 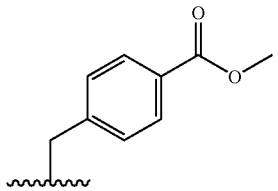 | H |
| Example 288. | Ac | 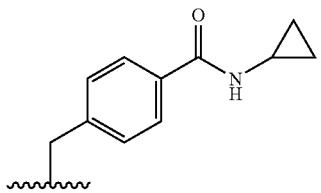 | H |

TABLE A2-continued
| Example | Q | -Ar₁-M-Ar₂ | Z |
|---|---|---|---|
| Example 289. | Ac | 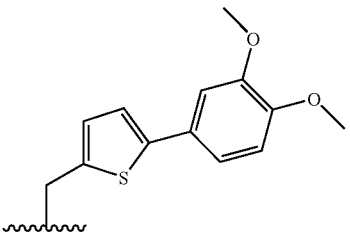 | H |
| Example 290. | Ac | 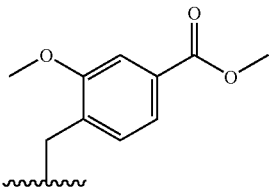 | H |
| Example 291. | Ac | 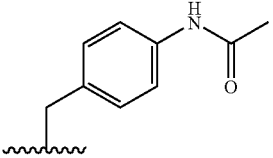 | H |
| Example 292. | Ac | 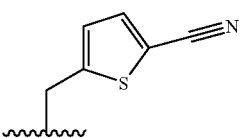 | H |
| Example 293. | Ac | 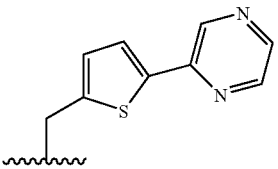 | H |
| Example 294. | Ac | 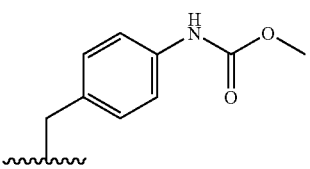 | H |
| Example 295. | Ac | 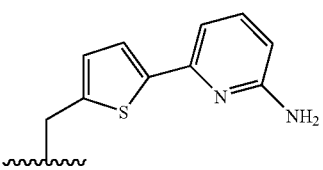 | F |
| Example 296. | Ac | 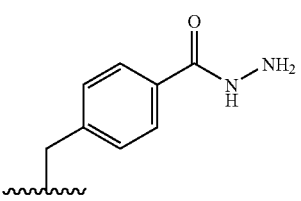 | H |

TABLE A2-continued
| Example | Q | -Ar₁-M-Ar₂ | Z |
|---|---|---|---|
| Example 297. | Ac | 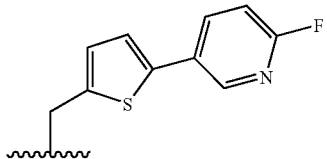 | H |
| Example 298. | Ac | 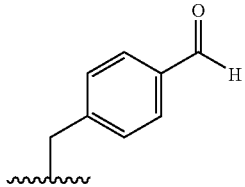 | H |
| Example 299. | Ac | 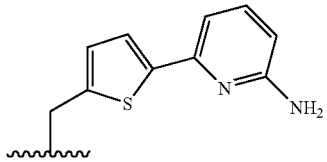 | H |
| Example 300. | H | 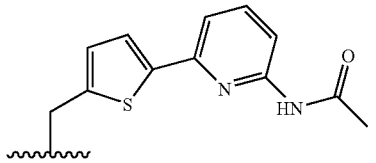 | H |
| Example 301. | Ac | 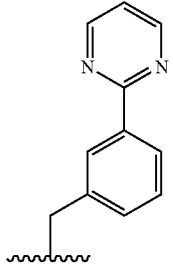 | H |
| Example 302. | Ac | 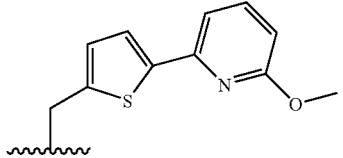 | H |
| Example 303. | H | 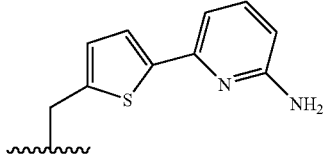 | H |
| Example 304. | H | 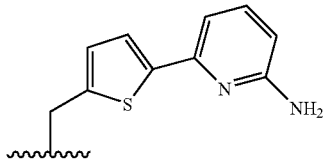 | F |

TABLE A2-continued
| Example | Q | -Ar₁-M-Ar₂ | Z |
|---|---|---|---|
| Example 305. | Ac | 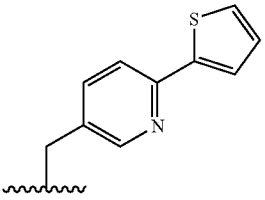 | H |
| Example 306. | Ac | 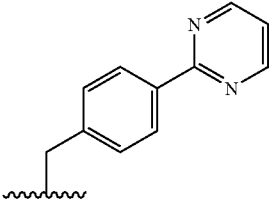 | H |
| Example 307. | Ac | 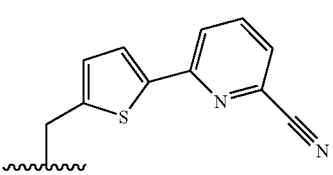 | H |
| Example 308. | Ac | 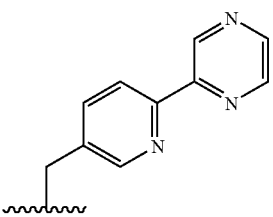 | H |
| Example 309. | Ac | 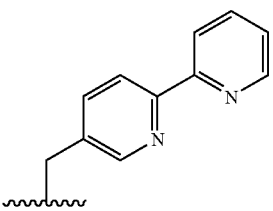 | H |
| Example 310. | Ac | 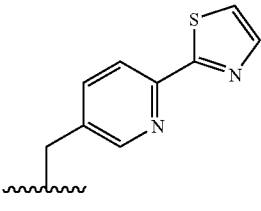 | H |
| Example 311. | Ac | 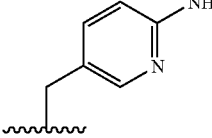 | H |
| Example 312. | Ac | 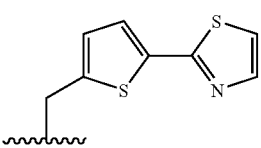 | H |

TABLE A2-continued

| Example | Q | -Ar₁-M-Ar₂ | Z |
| --- | --- | --- | --- |
| Example 313. | Ac | (5-(pyrazol-1-yl)pyridin-2-yl)methyl | F |
| Example 314. | Ac | (5-(pyrazol-1-yl)pyridin-2-yl)methyl | H |
| Example 315. | Ac | (3-(2,3-dimethoxyphenyl)isoxazol-5-yl)methyl | H |
| Example 316. | Ac | (6-amino-pyridin-3-yl)methyl | F |
| Example 317. | Ac | (4-(1,2,3-thiadiazol-5-yl)phenyl)methyl | H |
| Example 318. | Ac | (4-(1,2,3-thiadiazol-5-yl)phenyl)methyl | F |
| Example 319. | Ac | (5-(1,2,4-triazol-1-yl)pyridin-2-yl)methyl | H |

TABLE A2-continued
| Example | Q | -Ar₁-M-Ar₂ | Z |
|---|---|---|---|
| Example 320. | Ac | 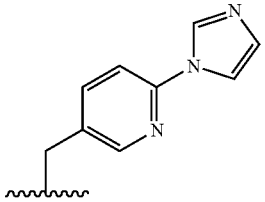 | H |
| Example 321. | Ac | 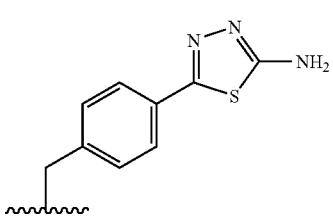 | H |
| Example 322. | Ac | 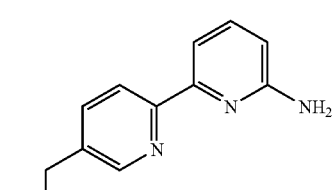 | H |
| Example 323. | Ac | 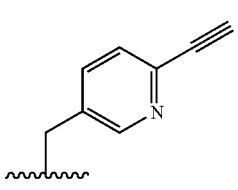 | H |
| Example 324. | Ac | 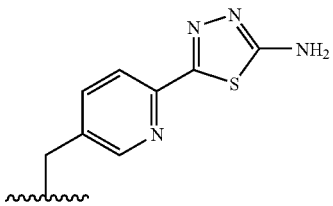 | H |
| Example 325. | Ac | 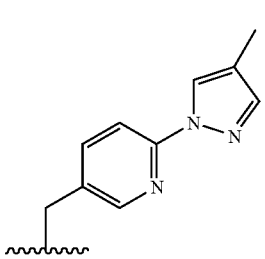 | H |
| Example 326. | Ac | 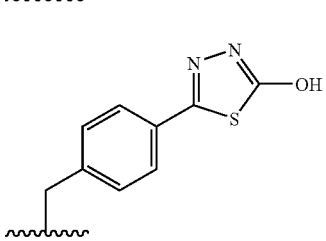 | H |

TABLE A2-continued
| Example | Q | -Ar₁-M-Ar₂ | Z |
| --- | --- | --- | --- |
| Example 327. | Ac | 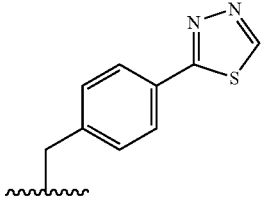 | H |
| Example 328. | Ac | 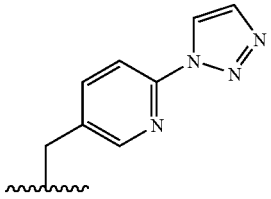 | H |
| Example 329. | Ac | 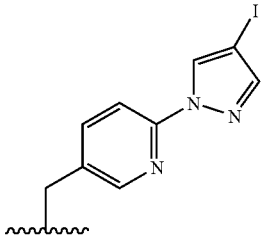 | H |
| Example 330. | Ac | 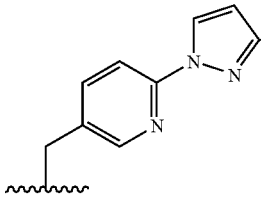 | H |
| Example 331. | Ac | 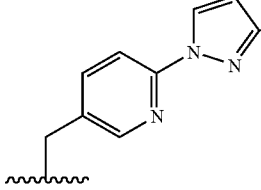 | H |
| Example 332. | Ac | 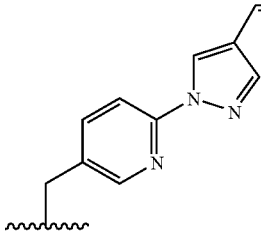 | H |

TABLE A2-continued

| Example | Q | -Ar₁-M-Ar₂ | Z |
| --- | --- | --- | --- |
| Example 333. | Ac | (pyridine-pyrazole-CN) | H |
| Example 334. | Ac | (pyridine-triazole-N=CH-N(CH₃)₂) | H |
| Example 335. | Ac | (pyridine-pyrazole-thiophene-Br) | H |
| Example 336. | Ac | (pyridine-pyrazole-thiophene) | H |
| Example 337. | H | (indazole) | H |
| Example 338. | Ac | (benzothiazole-NH₂) | H |

Example compounds 339–353 of formula B:
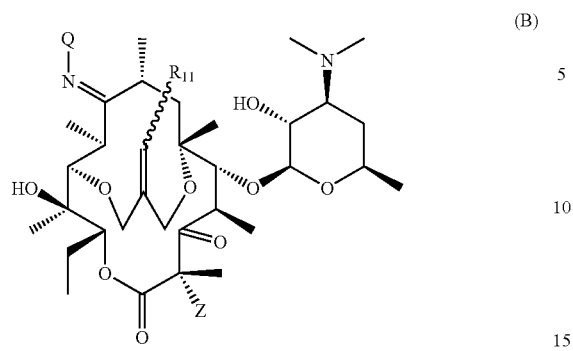
wherein $R_{11}$, Q, and Z are delineated for each example in Table B:
TABLE B
| Example | Q | $R_{11}$ | Z |
|---|---|---|---|
| Example 339. | H | H | H |
| Example 340. | OMOM | H | H |
| Example 341. | OMOM | phenyl | H |
| Example 342. | Ac | biphenyl-4-yl | H |
| Example 343. | Ac | biphenyl-3-yl | H |
| Example 344. | Ac | 4-phenoxyphenyl | H |
| Example 345. | Ac | 1-phenylvinyl | H |

TABLE B-continued
| Example | Q | R₁₁ | Z |
|---|---|---|---|
| Example 346. | Propionyl | 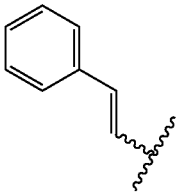 | H |
| Example 347. | Ac | 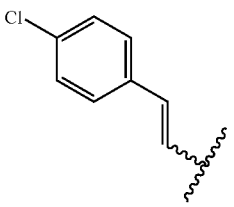 | H |
| Example 348. | Methyl carbamate | 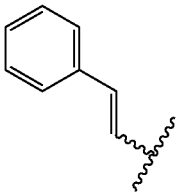 | H |
| Example 349. | urea | H | H |
| Example 350. | Me | H | H |
| Example 351. | BOM | H | H |
| Example 352. | Ac | 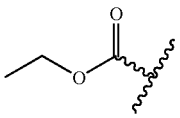 | H |
| Example 353. | Ac | 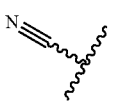 | H |

Example compounds 354–376 of formula B1:
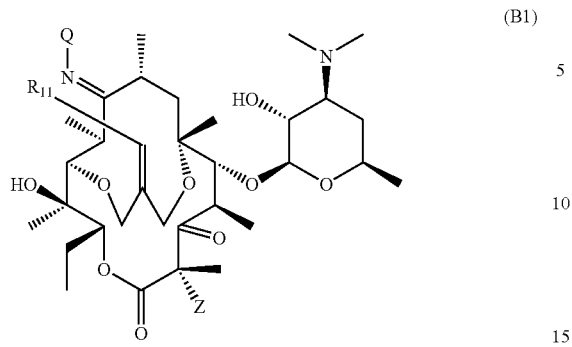
(B1)
wherein $R_{11}$, Q, and Z are delineated for each example in Table B1:
| Examples | Q | $R_{11}$ | Z |
|---|---|---|---|
| Example 354. | Ac | 2-pyridyl-C≡C- | H |
| Example 355. | Ac | 3-pyridyl-C≡C- | H |
| Example 356. | Ac | 6-amino-3-pyridyl-C≡C- | H |
| Example 357. | Ac | 4-aminophenyl-C≡C- | H |
| Example 358. | Ac | 4-methoxyphenyl-C≡C- | H |

-continued
| Examples | Q | R$_{11}$ | Z |
|---|---|---|---|
| Example 359. | Ac | 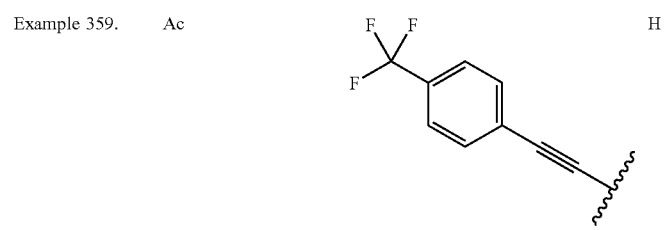 | H |
| Example 360. | Ac | 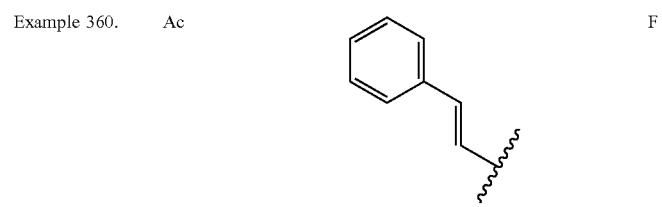 | F |
| Example 361. | Ac | 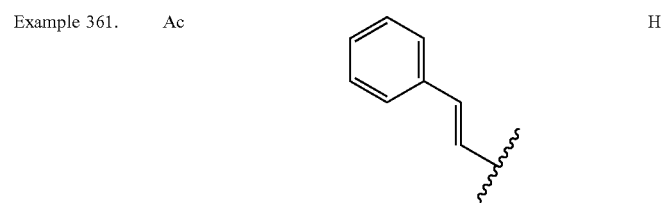 | H |
| Example 362. | Ac | 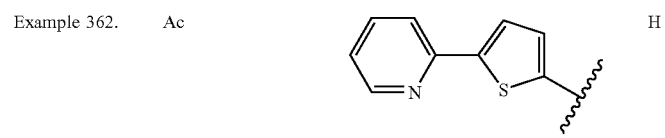 | H |
| Example 363. | Ac | 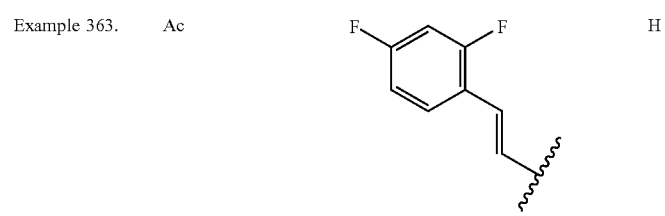 | H |
| Example 364. | 2-methoxyacetamide | 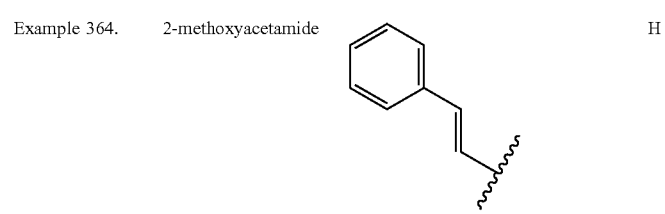 | H |
| Example 365. | 2-O-acyl-acetamide | 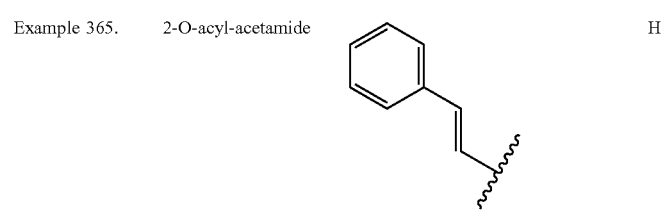 | H |

-continued
| Examples | Q | R$_{11}$ | Z |
|---|---|---|---|
| Example 366. | 2-Fmoc-acetamide | 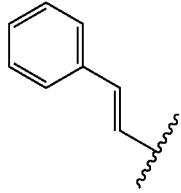 | H |
| Example 367. | Ac | 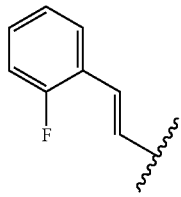 | H |
| Example 368. | Ac | 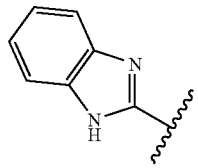 | H |
| Example 369. | 2-hydroxy acetyl | 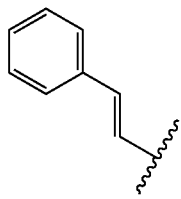 | H |
| Example 370. | 2-aminoacetyl | 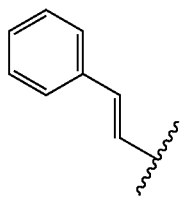 | H |
| Example 371. | Ac | 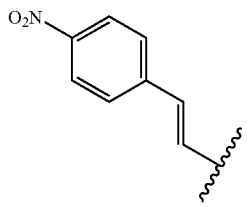 | H |
| Example 372. | Ac | 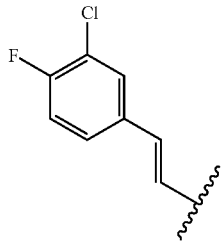 | H |

-continued
| Examples | Q | R$_{11}$ | Z |
|---|---|---|---|
| Example 373. | Ac | 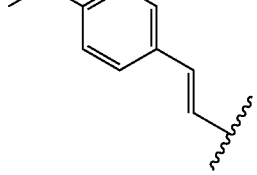 | H |
| Example 374. | Ac | 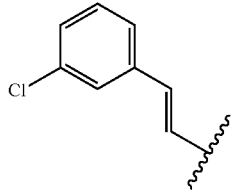 | H |
| Example 375. | Ac | 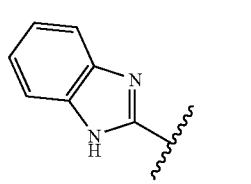 | H |
Example compounds 376–384 of formula B2:
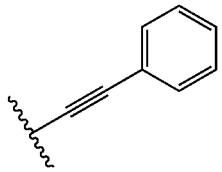
(B2)
wherein R$_{11}$, Q, and Z are delineated for each example in Table B2:
TABLE B2
| Example | Q | R$_{11}$ | Z |
|---|---|---|---|
| Example 376. | Ac | 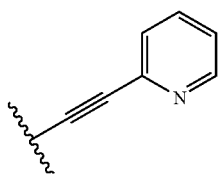 | H |
TABLE B2-continued
| Example | Q | R$_{11}$ | Z |
|---|---|---|---|
| Example 377. | Ac | 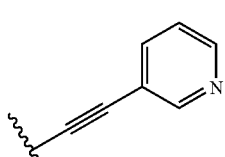 | H |
| Example 378. | Ac |  | H |
| Example 379. | Ac | | H |
| Example 380. | Ac | | H |

TABLE B2-continued

| Example | Q | $R_{11}$ | Z |
|---|---|---|---|
| Example 381. | Ac | (5-amino-pyridin-3-yl)ethynyl group | H |
| Example 382. | Ac | (4-aminophenyl)ethynyl group | H |
| Example 383. | Ac | (4-trifluoromethylphenyl)ethynyl group | H |
| Example 384. | Ac | [5-(pyridin-2-yl)isoxazol-3-yl... ethynyl group] | H |

Example compounds 385–391 of formula C:

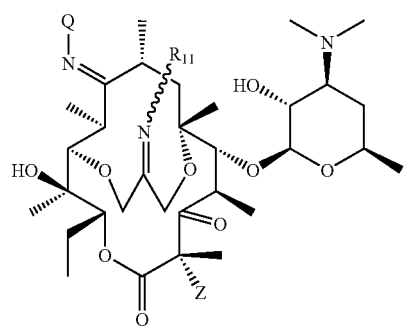
(C)

wherein $R_{11}$, Q, and Z are delineated for each example in Table C:

TABLE C

| Example | Q | $R_{11}$ | Z |
|---|---|---|---|
| Example 385. | Ac | benzyl | H |
| Example 386. | Ac | 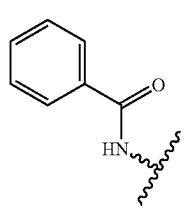 | H |
| Example 387. | Ac | (pyridin-2-yl)methyl | H |
| Example 388. | Ac | isoquinolin-3-ylmethylideneamino | H |
| Example 389. | Ac | phenylsulfonylamino | H |
| Example 390. | Ac | benzoylamino | H |
| Example 391. | Ac | 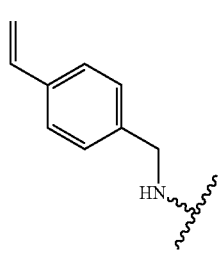 | H |

A further embodiment of the present invention includes pharmaceutical compositions comprising any single compound delineated herein, or a pharmaceutically acceptable salt, ester, or prodrug thereof, with a pharmaceutically acceptable carrier or excipient.

Yet another embodiment of the present invention is a pharmaceutical composition comprising a combination of two or more compounds delineated herein, or a pharmaceutically acceptable salt, ester, or prodrug thereof, with a pharmaceutically acceptable carrier or excipient.

Yet a further embodiment of the present invention is a pharmaceutical composition comprising any single compound delineated herein in combination with one or more antibiotics known in the art (such as penicillin, amoxicillin, azithromycin, erythromycin, ciproflaxin, telithromycin, cethromycin, and the like) or a pharmaceutically acceptable salt, ester, or prodrug thereof, with a pharmaceutically acceptable carrier or excipient.

Yet an additional aspect of the present invention relates to a method of treating a subject (e.g., mammal, human, horse, dog, cat, fish) having bacterial infection or disease or disease symptom related to having a bacterial infection (including diseases delineated herein). The method includes administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

Also within the scope of this invention is a packaged product. The packaged product includes a container, one of the aforementioned compounds in the container, and a legend (e.g., a label or an insert) associated with the container and indicating administration of the compound for treating a disorder associated with bacterial infection, including the diseases delineated herein.

In addition, the present invention contemplates processes of making any compound delineated herein via any synthetic method delineated herein.

Definitions

Listed below are definitions of various terms used to describe this invention. These definitions apply to the terms as they are used throughout this specification and claims, unless otherwise limited in specific instances, either individually or as part of a larger group.

An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

The terms "$C_1$–$C_3$ alkyl," "$C_1$–$C_6$ alkyl," or "$C_1$–$C_{12}$ alkyl," as used herein, refer to saturated, straight- or branched-chain hydrocarbon radicals containing between one and three, one and twelve, or one and six carbon atoms, respectively. Examples of $C_1$–$C_3$ alkyl radicals include methyl, ethyl, propyl and isopropyl radicals; examples of $C_1$–$C_6$ alkyl radicals include, but are not limited to, methyl, ethyl, propyl, isopropyl, n-butyl, tert-butyl, sec-butyl, n-pentyl, neopentyl and n-hexyl radicals; and examples of $C_1$–$C_{12}$ alkyl radicals include, but are not limited to, ethyl, propyl, isopropyl, hexyl, heptyl, octyl, nonyl, decyl, undecyl, dodecyl radicals and the like.

The term "substituted alkyl," as used herein, refers to an alkyl, such as a $C_1$–$C_{12}$ alkyl or $C_1$–$C_6$ alkyl group, substituted by one, two, three or more aliphatic substituents.

Suitable aliphatic substituents include, but are not limited to, —F, —Cl, —Br, —I, —OH, protected hydroxy, aliphatic ethers, aromatic ethers, oxo, —$NO_2$, —CN, —$C_1$–$C_{12}$-alkyl optionally substituted with halogen (such as perhaloalkyls), $C_2$–$C_{12}$-alkenyl optionally substituted with halogen, —$C_2$–$C_{12}$-alkynyl optionally substituted with halogen, —$NH_2$, protected amino, —NH—$C_1$–$C_{12}$-alkyl, —NH—$C_2$–$C_{12}$-alkenyl, —NH—$C_2$–$C_{12}$-alkenyl, —NH—$C_3$–$C_{12}$-cycloalkyl, —NH-aryl, —NH-heteroaryl, —NH-heterocycloalkyl, -dialkylamino, -diarylamino, -diheteroarylamino, —O—$C_1$–$C_{12}$-alkyl, —O—$C_2$–$C_{12}$-alkenyl, —O—$C_2$–$C_{12}$-alkynyl, —O—$C_3$–$C_{12}$-cycloalkyl, —O-aryl, —O-heteroaryl, —O-heterocycloalkyl, —C(O)—$C_1$–$C_{12}$-alkyl, —C(O)—$C_2$–$C_{12}$-alkenyl, —C(O)—$C_2$–$C_{12}$-alkynyl, —C(O)—$C_3$–$C_{12}$-cycloalkyl, —C(O)-aryl, —C(O)-heteroaryl, —C(O)-heterocycloalkyl, —$CONH_2$, —CONH—$C_1$–$C_{12}$-alkyl, —CONH—$C_2$–$C_{12}$-alkenyl, —CONH—$C_2$–$C_{12}$-alkynyl, —CONH—$C_3$–$C_{12}$-cycloalkyl, —CONH-aryl, —CONH-heteroaryl, —CONH-heterocycloalkyl, —$CO_2$—$C_1$–$C_{12}$-alkyl, —$CO_2$—$C_2$–$C_{12}$-alkenyl, —$CO_2$—$C_2$–$C_{12}$-alkynyl, —$CO_2$—$C_3$–$C_{12}$-cycloalkyl, —$CO_2$-aryl, —$CO_2$-heteroaryl, —$CO_2$-heterocycloalkyl, —$OCO_2$—$C_1$–$C_{12}$-alkyl, —$OCO_2$—$C_2$–$C_{12}$-alkenyl, —$OCO_2$—$C_2$–$C_{12}$-alkynyl, —$OCO_2$—$C_3$–$C_{12}$-cycloalkyl, —$OCO_2$-aryl, —$OCO_2$-heteroaryl, —$OCO_2$-heterocycloalkyl, —$OCONH_2$, —OCONH—$C_1$–$C_{12}$-alkyl, —OCONH—$C_2$–$C_{12}$-alkenyl, —OCONH—$C_2$–$C_{12}$-alkynyl, —OCONH—$C_3$–$C_{12}$-cycloalkyl, —OCONH-aryl, —OCONH-heteroaryl, —OCONH-heterocycloalkyl, —NHC(O)—$C_1$–$C_{12}$-alkyl, —NHC(O)—$C_2$–$C_{12}$-alkenyl, —NHC(O)—$C_2$–$C_{12}$-alkynyl, —NHC(O)—$C_3$–$C_{12}$-cycloalkyl, —NHC(O)-aryl, —NHC(O)-heteroaryl, —NHC(O)-heterocycloalkyl, —$NHCO_2$—$C_1$–$C_{12}$-alkyl, —$NHCO_2$—$C_2$–$C_{12}$-alkenyl, —$NHCO_2$—$C_2$–$C_{12}$-alkynyl, —$NHCO_2$—$C_3$–$C_{12}$-cycloalkyl, —$NHCO_2$-aryl, —$NHCO_2$-heteroaryl, —$NHCO_2$-heterocycloalkyl, —NHC(O)$NH_2$, NHC(O)NH—$C_1$–$C_{12}$-alkyl, —NHC(O)NH—$C_2$–$C_{12}$-alkenyl, —NHC(O)NH—$C_2$–$C_{12}$-alkynyl, —NHC(O)NH—$C_3$–$C_{12}$-cycloalkyl, —NHC(O)NH-aryl, —NHC(O)NH-heteroaryl, —NHC(O)NH-heterocycloalkyl, NHC(S)$NH_2$, NHC(S)NH—$C_1$–$C_{12}$-alkyl, —NHC(S)NH—$C_2$–$C_{12}$-alkenyl, —NHC(S)NH—$C_2$–$C_{12}$-alkynyl, —NHC(S)NH—$C_3$–$C_{12}$-cycloalkyl, —NHC(S) NH-aryl, —NHC(S)NH-heteroaryl, —NHC(S)NH-heterocycloalkyl, —NHC(NH)$NH_2$, NHC(NH)NH—$C_1$–$C_2$-alkyl, —NHC(NH)NH—$C_2$–$C_{12}$-alkenyl, —NHC(NH)NH—$C_2$–$C_{12}$-alkynyl, —NHC(NH)NH—$C_3$–$C_2$-cycloalkyl, —NHC(NH)NH-aryl, —NHC(NH)NH-heteroaryl, —NHC(NH)NH-heterocycloalkyl, NHC(NH)—$C_1$–$C_{12}$-aryl, —NHC(NH)—$C_2$–$C_{12}$-alkenyl, —NHC(NH)—$C_2$–$C_{12}$-alkynyl, —NHC(NH)—$C_3$–$C_{12}$-cycloalkyl, —NHC(NH)-aryl, —NHC(NH)-heteroaryl, —NHC(NH)-heterocycloalkyl, —C(NH)NH—$C_1$–$C_{12}$-alkyl, —C(NH)NH—$C_2$–$C_{12}$-alkenyl, —C(NH)NH—$C_2$–$C_{12}$-alkynyl, —C(NH) NH—$C_3$–$C_{12}$-cycloalkyl, —C(NH)NH-aryl, —C(NH)NH-heteroaryl, —C(NH)NH-heterocycloalkyl, —S(O)-$C_1$–$C_{12}$-alkyl, —S(O)—$C_2$–$C_{12}$-alkenyl, —S(O)—$C_2$–$C_{12}$-alkynyl, —S(O)—$C_3$–$C_{12}$-cycloalkyl, —S(O)-aryl, —S(O)-heteroaryl, —S(O)-heterocycloalkyl —$SO_2NH_2$, —$SO_2$NH—$C_1$–$C_{12}$-alkyl, —$SO_2$NH—$C_2$–$C_{12}$-alkenyl, —$SO_2$NH—$C_2$–$C_{12}$-alkynyl, —$SO_2$NH—$C_3$–$C_{12}$-cycloalkyl, —SO$_2$NH-aryl, —SO$_2$NH-heteroaryl, —SO$_2$NH-heterocycloalkyl, —NHSO$_2$—C$_1$–C$_{12}$-alkyl, —NHSO$_2$—C$_2$–C$_{12}$-alkenyl, —NHSO$_2$—C$_2$–C$_{12}$-alkynyl, —NHSO$_2$—C$_3$–C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$–C$_{12}$-cycloalkyl, polyalkoxyalkyl, polyalkoxy, -methoxymethoxy, -methoxyethoxy, —SH, —S—C$_1$–C$_{12}$-alkyl, —S—C$_2$–C$_{12}$-alkenyl, —S—C$_2$–C$_{12}$-alkynyl, —S—C$_3$–C$_{12}$-cycloalkyl, —S-aryl, —S-heteroaryl, —S-heterocycloalkyl, or methylthiomethyl. It is understood that the aryls, heteroaryls, alkyls and the like can be further substituted.

The terms "C$_2$–C$_{12}$ alkenyl" or "C$_2$–C$_6$ alkenyl," as used herein, denote a monovalent group derived from a hydrocarbon moiety containing from two to twelve or two to six carbon atoms having at least one carbon-carbon double bond by the removal of a single hydrogen atom. Alkenyl groups include, but are not limited to, for example, ethenyl, propenyl, butenyl, 1-methyl-2-buten-1-yl, alkadienes and the like.

The term "substituted alkenyl," as used herein, refers to a "C$_2$–C$_{12}$ alkenyl" or "C$_2$–C$_6$ alkenyl" group as previously defined, substituted by one, two, three or more aliphatic substituents.

The terms "C$_2$–C$_{12}$ alkynyl" or "C$_2$–C$_6$ alkynyl," as used herein, denote a monovalent group derived from a hydrocarbon moiety containing from two to twelve or two to six carbon atoms having at least one carbon-carbon triple bond by the removal of a single hydrogen atom. Representative alkynyl groups include, but are not limited to, for example, ethynyl, 1-propynyl, 1-butynyl, and the like.

The term "substituted alkynyl," as used herein, refers to a "C$_2$–C$_{12}$ alkynyl" or "C$_2$–C$_6$ alkynyl" group as previously defined, substituted by one, two, three or more aliphatic substituents.

The term "C$_1$–C$_6$ alkoxy," as used herein, refers to a C$_1$–C$_6$ alkyl group, as previously defined, attached to the parent molecular moiety through an oxygen atom. Examples of C$_1$–C$_6$-alkoxy include, but are not limited to, methoxy, ethoxy, propoxy, isopropoxy, n-butoxy, sec-butoxy, tert-butoxy, n-pentoxy, neopentoxy and n-hexoxy.

The terms "halo" and "halogen," as used herein, refer to an atom selected from fluorine, chlorine, bromine and iodine.

The term "aryl," as used herein, refers to a mono- or bicyclic carbocyclic ring system having one or two aromatic rings including, but not limited to, phenyl, naphthyl, tetrahydronaphthyl, indanyl, idenyl and the like.

The term "substituted aryl," as used herein, refers to an aryl group, as previously defined, substituted by one, two, three or more aromatic substituents.

Aromatic substituents include, but are not limited to, —F, —Cl, —Br, —I, —OH, protected hydroxy, aliphatic ethers, aromatic ethers, oxo, —NO$_2$, —CN, —C$_1$–C$_{12}$-alkyl optionally substituted with halogen (such as perhaloalkyls), C$_2$–C$_{12}$-alkenyl optionally substituted with halogen, —C$_2$–C$_{12}$-alkynyl optionally substituted with halogen, —NH$_2$, protected amino, —NH—C$_1$–C$_{12}$-alkyl, —NH—C$_2$–C$_{12}$-alkenyl, —NH—C$_2$–C$_{12}$-alkenyl, —NH—C$_3$–C$_{12}$-cycloalkyl, —NH-aryl, —NH-heteroaryl, —NH-heterocycloalkyl, -dialkylamino, -diarylamino, -diheteroarylamino, —O—C$_1$–C$_{12}$-alkyl, —O—C$_2$–C$_2$-alkenyl, —O—C$_2$–C$_2$-alkynyl, —O—C$_3$–C$_{12}$-cycloalkyl, —O-aryl, —O-heteroaryl, —O-heterocycloalkyl, —C(O)—C$_1$–C$_{12}$-alkyl, —C(O)—C$_2$–C$_{12}$-alkenyl, —C(O)—C$_2$–C$_{12}$-alkynyl, —C(O)—C$_3$–C$_{12}$-cycloalkyl, —C(O)-aryl, —C(O)-heteroaryl, —C(O)-heterocycloalkyl, —CONH$_2$, —CONH— C$_1$–C$_{12}$-alkyl, —CONH—C$_2$–C$_{12}$-alkenyl, —CONH—C$_2$–C$_2$-alkynyl, —CONH—C$_3$–C$_2$-cycloalkyl, —CONH-aryl, —CONH-heteroaryl, —CONH-heterocycloalkyl, —CO$_2$—C$_1$–C$_{12}$-alkyl, —CO$_2$—C$_2$–C$_{12}$-alkenyl, —CO$_2$—C$_2$–C$_{12}$-alkynyl, —CO$_2$—C$_3$–C$_{12}$-cycloalkyl, —CO$_2$-aryl, —CO$_2$-heteroaryl, —CO$_2$-heterocycloalkyl, —OCO$_2$—C$_1$–C$_{12}$-alkyl, —OCO$_2$—C$_2$–C$_{12}$-alkenyl, —OCO$_2$—C$_2$–C$_2$-alkynyl, —OCO$_2$—C$_3$–C$_2$-cycloalkyl, —OCO$_2$-aryl, —OCO$_2$-heteroaryl, —OCO$_2$-heterocycloalkyl, —OCONH$_2$, —OCONH—C$_1$–C$_{12}$-alkyl, —OCONH—C$_2$–C$_{12}$-alkenyl, —OCONH—C$_2$–C$_{12}$-alkynyl, —OCONH—C$_3$–C$_{12}$-cycloalkyl, —OCONH-aryl, —OCONH-heteroaryl, —OCONH-heterocycloalkyl, —NHC(O)—C$_1$–C$_{12}$-alkyl, —NHC(O)—C$_2$–C$_{12}$-alkenyl, —NHC(O)—C$_2$–C$_{12}$-alkynyl, —NHC(O)—C$_3$–C$_{12}$-cycloalkyl, —NHC(O)-aryl, —NHC(O)-heteroaryl, —NHC(O)-heterocycloalkyl, —NHCO$_2$—C$_1$–C$_{12}$-alkyl, —NHCO$_2$—C$_2$–C$_{12}$-alkenyl, —NHCO$_2$—C$_2$–C$_{12}$-alkynyl, —NHCO$_2$—C$_3$–C$_{12}$-cycloalkyl, —NHCO$_2$-aryl, —NHCO$_2$-heteroaryl, —NHCO$_2$-heterocycloalkyl, —NHC(O)NH$_2$, NHC(O)NH—C$_1$–C$_{12}$-alkyl, —NHC(O)NH—C$_2$–C$_{12}$-alkenyl, —NHC(O)NH—C$_2$–C$_{12}$-alkynyl, —NHC(O)NH—C$_3$–C$_2$-cycloalkyl, —NHC(O)NH-aryl, —NHC(O)NH-heteroaryl, —NHC(O)NH-heterocycloalkyl, NHC(S)NH$_2$, NHC(S)NH—C$_1$–C$_2$-alkyl, —NHC(S)NH—C$_2$–C$_{12}$-alkenyl, —NHC(S)NH—C$_2$–C$_{12}$-alkynyl, —NHC(S)NH—C$_3$–C$_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—C$_1$–C$_{12}$-alkyl, —NHC(NH)NH—C$_2$–C$_{12}$alkenyl, —NHC(NH)NH—C$_2$–C$_{12}$-alkynyl, —NHC(NH)NH—C$_3$–C$_{12}$-cycloalkyl, —NHC(NH)NH-aryl, —NHC(NH)NH-heteroaryl, —NHC(NH)NH-heterocycloalkyl, NHC(NH)-C$_1$–C$_{12}$-alkyl, —NHC(NH)—C$_2$–C$_{12}$-alkenyl, —NHC(NH)—C$_2$–C$_{12}$-alkynyl, —NHC(NH)—C$_3$–C$_{12}$-cycloalkyl, —NHC(NH)-aryl, —NHC(NH)-heteroaryl, —NHC(NH)-heterocycloalkyl, —C(NH)NH-C$_1$–C$_{12}$-alkyl, —C(NH)NH—C$_2$–C$_{12}$-alkenyl, —C(NH)NH—C$_2$–C$_{12}$-alkynyl, —C(NH)NH—C$_3$–C$_{12}$-cycloalkyl, —C(NH)NH-aryl, —C(NH)NH-heteroaryl, —C(NH)NH-heterocycloalkyl, —S(O)—C$_1$–C$_{12}$-alkyl, —S(O)—C$_2$–C$_{12}$-alkenyl, —S(O)—C$_2$–C$_{12}$-alkynyl, —S(O)—C$_3$–C$_{12}$-cycloalkyl, —S(O)-aryl, —S(O)-heteroaryl, —S(O)-heterocycloalkyl —SO$_2$NH$_2$, —SO$_2$NH-C$_1$–C$_{12}$-alkyl, —SO$_2$NH—C$_2$–C$_{12}$-alkenyl, —SO$_2$NH—C$_2$–C$_2$-alkynyl, —SO$_2$NH—C$_3$–C$_{12}$-cycloalkyl, —SO$_2$NH-aryl, —SO$_2$NH-heteroaryl, —SO$_2$NH-heterocycloalkyl, —NHSO$_2$—C$_1$–C$_{12}$-alkyl, —NHSO$_2$—C$_2$–C$_{12}$-alkenyl, —NHSO$_2$—C$_2$–C$_{12}$-alkynyl, —NHSO$_2$—C$_3$–C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$–C$_{12}$-cycloalkyl, polyalkoxyalkyl, polyalkoxy, -methoxymethoxy, -methoxyethoxy, —SH, —S—C$_1$–C$_{12}$-alkyl, —S—C$_2$–C$_{12}$-alkenyl, —S—C$_2$–C$_{12}$-alkynyl, —S—C$_3$–C$_{12}$-cycloalkyl, —S-aryl, —S-heteroaryl, —S-heterocycloalkyl, or methylthiomethyl. It is understood that the aryls, heteroaryls, alkyls and the like can be further substituted.

The term "arylalkyl," as used herein, refers to an aryl group attached to the parent compound via a C$_1$–C$_3$ alkyl or C$_1$–C$_6$ alkyl residue. Examples include, but are not limited to, benzyl, phenethyl and the like.

The term "substituted arylalkyl," as used herein, refers to an arylalkyl group, as previously defined, substituted by one, two, three or more aromatic substituents.

The term "heteroaryl," as used herein, refers to a mono-, bi-, or tri-cyclic aromatic radical or ring having from five to ten ring atoms of which at least one ring atom is selected from S, O and N; zero, one or two ring atoms are additional heteroatoms independently selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The heteroaromatic ring may be bonded to the chemical structure through a carbon or hetero atom.

The term "substituted heteroaryl," as used herein, refers to a heteroaryl group as previously defined, substituted by one, two, three or four aromatic substituents.

The term "$C_3$–$C_{12}$-cycloalkyl," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo[2.2.1]heptyl, and bicyclo[2.2.2] octyl.

The term "substituted $C_3$–$C_{12}$-cycloalkyl," as used herein, refers to a $C_3$–$C_{12}$-cycloalkyl group as previously defined, substituted by one, two, three or more aliphatic substituents.

The term "heterocycloalkyl," as used herein, refers to a non-aromatic 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (iv) any of the above rings may be fused to a benzene ring, and (v) the remaining ring atoms are carbon atoms which may be optionally oxo-substituted. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl.

The term "substituted heterocycloalkyl," as used herein, refers to a heterocycloalkyl group, as previously defined, substituted by one, two, three or more aliphatic substituents.

The term "heteroarylalkyl," as used herein, to an heteroaryl group attached to the parent compound via a $C_1$–$C_3$ alkyl or $C_1$–$C_6$ alkyl residue. Examples include, but are not limited to, pyridinylmethyl, pyrimidinylethyl and the like.

The term "substituted heteroarylalkyl," as used herein, refers to a heteroarylalkyl group, as previously defined, substituted by independent replacement of one, two, or three or more aromatic substituents.

The term "$C_1$–$C_3$-alkylamino," as used herein, refers to one or two $C_1$–$C_3$-alkyl groups, as previously defined, attached to the parent molecular moiety through a nitrogen atom. Examples of $C_1$–$C_3$-alkylamino include, but are not limited to, methylamino, dimethylamino, ethylamino, diethylamino, and propylamino.

The term "alkylamino" refers to a group having the structure —NH($C_1$–$C_{12}$ alkyl) where $C_1$–$C_{12}$ alkyl is as previously defined.

The term "dialkylamino" refers to a group having the structure —N($C_1$–$C_{12}$ alkyl) ($C_1$–$C_{12}$ alkyl), where $C_1$–$C_{12}$ alkyl is as previously defined. Examples of dialkylamino are, but not limited to, dimethylamino, diethylamino, methylethylamino, piperidino, and the like.

The term "alkoxycarbonyl" represents an ester group, i.e., an alkoxy group, attached to the parent molecular moiety through a carbonyl group such as methoxycarbonyl, ethoxycarbonyl, and the like.

The term "carboxaldehyde," as used herein, refers to a group of formula —CHO.

The term "carboxy," as used herein, refers to a group of formula —COOH.

The term "carboxamide," as used herein, refers to a group of formula —C(O)NH($C_1$–$C_{12}$ alkyl) or —C(O)N($C_1$–$C_{12}$ alkyl) ($C_1$–$C_{12}$ alkyl), —C(O)NH$_2$, NHC(O)($C_1$–$C_{12}$ alkyl), N($C_1$–$C_{12}$ alkyl)C(O)($C_1$–$C_{12}$ alkyl) and the like.

The term "hydroxy protecting group," as used herein, refers to a labile chemical moiety which is known in the art to protect a hydroxyl group against undesired reactions during synthetic procedures. After said synthetic procedure (s) the hydroxy protecting group as described herein may be selectively removed. Hydroxy protecting groups as known in the are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl) ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl(trityl), tetrahydrofuryl, methoxymethyl, methylthiomethyl, benzyloxymethyl, 2,2, 2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are acetyl (Ac or —C(O)CH$_3$), benzoyl (Bn or —C(O)C$_6$H$_5$), and trimethylsilyl (TMS or —Si(CH$_3$)$_3$).

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

The term "protogenic organic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)— or (S)—, or as (D)— or (L)— for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1–19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113–191 (1991); Bundgaard, et al., Journal of Drug Deliver Reviews, 8:1–38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This invention also encompasses pharmaceutical compositions containing, and methods of treating bacterial infections through administering, pharmaceutically acceptable prodrugs of compounds of the formula I. For example, compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula I. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

As used herein, unless otherwise indicated, the term "bacterial infection(s)" or "protozoa infections"; includes, but is not limited to, bacterial infections and protozoa infections that occur in mammals, fish and birds as well as disorders related to bacterial infections and protozoa infections that may be treated or prevented by administering antibiotics such as the compounds of the present invention. Such bacterial infections and protozoa infections and disorders related to such infections include, but are not limited to, the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus,* or *Peptostreptococcus* spp. *Pseudomonas* spp.; pharynigitis, rheumatic fever, and glomerulonephritis related to infection by *Streptococcus pyogenes*, Groups C and G streptococci, *Clostridium diptheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; uncomplicated skin and soft tissue infections, abscesses and osteomyelitis, and puerperal fever related to infection by *Staphylococcus aureus*, coagulase-positive staphylococci (i.e., *S. epidermidis, S. hemolyticus,* etc.), *S. pyogenes, S. agalactiae*, Streptococcal groups C–F (minute-colony streptococci), viridans streptococci, *Corynebacterium* spp., *Clostridium* spp., or *Bartonella henselae*; uncomplicated acute urinary tract infections related to infection by *S. saprophyticus* or *Enterococcus* spp.; urethritis and cervicitis; and sexually transmitted diseases related to infection by *Chlamydia trachomatis, Haemophilus ducreyi, Treponema pallidum, Ureaplasma urealyticum,* or *Nesseria gonorrheae*; toxin diseases related to infection by *S. aureus* (food poisoning and Toxic shock syndrome), or Groups A, S. and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *C. trachomatis, N. gonorrhoeae, S. aureus, S. pneumoniae, S. pyogenes, H. influenzae,* or *Listeria* spp.; disseminated *Mycobacterium avium* complex (MAC) disease related to infection by *Mycobacterium avium*, or *Mycobacterium intracellulare*; gastroenteritis related to infection by *Campylobacter jejuni*; intestinal protozoa related to infection by *Cryptosporidium* spp. odontogenic infection related to infection by viridans streptococci; persistent cough related to infection by *Bordetella pertussis*; gas gangrene related to infection by *Clostridium perfringens* or *Bacteroides* spp.; Skin infection by *S. aureus, Propionibacterium acne*; atherosclerosis related to infection by *Helicobacter pylori* or *Chlamydia pneumoniae*; or the like.

Bacterial infections and protozoa infections and disorders related to such infections that may be treated or prevented in animals include, but are not limited to, the following: bovine respiratory disease related to infection by *P. haemolytica.*, *P. multocida*, *Mycoplasma bovis*, or *Bordetella* spp.; cow enteric disease related to infection by *E. coli* or protozoa (i.e., coccidia, cryptosporidia, etc.), dairy cow mastitis related to infection by *S. aureus, S. uberis, S. agalactiae, S. dysgalactiae, Klebsiella* spp., *Corynebacterium*, or *Enterococcus* spp.; swine respiratory disease related to infection by *A. pleuropneumoniae.*, *P. multocida*, or *Mycoplasma* spp.; swine enteric disease related to infection by *E. coli, Lawsonia intracellularis, Salmonella* spp., or *Serpulina hyodyisinteriae*; cow footrot related to infection by *Fusobacterium* spp.; cow metritis related to infection by *E. coli*; cow hairy warts related to Infection by *Fusobacterium necrophorum* or *Bacteroides nodosus*; cow pink-eye related to infection by *Moraxella bovis*, cow premature abortion related to infection by protozoa (i.e. neosporium); urinary tract infection in dogs and cats related to infection by *E. coli*; skin and soft tissue infections in dogs and cats related to infection by *S. epidermidis, S. intermedius*, coagulase neg. *Staphylococcus* or *P. multocida*; and dental or mouth infections in dogs and oats related to infection by *Alcaligenes* spp., *Bacteroides* spp., *Clostridium* spp., *Enterobacter* spp., *Eubacterium* spp., *Peptostreptococcus* spp., *Porphfyromonas* spp., *Campylobacter* spp., *Actinomyces* spp., *Erysipelothrix* spp., *Rhodococcus* spp., *Trypanosoma* spp., *Plasmodium* spp., *Babesia* spp., *Toxoplasma* spp., *Pneumocystis* spp., *Leishmania* spp., and *Trichomonas* spp. or *Prevotella* spp. Other bacterial infections and protozoa infections and disorders related to such infections that may be treated or prevented in accord with the method of the present invention are referred to in J. P. Sanford at al., "The Sanford Guide To Antimicrobial Therapy," 26th Edition, (Antimicrobial Therapy, Inc., 1996).

Antibacterial Activity

Susceptibility tests can be used to quantitatively measure the in vitro activity of an antimicrobial agent against a given bacterial isolate. Compounds are tested for in vitro antibacterial activity by a micro-dilution method. Minimal Inhibitory Concentration (MIC) is determined in 96 well microtiter plates utilizing the appropriate Mueller Hinton Broth medium (CAMHB) for the observed bacterial isolates. Antimicrobial agents are serially diluted (2-fold) in DMSO to produce a concentration range from about 64 μg/ml to about 0.03 μg/ml. The diluted compounds (2 μl/well) are then transferred into sterile, uninoculated CAMHB (0.2 mL) by use of a 96 fixed tip-pipetting station. The inoculum for each bacterial strain is standardized to $5 \times 10^5$ CFU/mL by optical comparison to a 0.5 McFarland turbidity standard. The plates are inoculated with 10 μl/well of adjusted bacterial inoculum. The 96 well plates are covered and incubated at 35+/−2° C. for 24 hours in ambient air environment. Following incubation, plate wells are visually examined by Optical Density measurement for the presence of growth (turbidity). The lowest concentration of an antimicrobial agent at which no visible growth occurs is defined as the MIC. The compounds of the invention generally demonstrated an MIC in the range from about 64 μg/ml to about 0.03 μg/ml.

All in vitro testing follows the guidelines described in the Approved Standards M7-A4 protocol, published by the National Committee for Clinical Laboratory Standards (NCCLS).

Pharmaceutical Compositions.

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically exipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The pharmaceutical compositions of this invention can be administered orally to fish by blending said pharmaceutical compositions into fish feed or said pharmaceutical compositions may be dissolved in water in which infected fish are placed, a method commonly referred to as a medicated bath. The dosage for the treatment of fish differs depending upon the purpose of administration (prevention or cure of disease) and type of administration, size and extent of infection of the fish to be treated. Generally, a dosage of 5–1000 mg, preferably 20–100 mg, per kg of body weight of fish may be administered per day, either at one time or divided into several times. It will be recognized that the above-specified dosage is only a general range which may be reduced or increased depending upon the age, body weight, condition of disease, etc. of the fish.

Unless otherwise defined, all technical and scientific terms used herein are accorded the meaning commonly known to one of ordinary skill in the art. All publications, patents, published patent applications, and other references mentioned herein are hereby incorporated by reference in their entirety.

Abbreviations

Abbreviations which may be used in the descriptions of the scheme and the examples that follow are:

Ac for acetyl;
AIBN for azobisisobutyronitrile;
$Bu_3SnH$ for tributyltin hydride;
CDI for carbonyldiimidazole;
dba for dibenzylidene acetone;
dppb for diphenylphosphino butane;
DBU for 1,8-diazabicyclo[5.4.0]undec-7-ene;
DEAD for diethylazodicarboxylate;
DMAP for dimethylaminopyridine;
DMF for dimethyl formamide;
DPPA for diphenylphosphoryl azide;
EtOAc for ethyl acetate;
MeOH for methanol;
$NaN(TMS)_2$ for sodium bis(trimethylsilyl)amide;
NMMO for N-methylmorpholine N-oxide;
TEA for triethylamine;
THF for tetrahydrofuran;
TPP or $PPh_3$ for triphenylphosphine;
MOM for methoxymethyl;
Boc for t-butoxycarbonyl;
Bz for benzyl;
Ph for phenyl;
POPd for dihydrogen dichlorobis(di-tert-butylphosphinito-κP)palladate(II);
TBS for tert-butyl dimethylsilyl; or
TMS for trimethylsilyl.

Synthetic Methods

The compounds and processes of the present invention will be better understood in connection with the following synthetic schemes that illustrate the methods by which the compounds of the invention may be prepared.

A preferred intermediate for the preparation of compounds represented by formula I is a compound represented by formula IX as illustrated below

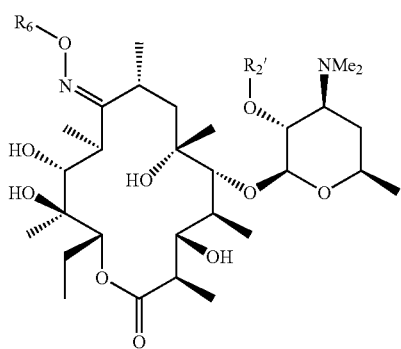

(IX)

wherein $R_6$ and $R_2'$ are as previously defined.

A second preferred intermediate for the preparation of compounds represented by formula I is a compound represented by formula X as illustrated below

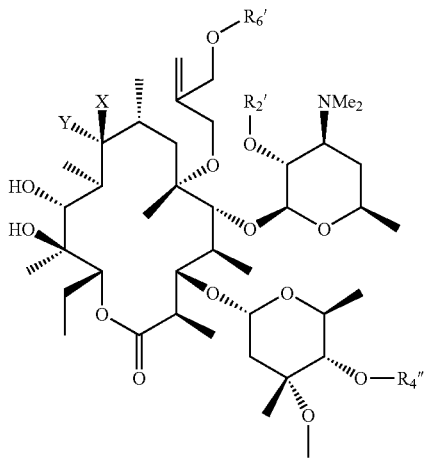

(X)

where X, Y, $R_2'$, $R_4''$ and $R_6'$ are as previously defined.

Schemes 1–4 describe processes for the preparation of intermediates which are useful in the preparation of compounds according to the invention.

Compounds of formula (1-2), which are useful as the starting materials for the preparation of compounds of the present invention, may be synthesized as detailed in Schemes 1 and 2 below. An erythromycin derivative (1-2) is prepared from erythromycin using the procedures described in U.S. Pat. Nos. 4,990,602; 4,331,803; 4,680,386; 4,670,549; and European Patent Application EP 260,938.

Scheme 1

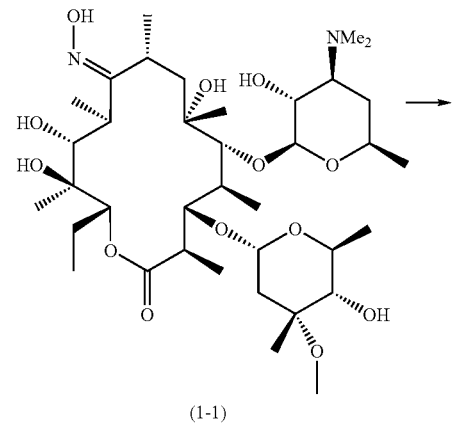

(1-1)

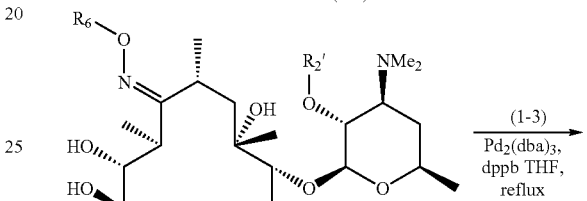

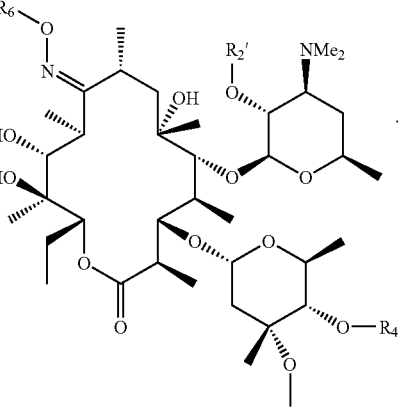

(1-2)

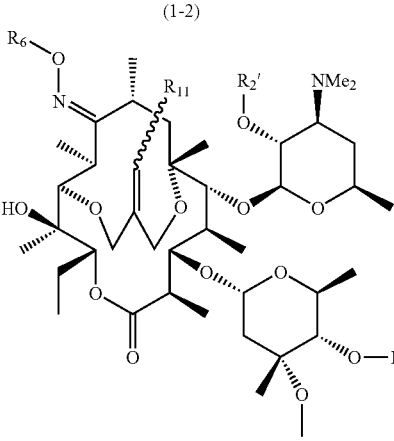

(1-4)

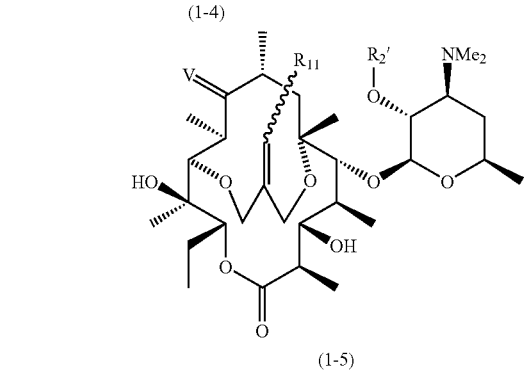

(1-5)

-continued

V = N—O—R$_6$

The erythromycin derivative of formula (1-2), is then reacted with an alkylating agent of the formula:

R$_{13}$—OC(O)O—CH$_2$[C=CH R$_{11}$]CH$_2$—OC(O)—OR$_{13}$ (1-3)

where R$_{13}$ is C$_1$–C$_{12}$-alkyl and R$_{11}$ is as previously defined.

Most palladium (0) catalysts are expected to work in this process. Some palladium (II) catalysts, such as palladium (II) acetate, which is converted into a palladium (0) species in-situ by the actions of a phosphine, will work as well. See, for example, Beller et al. *Angew. Chem. Int. Ed. Engl.*, 1995, 34 (17), 1848. The palladium catalyst can be selected from, but not limited to, the group consisting of palladium (II) acetate, tetrakis(triphenylphospine)palladium (0), tris(dibenzylideneacetone)dipalladium, tetradi(benzylideneacetone)dipalladium and the like. Palladium on carbon and palladium (II) halide catalysts are less preferred than other palladium catalysts for this process.

Suitable phosphines include, but are not limited to, triphenylphosphine, bis(diphenylphosphino)methane, bis(diphenylphosphino)ethane, bis(diphenylphosphino)propane, 1,4-bis(diphenylphosphino)butane, bis(diphenylphosphino)pentane, and tri(o-tolyl)phosphine, and the like.

The reaction is carried out in an aprotic solvent, preferably at elevated temperature, for example, at or above 50° C. Suitable aprotic solvents include, but are not limited to, tetrahydrofuran, N,N-dimethylformamide, dimethyl sulfoxide, N-methyl-2-pyrrolidone, hexamethylphosphoric triamide, 1,2-dimethoxyethane, methyl-tert-butyl ether, heptane, acetonitrile, isopropyl acetate and ethyl acetate. The most preferred solvents are tetrahydrofuran or toluene.

The alkylating agents useful in the processes of the invention are di-carbonates (1-3). Generally, the alkylating agents have the formula (1-3), previously described. The preferred alkylating agents are those wherein R$_{13}$ is a tert-butyl, isopropyl or isobutyl group. The alkylating reagents are prepared by reaction of a di-ol with a wide variety of compounds for incorporating the di-carbonate moiety. The compounds include, but are not limited to, tert-butyl chloroformate, di-tert-butyl dicarbonate, and 1-(tert-butoxycarbonyl)imidazole and the reaction is carried out in the presence of an organic or an inorganic base. The temperature of the reaction varies from about –30° C. to about 30° C. Preferably, the alkylating reagent is di-tert-butyl dicarbonate.

An alternative method of converting the alcohol into the carbonate involves treating the alcohol with phosgene or triphosgene to prepare the chloroformate derivative of the di-ol. The di-chloroformate derivative is then converted into the di-carbonate by the methods described in Cotarca, L., Delogu, P., Nardelli, A., Sunijic, V, *Synthesis*, 1996, 553. The reaction can be carried out in a variety of organic solvents such as dichloromethane, toluene, diethyl ether, ethyl acetate and chloroform in the presence of a base. Examples of suitable bases include, but are not limited to, sodium hydroxide, potassium hydroxide, ammonium hydroxide, sodium carbonate, potassium carbonate, ammonium carbonate, dimethylaminopyridine, pyridine, triethylamine and the like. The temperature conditions can vary from 0° C. to about 60° C. The reaction typically takes about 3 to 5 hours to run to completion.

The cladinose moiety of macrolide (1-4) is removed either by mild acid hydrolysis or by enzymatic hydrolysis to give compounds of formula (1-5). Representative acids include dilute hydrochloric acid, sulfuric acid, perchloric acid, chloroacetic acid, dichloroacetic acid or trifluoroacetic acid. Suitable solvents for the reaction include methanol, ethanol, isopropanol, butanol and the like. Reaction times are typically 0.5 to 24 hours. The reaction temperature is preferably –10° C. to 80° C.

Scheme 2

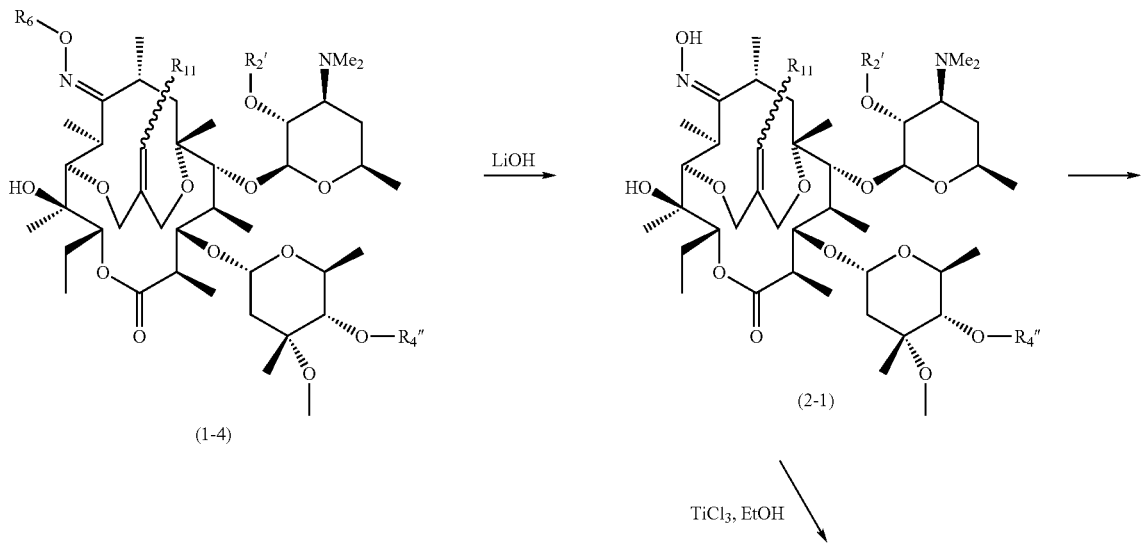

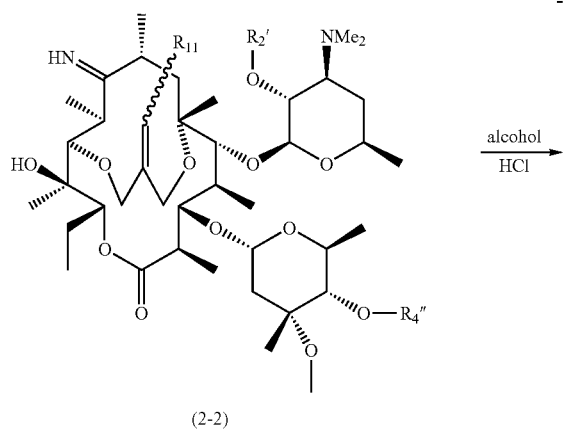

(2-2)

-continued

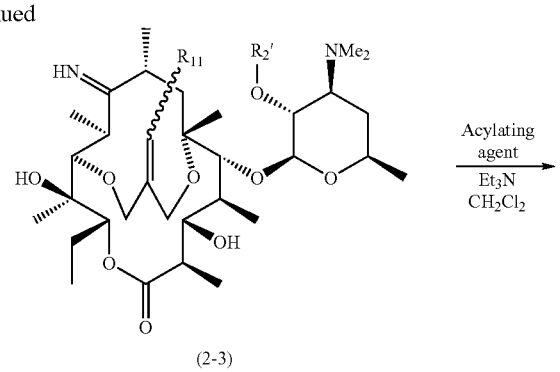

(2-3)

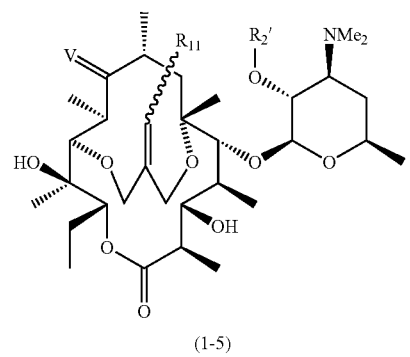

(1-5)

V: N—R$_{12}$

Compounds of formula (1-4), where R$_6$ is an acetyl group, can be converted into the corresponding imine as outlined in Scheme 2. Selective deprotection of the oxime is typically accomplished via alkaline hydrolysis in protic solvents. Representative alkali compounds include lithium hydroxide, sodium hydroxide, potassium hydroxide, and the like. Suitable solvents include, but are not limited to, tetrahydrofuran, 1,4-dioxane, 1,2-dimethoxyethane, isopropanol, ethanol, butanol and mixtures there of. The reaction temperature is preferably 0° to 35° C. and reaction time is preferably 0.5 to 8 hours.

In a like fashion, simultaneous deprotection of both the oxime and the 2' hydroxyl can be accomplished under a variety of conditions. Conditions for deprotection include, but not limited to, treating with an alcoholic solvent from room temperature to reflux, or treatment with a primary amine, such as butylamine. Alcoholic solvents preferred for the deprotection are methanol and ethanol. A more thorough discussion of the procedures, reagents and conditions for removing protecting groups is described in literature, for example, by T. W. Greene and P. G. M. Wuts in "Protective Groups in Organic Synthesis" 3$^{rd}$ ed., John Wiley & Son, Inc, 1999.

Deoxygenation of compounds of formula (2-1) under reducing conditions gives the macrolide imine of formula (2-2). Many reducing agents can be used to effect this transformation including, but not limited to, lithium aluminum hydride, titanium trichloride, borane, and various sulfides such as sodium hydrogen sulfide and sodium nitrite. For a more detailed account of oxime reduction see J. March in "Advanced Organic Chemistry" 4$^{th}$ ed., Wiley & Son, Inc, 1992.

A particularly useful method for the reduction of oximes to the corresponding imine uses a sulfite reducing agent, such as sodium hydrogensulfite, under acidic conditions, typically in protic solvents. Representative acids include, but are not limited to, acetic acid, formic acid, dilute hydrochloric acid, dilute phosphoric acid, dilute sulfuric acid, and the like. Suitable protic solvents include, but are not limited to, mixtures of water and methanol, ethanol, isopropanol, or butanol. The reaction is typically carried out at 500 to 110° C., preferably for between 1 and 10 hours.

Hydrolysis of the cladinose moiety can be accomplished as previously described in scheme 1 to give compounds of formula (2-3)

Alternatively compounds of formula (2-3) can be formed directly from compounds of formula (2-1) via treatment with TiCl$_3$ in alcoholic solvents, preferably methanol or ethanol Imines of formula (2-3) can be acylated under basic conditions using a suitable acylating agent in an aprotic solvent. Typical acylating agents include, but are not limited to, acetyl chloride, acetic anhydride, benzoyl chloride, benzoic anhydride, and benzyl chloroformate.

Examples of aprotic solvents are dichloromethane, chloroform, tetrahydrofuran, N-methylpyrrolidinone, dimethylsulfoxide, N,N-dimethylformamide, N,N-dimethylacetamide, hexamethylphosphoric triamide, a mixture thereof or a mixture of one of these solvents with ether, tetrahydrofuran, 1,2-dimethoxyethane, 1,2-dichloroethane, acetonitrile, ethyl acetate, acetone and the like. Aprotic solvents do not adversely affect the reaction. Preferably, the solvent is selected from dichloromethane, chloroform, N,N-dimethylformamide, tetrahydrofuran, N-methylpyrrolidinone or mixtures thereof.

Typical bases include, but are not limited to, pyridine, triethylamine, diisopropyl ethylaamine, N-methyl morpholine, N-methylpyrrolidine, 2,6-lutidine, 1,8-diazabicyclo [5.4.0]undec-7-ene. For a more extensive discussion of acylating conditions see, for example, T. W. Greene and P. G. M. Wuts in "Protective Groups in Organic Synthesis" 3$^{rd}$ ed., John Wiley & Son, Inc, 1999.

Scheme 3

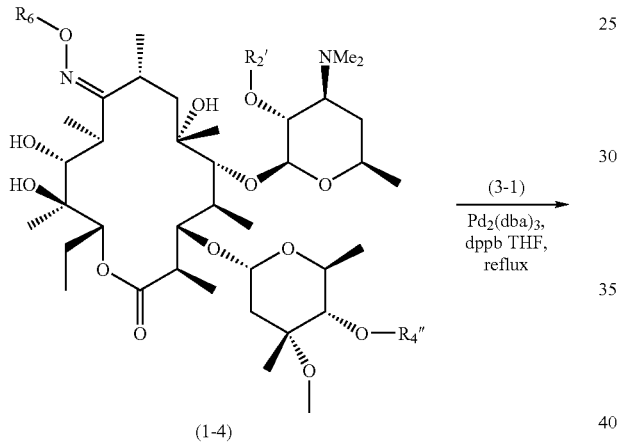

(1-4)

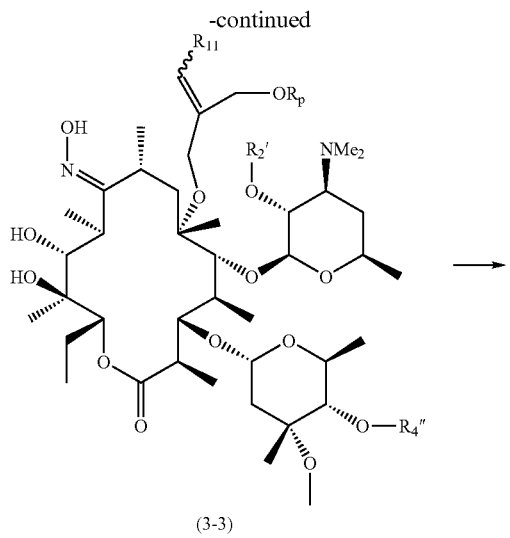

(3-3)

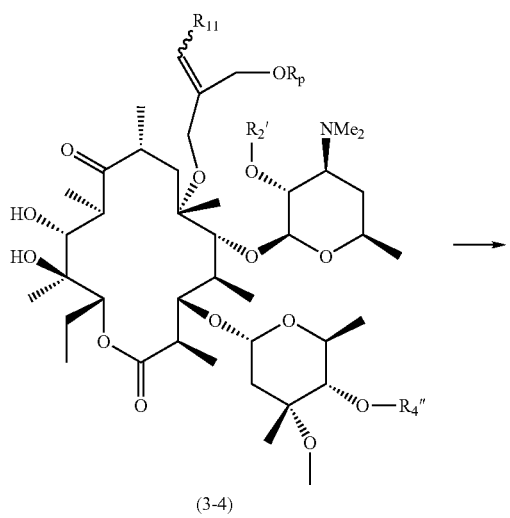

(3-4)

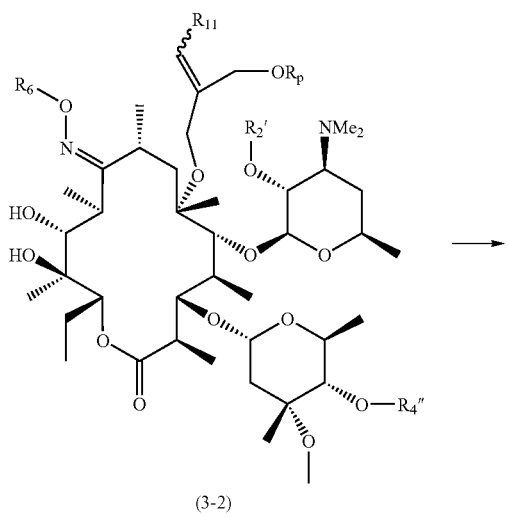

(3-2)

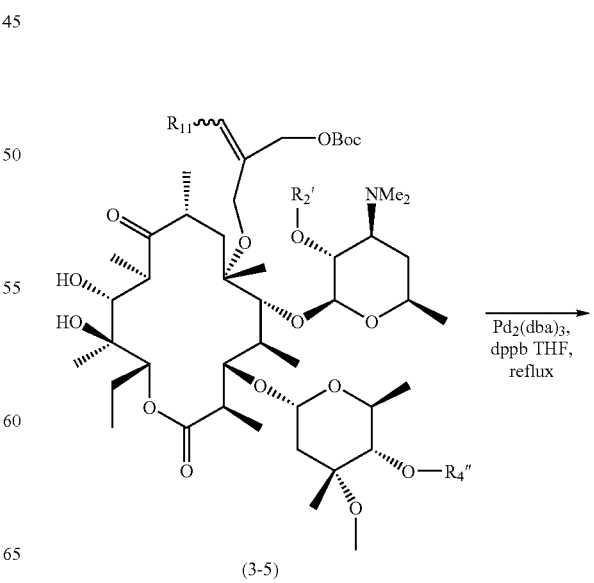

(3-5)

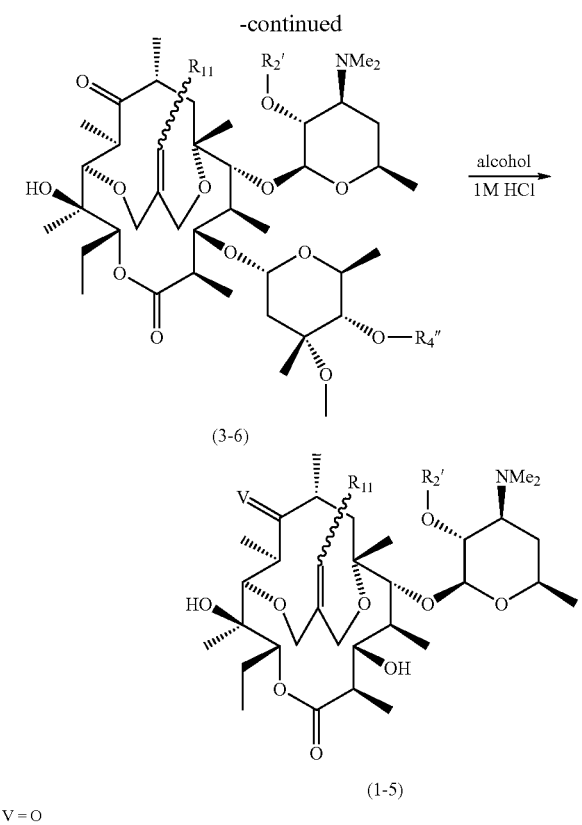

(3-6)

(1-5)

V=O

Stepwise formation of the 6–11 bridged macrolides is also possible as outlined in Scheme 3. In a similar manner as previously described, the procedure involves reacting a compound of formula (1-4) with a suitable alkylating agent. As before, the erythromycin derivative of formula (1-4) is reacted with an alkylating agent of the formula:

(3-1)

where $R_{13}$ is $C_1$–$C_{12}$-alkyl, and $R_{11}$ and $R_p$ are as previously defined.

As discussed previously, most palladium (0) catalysts are expected to work in this process and the reaction is carried out in an aprotic solvent, preferably at elevated temperature, preferably at or above 50° C. The most preferred solvents are tetrahydrofuran and toluene.

The alkylating agents useful in the process of the invention are the mixed silyl ether carbonates (3-1). Generally, the alkylating agents have the formula (3-1), previously described. The preferred alkylating agents are those wherein $R_{13}$ is tert-butyl, isopropyl or isobutyl and $R_p$ is tert-butyl dimethyl silyl, triisopropyl silyl, tert-butyl diphenyl silyl or the like.

The alkylating reagents of formula (3-1) are prepared by reaction of a diol sequentially with a wide variety of compounds for incorporating the carbonate moiety, followed by a wide variety of compounds for incorporating the silyl moiety. Alkylating reagents include, but not limited to, tert-butyl chloroformate, di-tert-butyl dicarbonate, and 1-(tert-butoxycarbonyl)imidazole; where as silylating reagents include, but are not limited to tert-butyl dimethyl silyl chloride, tert-butyl dimethyl silyl triflate, tert-butyl dimethyl silyl cyanide, and tert-butyl dimethyl silyl imida-zole. Both reactions are carried out in the presence of an organic or an inorganic base. The temperature of the reactions vary from about −30° C. to about 30° C. Preferably, the alkylating reagent is di-tert-butyl dicarbonate and the sily-lating reagent is tert-butyl dimethyl silyl chloride.

The free oxime (−3) is prepared using essentially the same procedure as for the deprotection of oxime (1-4) where $R_6$ is Ac in Scheme 2.

Compounds of formula (3-4) can be formed directly from compounds of formula (3-3) by the application of the previously described procedure for the reduction of oximes of formula (2-1) to the corresponding imine of formula (2-2).

The protecting group (Rp) is then removed from the hydroxyl of the compound of formula 3-4) using the appropriate conditions as outlined in T. W. Greene and P. G. M. Wuts in "Protective Groups in Organic Synthesis" $3^{rd}$ ed., John Wiley & Son, Inc, 1999. For example, when the protecting group is TBS, tetra-n-butyl ammonium fluoride, hydrofluoric acid or trifluoro acetic acid may be used. Using standard conditions, the primary hydroxyl is converted to the tert-butyl carbonate, and subsequently the 11-hydroxyl group is alkylated by means of a palladium (0) catalyst as described previously. In this way compounds of formula (3-6) can be prepared readily.

Removal of the cladinose sugar is accomplished as previously described in Scheme 1 to give a compound of formula (1-5).

Scheme 4

(1-5)

(5-1)

V: O, N, —O—$R_6$, NH, NC(O)$R_1$, NC(O)$R_2$ or N—$R_{12}$

Compounds according to the invention (5-1) may be prepared by oxidation of the secondary alcohol using Dess Martin periodinane as the oxidant. The reaction is typically run in an aprotic solvent at 0° to 25° C. The reaction time is typically between 1 and 12 hours.

Alternatively the oxidation can be accomplished using pyridinium chlorochromate, sulfur trioxide pyridine complex in dimethyl sulfoxide, tetra-n-propyl ammonium perruthenate and N-methyl morpholine N-oxide, Swern oxidation or the like. A more thorough discussion of the oxidation of secondary alcohols can be found in J. March in "Advanced Organic Chemistry" 4$^{th}$ ed., Wiley & Son, Inc, 1992.

An alternative method for the preparation of ketone (6-2) involves dihydroxylation of the alkene followed by diol cleavage. The glycol (6-3) is first prepared by reacting alkene (6-1) with osmium tetroxide. This reaction can be carried out with stochiometric amounts of osmium tetroxide, or, if an oxidant such as hydrogen peroxide, tert-butyl hydroperoxide, or N-methylmorpholine-N-oxide is present, with catalytic amounts of osmium tetroxide. These reactions

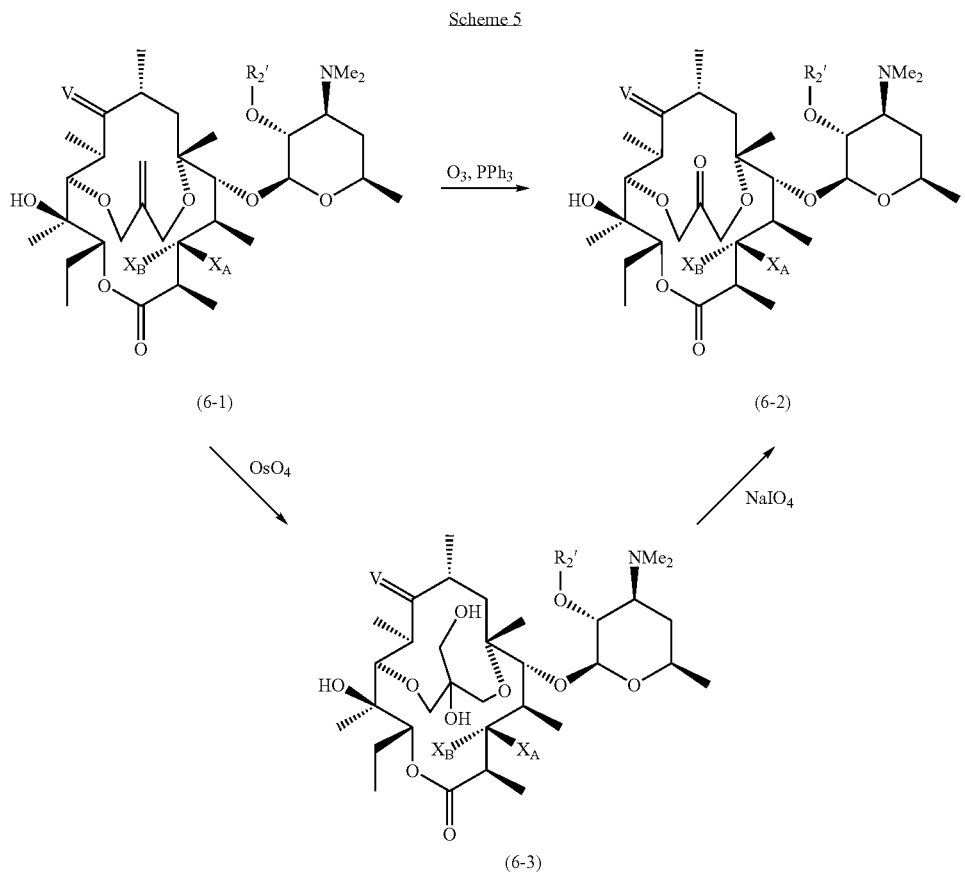

V = O, NH, NR$_{12}$, N—O—R$_6$, NC(O)R$_1$, NC(O)R$_2$, or N—R$_{12}$

X$_A$ = OH, X$_B$ = H or X$_A$ and X$_B$ taken together with the carbon to which they are attached is C═O Scheme 5 illustrates another process of the invention for the preparation of compounds according to the invention. Conversion of alkene (6-1) into ketone (6-2) can be accomplished by exposure of the alkene to ozone followed by decomposition of the ozonide with the appropriate reducing agent, as outlined in Scheme 3. The reaction is typically carried out in an inert solvent such as, but not limited to, methanol, ethanol, ethyl acetate, glacial acetic acid, chloroform, methylene chloride or hexanes or mixtures thereof, preferably methanol, preferably at −78° to −20° C. Representative reducing agents are, for example, triphenylphosphine, trimethyl phosphite, -thiourea, and dimethyl sulfide, preferably triphenylphosphine. A more thorough discussion of ozonolysis and the conditions there for can be found in J. March "Advanced Organic Chemistry" 4$^{th}$ ed., Wiley & Son, Inc, 1992.

can be carried out in a variety of solvents including: 1,4-dioxane, tetrahydrofuran, tert-butanol and diethyl ether, preferably at 0° C.

The glycol can be cleaved by a variety of reagents including, but not limited to, periodic acid, lead tetraacetate, manganesedioxide, potassium permanganate, sodium metaperiodate, and N-iodosuccinamide. Depending on the cleavage reagent, a variety of solvents can be used. Preferably the cleavage reagent is sodium metaperiodate, the solvent is preferably a mixture of ethanol, methanol, acetone, or 1,4-dioxane and water and the reaction temperature is 0 to 25° C.

Scheme 6

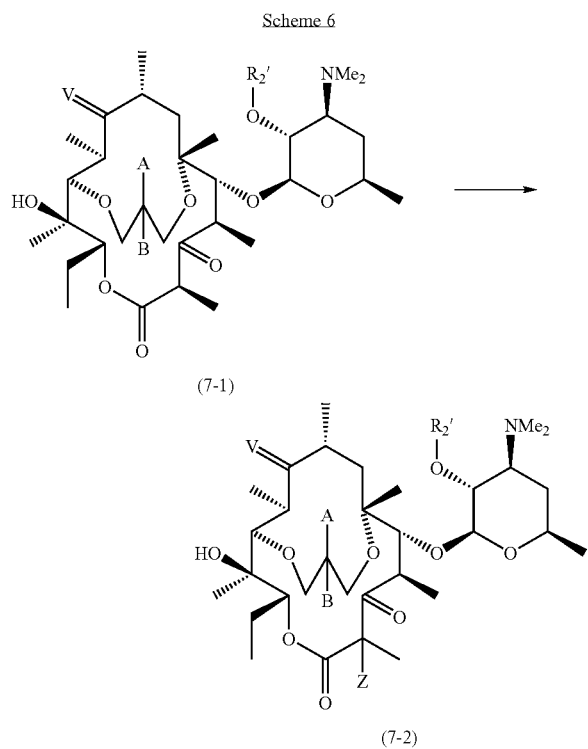

V = O, NH, NOR$_6$, NR$_{12}$, NC(O)R$_1$ or NC(O)R$_2$
Z = halogen

Scheme 6 illustrates the procedure by which compounds of formula (7-1) may be converted to compounds of formula (7-2) by treatment with a halogenating reagent. This reagent acts to replace a hydrogen atom with a halogen atom at the C-2 position of the ketolide. Various halogenating reagents may be suitable for this procedure.

Fluorinating reagents include, but are not limited to, N-fluorobenzenesulfonimide in the presence of base, 10% F$_2$ in formic acid, 3,5-dichloro-1-fluoropyridinium tetrafluoroborate, 3,5-dichloro-1-fluoropyridinium triflate, (CF$_3$SO$_2$)$_2$NF, N-fluoro-N-methyl-p-toluenesulfonamide in the presence of base, N-fluoropyridinium triflate, N-fluoroperfluoropiperidine in the presence of base.

Chlorinating reagents include, but are not limited to, hexachloroethane in the presence of base, CF$_3$CF$_2$CH$_2$ICl$_2$, SO$_2$Cl$_2$, SOCl$_2$, CF$_3$SO$_2$Cl in the presence of base, Cl$_2$, NaOCl in the presence of acetic acid.

Brominating reagents include, but are not limited to, Br$_2$.pyridine.HBr, Br$_2$/acetic acid, N-bromosuccinimide in the presence of base, LDA/BrCH$_2$CH$_2$Br, or LDA/CBr$_4$ A suitable iodinating reagent is N-Iodosuccinimide in the presence of base, or I$_2$, for example Suitable bases for the halogenating reactions requiring them are compounds such as alkali metal hydrides, such as NaH and KH, or amine bases, such as LDA or triethylamine, for example. Different reagents may require different type of base, but this is well known within the art.

A preferred halogenating reagent is N-fluorobenzenesulfonimide in the presence of sodium hydride.

Suitable solvents are dimethylformamide, dimethyl sulfoxide, pyrrolidinone and the like.

It will be appreciated by one skilled in the art that compounds of formula 7-1) or 7-2) can be substituted for compounds of formula (–1) or (6-2) in the preceding examples if the corresponding C-2 halogenated product is desired.

Scheme 7

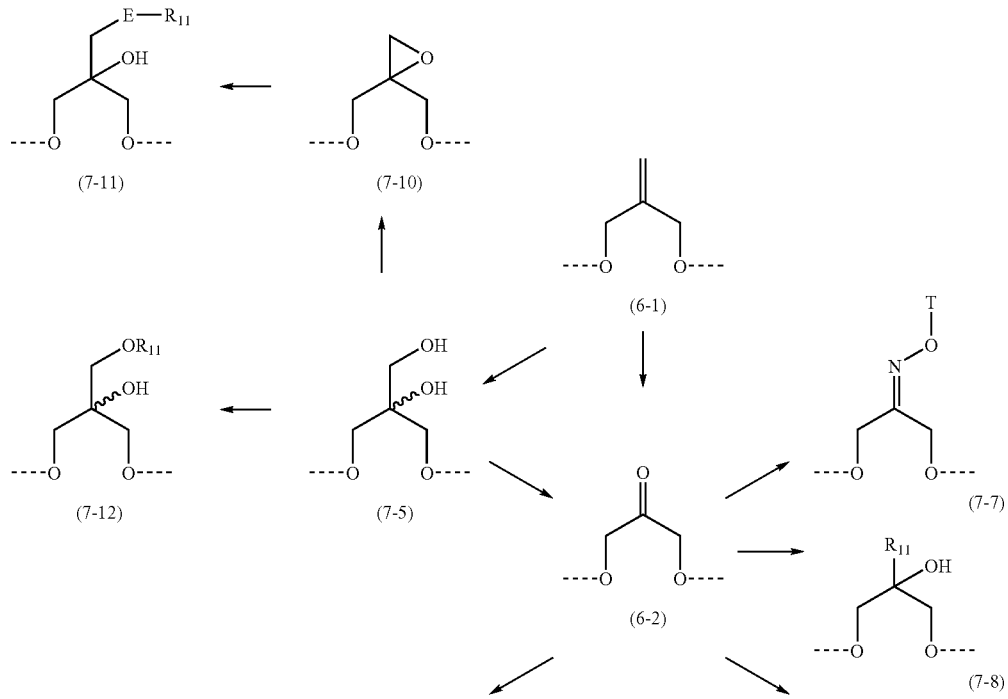

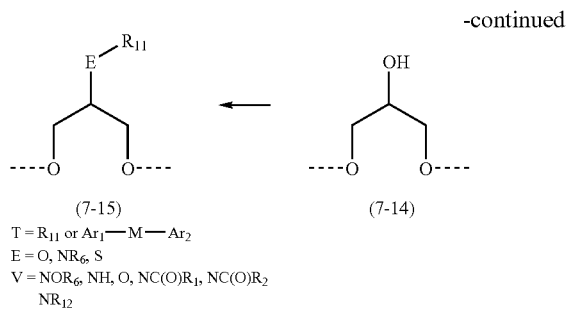

(7-15)     (7-14)

T = R$_{11}$ or Ar$_1$—M—Ar$_2$
E = O, NR$_6$, S
V = NOR$_6$, NH, O, NC(O)R$_1$, NC(O)R$_2$
    NR$_{12}$

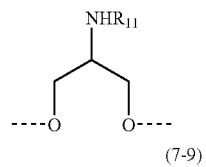

(7-9)

For ease of illustration, in Scheme 7 only the 6–11 bridged moiety of each particular compound according to formula I will be shown, it being understood that it is intended to illustrate a compound according to formula I with the specified bridged moiety. Compounds according to the invention of the formulas (6-1) and (6-2) can be further functionalized in a variety of ways. Scheme 7 details a procedure for the conversion of the ketone (6-2) into an oxime of formula (7-7). Oxime formation can be accomplished, using the appropriate substituted hydroxylamine, under either acidic or basic conditions in a variety of solvents. Representative acids include, but are not limited to, hydrochloric, phosphoric, sulfuric, p-toluenesulfonic, and pyridinium p-toluene sulfonate. Likewise, bases that are useful are, for example, triethylamaine, pyridine, diisopropylethyl amine, 1,5-lutidine, and the like. Appropriate solvents include, but are not limited to, methanol, ethanol, water, tetrahydrofuran, 1,2-dimethoxyethane, and ethyl acetate. Preferably the reaction is carried out in ethanol using triethylamine as the base. Reaction temperature is generally 25° C. and reaction time is 1 to 12 hours.

Ketone (6-2) can also be further utilized by conversion into the amine (2-9) via a reductive amination protocol. Thus, the ketone is treated with an amine in the presence of a reducing agent to obtain the product amine (7-9). The reaction can be carried out either with or without added acid. Examples of acids that are commonly used include, hydrochloric, phosphoric, sulfuric, acetic, and the like. Reducing agents that effect reductive amination include, but are not limited to, hydrogen and a catalyst, zinc and hydrochloric acid, sodium cyanoborohydride, sodium borohydride, iron petnatcarbonyl, and alcoholic potassium hydroxide. Generally alcoholic solvents are used. The preferred conditions use sodium cyanoborohydride in methanol with added acetic acid.

A still further way to functionalize ketone (6-2) is via addition of Grignard reagents to form alcohols of formula (7-8). Scheme 8 depicts this protocol. The requisite Grignard reagents are readily available via the reaction of a variety of alkyl or aryl halides with magnesium under standard conditions (see B. S. Fumiss, A. J. Hannaford, P. W. G. Smith, A. R. Tatchell "Vogel's Textbook of Practical Organic Chemistry" 5$^{th}$ ed., Longman, 1989). The addition is performed in an inert solvent, generally at low temperature. Suitable solvents include, but are not limited to tetrahydrofuran, diethylether, 1,4-dioxane, 1,2-dimethoxyethane, and hexanes. Preferably the solvent is tetrahydrofuran or diethylether. Preferably the reaction is run at −78° to 0° C.

In a similar way, reaction with other organometallic reagents gives rise to alcohols of type (7-8). Examples of organometallic reagents that may be used include, but are not limited to, organo-aluminum, organo-lithium, organo-cerium, organo-zinc, organo-thallium, and organo-boron reagents. A more thorough discussion of organometallic reagents can be found in B. S. Furniss, A. J. Hannaford, P. W. G. Smith, A. R. Tatchell "Vogel's Textbook of Practical Organic Chemistry" 5$^{th}$ ed., Longman, 1989.

Furthermore, alcohols of type (2-14) can be prepared by reduction of the corresponding ketone (6-2) under a variety of conditions. (see Hudlicky, M. *Reductions in Organic Chemistry*, Ellis Horwood Limited: Chichester, 1984). The alcohols thus derived can be further modified to give compounds of type (7-15). Processes to generate compounds of formula (7-15) include, but are not limited to: alkylation of the alcohol with an electrophile or conversion of the alcohol into a leaving group such as a triflate, tosylate, phosponate, halide, or the like followed by displacement with a heteroatom nucleophile (e.g. an amine, alkoxide, sulfide or the like).

It will be appreciated by one skilled in the art, that the unsaturated compounds represented by compounds (6-1) and (6-2) can be reduced to form the corresponding saturated compound (see Hudlicky, M. *Reductions in Organic Chemistry*, Ellis Horwood Limited: Chichester, 1984).

The glycol (7-5) can be prepared by reacting alkene (6-1) with osmium tetroxide. This reaction can be carried out either with stochiometric amounts of osmium tetroxide, or, if a oxidant such as hydrogen peroxide, tert-butyl hydroperoxide, or N-methylmorpholine-N-oxide are present, with catalytic amounts of osmium tetroxide. These reactions can be run in a variety of solvents including: 1,4-dioxane, tetrahydrofuran, tert-butanol and diethyl ether, preferably at 0° C. The glycols thus derived can be further modified to give compounds of type 7-12) by, for instance, selective alkylation of the primary alcohol with an electrophile (see B. S. Fumiss, A. J. Hannaford, P. W. G. Smith, A. R. Tatchell "Vogel's Textbook of Practical Organic Chemistry" 5$^{th}$ ed., Longman, 1989).

Epoxides of type (7-10) can be prepared by the conversion of the primary alcohol into a leaving group such as a triflate, tosylate, phosponate, halide, or the like, followed by intramolecular nucleophillic displacement (see *Tetrahedron Lett.*, 1983, 661–664). Epoxides of formula (7-10) can be further funtionalized via ring opening with a variety of nucleophiles. Representative nucleophiles include, but are not limited to, amines, alkoxides, sulfides, organometallic reagents and the like. Reactions can be carried out in the presence or absence of Lewis acid activators such as silver carbonate, silver triflate, boron trifluoride etherate, aluminum trichloride and the like. (see (a) *J. Med Chem.*, 1997, 2762–2769, (b) *J. Amer. Chem. Soc.*, 1999, 10251–10263, (c) *Tetrahedron Lett.*, 2000, 4229–4234)

Scheme 8

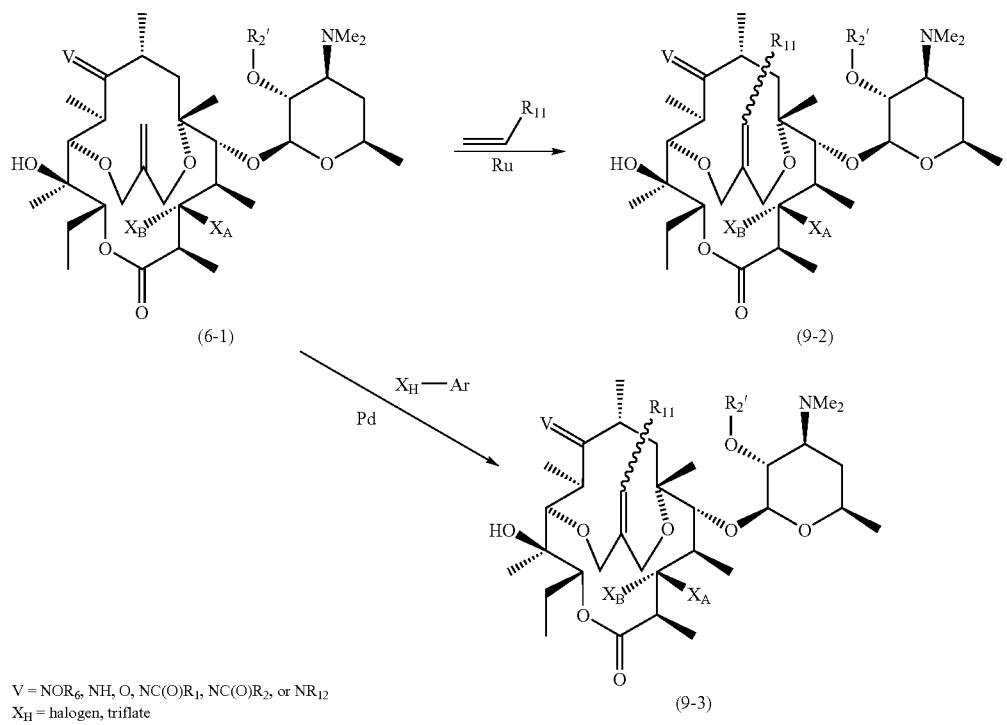

V = NOR₆, NH, O, NC(O)R₁, NC(O)R₂, or NR₁₂
X_H = halogen, triflate
X_A = OH, X_B = H or X_A and X_B taken together
  with the carbon to which they are attached is
  C=O Compounds of the invention according to formula (6-1) are also capable of further functionalization to generate compounds of the present invention. Alkene (6-1) can be treated with an aryl halide or aryl triflate in the presence of a palladium catalyst [Pd(0) or Pd(II)] to provide compound (9-3): (See (a) Heck, Palladium Reagents in Organic Synthesis, Academic Press: New York, 1985, Chapter 1; (b) Sonogashira, Comprehensive Organic Synthesis, Volume 3, Chapters 2,4; (c) Sonogashira, *Synthesis* 1977, 777.). Under the Heck coupling conditions, regioisomers and stereoisomers of the double bond are possible. Alternatively, compound (6-1) can undergo a cross metathesis reaction with vinyl aromatic derivatives using ruthenium catalysts to give compounds of formula (9-2) (see (a) *J. Org. Chem.* 2000, 65, 2204–2207; (b) Reviews: *Synlett.* 1999, 2, 267; (c) Reviews: Ivin, K. J.; Mol. J. C. *Olefin Metathesis and Metathesis Polymerization*, 2$^{nd}$ ed.; Academic Press: New York, 1997; (d) *J. Org. Chem.* 1999, 64, 4798–4816; (e) *Angew. Chem., rt. Ed. Engl.* 1997, 36, 2036–2056; (f) *Tetrahedron* 1998, 54, 4413–4450).

Scheme 9

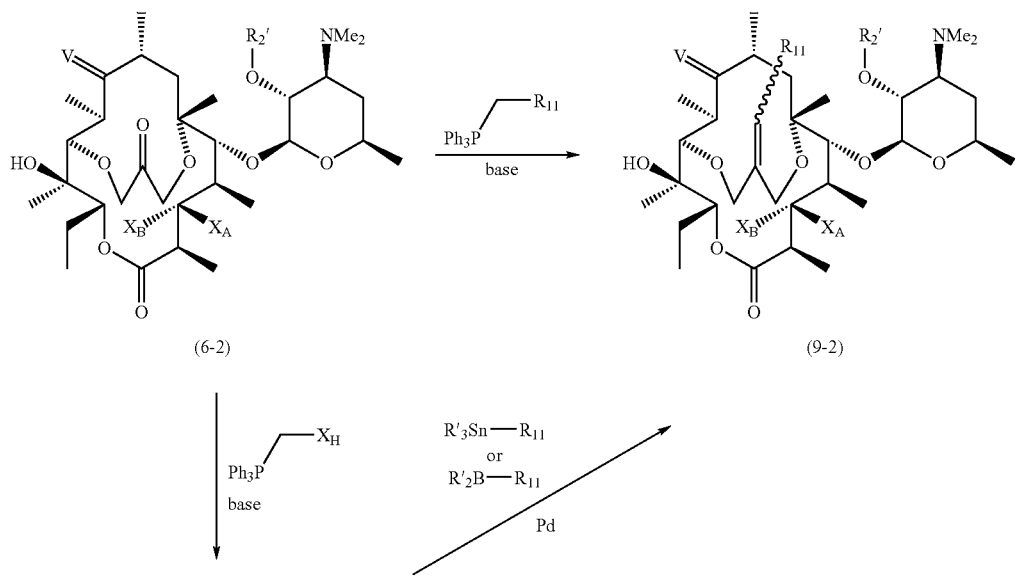

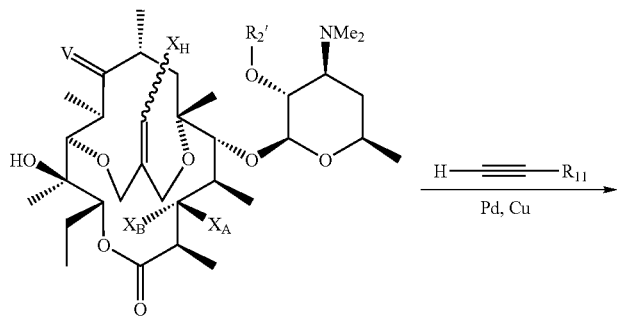

(8-1)

V = NOR₆, NH, O, NC(O)R₁, NC(O)R₂ or NR₁₂
X_H = halogen, triflate
R' = C1–C6 alkyl or cycloalkyl, aryl or heteroaryl
X_A = OH, X_B = H or X_A and X_B taken heteroaryl
   the carbon to which they are attached is
   C=O

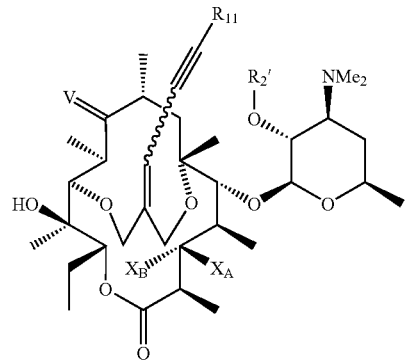

(8-2)

It will be appreciated that ketones of formula (6-2) can be transformed into alkenes of formula (9-2) and (8-1) via Wittig reaction with the appropriate phosphonium salt in the presence of a base. (see (a) Burke, *Tetrahedron Lett.*, 1987, 4143–4146, (b) Rathke and Nowak, *J. Org. Chem.*, 1985, 2624–2626, (c) Maryanoff and Reitz, *Chem. Rev.*, 1989, 863–927. Furthermore, vinyl halides of formula (8-1) can be functionalized by Sonogashira coupling with alkynes in the presence of a palladium catalyst, a copper halide and an amine base to give compounds of formula (8-2) (see (a) Sonogashira, Comprehensive Organic Synthesis, Volume 3, Chapters 2,4; (b) Sonogashira, *Synthesis* 1977, 777.). In a similar manner, alkenes of formula (9-2) can be obtained from vinyl halides (8-1) via Suzuki cross coupling with organoboron reagents in the presence of a palladium catalyst and a base, or via Stille cross coupling with organostananes in the presence of a palladium catalyst. (see (a) Suzuki, *J. Organomet. Chem.* 1999, 576,147–168, (b) Stille, *Angew. Chem. Int. Ed. Engl.*, 1986, 508–524 (c) Farina, *J. Am. Chem. Soc.*, 1991, 9585–9595).

It will be appreciated by one skilled in the art, that the unsaturated compounds represented by compounds (9-2) and (8-2) can be reduced to form the corresponding saturated compound (see Hudlicky, M. *Reductions in Organic Chemistry*, Ellis Horwood Limited: Chichester, 1984).

Scheme 10

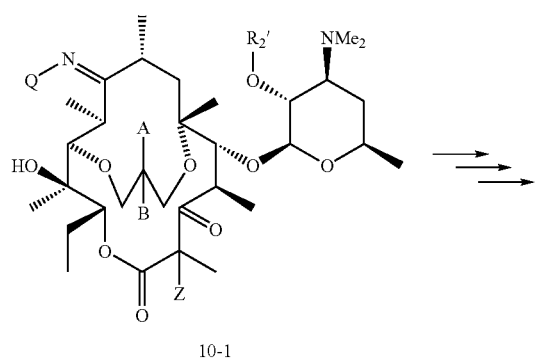

10-1

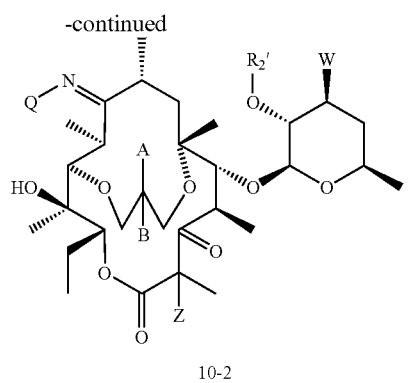

10-2

It will be appreciated that compounds of the present invention include modification of the 3' N of compounds of the formula (10-1). Compounds of formula (10-2), where W is as previously defined, can be made via the methods delineated in U.S. Pat. Nos. 6,034,069 and 6,387,885.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Compound of Formula I: A and B Taken Together with the Carbon Atom to Which They are Attached are C=CH$_2$, X and Y Taken Together with the Carbon Atom to Which They are Attached are C=N—Ac, L=CH$_2$CH$_3$, Z=H, and R$_2$'=Ac Step 1a: Compound of Formula 1-2: R$_6$=Ac, R$_2$'=Ac and R$_4$"=Ac To a solution of erythromycin A oxime (74.9 g, 0.1 mol) in 400 ml THF was added acetic anhydride (35.9 ml, 0.38 mol), triethylamine (55.7 ml, 0.4 mol) and DMAP (3.7 g, 0.03 mol) at room temperature. The mixture was stirred at room temperature for 16 hours and was condensed to ~200 ml, diluted with 300 ml of ethyl acetate and the resulting mixture washed with NaHCO$_3$ (Sat.) (500 ml×4) and brine (500 ml) and dried on anhydrous sodium sulfate. The solvent was evaporated and the residue was recrystallized from ethyl acetate to give title compound (78 g).

MS (ESI) m/z 875 (M+H)$^+$. $^{13}$C NMR(CDCl$_3$): δ 178.5, 175.4, 170.6, 170.2, 168.2, 100.2, 96.1, 83.3, 79.3, 78.7, 75.2, 74.5, 72.9, 70.0, 67.6, 63.4, 63.2, 60.6, 49.5, 44.7, 40.9, 35.4, 31.8, 28.5, 22.8, 21.7, 21.6, 21.5, 21.3, 21.2, 21.1, 19.9, 18.6, 18.4, 16.7, 14.9, 14.4, 14.3, 10.8, 9.2

Step 1b: Compound of Formula 1-3: R$_{11}$=H and R$_{13}$=t-Bu:

To a solution of 2-methylene-1,3-propane diol (5.28 g, 0.06 mmol) and di-tert-butyl dicarbonate (35 g, 0.16 mol) in 150 ml of dichloromethane was added 6N NaOH (70 ml) and tetrabutylammoniahydrogensulfate (3.4 g, 10 mmol). The mixture was stirred at room temperature overnight. The organic layer was separated, washed with NaHCO$_3$ (200 ml×3) and brine (200 ml), dried over anhydrous MgSO$_4$, concentrated and dried over vacuum to give the title compound.

$^1$H NMR (CDCl$_3$): δ 5.20(s, 2H); 4.44(s, 4H); 1.18(s, 18H). $^{13}$C NMR(CDCl$_3$): δ 153.3, 138.5, 117.3, 82.3, 66.9, 27.8.

Step 1c: Compound of Formula 1-4: R$_6$=Ac, R$_{11}$=H, R$_2$'=Ac and R$_4$"=Ac

To a solution of erythromycin oxime 2',4",9-triacetate from Step 1a (112 g, 128 mmol), the compound from step 1b (44.3 g, 154 mmol) and dppb (1.71 g, 4 mmol) in THF (500 ml), was added Pd$_2$(dba)$_3$ (1.83 g, 2 mmol) under nitrogen. The mixture was refluxed for 5 hours and concentrated. The residue was purified by flash chromatography (SiO$_2$ hexane:acetone/2:1) to give the title compound. (110 g).

MS (ESI) m/z 927.64 (M+H)$^{+13}$C NMR(CDCl$_3$): δ 176.5, 175.9, 170.7, 170.1, 169.9, 141.6, 124.7, 100.4, 96.0, 79.1, 78.7, 78.2, 78.0, 77.4, 76.5, 73.5, 73.0, 72.4, 72.1, 67.8, 66.1, 63.4, 63.3, 49.6, 44.1, 41.2, 40.9, 37.3, 35.4, 35.1, 31.3, 29.5, 28.5, 27.1, 23.4, 21.7, 21.3, 21.1, 20.9, 20.3, 18.8, 18.3, 17.4, 15.7, 13.4, 12.7, 8.6.

Step 1d: Compound of Formula 2-1: R$_{11}$=H, R$_2$'=H and R$_4$"=Ac

A solution of the compound of Step 1c (32 g) in 400 ml methanol was refluxed for 48 hours and then concentrated. The residue was purified by flash chromatography (SiO$_2$, CH$_2$Cl$_2$:2M ammonia in methanol=95:5) to give the title compound (28.5 g).

MS (ESI) m/z 843 (M+H)$^{+13}$C NMR(CDCl$_3$): δ 176.2, 170.8, 168.8, 142.0, 124.2, 102.5, 95.9, 79.4, 78.7, 78.1, 78.0, 76.6, 73.0, 71.8, 71.1, 68.2, 65.6, 63.2, 49.7, 44.2, 41.7, 40.5, 37.7, 35.0, 34.4, 29.3, 25.8, 23.5, 21.9, 21.3, 21.1, 19.0, 18.1, 17.5, 15.3, 13.2, 12.7, 8.7.

Step 1e: Compound of Formula 2-2: R$_{11}$=H and R$_2$'=H

Titanium trichloride (40 ml, 20% in 3% hydrochloric acid) was added dropwise over 10 minutes to a stirred solution of the compound from Step 1d (9.5 g, 11.3 mmol) and ammonium acetate (17.4 g, 226 mmol) in 120 ml of methanol at 0° C. The reaction mixture was allowed to warm up to room temperature and stirred over night. The pH of the reaction mixture was adjusted to pH=10 by slow addition of 3N aqueous sodium hydroxide. The aqueous solution was extracted with ethyl acetate (200 ml) and the organic phase was washed once with saturated sodium bicarbonate (200 ml), dried over sodium sulfate and solvent was removed in vacuo. The residue was purified by flash chromatography (SiO$_2$, CH$_2$Cl$_2$:2M ammonia in methanol/95:5) to give the title compound (3.0 g).

MS (ESI) m/z: 627 (M+H). $^{13}$C-NMR(100 MHz, CDCl$_3$): δ 188.5, 176.0, 143.9, 118.9, 106.9, 90.8, 79.8, 79.6, 79.2, 77.4, 75.9, 75.3, 70.8, 70.4, 65.8, 65.3, 44.6, 42.1, 40.4, 38.6, 36.4, 35.3, 28.2, 22.9, 21.5, 20.0, 19.7, 16.8, 15.1, 14.9, 11.5, 8.3.

Step 1f: Compound of Formula 1-5: V=N—O—Ac, R$_{11}$=H and R$_2$'=Ac

To a solution of the compound from Step 1e (3 g, 4.8 mmol) in 40 ml of dichloromethane was added acetic anhydride (1.36 ml, 14.4 mmol) and triethyl amine (2.8 ml, 20 mmol). The mixture was stirred at room temperature for 4 hours. The solvent was removed under vacuum and the residue was purified by flash chromatography (SiO$_2$, hexane:acetone/1:1) to give the title compound (2.9 g).

MS (ESI) m/z 711.50 (M+H)$^{+13}$C NMR(CDCl$_3$): δ 184.7, 176.9, 174.9, 170.1, 141.9, 122.2, 99.4, 81.2, 79.0, 77.8, 77.7, 76.1, 73.5, 71.7, 68.8, 65.7, 63.2, 43.7, 40.8, 39.9, 38.2, 36.2, 35.6, 31.0, 25.5, 23.2, 21.6, 21.2, 19.9, 19.5, 17.1, 15.8, 14.7, 11.8, 7.9.

Step 1g: Compound of Formula I: A and B Taken Together with the Carbon Atom to Which They are Attached are C=CH$_2$, X and Y Taken Together with the Carbon Atom to Which They are Attached are C=N—Ac, L=CH$_2$CH$_3$, Z=H and R$_2$'=Ac To a solution of the compound from Step 1f (2.9 g, 4.08 mmol) in 40 ml dichloromethane was added Dess-Martin reagent (1.9 g, 4.5 mmol) at room temperature. The mixture was stirred at room temperature for 2 hours. The reaction was quenched with sodium bicarbonate (50 ml) and Na$_2$S$_2$O$_3$ (2 g). The organic phase was separated and washed with brine (50 ml). The solvent was removed under vacuum and the residue was purified on chromatography (hexane:acetone/1:1) to give the title compound (2.0 g).

MS (ESI) m/z 709.28 (M+H)$^{+13}$C NMR(CDCl$_3$): 205.8, 184.5, 177.4, 170.0, 168.0, 141.2, 124.3, 100.5, 79.2, 78.1, 77.5, 76.2, 74.5, 73.4, 72.1, 71.4, 69.0, 65.7, 63.1, 50.5, 45.5, 40.3, 38.5, 30.7, 25.3, 23.4, 21.5, 21.1, 20.0, 19.4, 17.4, 15.4, 13.8, 13.3, 12.5.

Example 2

Compound of Formula I: A and B Taken Together with the Carbon Atom to Which They are Attached are C=CH$_2$, X and Y Taken Together with the Carbon Atom to Which They are Attached are C=N—Ac, L=CH$_2$CH$_3$, Z=H and R$_2$'=H A solution of the compound of Example 1 (2.0 g, 2.82 mmol) in 40 ml methanol was refluxed for 5 hours. The solvent was evaporated to give the crude title compound.

MS (ESI) m/z 667.40 (M+H)$^+$ $^{13}$C NMR(CDCl$_3$): 205.9, 184.5, 177.5, 168.1, 141.3, 124.4, 103.1, 79.1, 78.2, 77.5, 76.2, 75.6, 73.4, 72.1, 70.4, 69.6, 66.0, 65.7, 50.5, 46.2, 40.4, 38.7, 28.5, 25.4, 23.4, 21.4, 20.0, 19.6, 17.5, 15.4, 13.9, 13.5, 12.6.

Example 3

Compound of Formula I: A and B Taken Together with the Carbon Atom to Which They are Attached are C=O, X and Y Taken Together with the Carbon Atom to Which They Attached are C=N—Ac, L=CH$_2$CH$_3$, Z=H and R$_2$'=H A solution of the crude compound from Example 2 in methanol (10 ml) and dichloromethane (30 ml) was cooled to −78° C. and ozone was bubbled through the reaction until the solution became light blue. Then nitrogen was bubbled through the reaction mixture to remove excess ozone and triphenyl phosphine (5.64 mmol) was added. The solution was allowed to warm to room temperature over 1 hour. The solvent was evaporated and the residue was dissolved in 40 ml of THF. Triphenyl phosphine (5.64 mmol) was added and the mixture was refluxed overnight. The solvent was removed under vacuum and the residue was purified by flash chromatography (SiO$_2$, CH$_2$Cl$_2$:2M ammonia in methanol=95:5) to give the title compound (1.5 g).

MS (ESI) m/z 669.38 (M+H)$^+$ $^{13}$C NMR(CDCl$_3$): δ 205.6, 205.1, 184.4, 175.8, 169.7, 102.5, 80.2, 79.0, 78.8, 77.5, 76.1, 75.8, 75.5, 70.4, 69.7, 68.6, 66.0, 50.9, 45.9, 40.4, 39.7, 38.8, 36.6, 28.4, 25.5, 23.1, 21.4, 19.9, 19.7, 17.2, 15.4, 14.2, 13.1, 11.6.

Example 4

Compound of Formula I: A and B Taken Together with the Carbon Atom to Which They are Attached are C=N—O—CH$_2$-Ph, X and Y Taken Together with the Carbon Atom to Which They are Attached are C=N—Ac, L=CH$_2$CH$_3$, Z=H and R$_2$'=.H A solution of the crude compound from Example 3 (34 mg, 0.05 mmol), benzyl hydroxylamine (16 mg, 0.1 mmol) and pyridine (0.2 mmol) in 4 ml ethanol was stirred at room temperature for 1 hour. The reaction mixture was concentrated and purified by flash chromatography (SiO$_2$, CH$_2$Cl$_2$: 2M ammonia in methanol=95:5) to give the title compound (35 mg, 3:1 cis and trans mixture).

MS (ESI) m/z 774.48 (M+H)$^+$.

Example 5

Compound of Formula I: A and B Taken Together with the Carbon Atom to Which They are Attached are C=N—O—CH$_2$—(3-pyridyl), X and Y Taken Together with the Carbon Atom to Which They are Attached are C=N—Ac, L=CH$_2$CH$_3$, Z=H and R$_2$'=H Step 5a: N-phthaloyl-O-pyridin-3-ylmethyl-hydroxylamine To a solution of N-hydroxyphthalimide (653 mg, 4 mmol) and sodium carbonate (848 mg, 8 mmol) in DMF-CH$_3$CN—H$_2$O (5 ml/1 ml/5 ml) was added 3-(bromomethyl)pyridine hydrobromide (1.01 g, 4 mmol), portion by portion, at room temperature. The mixture was stirred at room temperature for 2 hours, diluted with ethyl acetate (30 ml), washed with 5% of Trisamine and dried over Na$_2$SO$_4$. The solvent was removed under vacuum and the residue was purified by silica gel chromatography (hexane:ethyl acetate/3:2) to give the title compound (0.8 g).

Step 5b: Compound of Formula I: A and B Taken Together with the Carbon Atom to Which They are Attached are C=N—O—CH$_2$—(3-pyridyl), X and Y Taken Together with the Carbon Atom to Which They are Attached are C=N—Ac, L=CH$_2$CH$_3$, Z=H and R$_2$'=H To a solution of N-phthaloyl-O-pyridin-3-ylmethyl-hydroxylamine (81.3 mg, 0.32 mmol) in 5 ml of ethanol was added hydrazine hydrate (12 mg, 0.24 mmol) at room temperature. The mixture was stirred at 40° C. for 2 hours and then cooled to room temperature. Acetic acid (7 µl, 0.12 mmol) was added followed by the compound of Example 3 (27 mg, 0.04 mmol). The mixture was stirred at 60° C. for 12 hours. The solvent was removed under vacuum and the residue was purified by flash chromatography (SiO$_2$, CH$_2$Cl$_2$:2M ammonia in CH$_3$OH=95:5) to give the title compound (24 mg).

MS (ESI) m/z 774.48 (M+H)$^+$.

Example 6

Compound of Formula I: A and B Taken Together with the Carbon Atom to Which They are Attached are C=N—O—CH$_2$—(2-pyridyl), X and Y Taken Together with the Carbon Atom to Which They are Attached are C=N—Ac, L=CH$_2$CH$_3$, Z=H and R$_2$'=H Using essentially the same procedure as for the preparation of the compound of Example 5, 81.3 mg (0.32 mmol) of N-phthaloyl-O-pyridin-2-ylmethyl-hydroxylamine was reacted with 12 mg (0.24 mmol) of hydrazine hydrate. Then 7 µl of glacial acetic acid was added followed by 27 mg (0.04 mmol) of the compound of Example 3. After isolation, 23 mg of the desired product were obtained.

MS: (ESI) m/z 774.48 (M+H)$^+$.

Example 7

Compound of Formula I: A and B Taken Together with the Carbon Atom to Which They are Attached are C=N—O—CH$_2$—(3-quinolyl), X and Y Taken Together with the Carbon Atom to Which They are Attached are C=N—Ac, L=CH$_2$CH$_3$, Z=H and R$_2$'=H Using essentially the same procedure as for the preparation of the compound of Example 5, 81.3 mg (0.32 mmol) of N-phthaloyl-O-quinolin-3-ylmethyl-hydroxylamine was reacted with 12 mg (0.24 mmol) of hydrazine hydrate. Then 7 µl of glacial acetic acid was added followed by 27 mg (0.04 mmol) of the compound of Example 3. After isolation, 24 mg of the desired product were obtained.

MS (ESI) m/z 846.98 (M+H)$^+$.

Example 8

Compound of Formula I: A and B Taken Together with the Carbon Atom to Which They are Attached are C=N—O—CH$_2$—(2-quinolyl), X and Y Taken Together with the Carbon Atom to Which They are Attached are C=N—Ac, L=CH$_2$CH$_3$, Z=H and R$_2$'=H Using essentially the same procedure as for the preparation of the compound of Example 5, 81.3 mg (0.32 mmol) of N-phthaloyl-O-quinolin-2-ylmethyl-hydroxylamine was reacted with 12 mg (0.24 mmol) of hydrazine hydrate. Then 7 µl of glacial acetic acid was added followed by 27 mg (0.04 mmol) of the compound of Example 3. After isolation, 24 mg of the desired product were obtained.

MS (ESI) m/z 846.96 (M+H)$^+$.

Example 9

Compound of Formula I: A and B Taken Together with the Carbon Atom to Which They are Attached are C=N—O-5-pyridin-2-ylthiophen-2yl-methyl, X and Y Taken Together with the Carbon Atom to Which They are Attached are C=N—Ac, L=$CH_2CH_3$, Z=H and $R_2'$=H Using essentially the same procedure as for the preparation of the compound of Example 4, 27 mg (0.04 mmol) of the compound of Example 3, 17 mg (0.08 mmol) of O-(5-pyridin-2-yl-thiophen-2-ylmethyl)-hydroxylamine and 2.3 μl (0.04 mmol) of glacial acetic acid were combined in 2 ml of ethanol. After isolation, 22 mg of the desired product were obtained.

MS (ESI) m/z 774.48 (M+H)$^+$.

Example 10

Compound of Formula I: A and B Taken Together with the Carbon Atom to Which They are Attached are C=N—O-3-pyrimidin-2-ylprop-2-ynyl, X and Y Taken Together with the Carbon Atom to Which They are Attached are C=N—Ac, L=$CH_2CH_3$, Z=H and $R_2'$=H Using essentially the same procedure as for the preparation of the compound of Example 4, 30 mg (0.04 mmol) of the compound of Example 3, 20 mg (0.1 mmol) of O-(3-pyrimidin-2-yl-prop-2-ynyl)-hydroxylamine and 2.3 μl (0.12 mmol) of triethyl amine were combined in 5 ml of ethanol. After isolation, 23 mg of the desired product were obtained.

MS (ESI) m/z 800.44 (M+H)$^+$.

Example 11

Compound of Formula I: A and B Taken Together with the Carbon Atom to Which They are Attached are C=N—O-Ph, X and Y Taken Together with the Carbon Atom to Which They are Attached are C=N—Ac, L=$CH_2CH_3$, Z=H and $R_2'$=H Using essentially the same procedure as for the preparation of the compound of Example 5, 81.3 mg (0.32 mmol) of N-phthaloyl-O-phenyl-hydroxylamine were reacted with 12 mg (0.24 mmol) of hydrazine hydrate. Then 7 μl of glacial acetic acid was added followed by 27 mg (0.04 mmol) of the compound of Example 4. After isolation, 24 mg of the desired product were obtained.

MS (ESI) m/z 760.12 (M+H)$^+$.

Example 12

Compound of Formula I: A=NHCH$_2$Ph, B=H, X and Y Taken Together with the Carbon Atom to Which They are Attached are C=N—Ac, L=$CH_2CH_3$, Z=H and $R_2'$=H To a solution of the compound of Example 3 (34 mg, 0.05 mmol), acetic acid (5.7 μl, 0.1 mmol) and benzyl amine (16.4 μl, 0.15 mmol) in 3 ml of methanol was added NaCNBH$_4$(6.6 mg, 0.1 mmol) at room temperature. The reaction mixture was stirred at room temperature for 5 hours and quenched with 5% Trisamine, extracted with ethyl acetate (15 ml), washed with brine (15 ml), and dried over Na$_2$SO$_4$. The solvent was removed under vacuum and the residue was purified by flash chromatography (SiO$_2$, CH$_2$Cl$_2$:2M ammonia in methanol=95:5) to give the title compound (25 mg)

MS (ESI) m/z 760.26 (M+H)$^+$.

Example 13

Compound of Formula I: A=NHCH$_2$CH$_2$Ph, B=H, X and Y Taken Together with the Carbon Atom to Which They are Attached are C=N—Ac, L=$CH_2CH_3$, Z=H and $R_2'$=H Using essentially the same procedure as for the preparation of the compound of Example 12, 53.5 mg (0.08 mmol) of the compound of Example 3, 30 g (0.24 mmol) of phenethyl amine, 9.2 μl of glacial acetic acid and 10 mg (0.16 mmol) of sodium cyanoborohydride were combined in 5 ml of methanol. After isolation, 40 mg of the desired product were obtained.

MS (ESI) m/z 774.25 (M+H)$^+$.

Example 14

Compound of Formula I: A and B Taken Together with the Carbon Atom to Which They are Attached are C=CH$_2$, X and Y Taken Together with the Carbon Atom to Which They are Attached are C=N—O—CH$_2$—O—CH$_3$, L=CH$_2$CH$_3$, Z=H, and $R_2'$=Ac Step 14a: Compound of Formula 1-5: V=N—O—H, R$_{11}$=H and $R_2'$=Ac To a solution of the compound from Step 1b (4.2 g, 4.5 mmol) in 50 ml methanol was added 2M HCl (10 ml). The mixture was refluxed for 1.5 hours, condensed to 30 ml, diluted with saturated NaHCO$_3$(30 ml), extracted with ethyl acetate (50 ml) and dried over Na$_2$SO$_4$. The solvent was evaporated and the residue was purified by silia gel chromatography (hexane:acetone/1:1) to give the title compound (2.5 g).

MS (ESI) m/z 685 (M+H)$^+$. $^{13}$C-NMR (100 MHz, CDCl$_3$): δ 175.2, 170.2, 166.3, 143.6, 119.3, 99.6, 82.2, 79.5, 78.1, 77.5, 76.0, 73.7, 71.7, 68.9, 65.5, 63.3, 43.8, 40.8, 37.4, 35.9, 34.3, 31.1, 25.6, 23.3, 21.7, 21.3, 19.9, 19.6, 17.1, 15.7, 14.7, 11.9, 7.9.

Step 14b: Compound of Formula 1-5: V=N—O—CH$_2$OCH$_3$, R$_{11}$=H and $R_2'$=Ac To a solution of the compound from Step 14a (6.85 g, 10 mmol) in 40 ml DMF was added NaH (303 mg, 1.3 mmol) at 0° C., portion by portion. After 10 minutes, MOM-Cl (900 ul, 1.15 mmol) was added at 0° C. during 15 minutes. The mixture was stirred at room temperature for 16 hours and quenched with saturated NaHCO$_3$ (60 ml), extracted with ethyl acetate (60 ml) and dried over Na$_2$SO$_4$. The solvent was evaporated and the residue was purified by silica gel chromatography (hexane:acetone/1:1) to give the title compound (4.5 g)

MS (ESI) m/z 729 (M+H)$^+$.

Step 14c. Compound of Formula I: A and B Taken with Together with the Carbon Atom to Which They are Attached are C=CH$_2$, X and Y Taken Together with the Carbon Atom to Which They are Attached are C=N—O—CH$_2$—O—CH$_3$, L=CH$_2$CH$_3$, Z=H, and $R_2'$=Ac To a solution of the compound from Step 14b (4.4 g, 6 mmol) in 50 ml dichloromethane was added a solution of Dess-Martin reagent (3.05 g, 7.2 mmol) in 20 ml of dichloromethane. The mixture was stirred at room temperature for 2 hours. The reaction was quenched by addition of saturated NaHCO$_3$(50 ml) and Na$_2$S$_2$O$_3$ (10.4 g, 42 mmol). The organic layer was separated and dried over Na$_2$SO$_4$. The solvent was removed and the residue was purified by flash chromatography (SiO$_2$, hexane:acetone/1:1) to give the title compound (3.0 g)

MS (ESI) m/z 727.32 (M+H)$^+$ $^{13}$C NMR(CDCl$_3$): δ 205.8, 169.8, 168.3, 168.1, 142.0, 123.5, 100.9, 98.4, 79.1, 78.5, 76.0, 73.4, 71.7, 69.1, 65.5, 63.5, 56.5, 50.8, 46.5, 40.7, 37.8, 34.4, 30.8, 26.9, 23.4, 21.5, 21.2, 20.1, 19.3, 17.4, 15.0, 14.0, 13.9, 12.5.

Example 15

Compound of Formula I: A and B Taken Together with the Carbon Atom to Which They are Attached are C=CH$_2$, X and Y Taken Together with the Carbon Atom to Which They are Attached are C=N—O—CH$_2$—O—CH$_3$, L=CH$_2$CH$_3$, Z=H and R$_2$'=H A solution of the compound of Example 14 (440 mg, 0.6 mmol) in 5 ml methanol was refluxed for 4 hours and concentrated to give the desired compound without purification.

MS (ESI) m/z 685.18 (M+H)$^+$

Example 16

Compound of Formula I: A and B Taken Together with the Carbon Atom to Which They are Attached are C=O, X and Y Taken Together with the Carbon Atom to Which They are Attached are C=N—O—CH$_2$—O—CH$_3$, L=CH$_2$CH$_3$, Z=H and R$_2$'=H A solution of the compound of Example 15 (420 mg, 0.6 mmol) in 7 ml methanol and 20 ml CH$_2$Cl$_2$ was purged with O3 at −78° C. until the solution became light blue. Nitrogen was bubbled through the solution to remove excess O3 and then PPh$_3$ (2 eq) was added. The mixture was warmed to room temperature and stirred at room temperature for 2 hours, concentrated and the residue dissolved in 10 ml THF and another 2 eq. of PPh$_3$ was added. The resulting mixture was refluxed overnight and concentrated. The residue was purified by flash chromatography (SiO$_2$, CH$_2$Cl$_2$:2M ammonia in CH$_3$OH=95:5) to give the title compound (280 mg).

MS (ESI) m/z 687.25 (M+H)$^+$ $^{13}$C NMR(CDCl$_3$): δ 205.8, 205.8, 170.2, 166.7, 102.4, 98.8, 80.6, 80.5, 78.8, 76.7, 76.0, 75.6, 70.5, 69.7, 69.5, 66.1, 60.6, 57.1, 50.8, 45.8, 40.5, 38.2, 34.3, 28.6, 26.9, 23.1, 21.5, 21.3, 19.9, 19.4, 17.0, 15.4, 14.5, 14.4, 13.0, 11.7.

Example 17

Compound of Formula I: A and B Taken Together with the Carbon Atom to Which They are Attached are C=NOCH$_2$Ph, X and Y Taken Together with the Carbon Atom to Which They are Attached are C=N—O—CH$_2$—O—CH$_3$, L=CH$_2$CH$_3$, Z=H and R$_2$'=H Using essentially the same procedure as for the preparation of the compound of Example 4, 87 mg (0.13 mmol) of the compound of Example 16, 41.5 mg (0.26 mmol) of O-benzyl hydroxylamine and 21 μl (0.26 mmol) of pyridine were combined in 10 ml of ethanol. After isolation, 75 mg of the desired product was obtained.

ESMS: 774.35 (M+H)$^+$

Example 18

Compound of Formula I: A and B Taken Together with the Carbon Atom to Which They are Attached are C=O, X and Y Taken Together with the Carbon Atom to Which They are Attached are C=O, L=CH$_2$CH$_3$, Z=H, and R$_2$'=Ac Step 18a. Compound of Formula 3-1: R$_{11}$=H, R$_{13}$=H and R$_p$=Tert-butyl Dimethyl Silyl To a suspension of NaH (1.26 g, 50 mmol) in 40 ml of THF was added a solution of 2-methylene-1,3-propane diol (4.4 g, 50 mmol) in 30 ml of THF. The mixture was stirred at room temperature for 45 minutes and then a solution of tert-butyl dimethylsilyl chloride (7.54 g, 50 mmol) in 30 ml of THF added. The mixture was stirred at room temperature for 1 hour and then quenched with saturated NaHCO$_3$ (200 ml), extracted with diethylether (150 ml×2) and the combined organic layers were dried over MgSO$_4$. The solvent was removed and the resulting oil was purified by flash chromatography (SiO$_2$, hexane:ethyl acetate/10:1) to give the title compound (8.4 g).

Step 18b: Compound of Formula 3-1: R$_{11}$=H, R$_{13}$=t-butoxycarbonyl and R$_p$=Tert-butyl Dimethyl Silyl To a solution of the compound from Step 18a (81 g, 40 mmol) in 100 ml of methylenechloride was added di-tertbutyl dicarbonate (13.1 g, 60 mmol), tetrabutylammoniahydrogensulfate (1.2 g, 3.5 mmol) and 30 ml of 6N NaOH. The mixture was stirred at room temperature for 16 hours, diluted with 100 ml of methylene chloride and washed with saturated NaHCO$_3$ (200 ml×3). The organic layer was dried over Na$_2$SO$_4$ and the solvent was removed under vacuum. The residue was purified by flash chromatography (SiO$_2$, hexane:ethylacetate/96:4) to give the title compound (6.8 g).

Step 18c. Compound of Formula 3-2: R$_p$=Tert-butyl Dimethyl Silyl, R$_{6}$=Ac, R$_{11}$=H, R$_2$'=Ac and R$_4$"=Ac To a solution of erythromycin A oxime 9,2',4"-triacetate from Step 1a (22 g, 25 mmol), the compound from Step 18b (9.1 g, 30 mmol) and dppb (853 mg, 1 mmol) in 250 ml THF was added Pd$_2$(dba)$_3$ (916 mg, 1 mmol). The mixture was refluxed overnight, concentrated and purified by flash chromatography (SiO$_2$, acetone:hexane/1:3) to give the title compound (25 g).

MS (ESI) m/z 1059.65 (M+H)$^+$ $^{13}$C NMR(CDCl$_3$): δ 181.2, 179.3, 175.9, 175.5, 173.5, 148.5, 116.5, 104.8, 102.0, 85.2, 84.3, 83.9, 83.6, 82.8, 82.2, 79.7, 78.1, 77.6, 75.6, 72.4, 70.4, 69.0, 68.6, 54.6, 49.9, 46.2, 43.2, 40.8, 36.5, 33.6, 31.4, 27.1, 27.0, 26.6, 26.3, 25.2, 25.1, 24.0, 23.7, 22.0, 20.4, 16.0, 15.2, 0.5, 0.0.

Step 18d: Compound of Formula (3-2) Rp=Tert-butyl Dimethyl Silyl, R$_6$=H, R$_{11}$=H, R$_2$'=H, R$_4$"=Ac A solution of the compound of Step 18c (3.18 g, 3 mmol) in 80 ml methanol was refluxed for 8 hours. The solution was concentrated and purified by flash chromatography (SiO$_2$, 2M ammonia in methanol:dichloromethane/3:97) to give the title compound (2.6 g, 89%).

MS (ESI) m/z 975.47 (M+H)$^+$ $^{13}$C NMR(CDCl$_3$): δ 179.5, 178.9, 175.7, 150.6, 121.5, 106.8, 101.4, 85.3, 83.9, 83.7, 82.4, 82.0, 79.3, 77.8, 76.7, 76.5, 72.7, 70.4, 70.1, 69.3, 68.3, 54.6, 49.8, 45.5, 43.0, 42.9, 40.6, 38.1, 34.0, 31.1, 30.5, 27.1, 26.3, 26.1, 26.0, 24.3, 23.7, 23.5, 21.5, 19.9, 15.7, 14.8, 0.5, 0.0.

Step 18e. Compound of Formula 3-4: R$_p$=H, R$_{11}$=H, R$_2$'=H and R$_4$"=Ac

To an emulsion of the compound of Step 18d (2.44 g, 2.5 mmol) in 25 ml of isopropanol and 30 ml of water was added formic acid (380 μl, 10 mmol) and Na$_2$S$_2$O$_4$ (1.39, 8 mmol). The reaction mixture was heated to 90° C. and stirred for 8 hours. The solution was diluted with ethyl acetate (60 ml) and washed with saturated NaHCO$_3$ (60 ml×3). The organic layer was separated and dried over anhydrous Na$_2$SO$_4$(~5 g), concentrated and purified by flash chromatography (SiO$_2$, 2M ammonia in methanol:dichloromethane/3:97) to give the title compound (1.7 g).

MS (ESI) m/z 846.54 (M+H)$^+$. $^{13}$C NMR(CDCl$_3$): δ 221.3, 175.3, 170.6, 147.0, 114.1, 101.8, 96.6, 79.9, 79.2, 78.8, 78.7, 77.4, 75.0, 72.8, 71.4, 68.8, 67.8, 65.4, 65.3, 63.7, 63.4, 60.6, 49.6, 45.5, 44.8, 40.4, 38.2, 38.0, 35.6, 22.0, 21.2, 21.1, 19.6, 18.6, 16.5, 14.4, 12.2, 10.6, 9.8.

Step 18f. Compound of Formula 3-4: $R_p$=H, $R_{11}$=H, $R_2'$=Ac and $R_4''$=Ac Acetic anhydride (94 ul, 1 mmol) was added to a solution of the compound of Step 18e (338.4 mg, 0.4 mmol) in dichloromethane (5 ml). The mixture was stirred at room temperature for 16 hours. Solvent was removed under vacuum and the product was purified by flash chromatography (SiO$_2$, acetone:hexane/4:6 vl) to give the title compound (330 mg).

MS (ESI) m/z 888.58 (M+H)$^{+13}$C NMR(CDCl$_3$): δ 221.3, 175.1, 170.6, 170.3, 146.8, 114.2, 99.6, 96.5, 79.9, 79.1, 78.5, 78.4, 77.1, 74.9, 72.8, 72.1, 68.9, 67.1, 65.1, 63.7, 63.5, 63.1, 49.3, 45.5, 44.8, 40.6, 38.0, 37.7, 37.6, 35.5, 29.4, 21.8, 21.3, 21.1, 21.0, 19.4, 18.6, 16.6, 12.2, 10.6, 9.6.

Step 18g. Compound of Formula 3-4: $R_p$=Tert-butoxycarbonyl, $R_{11}$=H, $R_2'$=Ac and $R_4''$=Ac Di-tert-butyl-dicarbonate (69 μl, 0.3 mmol) was added to a solution of the compound of Step 18f (178 mg, 0.2 mmol) and triethylamine (56 μl, 0.4 mmol) in dichloromethane (8 ml) at room temperature. After 10 minutes, DMAP (12.2 mg, 0.1 mmol) was added. The resulting solution was stirred at room temperature for 2 hours. Solvent was removed under vacuum and the product was purified by flash chromatography (SiO$_2$, acetone:hexane/1:3 vl) to give the title compound (180 mg).

MS (ESI) m/z 988.41 (M+H)$^{+13}$C NMR(CDCl$_3$): δ 219.6, 174.6, 170.6, 170.3, 153.8, 141.3, 116.8, 99.6, 96.5, 82.0, 80.2, 79.4, 78.7, 78.6, 76.8, 74.9, 72.9, 72.4, 69.1, 67.9, 67.2, 64.8, 63.6, 63.4, 49.4, 45.2, 44.8, 41.0, 37.9, 37.7, 37.6, 35.6, 31.8, 31.3, 31.2, 28.2, 28.1, 22.9, 21.8, 21.5, 21.4, 21.1, 19.4, 18.7, 16.7, 16.6, 14.4, 12.5, 10.7, 9.7

Step 18h. Compound of Formula 3-6: $R_{11}$=H, $R_2'$=Ac and $R_4''$=Ac 1,4-Bis(diphenylphosphino)butane (8.5 mg, 0.02 mmol) and Pd$_2$(dba)$_3$ (9.2 mg, 0.01 mmol) were added to a solution of the compound of Step 18g (98.8 mg, 0.1 mmol) in 2 ml anhydrous THF at room temperature. The resulting mixture was refluxed for 30 minutes. Solvent was removed under vacuum to give the title compound (85 mg).

MS (ESI) m/z 870.49 (M+H)$^+$

Step 18i. Compound of Formula 1-5: V=O, $R_{11}$=H and $R_2'$=Ac

To a solution of the compound of Step 18h (700 mg, 0.8 mmol) in 10 ml ethanol was added 25 ml of 1M HCl. The mixture was refluxed for 2 hours and then cooled to room temperature. The pH of the mixture was adjusted to 10 by addition of 2M NaOH and then extracted with ethyl acetate. The extract was dried over Na$_2$SO$_4$, concentrated and the residue purified by flash chromatography (SiO$_2$, hexane:acetone/1:1) to give the title compound (480 mg).

MS (ESI) m/z 670.23 (M+H)$^{+13}$C NMR(CDCl$_3$): δ 216.3, 175.0, 170.1, 141.8, 122.1, 99.4, 81.1, 79.0, 77.7, 77.5, 76.2, 75.6, 72.1, 71.7, 68.8, 65.6, 63.2, 60.5, 46.5, 43.7, 40.8, 39.1, 38.6, 35.9, 31.1, 23.0, 21.6, 21.2, 19.8, 18.5, 17.3, 14.8, 14.3, 13.0, 11.7, 7.9.

Step 18j. Compound of Formula I: A and B Taken Together with the Carbon Atom to Which They are Attached are C=O, X and Y Taken Together with the Carbon Atom to Which They are Attached are C=O, L=CH$_2$CH$_3$, Z=H and $R_2'$=Ac To a solution of the compound of Step 18i (480 mg, 0.7 mmol) in 10 ml of dichloromethane was added Dess-Martin reagent (385 mg, 0.9 mmol) at room temperature. The reaction mixture was stirred at room temperature for 2 hours and quenched with saturated NaHCO$_3$ (15 ml) and sodium thiosulfate (0.4 g). The organic phase was separated, washed with brine (15 ml), dried over Na$_2$SO$_4$ and concentrated. The residue was purified by flash chromatography (SiO$_2$, hexanes:acetone/2:1) to give the title compound (400 mg).

MS (ESI) m/z 668.02 (M+H)$^{+13}$C NMR(CDCl$_3$): δ 218.2, 205.8, 170.0, 168.1, 140.9, 125.1, 101.0, 78.9, 78.3, 76.5, 75.0, 72.7, 70.4, 69.3, 65.7, 63.6, 50.8, 46.6, 46.3, 40.9, 39.3, 39.1, 30.8, 23.4, 21.6, 21.3, 19.9, 18.5, 17.8, 14.2, 14.0, 12.5, 12.4.

Example 19

Compound of Formula I: A and B Taken Together with the Carbon Atom to Which They are Attached are C=CH$_2$, X and Y Taken Together with the Carbon Atom to Which They are Attached are C=O, L=CH$_2$CH$_3$, Z=1H and $R_2'$=H A solution of the compound of Example 18 (300 mg, 0.45 mmol) in 10 ml of methanol was refluxed for 8 hours. Solvent was removed under vacuum and the residue was purified by silica gel chromatography (CH$_2$Cl$_2$:2M ammonia in methanol/97:3 vl) to give the title compound (270 mg).

MS (ESI) m/z 626.10 (M+H)$^+$. $^{13}$C NMR(CDCl$_3$): δ 218.4, 205.9, 168.1, 141.0, 125.2, 103.5, 78.7, 78.3, 76.6, 76.1, 72.6, 70.6, 70.3, 69.8, 66.1, 65.7, 50.9, 47.3, 46.4, 40.5, 39.4, 39.3, 28.5, 23.4, 21.5, 20.0, 18.5, 17.9, 14.6, 14.1, 12.5, 12.4.

Example 20

Compound of Formula I: A and B Taken Together with the Carbon Atom to Which They are Attached are C=O, X and Y Taken Together with the Carbon Atom to Which They are Attached are C=O, L=CH$_2$CH$_3$, Z=H, and $R_2'$=H A solution of the compound of Example 19 (94 mg, 0.15 mmol) in 2 ml of methanol and 4 ml of CH$_2$Cl$_2$ was purged with O3 at –78° C. until the solution became light blue. Nitrogen was bubbled through the solution to remove excess O3 and then PPh$_3$ (2 eq) was added. The mixture was warmed to room temperature and stirred at room temperature for 2 hours. The mixture was concentrated and the residue was dissolved in 5 ml of THF and another 2 eq of PPh$_3$ was added. The resulting mixture was refluxed overnight and concentrated. The residue was purified by flash chromatography (SiO$_2$, CH$_2$Cl$_2$:2M ammonia in methanol/95:5) to give the title compound (80 mg).

MS (ESI) m/z 628.10 (M+H)$^{+13}$C-NMR(CDCl$_3$): δ 215.2, 205.6, 205.3, 169.9, 102.5, 80.5, 79.4, 78.6, 77.5, 76.3, 76.1, 75.3, 70.5, 69.8, 68.5, 66.1, 51.0, 46.3, 46.2, 40.5, 39.8, 39.0, 28.5, 22.9, 21.5, 19.8, 18.3, 17.3, 14.4, 13.6, 12.4, 11.6

Example 21

Compound of Formula I: A and B Taken Together with the Carbon Atom to Which They are Attached are C=N—O—

$CH_2Ph$, X and Y Taken Together with the Carbon Atom to Which They are Attached are C=O, L=$CH_2CH_3$, Z=H, and $R_2'$=H Using essentially the same procedure as for the preparation of the compound of Example 4, 19 mg (0.03 mmol) of the compound of Example 20, 10 mg (0.06 mmol) of O-benzyl hydroxylamine and 5 µl (6 mmol) of pyridine were combined in 5 ml of ethanol. After isolation, 20 mg of the desired product was obtained.

MS (ESI) m/z 733.24 $(M+H)^+$

Example 22

Compound of Formula I: A and B Taken Together with the Carbon Atom to Which They are Attached are C=$CH_2$, X and Y Taken Together with the Carbon Atom to Which They are Attached are C=NH, L=$CH_2CH_3$, Z=H, and $R_2'$=H Potassium carbonate (50 mg) was added to a solution of the compound of Example 2 in methanol (6 ml). The mixture was stirred at room temperature for 3 days. The solvent was removed in vacuo and the residue was purified by flash chromatography ($SiO_2$, $CH_2Cl_2$:2M ammonia in methanol/95:5) to give the title compound (70 mg).

MS (ESI) m/z: 625.36$(M+H)^+$

Example 23

Compound of Formula I: A and B Taken Together with the Carbon Atom to Which They are Attached are C=N—O—$CH_2$-p-$NO_2Ph$, X and Y Taken Together with the Carbon Atom to Which They are Attached are C=N—Ac, L=$CH_2CH_3$, Z=H, and $R_2'$=H A solution of the compound of Example 3 (53.5 mg, 0.08 mmol), benzyl hydroxylamine HCl salt (33 mg, 0.16 mmol) and pyridine (0.16 mmol) in 4 ml ethanol was stirred at room temperature for 1 hour. The solvent was removed in vacuo and the residue was purified by flash chromatography ($SiO_2$, $CH_2Cl_2$:2M ammonia in methanol/95:5) to give the title compound (52 mg) as a 3:1 mixture of cis and trans.

MS (ESI) m/z: 819.22$(M+H)^+$

Example 24

Compound of Formula I: A and B Taken Together with the Carbon Atom to Which They are Attached are C=N—O—$(CH_2)_2$-Ph, X and Y Taken Together with the Carbon Atom to Which They are Attached are C=N—Ac, L=$CH_2CH_3$, Z=H, and $R_2'$=H Using essentially the same procedure as for the preparation of the compound of Example 5, 50 mg (0.074 mmol) of the compound of Example 3, and 100 mg (0.37 mmol) of N-phthaloyl-O-phenethyl-hydroxylamine were reacted to give the title compound.

MS (ESI) m/z: 788$(M+H)^+$

Example 25

Compound of Formula I: A and B Taken Together with the Carbon Atom to Which They are Attached are C=N—O—$(CH_2)_3$-Ph, X and Y Taken Together with the Carbon Atom to Which They are Attached are C=N—Ac, L=$CH_2CH_3$, Z=H, and $R_2'$=H Using essentially the same procedure as for the preparation of the compound of Example 5, 50 mg (0.074 mmol) of the compound of Example 3, and 105 mg (0.37 mmol) of N-phthaloyl-0-1-(3-phenyl)propyl-hydroxylamine were reacted to give the title compound.

MS (ESI) m/z: 802$(M+H)^+$

Example 26

Compound of Formula I: A and B Taken Together with the Carbon Atom to Which They are Attached are C=N—O—$CH_2$—CH=CH-Ph, X and Y Taken Together with the Carbon Atom to Which They are attached are C=N—Ac, L=$CH_2CH_3$, Z=H, and $R_2'$=H Using essentially the same procedure as for the preparation of the compound of Example 5, 50 mg (0.074 mmol) of the compound of Example 3, and 105 mg (0.37 mmol) of N-phthaloyl-O-1-(3-phenyl)prop-2-enyl-hydroxylamine were reacted to give the title compound.

MS (ESI) m/z: 800$(M+H)^+$

Example 27

Compound of Formula I: A is NH—$(CH_2)_3$-Ph, B is H, X and Y Taken Together with the Carbon Atom to Which They are Attached are C=N—Ac, L=$CH_2CH_3$, Z=H, and $R_2'$=H Using essentially the same procedure as for the preparation of the compound of Example 12, 33.5 mg (0.05 mmol) of the compound of Example 3, and 21.8 µl (0.1 mmol) of 3-phenyl propylamine were reacted to give 18 mg of the title compound.

MS (ESI) m/z: 788$(M+H)^+$

Example 28

Compound of Formula I: A is NH—$(CH_2)_3$-Ph, B is H, X and Y Taken Together with the Carbon Atom to Which They are Attached are C=N—Ac, L=$CH_2CH_3$, Z=H, and $R_2'$=H Using essentially the same procedure as for the preparation of the compound of Example 12, 24 mg (0.05 mmol) of the compound of Example 3, and 33.5 µL (0.15 mmol) of 4-phenyl butylamine were reacted to give 12 mg of the title compound.

MS (ESI) m/z: 802$(M+H)^+$

Example 29

Compound of Formula I: A is $CH_2$—CH=$CH_2$, B is OH, X and Y Taken Together with the Carbon Atom to Which They are Attached are C=N—Ac, L=$CH_2CH_3$, Z=H, and $R_2'$=H A solution of the compound of Example 3 (0.23 g, 0.34 mmol) in 20 mL anhydrous THF was cooled to −78° C. Allylmagnesium bromide in THF (1.0 M, 1.5 mL, 1.5 mmol) was added via syringe. The reaction mixture was stirred for 1 hour at −78° C. and then was quenched with aqueous $NaHCO_3$. The mixture was warmed to room temperature slowly and then extracted with $CH_2Cl_2$ (3×30 mL). The combined organic layers were dried over anhydrous $Na_2SO_4$. The solvent was evaporated and the residue was purified by flash chromatography ($SiO_2$, $CH_2Cl_2$ containing 5% 2M ammonia solution in methanol) to provide the title compound (0.21 g, 86%).

MS (ESI) m/z 711 $(M+H)^+$ $^{13}$C-NMR (100 MHz, $CDCl_3$): δ 205.5, 186.1, 179.9, 169.7, 132.9, 118.3, 102.3, 80.0, 79.4, 76.1, 73.7, 72.7, 70.4, 70.4, 69.7, 66.2, 50.8, 44.9, 41.2, 40.5, 39.8, 39.4, 37.1, 28.6, 25.5, 23.6, 21.5, 20.2, 20.0, 17.3, 15.9, 14.3, 12.6, 12.0.

Example 30

Compound of Formula I: A=$CH_2$-Ph, B is OH, X and Y Taken Together with the Carbon Atom to Which They are Attached are C=N—Ac, L=$CH_2CH_3$, Z=H, and $R_2'$=H The compound of Example 3 (70 mg, 0.1 mmol) was treated with benzylmagnesium bromide (0.85 M in THF, 0.6 µL, 0.5 mmol) as described in Example 29. After the same work up, the crude mixture was purified by flash chromatography ($SiO_2$, $CH_2Cl_2$ containing 5% 2M ammonia solution in methanol) to provide the title compound (12 mg, 18%).

MS (ESI) m/z 761 (M+H)$^+$ $^{13}$C-NMR (100 MHz, $CDCl_3$): δ 205.7, 186.3, 179.5, 169.8, 136.3, 131.0, 128.1, 126.5, 101.8, 80.1, 79.3, 76.0, 73.5, 73.1, 70.6, 70.1, 69.2, 66.6, 50.9, 44.8, 42.4, 40.5, 39.8, 39.3, 37.1, 29.9, 25.6, 23.6, 21.3, 20.2, 20.1, 17.3, 15.9, 14.4, 12.7, 12.0.

Example 31

Compound of Formula I: A=$(CH_2)_2$-Ph, B=OH, X and Y Taken Together with the Carbon Atom to Which They are Attached are C=N—Ac, L=$CH_2CH_3$, Z=H, and $R_2'$=H The compound of Example 3 (70 mg, 0.1 mmol) was treated with phenethylmagnesium bromide (1.0 M in THF, 0.5 mL, 0.5 mmol) as described in Example 29. After the same work up, the crude mixture was purified by flash chromatography ($SiO_2$, $CH_2Cl_2$ containing 5% 2M ammonia solution in methanol) to provide the title compound (12 mg, 16%).

MS (ESI) m/z 775 (M+H)$^+$

Example 32

Compound of Formula I: A=Ph, B=OH, X and Y Taken Together with the Carbon Atom to Which They are Attached are C=N—Ac, L=$CH_2CH_3$, Z=H, and $R_2$=H The compound of Example 3 (70 mg, 0.1 mmol) was treated with phenylmagnesium bromide (1.0 M in THF, 0.5 mL, 0.5 mmol) as described in Example 29. After the same work up, the crude mixture was purified by flash chromatography ($SiO_2$, $CH_2Cl_2$ containing 5% 2M ammonia solution in methanol) followed by a semi-prep. HPLC to provide the title compound (5 mg).

MS (ESI) m/z 747 (M+H)$^+$

Example 33

Compound of Formula I: A is $CH_2$—CH=CH-Ph, B is OH, X and Y Taken Together with the Carbon Atom to Which They are Attached are C=N—Ac, L=CH)$CH_3$, Z=H, and $R_2'$=H The compound from Example 29 (50 mg, 0.07 mmol), iodobenzene (32 mg, 0.15 mmol), Pd(OAc)$_2$ (2.5 mg), (o-Tolyl)$_3$P (10 mg) and triethyl amine (0.1 mL, excess) were dissolved in 3 ml $CH_3CN$ and the solution was degassed at −40° C. The reaction mixture was warmed to room temperature under nitrogen, heated at 50° C. for 1 hour, and then left at 80° C. for 12 hours. The reaction mixture was diluted with ethyl acetate, washed with saturated aqueous $NaHCO_3$, and dried over anhydrous $Na_2SO_4$. The solvent was evaporated and the residue was purified by flash chromatography ($SiO_2$, $CH_2Cl_2$ containing 5% 2M ammonia solution in methanol) to provide the title compound (40 mg, 76%).

MS (ESI) m/z 787 (M+H)$^+$

Selected $^{13}$C-NMR (100 MHz, $CDCl_3$): δ 205.5, 186.3, 179.7, 169.9, 137.7, 133.2, 128.6, 127.2, 126.5, 124.8, 101.9, 80.0, 79.4, 76.1, 73.9, 73.2, 70.5, 70.1, 69.3, 66.3, 50.9, 46.5, 44.8, 40.7, 40.2, 39.8, 39.4, 37.0, 29.4, 25.6, 23.6, 21.3, 20.2, 20.1, 17.3, 16.0, 14.5, 12.6, 11.9, 8.9.

Example 34

Compound of Formula I: A is $(CH_{12})_3$-Ph, B is OH, X and Y Taken Together with the Carbon Atom to Which They are Attached are C=N—Ac, L=$CH_2CH_3$, Z=H, and $R_2'$=H The compound from Example 24 (15 mg, 0.02 mmol) was hydrogenated under 1 atm $H_2$ over Pd-C in ethanol at room temperature for 24 hours. The solvent was evaporated under vacuum. Purification by flash chromatography ($SiO_2$, $CH_2Cl_2$ containing 5% 2M ammonia solution in methanol) gave the title compound (13.2 mg, 88%).

MS (EST) m/z 789 (M+H)$^+$

Example 35

Compound of Formula I: A and B Taken Together with the Carbon Atom to Which They are Attached are C=CH—CH=CH-Ph, X and Y Taken Together with the Carbon Atom to Which They are Attached are C=N—Ac, L=$CH_2CH_3$, Z=H, and $R_2'$=H Step 35a: Compound of Formula (1-5): V is N—Ac, $R_{11}$ is CH—CH-Ph, $R_2'$=Ac To a solution of the compound of formula (1-5), wherein V=N—Ac, $R_{11}$=H, and $R_2'$=Ac (0.5 g, 0.7 mmol) in 8 ml anhydrous DMF, β-bromostyrene (0.15 ml, 1.2 mmol) and $K_2CO_3$ (200 mg, 1.5 mmol) were added at room temperature. The mixture was degassed briefly and a catalytic amount of dihydrogen dichlorobis(di-tert-butylphosphinito-κP)palladate(II) (POPd from Combiphos catalysts, Inc.) was added. The reaction mixture was heated to 100° C. in a sealed tube for 48 hours. Ethyl acetate (50 mL) was added and the solution was washed 3 times with aqueous $NaHCO_3$. The organic layer was dried over anhydrous $Na_2SO_4$. The solvent was evaporated under vacuum and the residue was purified by flash chromatography ($SiO_2$, acetone:hexanes/1:1) to provide the title compound.

MS (ESI) m/z 813 (M+H)$^+$

Step 35b: Compound of Formula I: A and B Taken Together with the Carbon Atom to Which They are Attached are C=CH—CH=CH-Ph, X and Y Taken Together with the Carbon Atom to Which They are Attached are C=N—Ac, L=$CH_2CH_3$, Z=H, and $R_2'$=Ac The compound from Step 35a was dissolved in $CH_2Cl_2$ and Dess-Martin periodinane (1,1,1-triacetoxy-1,1-dihydro-1,2-benziodoxol-3(1H)-one) (0.3 g, 0.7 mmol) was added. The mixture was stirred for 1 hour and then aqueous $NaHCO_3$ was added. The mixture was extracted 3 times with $CH_2Cl_2$ and the combined organic layers were dried over anhydrous $Na_2SO_4$. The solvent was evaporated under vacuum and the residue was purified by flash chromatography ($SiO_2$, acetone:hexanes/2:3) to provide the title compound (0.24 g, 42%).

MS (ESI) m/z 811 (M+H)$^+$

Step 35c: Compound of Formula I: A and B Taken Together with the Carbon Atom to Which They are Attached are C=CH—CH=CH-Ph, X and Y Taken Together with the Carbon Atom to Which They are Attached are C=N—Ac, L=CH$_2$CH$_3$, Z=H, and R$_2$'=H A solution of the compound from Step 35b (0.16 g, 0.05 mmol) in 10 mL of methanol was stirred for 48 hours at room temperature. The solvent was evaporated under vacuum. Purification by flash chromatography (SiO$_2$, CH$_2$Cl$_2$ containing 3% 2M ammonia solution in methanol) gave the title compound (0.12 g, 79%).

MS (ESI) m/z 769 (M+H)$^+$ $^{13}$C-NMR (100 MHz, CDCl$_3$): δ 206.4, 184.7, 177.9, 167.8, 137.6, 136.4, 136.2, 134.2, 128.7, 128.0, 127.0, 124.0, 103.4, 79.8, 76.4, 72.5, 70.5, 69.7, 66.8, 66.6, 66.2, 51.1, 47.2, 40.5, 38.8, 28.6, 25.4, 23.9, 21.5, 20.0, 17.7, 15.2, 14.1, 13.1.

Example 36

Compound of Formula I: A is (CH$_2$)$_3$-Ph, B is H, X and Y Taken Together with the Carbon Atom to Which They are Attached are C=N—Ac, L=CH$_2$CH$_3$, Z=H, and R$_2$'=H The compound of Example 35 (15 mg, 0.02 mmol) was hydrogenated under H$_2$ (30 psi) over Pd-C in ethanol at room temperature for 12 hours. The solvent was evaporated under vacuum. Purification by flash chromatography (SiO$_2$, CH$_2$Cl$_2$ containing 5% 2M ammonia solution in methanol) gave the title compound (7.0 mg, 50%).

MS (ESI) m/z 773 (M+H)$^+$

Example 37

Compound of Formula I: A and B Taken Together with the Carbon Atom to Which They are Attached are C=CH—CH=CH-3-pyridyl, X and Y Taken Together with the Carbon Atom to Which They are Attached are C=N—Ac, L=CH$_2$CH$_3$, Z=H, and R$_2$'=H Using essentially the same procedure as for the preparation of the compound of Example 35, 190 mg (0.2 mmol) of the compound of Example 1, and 35 mg (0.2 mmol) of 1-bromo-2-(3-pyridyl)ethylene were reacted to give the title compound.

MS (ESI) m/z 770 (M+H)$^+$

Example 38

Compound of Formula I: A and B Taken Together with the Carbon Atom to Which They are Attached are C=CH—CH=CH-3-quinolyl, X and Y Taken Together with the Carbon Atom to Which They are Attached are C=N—Ac, L=CH$_2$CH$_3$, Z=H, and R$_2$'=H Using essentially the same procedure as for the preparation of the compound of Example 35, 240 mg (0.35 mmol) of the compound of Example 1, and 100 mg (0.43 mmol) of 1-bromo-2-(3-quinolyl)ethylene were reacted to give the title compound.

MS (ESI) m/z 794 (M+H)$^+$

Example 39

Compound of Formula I: A and B Taken Together with the Carbon Atom to Which They are Attached are C=CH-2-quinolyl, X and Y Taken Together with the Carbon Atom to Which They are Attached are C=N—Ac, L=CH$_2$CH$_3$, Z=H, and R$_2$'=H Using essentially the same procedure as for the preparation of the compound of Example 35, 500 mg (0.7 mmol) of the compound of Example 1, and 25 mg (1.2 mmol) of 3-bromoquinoline were reacted to give the title compound.

MS (ESI) m/z 820 (M+H)$^+$

Example 40

Compound of Formula I: A and B Taken Together with the Carbon Atom to Which They are Attached are C=CH-2-quinolyl, X and Y Taken Together with the Carbon Atom to Which They are Attached are C=N—H, L=CH$_2$CH$_3$, Z=H, and R$_2$'=H Using essentially the same procedure as for the preparation of the compound of Example 35, 63 mg (0.1 mmol) of the compound of Example 22, and 42 mg (0.2 mmol) of 3-bromoquinoline were reacted to give 7.5 mg of the title compound.

MS (ESI) m/z 742 (M+H)$^+$

Example 41

Compound of Formula I: A and B Taken Together with the Carbon Atom to Which They are Attached are C=CH-4-biphenyl, X and Y Taken Together with the Carbon Atom to Which They are Attached are C=N—Ac, L=CH$_2$CH$_3$, Z=H, and R$_2$'=H Using essentially the same procedure as for the preparation of the compound of Example 35, 213 mg (0.3 mmol) of the compound of Example 1, and 142 mg (0.6 mmol) of 4-bromobiphenyl were reacted to give the title compound.

MS (ESI) m/z 819 (M+H)$^+$

Example 42

Compound of Formula I: A and B Taken Together with the Carbon Atom to Which They are Attached are C=CH-3-biphenyl, X and Y Taken Together with the Carbon Atom to Which They are Attached are C=N—Ac, L=CH$_2$CH$_3$, Z=H, and R$_2$'=H Using essentially the same procedure as for the preparation of the compound of Example 35, 213 mg (0.3 mmol) of the compound of Example 1, and 103 μL (0.6 mmol) of 3-bromobiphenyl were reacted to give the title compound.

MS (ESI) m/z 819 (M+H)$^+$

Example 43

Compound of Formula I: A and B Taken Together with the Carbon Atom to Which They are Attached are C=CH-4-phenoxyphenyl, X and Y Taken Together with the Carbon Atom to Which They are Attached are C=N—Ac, L=CH$_2$CH$_3$, Z=H, and R$_2$'=H Using essentially the same procedure as for the preparation of the compound of Example 35, 142 mg (0.2 mmol) of the compound of Example 1, and 71 μL (0.4 mmol) of 4-bromodiphenyl ether were reacted to give the title compound.

MS (ESI) m/z 835 (M+H)$^+$

Example 44

Compound of Formula I: A and B Taken Together with the Carbon Atom to Which They are Attached are C=CH-Ph, X and Y Taken Together with the Carbon Atom to Which They are Attached are C=N—Ac, L=CH$_2$CH$_3$, Z=H, and R$_2$'=H Step 44a: 3-propanone-1,3-di-t-butyldicarbonate To a solution of 1,3-dihydroxyacetone dimer (36.03 g, 0.20 mol) and DMAP (1.22 g, 10.0 mmol) in dichloromethane (80 mL) and pyridine (97.0 mL, 1.20 mol) was added a solution of di-tert-butyl dicarbonate (200.0 g, 0.92 mol) in dichloromethane (40 mL) via a dropping funnel over 3 hours at room temperature. After stirring at room temperature for 15 hours, the reaction mixture was condensed in vacuo. The residue was diluted with a 1:1 mixture of hexanes and diethyl ether, washed with saturated aqueous CuSO$_4$, water and brine. The organic phase was dried over Na$_2$SO$_4$ and the solvent was removed in vacuo. The residue was purified by flash chromatography (SiO$_2$, hexane:ethyl acetate gradient from 95:5 to 85:15) to give the title compound (45.0 g, 39%).

$^{13}$C-NMR (125 MHz, CDCl$_3$): δ 198.5, 152.6, 83.5, 68.5, 27.6.

Step 44b: Compound of Formula 1-3: R$_{11}$=Ph and R$_{13}$=t-Bu

A suspension of benzyltriphenylphosphonium bromide (520 mg, 1.20 mmol) in THF (5.0 mL) was treated with n-butyl lithium (1.6 M in hexanes, 0.81 mL, 1.30 mmol) at −78° C. under nitrogen. The mixture was warmed to −15° C. over 1 hour before a solution of the compound from Step 44a (290 mg, 1.0 mmol) in THF (2.5 mL) was added at −70° C. The reaction mixture was warmed to room temperature over 1 hour and stirred for a further 14 hours at room temperature. The reaction mixture was diluted with ethyl acetate and the organic phase was washed with water and brine, and dried over Na$_2$SO$_4$. The solvent was evaporated and the residue was purified by flash chromatography (SiO$_2$, hexanes: CH$_2$Cl$_2$/1:1) to give the title compound (253 mg, 70% yield).

$^{13}$C-NMR (125 MHz, CDCl$_3$): δ 153.1, 153.0, 135.1, 134.6, 130.4, 128.6, 128.2, 127.6, 82.0, 81.9, 68.4, 62.7, 27.6, 27.5.

Step 44c: Compound of Formula 1-4: R$_6$=Ac, R$_{11}$=Ph, R$_2$'=Ac, R$_4$"=Ac

A mixture of Erythromycin A oxime triacetate (525 mg, 0.60 mmol), the compound from Step 44b (250 mg, 0.69 mmol), 1,4-bis(diphenylphosphino)butane (51.2 mg, 0.12 mmol), and tris(dibenzylideneacetone)dipalladium (54.9 mg, 0.06 mmol) in THF (5.0 mL) was degassed and heated to 75° C. for 15 hours. The solvent was removed under vacuum and the resulting residue was purified by flash chromatography (SiO$_2$, hexanes:acetone/4:11~5:1) to give the title compounds as a 2.6:1 mixture of double bond isomers (330 mg, 55% yield).

MS (ESI) m/z: 1003 (M+H)$^+$

Step 44d: Compound of Formula 1-4: R$_6$=Ac, R$_{11}$=Ph, R$_2$'=H, R$_4$"=Ac

The title compound was prepared by refluxing the compound from Step 44c in methanol according to the procedure described in Step 1 of Example 1.

MS (ESI) m/z: 919 (M+H)$^+$

Step 44e: Compound of Formula 2-2: R$_{11}$=Ph, R$_{11}$'=H

A solution of the compound from Step 44d (0.30 mmol) in methanol (5.0 mL) was treated with titanium (III) chloride (20% in 3% HCl, 0.77 mL) for 2 hours at room temperature, then for 1 hour at 50° C. The mixture was then partitioned between CH$_2$Cl$_2$ and aqueous saturated NaHCO$_3$. The aqueous solution was extracted with CH$_2$Cl$_2$ and the combined extracts were washed with brine and dried over Na$_2$SO$_4$. After evaporation, the residue was purified by flash chromatography (SiO$_2$, CH$_2$Cl$_2$:2 M NH$_3$ in MeOH/98:2~93:7) to give the title compounds as a 4:1 mixture of double bond isomers (105 mg, 50% yield).

MS (ESI) m/z: 703 (M+H)$^+$

Step 44f: Compound of Formula 1-5: V=N—Ac, R$_{11}$=Ph, R$_2$'=Ac

A solution of the compound from Step 44e (105 mg, 0.15 mmol) in CH$_2$Cl$_2$ (3.0 mL) was treated with triethylamine (104 μL, 0.74 mmol) and acetic anhydride (42 μL, 0.45 mmol) at room temperature for 19 hours before evaporation and drying in vacuo to give the title compound.

MS (ESI) m/z 787 (M+H)$^+$

Step 44 g: Compound of Formula I: A and B Taken Together with the Carbon Atom to Which They are Attached are C=CH-Ph, X and Y Taken Together with the Carbon Atom to Which They are Attached are C=N—Ac, L=CH$_2$CH$_3$, Z=H, and R$_2$'=Ac A solution of the compound from Step 44f (0.15 mmol at most) in CH$_2$Cl$_2$ (3.0 mL) was treated with Dess-Martin periodinane (108 mg, 0.25 mL) for 4.5 hours at room temperature. The resulting mixture was partitioned between ethyl aceate and aqueous saturated NaHCO$_3$:Na$_2$S$_2$O$_3$/3:1. The organic phase was washed with water and brine. After drying (Na$_2$SO$_4$) and evaporation, the residue was purified by flash chromatography (SiO$_2$, hexanes:acetone/4:1~1.5:1) to give the title compound as a 5:1 mixture of double bond isomers (62.7 mg, 54% yield).

MS (ESI) m/z 785 (M+H)$^+$

Step 44h: Compound of Formula I: A and B Taken Together with the Carbon Atom to Which They are Attached are C=CH-Ph, X and Y Taken Together with the Carbon Atom to Which They are Attached are C=N—Ac, L=CH$_2$CH$_3$, Z=H, and R$_2$'=H A solution of the compound from Step 44g (62.7 mg, 0.08 mmol) in methanol (3.0 mL) was stirred at room temperature for 5 days before evaporation. Purification by flash chromatography (SiO$_2$, CH$_2$Cl$_2$:2 M NH$_3$ in MeOH/99:1~96:4) gave the title compound as a 5:1 mixture of double bond isomers (49.6 mg, 84%).

MS (ESI) m/z 743 (M+H)$^+$

Example 45

Compound of Formula I: A and B Taken Together with the Carbon Atom to Which They are Attached are C=CH-2-(2pyridyl)-thiophen-5-yl, X and Y Taken Together with the Carbon Atom to Which They are Attached are C=N—Ac, L=CH$_2$CH$_3$, Z=H, and R$_2$'=H Step 45a: Compound of Formula 6-3: V is N—Ac, X$_A$=OH, X$_B$=H, R$_2$'=Ac To a solution of the compound from Step 1f of Example 1 (8.70 g, 12.25 mmol) in t-BuOH (18 mL) was added 4-methylmorpholine N-oxide (2.07 g, 14.7 mmol) and OsO$_4$ (4% in water, 0.78 ml). The mixture was stirred at room temperature for 1 hour and then partitioned between CH$_2$Cl$_2$ and aqueous saturated NaHCO$_3$. The aqueous layer was extracted with CH$_2$Cl$_2$ and the combined organic extracts were dried over NaSO$_4$ and condensed in vacuo. Purification by flash chromatography (SiO$_2$, hexanes:acetone/1:1~1:3) afforded the title compound (6.90 g, 76% yield) as a 1:1 mixture of diastereoisomers.

MS (ESI) m/z 745 (M+H)$^+$

Step 45b: Compound of Formula 6-2: V is N—Ac, $X_A$=OH, $X_B$=H, $R_2'$=Ac

A solution of the compound from Step 45a (2.00 g, 2.69 mmol) in acetone and water (1:1, 20.0 mL) was treated with sodium periodate (1.15 g, 5.37 mmol). The mixture was stirred at room temperature for 3.5 hours and then partitioned between $CH_2Cl_2$ and aqueous saturated $NaHCO_3$. The aqueous layer was extracted with $CH_2Cl_2$ and the combined organic extracts were dried over $NaSO_4$ and condensed in vacuo. Purification by flash chromatography ($SiO_2$, hexanes:acetone/1:1) afforded the title compound (1.50 g, 78% yield).

MS (ESI) m/z 713 (M+H)$^+$ $^{13}$C NMR (CDCl$_3$): δ 205.4, 184.4, 175.8, 175.4, 169.9, 99.2, 81.8, 80.6, 79.4, 78.2, 77.4, 76.5, 75.7, 71.4, 69.0, 68.8, 63.0, 43.8, 50.6, 39.1, 38.3, 36.1, 36.0, 30.8, 25.3, 22.6, 21.4, 21.0, 19.6, 19.2, 16.7, 15.5, 14.6, 11.1, 7.6.

Step 45c: Compound of Formula 8-1: V is N—Ac, $X_A$=OH, $X_B$=H, $X_H$=Br, $R_2'$=Ac A suspension of bromomethyltriphenylphosphonium bromide (443 mg, 1.01 mmol) in THF (4.0 mL) was treated with sodium bis(trimethylsilyl)amide (1.0 M in THF, 1.00 mL, 1.00 mmol) at −78° C. under nitrogen. The mixture was stirred at −70~−60° C. for 1 hour before a solution of the compound from Step 45b (127 mg, 0.18 mmol) in THF (5.0 mL) was added. The reaction mixture was warmed to room temperature over 1 hour and stirred at that temperature for 5 hours. The mixture was then partitioned between ethyl acetate and water. The organic extract was washed with water and brine, dried over $Na_2SO_4$, and condensed in vacuo. Purification by flash chromatography ($SiO_2$, hexanes:acetone/9:1~1.5:1) gave the title compound (87 mg, 62% yield) as a 2.5~4:1 mixture of double bond isomers.

MS (ESI) m/z 789/791 (M+H)$^+$

Step 45d: 2-(2-pyridine)thiophenyl-5-bromide

A solution of 2-(2-thiophenyl)pyridine (3.00 g, 18.6 mmol) in $CH_2Cl_2$ (90 mL) was added dropwise to a solution of bromine (0.95 mL) in $CH_2Cl_2$ (5 mL) at 0° C. The mixture was warmed to room temperature with vigorous stirring over 1.5 hours before dilution with $CH_2Cl_2$ (200 mL). The mixture was washed with saturated $NaHCO_3$, $Na_2SO_3$, brine and dried over $Na_2SO_4$. Evaporation gave the title compound (4.40 g, 100%).

MS (ESI) m/z 240, 242 (M+H)$^+$ $^{13}$C NMR (CDCl$_3$): δ 152.0, 149.8, 146.5, 136.9, 131.1, 124.6, 122.4, 118.3, 115.3.

Step 45e: 2-(2-pyridine)thiophenyl-5-tributylstannane

A solution of the compound from Step 45d (600 mg, 2.50 mmol) in dry THF (8.0 mL) was treated with n-butyl lithium (1.6 M in hexanes, 1.56 mL, 2.50 mL) at −78° C. with stirring for 30 minutes before tri(n-butyl)tin chloride (0.80 mL, 2.95 mmol) was added. The mixture was warmed to room temperature over 1.5 hours and then partitioned between ethyl acetate and aqueous saturated $NaHCO_3$. The organic layer was washed with water and brine, dried over $Na_2SO_4$, and condensed in vacuo. Purification by flash chromatography ($SiO_2$, hexanes:ethyl acetate/98:2) gave the title compound (998 mg, 89% yield).

MS (ESI) m/z 448/449/450/451/452 (M+H)$^+$ $^{13}$C NMR (CDCl$_3$): δ 152.7, 150.1, 149.6, 140.4, 136.6, 136.3, 125.6, 121.5, 118.8, 28.9, 27.2, 13.6, 10.8.

Step 45f: Compound of Formula 9-2: V is N—Ac, $X_A$=OH, $X_B$=H, $R_{11}$=2-(2pyridyl)-thiophen-5-yl, $R_2'$=Ac A solution of the compound from Step 42c (210 mg, 0.26 mmol), the compound from Step 45e (150 mg, 0.33 mmol), and tetrakis(triphenylphosphine)palladium (61 mg, 0.05 mmol) in toluene (8.0 mL) was degassed and then stirred under nitrogen for 14 hours at 100° C. The resulting material was purified by flash chromatography ($SiO_2$, hexanes:acetone/9:1~1:1.5) to give the title compounds as a 1:3.8 mixture of double bond isomers (140 mg, 61% yield).

MS (ESI) m/z 870 (M+H)$^+$

Step 45g: Compound of Formula I: A and B Taken Together with the Carbon Atom to Which They are Attached are C=CH-2-(2pyridyl)-thiophen-5-yl, X and Y Taken Together with the Carbon Atom to Which They are Attached are C=N—Ac, L=$CH_2CH_3$, Z=H, and $R_2'$=Ac A solution of the compound from Step 45f (140 mg, 0.16 mmol) in $CH_2Cl_2$ (5.0 mL) was treated with Dess-Martin periodinane (122 mg, 0.29 mmol) for 1 hour at room temperature and then partitioned between ethyl acetate and aqueous saturated $NaHCO_3$:$Na_2S_2O_3$/3:1. The organic layer was washed with water and brine. After drying over $Na_2SO_4$ and evaporation the crude title compound was obtained as a 1:3.8 mixture of double bond isomers (140 mg, 100% yield).

MS (ESI) m/z 868 (M+H)$^+$

Step 45h: Compound of Formula I: A and B Taken Together with the Carbon Atom to Which They are Attached are C=CH-2-(2pyridyl)-thiophen-5-yl, X and Y Taken Together with the Carbon Atom to Which They are Attached are C=N—Ac, L=$CH_2CH_3$, Z=H, and $R_2'$=H A solution of the compound from Step 45g (140 mg, 0.16 mmol) in methanol (4.0 mL) was stirred at room temperature for 64 hours and then condensed in vacuo. Purification by flash chromatography ($SiO_2$, $CH_2Cl_2$:2 M $NH_3$ in MeOH/ 99:1~96:4) gave the title compound as a 1:3 mixture of double bond isomers (97 mg, 73%).

MS (ESI) m/z 826 (M+H)$^+$

Example 46

Compound of Formula I: A and B Taken Together with the Carbon Atom to Which They are Attached are C=O, X and Y Taken Together with the Carbon Atom to Which They are Attached are C=N—Ac, L=$CH_2CH_3$, Z=F, and $R_2'$=Ac.

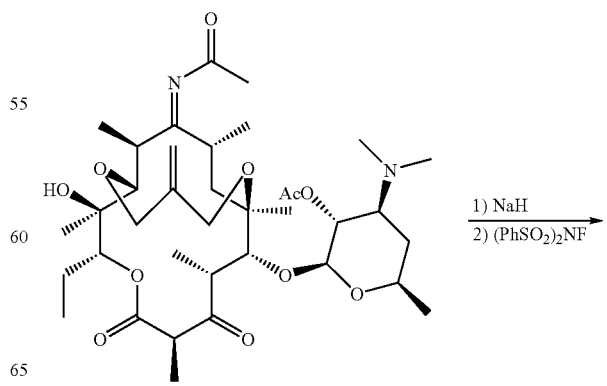

-continued

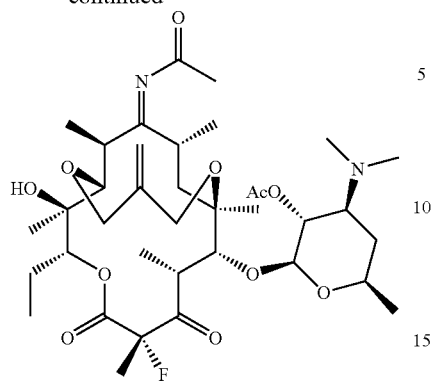

Step 46a: Fluorination of the 3 Position.

To a solution of the 3-keto compound of Example 1 (12.04 g, 17.0 mmol) in anhydrous DMF (70 mL) at 0° C., sodium hydride (60% in mineral oil, 1.50 g, 37.5 mmol) was added in one portion. Then the cooling bath was removed following the addition of sodium hydride. The reaction mixture was allowed to stir at room temperature for 30 minutes, during which period the reaction mixture turned into greenish color and then to light yellow. Upon recooling to 0° C., N-fluorobenzenesulfonimide (5.90 g, 18.7 mmol) was added as solid and stirred at 0° C. for 2 hours. Then it was diluted with isopropyl acetate (600 mL), washed with water (200 mL×2), dried ($Na_2SO_4$), and evaporated. The residue was purified by flash column chromatography (silica gel, acetone/hexanes, 40:60) to give 7.77 g (63%) of the title compound as a white solid.

$^{13}$C-NMR (125 MHz, $CDCl_3$): δ 205.1, 204.9, 184.1, 177.1, 170.0, 165.1, 164.9, 141.9, 125.3, 101.6, 99.8, 98.2, 79.8, 79.3, 78.5, 76.1, 71.9, 71.0, 69.4, 65.5, 63.4, 41.2, 40.8, 38.8, 31.1, 30.8, 25.3, 24.4, 24.3, 23.0, 21.6, 21.3, 20.9, 17.3, 14.5, 12.5. MS (ESI) m/z=727 (M+H)$^+$.

Step 46b: Deprotection of 2'-Hydroxy

The fluorinated compound from Step 46a is refluxed in MeOH according to the procedure set forth in Example 2 to yield the 2' hydroxy compound.

Step 46c: Ozonolysis

The compound prepared in Step 46b is converted to the title compound via ozonolysis according to the procedure elucidated in Example 3.

Example compounds 47–114 of the formula A:

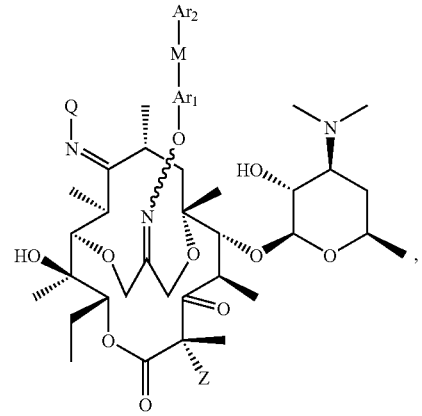

(A)

wherein $Ar_1$, $Ar_2$, M, Q, and Z are as delineated for each example in Table A.

Example compounds 47–114, where Z=H, are made from the title compound of Example 3 and the appropriate hydroxylamine of formula $Ar_2$—M—$Ar_1$—O—$NH_2$ via the method delineated in Example 4.

Example compounds 47–114, where Z=F, are made from the title compound of Example 46 and the appropriate hydroxylamine of formula $Ar_2$—M—$Ar_1$—O—$NH_2$ via the method delineated in Example 4.

In all of the following examples a mixture of E and Z isomers are present which may be separated by HPLC.

The substituted hydroxylamines used in the following examples are either commercially available or can be made from readily-available starting materials via synthetic methods well known by one of ordinary skill in the art.

TABLE A

| Example | Q | -Ar$_1$-M-Ar$_2$ | Z | MS (ESI): m/z (M +H)$^+$ | $^{13}$C NMR (125 MHz, CDCl$_3$): δ |
|---|---|---|---|---|---|
| Example 47. | Ac | ⌬-CH$_2$- (benzyl) | H | 774 | N/A |
| Example 48. | Ac | O$_2$N-⌬-CH$_2$- | H | 819 | N/A |

TABLE A-continued

| Example | Q | -Ar₁-M-Ar₂ | Z | MS (ESI): m/z (M +H)⁺ | ¹³C NMR (125 MHz, CDCl₃): δ |
|---|---|---|---|---|---|
| Example 49. | Ac | phenyl-C≡C-CH₂-CH₂- | H | 800 | N/A |
| Example 50. | Ac | 3-pyridyl-CH₂-CH₂- | H | 775 | N/A |
| Example 51. | Ac | 2-pyridyl-thiophene-CH₂-CH₂- | H | 857 | N/A |
| Example 52. | Ac | quinolin-3-yl-CH₂-CH₂- | H | 825 | N/A |
| Example 53. | Ac | quinolin-2-yl-CH₂-CH₂- | H | 825 | N/A |
| Example 54. | Ac | 2-pyridyl-CH₂-CH₂- | H | 775 | N/A |
| Example 55. | MOM | phenyl-CH₂-CH₂- | H | 792 | N/A |
| Example 56. | Ac | phenyl-CH(-)- | H | 760 | N/A |
| Example 57. | Ac | phenyl-CH₂-CH₂-CH(-)- | H | 787 | N/A |

TABLE A-continued
| Example | Q | -Ar₁-M-Ar₂ | Z | MS (ESI): m/z (M +H)⁺ | ¹³C NMR (125 MHz, CDCl₃): δ |
|---|---|---|---|---|---|
| Example 58. | Ac | 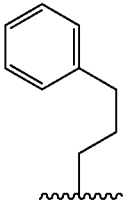 | H | 802 | N/A |
| Example 59. | Ac | 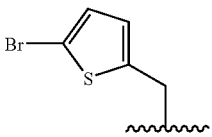 | H | 800 | N/A |
| Example 60. | Ac | 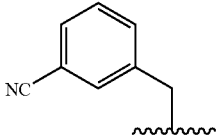 | H | 858 | N/A |
| Example 61. | Ac | 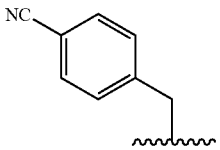 | H | 799 | N/A |
| Example 62. | Ac | 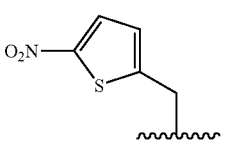 | H | 799 | N/A |
| Example 63. | Ac | 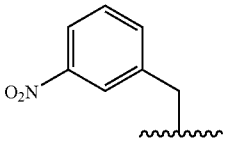 | H | 809 | N/A |
| Example 64. | Ac | 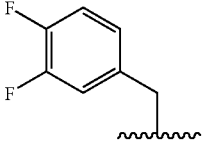 | H | 819 | N/A |
| Example 65. | Ac | 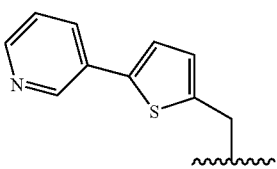 | H | 810 | N/A |
| Example 66. | Ac |  | H | 857 | N/A |

TABLE A-continued
| Example | Q | -Ar₁-M-Ar₂ | Z | MS (ESI): m/z (M +H)⁺ | ¹³C NMR (125 MHz, CDCl₃): δ |
|---|---|---|---|---|---|
| Example 67. | Ac | 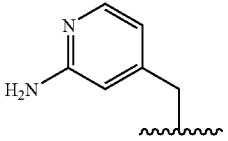 | H | 790 | N/A |
| Example 68. | Ac | 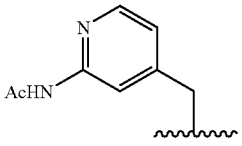 | H | 832 | N/A |
| Example 69. | Ac | 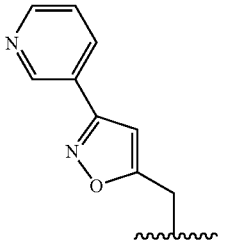 | H | 842 | N/A |
| Example 70. | Ac | 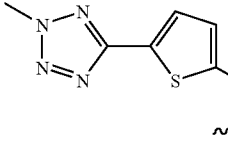 | H | 862 | N/A |
| Example 71. | Ac | 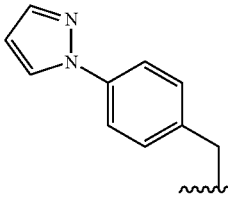 | H | 840 | N/A |
| Example 72. | Ac | 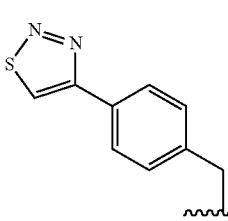 | H | 858 | N/A |
| Example 73. | Ac | 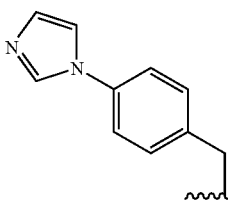 | H | 840 | N/A |

TABLE A-continued
| Example | Q | -Ar$_1$-M-Ar$_2$ | Z | MS (ESI): m/z (M +H)$^+$ | $^{13}$C NMR (125 MHz, CDCl$_3$): δ |
|---|---|---|---|---|---|
| Example 74. | Ac | 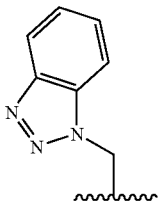 | H | 815 | N/A |
| Example 75. | Ac | 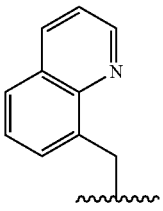 | H | 825 | N/A |
| Example 76. | Ac | 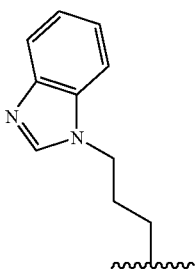 | H | 844 | N/A |
| Example 77. | Ac | 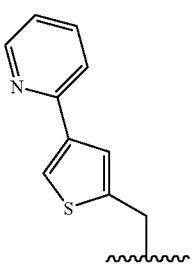 | H | 857 | N/A |
| Example 78. | Ac | 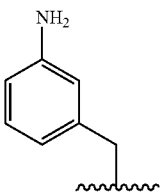 | H | 789 | N/A |
| Example 79. | Ac | 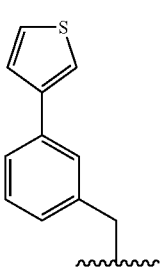 | H | 856 | N/A |

TABLE A-continued
| Example | Q | -Ar₁-M-Ar₂ | Z | MS (ESI): m/z (M +H)⁺ | ¹³C NMR (125 MHz, CDCl₃): δ |
|---|---|---|---|---|---|
| Example 80. | Ac | 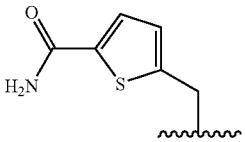 | F | 841 | N/A |
| Example 81. | H | 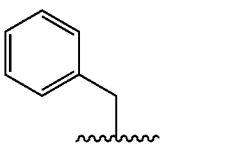 | H | 732 | N/A |
| Example 82. | Ac | 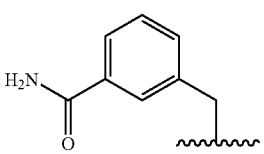 | H | 817 | N/A |
| Example 83. | Ac | 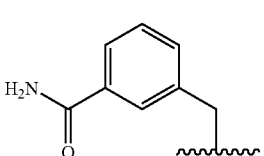 | F | 835 | N/A |
| Example 84. | Ac | 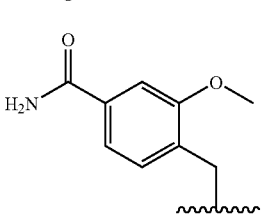 | H | 847 | N/A |
| Example 85. | Ac | 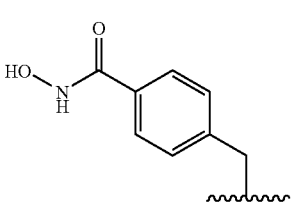 | H | 831 | N/A |
| Example 86. | Ac | 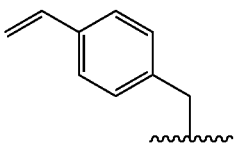 | H | 800 | N/A |
| Example 87. | Ac | 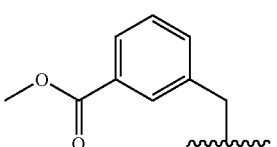 | H | 832 | N/A |
| Example 88. | Ac |  | H | 871 | N/A |

TABLE A-continued
| Example | Q | -Ar₁-M-Ar₂ | Z | MS (ESI): m/z (M +H)⁺ | ¹³C NMR (125 MHz, CDCl₃): δ |
|---|---|---|---|---|---|
| Example 89. | Ac | 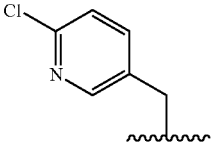 | H | 809 | N/A |
| Example 90. | H | 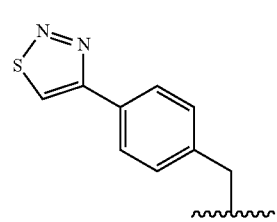 | H | 816 | N/A |
| Example 91. | H | 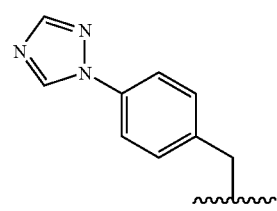 | H | 799 | N/A |
| Example 92. | OMe | 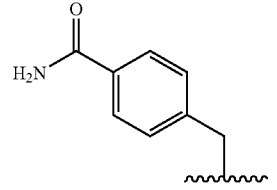 | H | 805 | N/A |
| Example 93. | MOM | 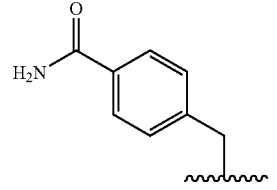 | H | 835 | N/A |
| Example 94. | —OCH₂CN | 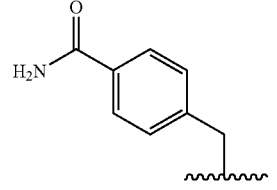 | H | 830 | N/A |
| Example 95. | —OCH₂CH₂OH | 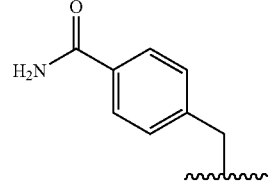 | H | 837 | N/A |
| Example 96. | H | 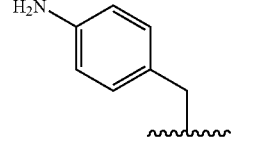 | H | 747 | N/A |

TABLE A-continued
| Example | Q | -Ar₁-M-Ar₂ | Z | MS (ESI): m/z (M +H)⁺ | ¹³C NMR (125 MHz, CDCl₃): δ |
|---|---|---|---|---|---|
| Example 97. | Ac | 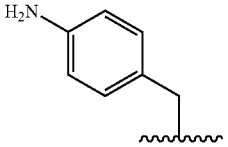 | H | 789 | N/A |
| Example 98. | Ac | 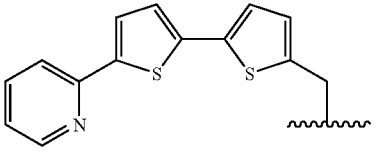 | H | 939 | N/A |
| Example 99. | Ac | 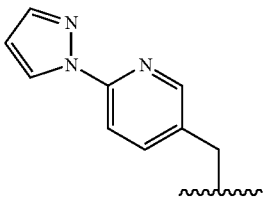 | H | 841 | N/A |
| Example 100. | Ac | 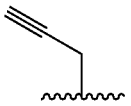 | H | 722 | N/A |
| Example 101. | Ac | 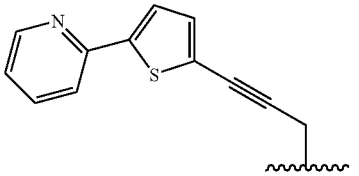 | H | 881 | N/A |
| Example 102. | Ac | 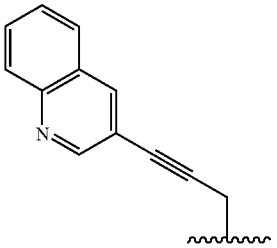 | H | 849 | N/A |
| Example 103. | Ac | 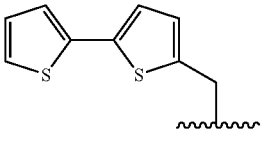 | H | 862 | N/A |
| Example 104. | Ac | 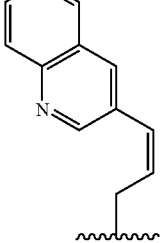 | H | 851 | N/A |

TABLE A-continued

| Example | Q | -Ar₁-M-Ar₂ | Z | MS (ESI): m/z (M +H)⁺ | ¹³C NMR (125 MHz, CDCl₃): δ |
|---------|---|------------|---|----------------------|------------------------------|
| Example 105. | Ac | 2-amino-pyridin-3-yl-methylene | H | 790.55 | N/A |
| Example 106. | Ac | 5-phenyl-1,2,4-oxadiazol-3-yl-methylene | H | 842 | N/A |
| Example 107. | Ac | 3-phenyl-1,2,4-oxadiazol-5-yl-methylene | H | 843 | N/A |
| Example 108. | Ac | 5-(4-methoxyphenyl)-1,2,4-oxadiazol-3-yl-methylene | H | 872 | N/A |
| Example 109. | Ac | 6-amino-pyridin-2-yl-methylene | H | 790 | N/A |
| Example 110. | Ac | 5-(5-formylthiophen-2-yl)pyridin-2-yl-methylene | H | 885 | N/A |

TABLE A-continued

| Example | Q | -Ar₁-M-Ar₂ | Z | MS (ESI): m/z (M +H)⁺ | ¹³C NMR (125 MHz, CDCl₃): δ |
|---|---|---|---|---|---|
| Example 111. | Ac | 2-amino-3-cyanopyridin-6-yl | H | 815 | N/A |
| Example 112. | Ac | 6-chloro-5-fluoro-2-(1H-pyrazol-1-yl)pyridin-3-yl | H | 893 | N/A |
| Example 113. | Ac | 6-chloropyridin-3-yl N-oxide | H | 825 | N/A |
| Example 114. | Ac | 5-(5-acetylthiophen-2-yl)pyridin-2-yl | H | 900 | N/A |

Example compounds 115–263 of formula A1:

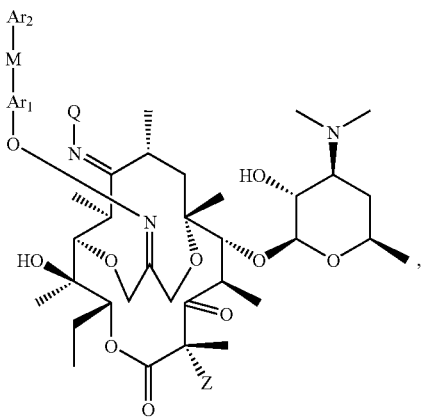

Example compounds 115–262, where Z=H, are made from the title compound of Example 3 and the appropriate hydroxylamine of formula $Ar_2$—M—$Ar_1$—O—$NH_2$ via the method delineated in Example 4.

Example compounds 115–262, where Z=F, are made from the title compound of Example 46 and the appropriate hydroxylamine of formula $Ar_2$—M—$Ar_1$—O—$NH_2$ via the method delineated in Example 4.

The Examples described in Table A1 are single isomers of the E designation, which are separated from the E/Z mixture via silica chromatography or HPLC.

The substituted hydroxylamines used in the following examples are either commercially available or can be made from readily-available starting materials via synthetic methods well known by one of ordinary skill in the art.

wherein $Ar_1$, $Ar_2$, M, Q, and Z are as delineated for each example in Table A1.

TABLE A1

| Example | Q | -$Ar_1$-M-$Ar_2$ | Z | MS (ESI): m/z (M + H)+ | $^{13}$C NMR (125 MHz. CDCl$_3$) δ |
|---|---|---|---|---|---|
| Example 115. | Ac | (2-pyridyl-thiophene-CH2) | H | 857 | 205.8, 184.7, 178.1, 169.3, 156.2, 153.9, 149.7, 145.3, 142.9, 136.8, 128.3, 124.5, 122.0, 119.0, 103.0. |
| Example 116. | Ac | (pentafluorophenyl-CH2) | H | 864 | Selected data: 205.7, 184.7, 178.0, 167.7, 154.5, 147.1, 145.1, 138.6, 136.6, 103.1, 79.1, |
| Example 117. | Ac | (3-fluorophenyl-CH2) | H | 792 | Selected: 205.8, 184.8, 178.0, 167.8, 153.8, 140.9, 134.5, 130.0, 123.5, 114.9, 114.7(2), 114.5, 110.0, 103.0, 79.4, 76.7, 75.3, 74.7, 70.5, 69.7, 66.1, 63.1, 62.9, 50.7, 46.2, 40.5, 38.8, 32.0, 29.9, 28.5, 25.4, 23.8, 21.5, 20.3, 19.5, 17.8, 15.1, 14.1, 13.7, 12.8. |
| Example 118. | Ac | (3-pyridyl-thiophene-CH2) | H | 857 | 205.8, 184.7, 178.0, 167.7, 154.0, 148.6, 147.0, 141.5, 141.0, 133.0, 130.7, 128.2, 124.0, 123.8, 103.1, 79.3, 79.1, 76.7, 75.5, 74.5, 70.7, 70.5, 69.7, 66.0, 63.1, 62.8, 50.7, 46.2, 40.4, 38.7, 37.2, 31.1, 29.5, 28.5, 25.3, 23.8, 21.5, 20.3, 19.5, 17.8, 15.0, 14.1, 13.7, 13.0. |

TABLE A1-continued
| Example | Q | -Ar₁-M-Ar₂ | Z | MS (ESI): m/z (M + H)⁺ | ¹³C NMR (125 MHz. CDCl₃) δ |
|---|---|---|---|---|---|
| Example 119. | Ac | 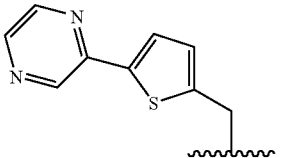 | H | 858 | 205.8, 184.7, 178.1, 167.8, 154.2, 148.8, 144.8, 144.2, 142.5, 141.6, 140.7, 128.0, 125.7, 103.1, 79.5, 79.2, 76.8, 75.6, 74.5, 70.9, 70.5, 69.8, 66.1, 63.1, 62.9, 50.7, 46.2, 40.5, 38.8, 37.3, 29.5, 28.5, 25.4, 23.9, 21.5, 20.3, 19.5, 17.8, 15.1, 14.1, 13.6, 13.0. |
| Example 120. | Ac | 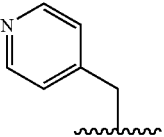 | H | 775 | Selected: 84.5, 177.6, 167.7, 154.1, 149.7, 147.3, 121.9, 102.8, 79.1, 76.5, 75.3, 73.9, 70.3, 69.5, 65.8, 62.8, 62.7, 50.5, 46.1, 40.2, 38.5, 28.2, 25.1, 23.6, 21.2, 20.0, 19.3, 17.5, 14.9, 13.8, 13.4, 12.7. |
| Example 121. | Ac | 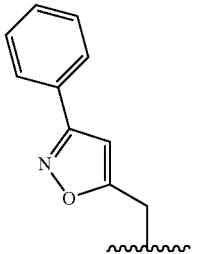 | H | 842 | 205.8, 184.7, 178.0, 170.0, 167.8, 163.3, 154.8, 150.0, 148.8, 137.0, 124.6, 124.6, 121.9, 103.0, 102.5, 7935, 79.2, 76.8, 74.6, 70.4, 69.6, 66.9, 66.2, 63.0, 62.7, 50.7, 46.1, 40.5, 38.8, 28.7, 25.4, 23.9, 21.5, 20.2, 19.5, 17.8, 15.1, 14.1, 13.6, 13.0. |
| Example 122. | Ac | 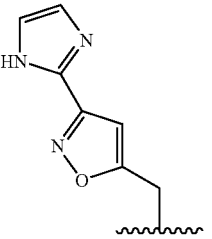 | H | 831 | 205.7, 184.8, 178.0, 169.8, 167.9, 155.4, 154.9, 139.9, 137.4, 103.1, 102.2, 79.5, 79.3, 76.7, 74.7, 70.5, 69.7, 66.7, 66.0, 62.9, 62.7, 50.7, 46.1, 40.4, 38.7, 28.5, 25.3, 23.9, 21.5, 20.2, 19.5, 17.8, 15.1, 14.0, 13.6, 13.0, 10.9. |
| Example 123. | Ac | 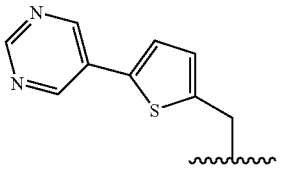 | H | 858 | N/A |
| Example 124. | Ac | 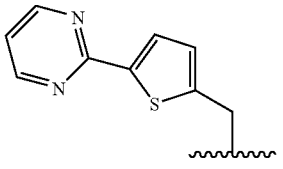 | H | 858 | 205.8, 184.7, 178.1, 167.8, 161.8, 157.4, 154.1, 145.6, 143.3, 128.9, 127.8, 118.6, 103.1, 79.5, 79.2, 76.8, 75.5, 74.5, 71.1, 70.5, 69.7, 66.1, 63.1, 62.9, 50.7, 46.2, 40.5, 38.8, 37.3, 31.2, 28.5, 25.3, 23.9, 21.5, 20.3, 19.5, 17.8, 15.1, 14.1, 13.6, 13.0. |
| Example 125. | Ac | 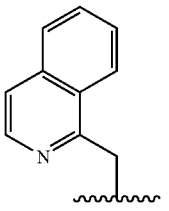 | H | 825 | Selected: 205.8, 184.6, 177.9, 167.9, 156.8, 153.7, 142.0, 136.6, 130.2, 127.4, 127.2, 126.4, 121.3, 103.0, 79.2, 76.6, 76.3, 74.9, 70.5, 69.7, 66.0, 63.1, 62.8, 50.8, 46.2, 40.4, 38.7, 28.4, 25.3, 23.7, 21.4, 20.3, 19.6, 17.7, 15.1, 14.1, 13.7, 12.7. |

TABLE A1-continued

| Example | Q | -Ar₁-M-Ar₂ | Z | MS (ESI): m/z (M + H)⁺ | ¹³C NMR (125 MHz. CDCl₃) δ |
|---|---|---|---|---|---|
| Example 126. | Ac | benzimidazol-2-ylmethyl | H | 831 | Selected: 205.8, 184.8, 178.0, 169.5, 167.7, 155.2, 153.3, 135.3, 126.1, 125.2, 123.3, 121.9, 103.1, 79.3, 76.7, 74.7, 73.5, 70.5, 69.8, 66.1, 62.9, 50.7, 40.5, 38.8, 28.5, 25.4, 23.8, 21.5, 20.3, 19.5, 17.7, 15.1, 14.1, 12.9. |
| Example 127. | Ac | 1-(pyrimidin-2-yl)pyrazol-3-ylmethyl | H | 843 | 205.8, 184.8, 177.7, 167.9, 159.3, 155.8, 154.6, 136.6, 134.5, 120.7, 102.9, 79.3, 76.7, 75.0, 70.4, 69.7, 67.9, 66.2, 62.9, 62.8, 50.8, 46.3, 40.5, 38.8, 28.7, 25.4, 23.8, 25.4, 23.8, 21.5, 20.2, 19.5, 17.7, 15.1, 14.1, 13.7, 12.9. |
| Example 128. | Ac | thiophen-2-ylmethyl | H | 780 | N/A |
| Example 129. | Ac | 1-(4-fluoro-3-nitrophenyl)-1,2,3-triazol-4-ylmethyl | H | 904 | N/A |
| Example 130. | Ac | imidazo[4,5-b]pyridin-1-ylpropyl | H | 829 | Selected: 205.8, 184.6, 177.5, 168.2; 154.8, 147.2, 145.6, 144.2, 135.6, 128.0, 118.3, 103.0, 79.4, 79.1, 76.5, 75.5, 72.0, 70.5, 69.7, 66.1, 63.0, 62.9, 50.8, 46.4, 43.0, 40.5, 38.7, 28.5, 25.4, 23.5, 21.5, 20.2, 19.7, 17.7, 15.2, 14.1, 13.8, 12.6. |
| Example 131. | Ac | purin-9-ylpropyl | H | 830 | Selected: 205.7, 184.6, 177.3, 168.4, 155.2, 152.6, 151.6, 148.6, 147.1, 134.2, 103.1, 79.5, 79.1, 76.5, 75.9, 71.8, 70.5, 69.8, 66.1, 63.0, 50.8, 43.1, 40.5, 38.7, 28.5, 25.5, 23.5, 21.5, 19.8, 17.7, 15.2, 14.0, 12.6. |
| Example 132. | Ac | 1-benzylimidazol-2-ylmethyl | H | 854 | E oxime isomer: Selected: 205.6, 184.6, 177.9, 167.9, 153.8, 145.0, 137.5, 128.9 128.6, 127.9, 127.3, 121.3, 103.2, 9.2, 76.6, 75.9, 74.6, 70.5, 69.7, 67.2, 66.0, 63.1, 62.4, 50.7, 50.1, 46.3, 40.6, 38.7, 28.6, 25.3, 23.6, 21.5, 20.3, 19.6, 17.7, 15.0, 14.1, 12.8. |

TABLE A1-continued

| Example | Q | -Ar₁-M-Ar₂ | Z | MS (ESI): m/z (M + H)⁺ | ¹³C NMR (125 MHz, CDCl₃) δ |
|---|---|---|---|---|---|
| Example 133. | Ac | pyridine-thiophene-CH(=CH₂)- | H | 871 | 206.0, 184.6, 178.0, 167.8, 153.6, 153.0, 149.7, 148.1, 143.9, 136.7, 125.6, 124.2, 121.9, 118.8, 102.9, 78.7, 76.7, 74.8, 70.4, 69.6, 66.2, 63.3, 51.0, 40.5, 38.9, 29.9, 28.9, 25.4, 23.6, 23.3, 22.7, 22.2, 21.5, 20.4, 19.7, 17.7, 15.1, 14.2, 12.6, 11.7. |
| Example 134. | Ac | pyridine-thiophene-CH(CH₃)- | H | 871 | 205.9, 184.7, 178.2, 167.7, 153.4, 153.0, 150.2, 149.7, 143.8, 136.7, 125.6, 124.2, 121.9, 118.8, 102.6, 78.9, 76.9, 74.4, 70.3, 69.2, 66.5, 63.2, 62.7, 50.7, 46.0, 40.5, 38.9, 29.6, 29.5, 25.3, 23.6, 22.2, 21.4, 20.3, 19.4, 17.9, 15.1, 14.3, 13.5, 12.6. |
| Example 135. | Ac | thiophene-oxadiazole-CH₂- | H | 848 | 205.8, 184.7, 178.1, 171.8, 168.1, 167.8, 154.8, 132.3, 132.1, 128.7, 125.9, 102.9, 79.4, 76.7, 74.6, 70.5, 69.7, 67.0, 66.1, 62.9, 62.7, 50.7, 46.1, 40.5, 38.8, 28.5, 25.3, 23.9, 21.5, 20.2, 19.5, 17.8, 15.1, 14.1, 12.9. |
| Example 136. | Ac | H₂N(C=O)-thiophene-CH₂- | H | 823 | 205.6, 184.5, 177.8, 167.6, 163.3, 154.2, 146.5, 137.3, 129.3, 126.8, 102.9, 79.2, 76.5, 74.4, 70.4, 70.3, 69.6, 69.5, 65.8, 62.8, 62.6, 53.8, 50.8, 50.5, 46.1, 40.2, 38.5, 31.7, 29.3, 28.3, 25.1, 23.6, 21.3, 20.1, 19.3, 17.5, 14.8, 13.9, 12.8. |
| Example 137. | Ac | phenyl-CH₂- | H | 774 | 205.9, 184.8, 178.0, 167.8, 153.3, 138.1, 128.4, 128.2, 127.8, 102.9, 79.4, 76.8, 76.2, 74.6, 70.5, 69.6, 66.2, 63.2, 62.9, 50.8, 40.5, 38.8, 28.7, 25.3, 23.8, 21.5, 20.3, 19.5, 17.8, 15.1, 14.1, 12.8. |
| Example 138. | Ac | quinoline-CH₂- | F | 843 | 205.3, 205.1, 184.2, 153.6, 149.8, 146.3, 136.5, 136.3, 128.4, 128.2, 127.5, 126.4, 121.2, 104.1, 99.7, 98.1, 79.6, 76.6, 73.7, 72.8, 70.7, 69.4, 66.0, 63.3, 62.7, 41.2, 40.5, 39.1, 28.4, 25.3, 24.7, 24.5, 23.2, 21.4, 21.1, 17.4, 15.1, 14.3, 12.5. |
| Example 139. | Ac | pyridine-thiophene-CH₂- | H | 857 | 205.8, 184.8, 178.0, 167.7, 154.5, 153.9, 149.7, 139.4, 138.6, 136.8, 128.6, 124.9, 123.3, 121.8, 103.1, 79.2, 76.7, 74.7, 70.5, 70.2, 69.7, 66.1, 63.1, 63.0, 50.9, 46.4, 40.5, 38.8, 28.5, 25.4, 23.7, 21.5, 20.4, 19.6, 17.7, 15.1, 14.1, 13.8, 12.7. |

TABLE A1-continued

| Example | Q | -Ar₁-M-Ar₂ | Z | MS (ESI): m/z (M + H)⁺ | ¹³C NMR (125 MHz. CDCl₃) δ |
|---|---|---|---|---|---|
| Example 140. | Ac | (pyrimidine-thiophene) | F | 876 | 205.2(d), 184.1, 177.4, 165.1(d), 161.7, 157.4, 154.3, 145.3, 143.4, 128.9, 127.8, 118.6, 104.0, 99.8, 98.1, 79.8, 76.6, 73.6, 71.2, 70.6, 69.7, 66.1, 63.2, 62.7, 41.3, 40.5, 39.0, 29.9, 28.7, 25.3, 24.6, 24.4, 23.2, 21.4, 21.0, 17.4, 15.0, 14.3, 12.8. |
| Example 141. | Ac | (pyrazine-thiophene) | F | 876 | (205.1, 204.9), 183.9, 176.5, (164.9, 164.7), 154.1, 148.6, 144.2, 144.0, 142.3, 141.4, 140.5, 127.7, 125.5, 103.9, (99.5, 97.9), 79.5, 76.3, 73.4, 70.7, 70.4, 69.6, 65.8, 62.9, 62.4, 53.8, 41.1, 40.2, 38.7, 29.7, 29.3, 28.2, 25.1, 24.4, 24.2, 23.0, 21.2, 20.8, 17.1, 14.8, 14.1, 12.6. |
| Example 142. | Ac | (carboxamide-thiophene) | F | 841 | N/A |
| Example 143. | Ac | (acetamido-pyridine-thiophene) | H | 914 | 205.9, 184.8, 178.0, 169.0, 167.8, 154.0, 151.1, 151.0, 144.4, 143.2, 139.2, 127.3, 124.5, 114.6, 111.6, 102.8, 79.4, 79.3, 76.8, 74.6, 71.1, 70.4, 69.4, 66.4, 63.0, 62.8, 50.8, 46.1, 40.5, 38.8, 29.9, 29.1, 25.4, 25.0, 23.8, 21.4, 20.3, 19.5, 17.8, 15.1, 14.2, 13.8, 12.9. |
| Example 144. | Ac | (pyridyl-amide-thiophene) | H | 900 | 205.8, 184.7, 178.1, 167.8, 160.2, 154.5, 151.5, 148.1, 147.6, 138.7, 138.6, 129.0, 127.2, 120.1, 114.4, 103.1, 79.5, 79.2, 76.8, 74.6, 70.7, 70.5, 69.8, 66.1, 63.1, 62.8, 50.7, 46.3, 40.5, 38.8, 28.5, 25.3, 23.9, 21.5, 20.3, 19.5, 17.8, 15.1, 14.1, 13.6, 13.0 |
| Example 145. | Ac | (benzyl-amide-thiophene) | H | 913 | 205.6, 184.5, 177.8, 167.6, 161.8, 154.1, 145.5, 138.2, 138.1, 128.8, 128.2, 127.9, 127.6, 126.8, 102.8, 79.2, 76.5, 74.3, 70.4, 70.3, 69.5, 65.9, 62.8, 62.6, 50.5, 46.0, 44.0, 40.2, 38.5, 29.3, 28.3, 25.1, 23.6, 21.3, 20.0, 19.3, 17.5, 14.8, 13.9, 13.4, 12.8. |
| Example 146. | Ac | (carboxamido-phenyl) | H | 817.28 | 205.9, 184.8, 169.4, 167.9, 153.9, 142.6, 132.7, 103.1, 79.4, 75.3, 74.8, 70.5, 69.7, 66.1, 63.1, 63.0, 50.8, 38.8, 28.5, 25.3, 23.8, 21.5, 20.3, 19.6, 17.8, 15.1, 14.1, 12.9 |

TABLE A1-continued

| Example | Q | -Ar₁-M-Ar₂ | Z | MS (ESI): m/z (M + H)⁺ | ¹³C NMR (125 MHz. CDCl₃) δ |
|---|---|---|---|---|---|
| Example 147. | Ac | (2-pyridyl-NH-C(O)-CH₂-CH₂-) | H | 818 | Selected: 205.6, 184.4, 168.4, 168.3, 157.0, 150.8, 148.1, 138.8, 120.3, 114.2, 110.0, 103.1, 78.3, 76.5, 72.7, 70.5, 69.8, 66.1, 62.5, 62.1, 50.9, 40.4, 31.2, 28.5, 25.4, 23.3, 21.5, 19.8, 18.4, 15.1, 14.2, 11.9. |
| Example 148. | Ac | (2-pyridyl-NH-C(O)-CH₂-CH₂-) | F | 836 | Selected: 203.1, 202.8, 181.8, 175.1, 165.9, 163.2, 163.0, 154.8, 148.5, 146.0, 136.7, 118.3, 112.0, 102.0, 76.8, 72.6, 70.6, 68.5, 67.8, 63.9, 38.3, 26.3, 19.3, 19.3, 16.3, 12.9, 9.7. |
| Example 149. | Ac | (phenyl-NH-C(O)-thiophene-CH₂-) | H | 899 | 205.8, 184.8, 178.0, 167.8, 160.1, 154.4, 146.6, 138.8, 137.9, 129.3, 129.3, 128.9, 127.2, 124.7, 120.4, 103.1, 79.5, 76.8, 74.6, 70.7, 70.5, 69.8, 69.7, 66.1, 63.1, 62.9, 54.0, 50.7, 40.5, 38.8, 32.0, 29.9, 29.5, 28.6, 25.4, 23.9, 21.5, 20.3, 19.5, 17.8, 15.1, 14.1, 13.0. |
| Example 150. | Ac | (H₂N-C(O)-phenyl-CH₂-CH₂-) | F | 835.39 | 205.4, 184.3, 169.3, 154.1 142.4, 132.7, 128.4, 127.9 127.6, 104.1, 79.7, 76.6, 66.1, 62.6, 41.3, 40.5, 28.5, 25.3, 23.2, 21.4, 21.0, 17.4, 12.7 |
| Example 151. | Ac | (H₂N-C(O)-thiophene-CH₂-) | H | 808 | 205.5, 184.5, 182.9, 177.7, 167.6, 154.4, 151.6, 143.5, 136.2, 126.9, 102.8, 79.2, 79.0, 76.5, 74.3, 70.5, 70.2, 69.4, 65.9, 62.7, 50.6, 45.9, 40.2, 38.5, 28.4, 25.1, 23.6, 21.2, 20.0, 19.2, 17.5, 14.8, 13.8, 13.3, 12.8 |
| Example 152. | Ac | (HO-CH=thiophene-CH₂-) | H | 823 | N/A |
| Example 153. | Ac | (phenyl-NH-C(O)-phenyl-CH₂-CH₂-) | H | 893 | 205.9, 184.9, 177.8, 167.9, 165.9, 153.9, 142.4, 138.3, 134.4, 129.3, 128.2, 127.3, 124.7, 120.4, 102.8, 79.4, 79.2, 76.7, 75.3, 74.9, 70.4, 69.5, 66.3, 63.1, 63.0, 50.7, 46.2, 40.5, 38.8, 32.0, 28.9, 25.3, 23.8, 21.4, 20.3, 19.5, 17.8, 15.1, 14.1, 13.6, 12.9. |

TABLE A1-continued

| Example | Q | -Ar₁-M-Ar₂ | Z | MS (ESI): m/z (M + H)⁺ | ¹³C NMR (125 MHz. CDCl₃) δ |
|---|---|---|---|---|---|
| Example 154. | Ac | (pyridin-2-yl aminocarbonyl phenyl methyl) | H | 894 | N/A |
| Example 155. | Ac | (N,N-dimethyl aminocarbonyl phenyl methyl) | H | 845 | 205.9, 184.8, 178.0, 171.8, 167.8, 153.7, 139.8, 135.7, 129.9, 127.9, 127.3, 103.0, 79.4, 79.2, 76.8, 75.6, 74.7, 70.5, 69.7, 66.1, 63.1, 62.9, 50.7, 46.2, 40.5, 38.8, 28.5, 25.4, 23.8, 21.5, 20.3, 19.5, 17.8, 15.1, 14.1, 13.7, 12.9. |
| Example 156. | Ac | (uracil-6-ylmethyl) | H | 808 | 205.5, 184.8, 177.7, 168.4, 164.3, 156.3, 151.8, 103.2, 99.9, 79.4, 79.2, 76.8, 75.2, 71.1, 70.5, 69.6, 66.0, 62.9, 62.7, 50.7, 46.4, 40.4, 38.7, 29.9, 28.6, 25.4, 23.5, 21.5, 20.2, 19.6, 17.9, 15.0, 14.0, 13.7, 12.7. |
| Example 157. | Ac | (N-methyl aminocarbonyl phenyl methyl) | H | 831.60 | 205.8, 184.8, 177.9, 168.3, 167.9, 153.8, 141.8, 134.0, 128.0, 127.0, 103.0, 79.4, 79.2, 76.7, 75.4, 74.8, 70.5, 69.8, 66.1, 63.1, 63.0, 50.7, 46.2, 40.5, 23.8, 21.5, 20.3, 19.5, 17.8, 15.1, 14.1, 13.7, 12.9 |
| Example 158. | Ac | (N-ethyl aminocarbonyl phenyl methyl) | H | 845.61 | 205.8, 184.8, 177.9, 167.8, 167.5, 153.8, 141.7, 134.2, 128.0, 127.0, 103.0, 79.4, 79.2, 76.7, 75.4, 74.7, 70.5, 69.7, 66.1, 63.1, 63.0, 50.7, 46.2, 40.5, 38.8, 35.1, 28.5, 25.3, 23.8, 21.5, 20.3, 19.5, 17.8, 15.1, 14.1, 13.7, 12.9 |
| Example 159. | Ac | (methoxycarbonyl phenyl methyl) | H | 832 | 204.6, 183.5, 176.7, 166.6, 166.0, 152.6, 142.3, 128.5, 128.2, 126.4, 101.8, 78.1, 77.9, 75.5, 74.2, 73.4, 69.2, 68.5, 64.8, 61.8, 61.7, 51.0, 49.5, 45.0, 39.2, 37.5, 27.3, 24.1, 22.6, 20.2, 19.0, 18.3, 16.5, 13.9, 12.8, 12.4, 11.6 |
| Example 160. | Ac | (N-cyclopropyl aminocarbonyl phenyl methyl) | H | 857 | 205.8, 184.8, 177.9, 168.9, 167.8, 153.8, 142.0, 133.8, 128.0, 127.0, 103.0, 79.4, 76.7, 75.4, 74.8, 70.5, 63.0, 50.7, 46.2, 40.5, 38.8, 28.5, 25.3, 23.8, 23.3, 21.5, 20.3, 19.5, 17.8, 15.1, 14.1, 13.7, 12.9, 7.0 |

TABLE A1-continued

| Example | Q | -Ar₁-M-Ar₂ | Z | MS (ESI): m/z (M + H)⁺ | ¹³C NMR (125 MHz, CDCl₃) δ |
|---|---|---|---|---|---|
| Example 161. | Ac | | H | 913 | N/A |
| Example 162. | Ac | | H | 899 | N/A |
| Example 163. | Ac | | H | 837 | N/A |
| Example 164. | Ac | | H | 872 | 205.9, 184.7, 178.1, 167.7, 158.2, 153.7, 151.2, 145.6, 142.0, 138.5, 127.7, 124.0, 109.3, 107.1, 102.7, 79.5, 79.1, 76.8, 74.6, 71.1, 70.3, 69.3, 66.5, 63.1, 62.9, 50.8, 46.0, 40.6, 38.8, 29.9, 29.3, 25.4, 23.8, 21.4, 20.3, 19.5, 17.8, 15.1, 14.2, 13.5, 13.0. |
| Example 165. | Ac | | H | 817 | 205.5, 184.7, 177.4, 168.7, 168.2, 157.0, 137.4, 128.9, 124.8, 121.4, 103.0, 79.7, 78.9, 76.6, 75.9, 73.6, 70.5, 69.7, 63.0, 62.9, 51.0, 46.4, 40.5, 38.7, 36.9, 28.6, 25.3, 23.4, 21.5, 20.3, 19.7, 17.7, 15.2, 14.2, 12.3. |
| Example 166. | Ac | | H | 916 | 205.8, 184.6, 176.6, 169.3, 156.2, 149.3, 148.9, 145.5, 138.8, 128.4, 128.0, 122.1, 118.7, 111.7, 109.7, 102.4, 79.6, 79.0, 76.2, 75.4, 71.0, 70.6, 70.4, 69.5, 66.3, 58.4, 56.22, 56.20, 50.9, 45.2, 40.5, 39.6, 39.0, 36.8, 29.9, 28.9, 25.5, 23.4, 21.5, 20.2, 19.7, 17.2, 15.7, 14.5, 12.8, 12.0. |
| Example 167. | Ac | | H | 862 | 205.8, 184.8, 177.9, 167.8, 156.9, 153.6, 132.3, 130.3, 128.2, 122.0, 110.9, 103.0, 79.3, 79.2, 76.7, 74.8, 71.0, 70.5, 69.7, 66.0, 63.1, 55.7, 52.3, 50.8, 46.2, 40.4, 38.8, 28.5, 25.3, 23.8, 21.4, 20.3, 19.6, 17.7, 15.1, 14.1, 13.7, 12.8 |

TABLE A1-continued
| Example | Q | -Ar₁-M-Ar₂ | Z | MS (ESI): m/z (M + H)⁺ | ¹³C NMR (125 MHz. CDCl₃) δ |
|---|---|---|---|---|---|
| Example 168. | Ac | 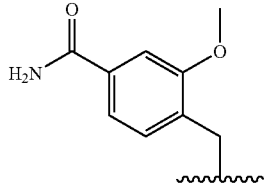 | H | 847 | 205.8, 184.9, 177.8, 169.4, 167.8, 157.3, 153.6, 133.7, 131.3, 128.4, 118.7, 109.7, 103.0, 79.3, 79.2, 76.7, 75.0, 70.9, 70.4, 69.7, 66.0, 63.0, 55.7, 50.8, 46.2, 40.4, 38.7, 28.4, 25.3, 23.8, 21.4, 20.3, 19.6, 17.7, 15.0, 14.0, 13.7, 12.8. |
| Example 169. | Ac | 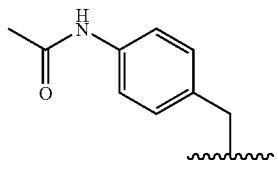 | H | 831 | 204.7, 183.5, 176.8, 167.2, 166.5, 152.0, 136.3, 132.8, 127.9, 118.6, 101.5, 78.1, 77.8, 75.5, 74.5, 73.4, 69.1, 68.1, 65.2, 61.9, 61.6, 52.4, 49.5, 44.8, 39.3, 37.6, 30.8, 28.7, 28.0, 24.1, 23.6, 22.5, 20.1, 19.0, 18.2, 16.5, 13.9, 12.9, 12.3, 11.6. |
| Example 170. | Ac | 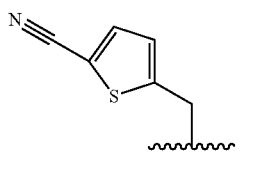 | H | 805 | 205.5, 184.4, 177.7, 167.6, 154.6, 148.7, 137.2, 126.4, 114.3, 109.6, 102.9, 79.1, 76.4, 74.3, 70.2, 69.8, 69.5, 65.8, 62.7, 62.5, 50.4, 46.1, 40.2, 38.5, 28.2, 25.1, 23.5, 21.2, 20.0, 19.2, 17.5, 14.8, 13.8, 12.7 |
| Example 171. | Ac | 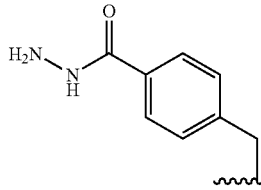 | H | 832 | 205.8, 184.8, 177.9, 168.7, 167.9, 153.9, 142.4, 132.0, 128.1, 127.1, 79.3, 76.7, 75.3, 74.8, 70.5, 69.7, 66.0, 63.0, 50.8, 46.3, 40.4, 38.7, 28.5, 25.3, 23.8, 21.5, 20.3, 19.5, 17.8, 15.1, 14.1, 13.7, 12.9 |
| Example 172. | Ac | 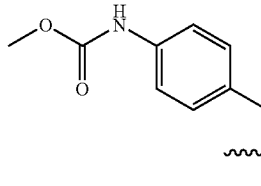 | H | 847 | 203.7, 182.6, 175.9, 165.6, 151.1, 135.4, 131.0, 127.2, 116.5, 100.8, 77.2, 77.1, 74.6, 73.7, 72.5, 68.3, 67.6, 64.0, 61.0, 60.8, 50.4, 48.6, 44.0, 38.3, 36.7, 27.8, 26.4, 23.2, 21.6, 19.3, 18.2, 17.4, 15.6, 13.0, 12.0, 11.5, 10.7. |
| Example 173. | Ac | 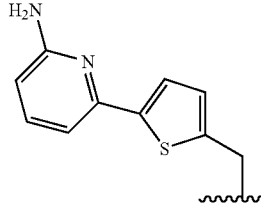 | F | 890 | (205.1, 204.9), 183.9, 164.4, 158.0, 153.8, 151.0, 145.5, 141.5, 138.2, 127.4, 123.7, 109.1, 106.8, 103.9, 99.5, 97.9, 79.5, 76.3, 73.3, 71.0, 70.4, 69.6, 65.8, 62.9, 62.4, 41.0, 40.2, 29.7, 28.2, 25.1, 24.4, 24.2, 23.0, 21.2, 20.8, 17.1, 14.8, 14.0, 12.5. |
| Example 174. | Ac | 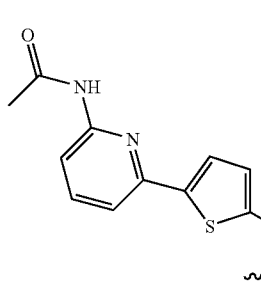 | F | 932 | Selected data: (205.1, 204.9), 184.0, 168.7, 154.1, 150.8, 144.2, 139.0, 124.1, 111.6, 103.9, 79.3, 73.4, 71.1, 70.4, 69.6, 65.8, 62.3, 41.0, 40.2, 29.7, 28.2, 25.1, 22.9, 21.2, 17.2, 14.9, 14.0, 12.3. |

TABLE A1-continued
| Example | Q | -Ar₁-M-Ar₂ | Z | MS (ESI): m/z (M + H)⁺ | $^{13}$C NMR (125 MHz. CDCl₃) δ |
|---|---|---|---|---|---|
| Example 175. | Ac | 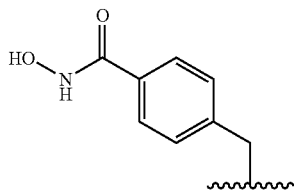 | H | 831 | N/A |
| Example 176. | Ac | 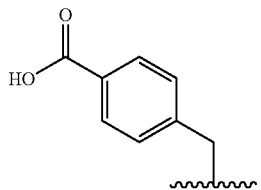 | H | 818 | 205.9, 184.8, 178.1, 173.2, 167.8, 153.6, 141.9, 129.9, 127.4, 102.5, 79.4, 79.1, 76.8, 75.7, 74.7, 70.1, 68.8, 66.3, 63.1, 62.9, 50.7, 46.1, 39.9, 38.8, 29.9, 29.6, 25.4, 23.8, 21.4, 20.3, 19.5, 17.8, 15.1, 14.2, 13.6, 12.9. |
| Example 177. | Ac | 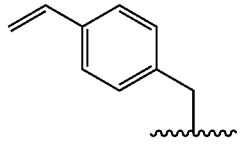 | H | 800 | 205.8, 184.7, 178.0, 167.8, 153.4, 137.8, 136.9, 128.5, 126.4, 113.9, 103.0, 79.4, 76.7, 75.9, 74.6, 70.5, 69.7, 66.0, 63.1, 50.8, 40.5, 38.8, 28.5, 25.3, 23.8, 21.5, 20.3, 19.5, 17.8, 15.1, 14.1, 13.7, 12.9 |
| Example 178. | Ac | 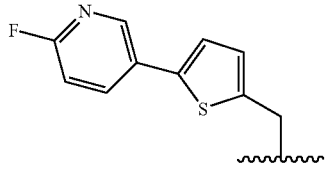 | H | 876 | 205.8, 184.7, 178.0, 167.8, 164.0, 162.1, 154.1, 144.7, 144.6, 141.6, 139.7, 138.7, 138.6, 128.2, 124.1, 110.0, 109.7, 103.1, 79.4, 79.3, 76.8, 75.9, 74.5, 70.7, 70.5, 69.8, 66.1, 63.1, 62.9, 50.7, 46.3, 40.5, 38.8, 28.5, 25.4, 23.8, 21.5, 20.3, 19.5, 17.8, 15.1, 14.1, 13.7, 13.0. |
| Example 179. | Ac | 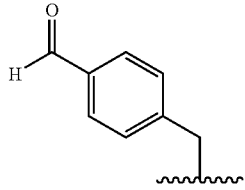 | H | 801 | N/A |
| Example 180. | H | 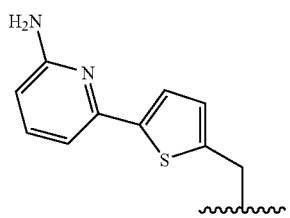 | H | 830 | 205.2, 170.0, 169.2, 158.3, 154.1, 151.2, 145.9, 141.7, 138.4, 127.9, 124.0, 109.3, 107.1, 103.6, 80.5, 79.0, 78.8, 75.8, 71.1, 70.6, 69.8, 66.1, 64.7, 63.0, 51.7, 48.1, 40.5, 38.3, 28.4, 23.0, 21.5, 21.1, 20.2, 17.4, 16.0, 14.4, 14.0, 11.9. |
| Example 181. | Ac | 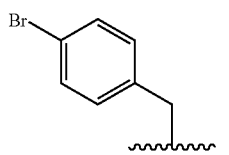 | H | 852, 854 | 205.4, 184.5, 177.6, 169.8, 167.3, 153.4, 136.9, 131.3, 75.1, 74.3, 71.5, 69.0, 63.3, 62.8, 50.4, 40.6, 31.6, 30.6, 25.1, 23.5, 22.6, 21.0, 17.5, 14.8, 14.1, 13.7, 12.6. |

TABLE A1-continued

| Example | Q | -Ar₁-M-Ar₂ | Z | MS (ESI): m/z (M + H)⁺ | $^{13}$C NMR (125 MHz. CDCl$_3$) δ |
|---|---|---|---|---|---|
| Example 182. | Ac | (pyrazine-phenyl) | H | 852 | N/A |
| Example 183. | Ac | (3-bromophenyl) | H | 895, 897 | 205.5, 184.5, 177.7, 169.9, 168.5, 167.5, 153.5, 140.3, 130.8, 130.7, 130.6, 130.0, 129.8, 126.4, 123.2, 102.8, 101.8, 79.0, 76.5, 75.0, 74.9, 74.4, 70.2, 69.5, 65.8, 62.8, 50.5, 47.4, 45.9, 44.2, 40.3, 40.2, 38.5, 34.9, 33.3, 30.8, 28.2, 25.1, 23.5, 21.2, 17.5, 14.8, 14.5, 13.8, 12.5. |
| Example 184. | Ac | (dimethylamino-pyridyl-thiophene) | F | 918 | N/A |
| Example 185. | Ac | (carbamoyl-phenyl-N,N-dihydroxy) | H | 862 | 205.9, 184.9, 177.5, 168.1, 167.0, 155.1, 147.4, 139.1, 133.6, 132.4, 129.9, 123.9, 102.8, 79.5, 79.2, 76.7, 75.7, 72.6, 70.4, 69.5, 66.2, 63.2, 62.9, 60.7, 50.8, 46.3, 40.5, 38.7, 29.9, 28.9, 25.4, 23.8, 21.4, 20.3, 19.7, 17.7, 15.2, 14.1, 12.8. |
| Example 186. | Ac | (bromo-pyridyl-isoxazole) | H | 921 | 205.53, 184.45, 177.74, 169.96, 167.57, 162.00, 154.51, 149.41, 141.94, 139.01, 128.79, 120.30, 102.58, 102.51, 79.19, 78.94, 76.49, 74.40, 70.08, 69.15, 66.52, 66.12, 62.72, 62.41, 50.42, 45.81, 40.26, 38.50, 28.87, 25.10, 23.62, 21.15, 19.95, 19.18, 17.52, 14.85, 13.86, 12.75 |
| Example 187. | Ac | (ethynyl-pyridyl-isoxazole) | H | 867 | 205.48, 184.43, 177.67, 170.41, 167.61, 161.75, 154.70, 150.29, 137.87, 133.77, 128.81, 124.82, 102.70, 102.48, 79.13, 79.00, 76.47, 74.41, 70.15, 69.35, 66.43, 65.91, 62.69, 62.42, 50.40, 45.90, 40.21, 38.46, 30.89, 29.23, 28.44, 25.08, 23.59, 21.18, 19.93, 19.20, 17.49, 14.81, 13.80, 13.31, 12.74 |

TABLE A1-continued

| Example | Q | -Ar₁-M-Ar₂ | Z | MS (ESI): m/z (M + H)⁺ | ¹³C NMR (125 MHz. CDCl₃) δ |
|---|---|---|---|---|---|
| Example 188. | Ac | (3-(pyrimidin-2-yl)phenyl)methyl group | H | 851 | N/A |
| Example 189. | Ac | (6-(methylamino)pyridin-2-yl)thiophen-2-yl)methyl group | F | 904 | N/A |
| Example 190. | Ac | (6-methoxypyridin-2-yl)thiophen-2-yl)methyl group | H | 887 | 205.9, 184.7, 178.1, 167.8, 163.7, 153.8, 150.3, 145.6, 142.2, 139.2, 127.9, 124.1, 111.3, 109.1, 103.0, 79.4, 76.8, 74.5, 71.1, 70.4, 69.6, 66.3, 63.1, 62.9, 53.6, 50.8, 46.1, 40.5, 38.8, 30.0, 28.8, 25.4, 23.8, 21.5, 20.3, 19.5, 17.8, 15.1, 14.2, 13.6, 12.9. |
| Example 191. | H | (6-acetamidopyridin-2-yl)thiophen-2-yl)methyl group | H | 872 | 205.2, 187.9, 169.3, 169.0, 154.5, 151.0, 144.7, 142.9, 139.2, 127.5, 124.5, 114.7, 112.0, 103.6, 80.6, 78.8, 77.8, 76.0, 71.1, 70.6, 69.8, 66.1, 64.7, 63.0, 51.6, 48.1, 41.7, 40.5, 38.3, 35.3, 30.0, 28.5, 25.0, 23.0, 21.5, 21.2, 20.2, 17.3, 16.0, 14.4, 14.1, 11.9. |
| Example 192. | Ac | (5-(thiophen-2-yl)pyridin-2-yl)methyl group | H | 857 | 205.8, 184.7, 178.0, 167.8, 154.0, 152.2, 149.7, 145.0, 137.0, 131.8, 128.2, 127.7, 124.7, 118.6, 103.1, 79.4, 74.6, 73.5, 70.5, 69.8, 66.1, 63.1, 62.8, 50.7, 40.5, 28.5, 25.4, 23.8, 21.5, 19.5, 17.8, 15.1, 14.1, 13.0 |
| Example 193. | Ac | (4-(pyrimidin-2-yl)phenyl)methyl group | H | 852 | 205.8, 184.7, 178.1, 167.8, 164.9, 157.5, 153.6, 141.0, 137.1, 128.3, 119.2, 103.0, 79.4, 76.8, 75.8, 74.6, 63.0, 50.8, 40.5, 38.8, 70.5, 69.8, 66.1, 63.1, 12.9 |

TABLE A1-continued

| Example | Q | -Ar₁-M-Ar₂ | Z | MS (ESI): m/z (M + H)⁺ | ¹³C NMR (125 MHz. CDCl₃) δ |
|---|---|---|---|---|---|
| Example 194. | H | | H | 857 | 204.82, 169.43, 168.98, 166.28, 162.73, 148.03, 147.32, 138.23, 123.11, 121.60, 103.20, 102.74, 80.34, 78.59, 75.61, 70.22, 69.43, 66.51, 65.98, 62.66, 53.92, 51.34, 47.70, 40.25, 28.40, 22.74, 21.18, 20.88, 19.81, 17.10, 14.09, 13.75, 11.63 |
| Example 195. | Ac | | H | 913 | 205.66, 184.49, 177.58, 169.88, 167.64, 162.38, 154.66, 150.06, 147.03, 138.27, 124.01, 122.92, 102.37, 79.06, 76.46, 74.36, 70.13, 69.34, 66.40, 65.94, 62.63, 62.44, 50.47, 46.02, 40.22, 38.45, 35.21, 34.34, 28.51, 25.06, 23.49, 21.15, 19.94, 19.21, 17.46, 15.47, 14.95, 14.80, 13.79, 12.62 |
| Example 196. | H | | H | 871 | 204.90, 169.61, 168.96, 163.60, 162.46, 154.94, 150.06, 146.95, 138.29, 123.97, 122.96, 103.31, 102.46, 80.35, 78.54, 75.61, 70.24, 69.52, 66.45, 65.86, 62.51, 51 35, 47.82, 40.21, 34.33, 28.17, 22.72, 21.16, 20.82, 19.84, 17.09, 15.72, 14.96, 14.06, 13.63, 11.63 |
| Example 197. | H | | H | 816 | 205.1, 169.3, 154.3, 148.8, 148.7, 147.1, 141.4, 141.3, 133.1, 130.7, 128.5, 128.4, 124.1, 123.9, 123.8, 103.5, 80.6, 78.8, 75.9, 70.8, 70.6, 69.8, 66.2, 63.0, 51.7, 48.1, 40.5, 38.3, 28.5, 23.0, 21.5, 21.2, 20.1, 17.4, 16.0, 14.4, 14.0, 11.9. |
| Example 198. | H | | H | N/A | |

TABLE A1-continued
| Example | Q | -Ar₁-M-Ar₂ | Z | MS (ESI): m/z (M + H)⁺ | ¹³C NMR (125 MHz. CDCl₃) δ |
|---|---|---|---|---|---|
| Example 199. | Ac | 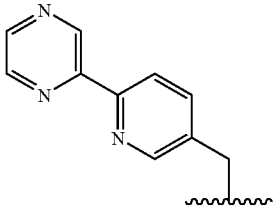 | H | 853 | 205.8, 184.7, 178.0, 167.9, 154.2, 153.7, 151.3, 149.5, 144.6, 143.8, 143.6, 137.1, 134.6, 121.3, 103.1, 79.4, 76.8, 74.7, 73.4, 70.5, 69.8, 66.1, 63.1, 62.8, 50.7, 46.3, 40.5, 38.8, 28.5, 25.4, 23.8, 21.5, 20.3, 19.5, 17.8, 15.1, 14.1, 13.7, 13.0. |
| Example 200. | Ac | 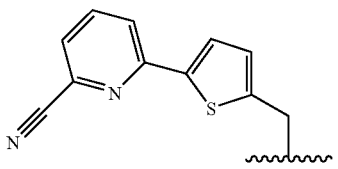 | H | 882 | 205.9, 184.6, 176.5, 169.4, 156.6, 154.6, 144.7, 142.9, 137.7, 133.8, 128.4, 126.5, 126.4, 122.2, 117.5, 102.5, 79.7, 79.1, 76.2, 75.5, 70.9, 70.4, 69.6, 66.4, 58.5, 50.9, 45.4, 40.6, 40.0, 39.1, 36.8, 30.0, 29.0, 25.6, 23.4, 21.6, 20.2, 19.8, 17.3, 15.7, 14.5, 12.9, 12.0. |
| Example 201. | Ac | 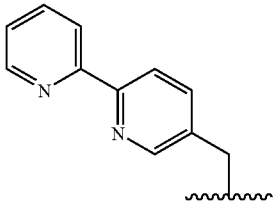 | H | 852 | 205.8, 184.7, 178.0, 167.8 156.3, 155.8, 154.0, 149.4, 149.2, 137.1, 133.7, 123.9, 121.3, 120.9, 103.1, 79.4, 76.8, 74.6, 73.6, 70.5, 69.8, 66.1, 63.1, 50.7, 40.5, 28.5, 25.4, 23.8, 21.5, 19.5, 17.8, 15.1, 14.1, 13.0 |
| Example 202. | H | 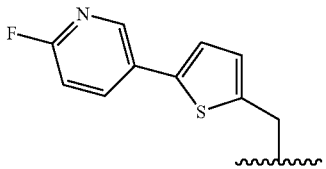 | H | 833 | N/A |
| Example 203. | H | 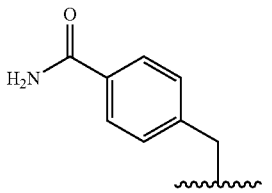 | H | 775 | 205.2, 188.5, 169.5, 169.4, 154.2, 142.1, 133.0, 128.2, 127.8, 103.5, 80.5, 78.8, 78.6, 77.9, 75.9, 75.6, 70.6, 69.8, 66.1, 64.7, 63.0, 51.6, 48.0, 40.5, 31.2, 28.5, 23.0, 21.4, 21.1, 20.0, 17.4, 15.9, 14.3, 14.0, 11.8 |
| Example 204. | H | 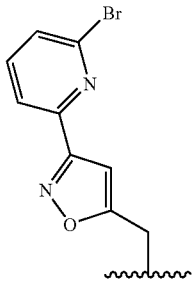 | H | 880 | 204.84, 169.57, 169.01, 162.08, 154.68, 149.35, 141.96, 139.04, 128.85, 120.37, 103.17, 102.78, 80.34, 78.60, 75.60, 70.23, 69.44, 66.54, 65.99, 64.25, 62.67, 51.34, 47.68, 40.25, 38.08, 35.06, 28.41, 22.73, 21.18, 20.87, 19.80, 17.09, 15.57, 14.09, 13.78, 12.63, 11.62 |

TABLE A1-continued

| Example | Q | -Ar₁-M-Ar₂ | Z | MS (ESI): m/z (M + H)⁺ | $^{13}$C NMR (125 MHz. CDCl$_3$) δ |
|---|---|---|---|---|---|
| Example 205. | Ac | (thiophene-pyridine) | H | 858 | 205.8, 184.7, 178.0, 169.5, 167.9, 154.2, 151.0, 149.5, 144.3, 137.2, 134.7, 121.5, 119.5, 103.1, 79.4, 79.2, 76.8, 74.7, 73.4, 70.5, 69.8, 66.1, 63.1, 62.8, 50.7, 46.3, 40.5, 38.8, 28.5, 25.4, 23.9, 21.5, 20.3, 19.5, 17.8, 15.1, 14.1, 13.7, 13.0. |
| Example 206. | H | (thiazole-pyridine) | H | 816 | N/A |
| Example 207. | Ac | (carboxamide-pyridine-isoxazole) | H | 885 | 205.68, 184.54, 177.56, 170.00, 167.59, 162.28, 154.63, 149.44, 147.27, 138.27, 124.27, 123.10, 102.25, 101.99, 79.11, 78.92, 76.41, 74.36, 69.71, 68.49, 66.43, 66.06, 62.61, 62.36, 50.41, 40.29, 38.37, 30.01, 25.05, 23.48, 20.94, 19.89, 19.14, 17.44, 14.76, 13.86, 12.63 |
| Example 208. | Ac | (aminopyridine) | H | 790 | 203.7, 182.6, 175.9, 165.6, 156.3, 151.3, 146.7, 137.0, 121.1, 106.3, 101.0, 77.2, 77.0, 74.6, 73.5, 72.5, 71.7, 68.4, 67.6, 63.9, 61.0, 60.6, 48.6, 44.1, 38.3, 36.7, 35.2, 26.4, 23.2, 21.6, 19.4, 18.2, 17.4, 15.7, 12.9, 12.0, 11.5, 10.7. |
| Example 209. | Ac | (cyanopyridine) | H | 800 | 205.7, 184.7, 177.8, 168.0, 154.9, 150.8, 137.9, 136.5, 133.0, 128.3, 117.5, 103.1, 79.3, 76.7, 72.6, 50.6, 46.4, 40.5, 38.7. |
| Example 210. | Ac | (thiazole-thiophene) | H | 863 | 205.5, 184.4, 177.8, 167.5, 162.0, 153.8, 143.2, 143.0, 137.4, 127.1, 126.1, 117.9, 102.5, 79.2, 78.9, 76.5, 74.3, 70.4, 70.1, 69.2, 66.0, 62.8, 62.6, 50.4, 45.8, 40.2, 38.5, 28.8, 25.1, 23.6, 21.1, 20.0, 19.2, 17.5, 14.8, 13.9, 13.3, 12.7. |
| Example 211. | Ac | (thiazole-phenyl) | F | 875 | Selected data: (205.1, 204.9), 184.0, 168.2, 164.7(d), 153.6, 143.7, 139.8, 132.9, 128.7, 128.3, 126.5, 118.7, 103.9, 99.5, 97.9. |

TABLE A1-continued

| Example | Q | -Ar₁-M-Ar₂ | Z | MS (ESI): m/z (M + H)⁺ | ¹³C NMR (125 MHz. CDCl₃) δ |
|---|---|---|---|---|---|
| Example 212. | H | thiazole-pyridine | F | 833 | Selected data: (204.3, 204.0), 187.4, 165.8, 153.5, 143.7, 139.6, 133.1, 128.5, 126.6, 118.8, 104.1, 99.0, 97.3. |
| Example 213. | H | thiazole-thiophene | H | 821 | 204.9, 187.4, 169.0, 162.0, 154.3, 143.3, 142.7, 137.7, 127.4, 126.1, 118.1, 103.4, 80.3, 78.7, 78.6, 75.6, 70.5, 70.3, 69.6, 65.9, 64.4, 62.8, 51.4, 47.8, 40.3, 38.1, 28.2, 22.8, 21.2, 20.9, 19.9, 17.1, 15.7, 14.1, 13.7, 11.7. |
| Example 214. | Ac | pyrazole-pyridine | F | 859 | 205.1, 204.9, 183.9, 176.7, 164.9, 164.7, 154.0, 151.1, 147.8, 142.0, 138.9, 131.0, 127.0, 112.0, 107.1, 103.9, 99.5, 97.9, 79.4, 76.3, 73.4, 73.0, 70.4, 69.6, 65.8, 62.9, 62.4, 41.1, 40.2, 38.8, 37.2, 30.9, 28.2, 25.1, 24.4, 24.2, 23.0, 21.2, 20.7, 17.2, 14.8, 14.7, 14.1, 12.5 |
| Example 215. | Ac | pyrazole-pyridine | H | 841 | 205.8, 184.7, 178.0, 167.8, 154.0, 151.3, 148.2, 142.2, 139.2, 131.3, 127.3, 112.2, 107.9, 103.1, 79.3, 79.2, 76.8, 75.5, 74.6, 73.2, 70.5, 69.8, 66.1, 63.1, 62.8, 50.7, 46.2, 40.5, 38.8, 37.2, 28.5, 25.4, 23.8, 21.5, 20.2, 19.5, 17.8, 15.1, 14.1, 13.7, 13.0. |
| Example 216. | Ac | H₂N-pyridine | F | 808 | Selected: 205.3, 205.1, 184.1, 158.4, 153.5, 148.7, 139.0, 123.2, 108.4, 104.2, 99.7, 98.1, 79.6, 76.5, 74.0, 73.6, 70.6, 69.9, 66.0, 63.1, 62.7, 41.3, 40.5, 28.4, 25.3, 24.6, 24.4, 23.2, 21.4, 21.0, 17.4, 15.0, 14.3, 12.7 |
| Example 217. | Ac | Br, dimethoxyphenyl-isoxazole | H | 979 | 205.5, 184.4, 177.7, 168.3, 167.5, 159.0, 154.3, 152.3, 148.8, 128.0, 126.0, 114.5, 113.6, 105.0, 102.7, 79.1, 78.9, 76.4, 74.2, 70.1, 69.4, 66.8, 65.8, 62.6, 62.4, 61.7, 56.0, 50.4, 45.9, 40.1, 38.4, 28.3, 25.0, 23.5, 21.1, 19.9, 19.1, 17.4, 14.7, 13.7, 13.3, 12.8, |

TABLE A1-continued
| Example | Q | -Ar₁-M-Ar₂ | Z | MS (ESI): m/z (M + H)⁺ | ¹³C NMR (125 MHz. CDCl₃) δ |
|---|---|---|---|---|---|
| Example 218. | Ac | 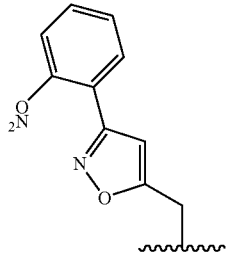 | H | 886 | N/A |
| Example 219. | Ac | 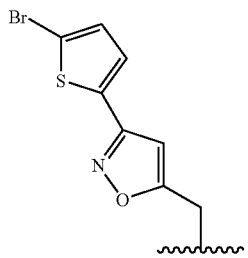 | H | 927 | 205.61, 184.49, 177.64, 169.80, 167.64, 156.83, 154.72, 130.37, 127.62, 114.93, 102.60, 101.03, 79.17, 76.47, 74.47, 70.11, 69.26, 66.47, 66.10, 62.68, 62.43, 53.41, 50.44, 45.90, 40.26, 38.48, 28.70, 25.11, 23.59, 21.16, 19.94, 19.20, 17.50, 14.84, 13.84, 13.31, 12.74 |
| Example 220. | Ac | 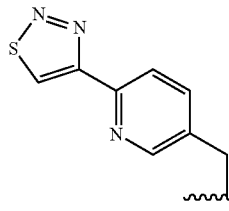 | F | 876 | 204.1, 203.9, 183.0, 161.7, 152.6, 138.2, 129.1, 128.9, 127.5, 126.3, 102.9, 98.5, 96.9, 78.4, 72.4, 69.4, 68.6, 64.8, 61.4, 40.0, 39.2, 27.1, 24.1, 23.4, 23.2, 21.9, 20.2, 19.8, 16.1, 13.7, 13.1, 11.4, |
| Example 221. | Ac | 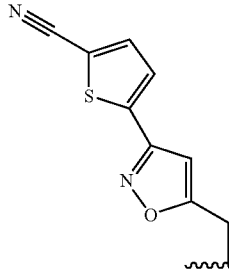 | H | 872 | 205.63, 184.51, 177.58, 170.82, 167.69, 156.01, 155.00, 131.90, 127.11, 113.71, 111.05, 102.55, 101.54, 79.18, 76.46, 74.51, 70.06, 69.18, 66.34, 69.18, 66.34, 62.41, 50.44, 45.93, 40.28, 38.47, 25.12, 23.59, 21.15, 19.94, 19.21, 17.51, 14.84, 13.84, 12.76 |
| Example 222. | Ac | 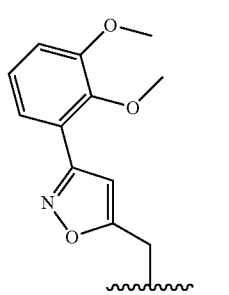 | H | 901 | 205.7, 184.5, 177.8, 168.4, 167.5, 159.8, 154.2, 153.2, 147.5, 124.4, 123.4, 121.0, 113.7, 104.6, 101.9, 79.3, 76.5, 74.4, 69.8, 68.4, 66.6, 60.9, 55.9, 50.5, 45.6, 40.1, 38.5, 34.6, 30.1, 29.7, 25.1, 23.6, 21.0, 19.9, 19.1, 17.5, 14.9, 13.9, 12.8, 6.6, 5.8, |
| Example 223. | Ac | 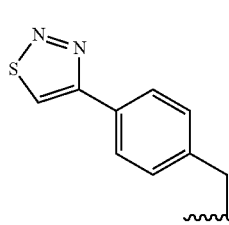 | H | 858 | 204.6, 183.5, 176.7, 166.6, 161.7, 152.4, 138.4, 129.0, 128.9, 127.6, 126.3, 101.8, 78.1, 75.5, 74.4, 73.4, 69.2, 68.5, 64.8, 61.9, 61.7, 49.5, 45.0, 39.2, 37.5, 27.2, 24.1, 22.6, 20.2, 19.0, 18.3, 16.5, 13.9, 12.8, 12.4, 11.7, |

TABLE A1-continued
| Example | Q | -Ar₁-M-Ar₂ | Z | MS (ESI): m/z (M + H)⁺ | $^{13}$C NMR (125 MHz. CDCl₃) δ |
|---|---|---|---|---|---|
| Example 224. | Ac | 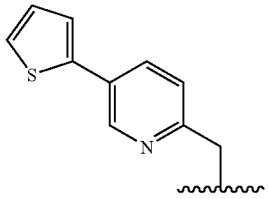 | H | 857 | 205.4, 184.4, 177.6, 169.7, 167.3, 153.1, 144.2, 137.1, 133.7, 132.0, 128.4, 127.9, 125.8, 124.6, 123.0, 100.3, 79.2, 76.4, 75.5, 74.3, 71.5, 69.0, 63.3, 62.8, 50.4, 40.6, 38.3, 30.5, 25.0, 23.5, 22.6, 21.3, 21.0, 17.4, 14.8, 14.1, 13.7, 12.6. |
| Example 225. | Ac | 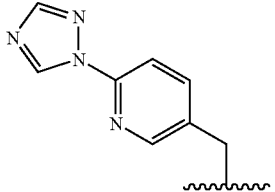 | H | 842 | 205.8, 184.7, 177.9, 167.9, 054.3, 153.0, 149.1, 148.5, 141.8, 139.6, 133.3, 112.8, 103.1, 79.3, 79.2, 76.8, 74.7, 72.9, 70.5, 69.8, 66.1, 63.1, 62.8, 50.7, 46.3, 40.5, 38.7, 28.5, 25.4, 23.8, 21.5, 20.2, 19.5, 17.8, 15.1, 14.1, 13.7, 13.0 |
| Example 226. | Ac | 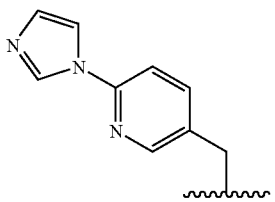 | H | 841 | 205.8, 184.7, 177.9, 167.9, 154.3, 149.3, 148.8, 139.5, 135.2, 132.2, 130.9, 116.4, 112.1, 103.1, 79.3, 79.2, 76.8, 75.6, 74.7, 72.8, 70.5, 69.8, 66.1, 63.1, 62.8, 50.7, 46.3, 40.5, 38.7, 37.2, 28.5, 25.4, 23.8, 21.5, 20.2, 19.5, 17.8, 15.1, 14.1, 13.7, 13.0. |
| Example 227. | Ac | 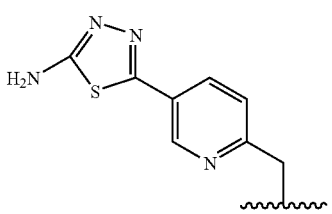 | H | 873 | 205.61, 184.52, 177.70, 167.61, 159.73, 153.56, 140.14, 129.94, 128.25, 126.88, 102.69, 79.11, 78.95, 75.21, 74.47, 70.18, 69.35, 65.88, 62.80, 62.67, 50.80, 50.52, 46.03, 40.21, 38.51, 28.47, 25.10, 23.54, 21.17, 20.04, 19.28, 17.52, 14.84, 13.83, 13.47, 12.62 |
| Example 228. | Ac | 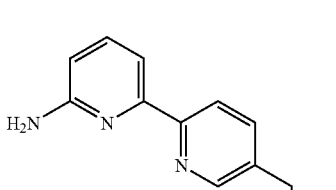 | H | 867 | 205.8, 184.7, 178.0, 167.8, 158.2, 156.1, 154.8, 153.9, 149.2, 138.8, 136.9, 133.2, 120.8, 111.9, 109.0, 103.1, 79.4, 79.2, 76.8, 75.9, 74.6, 73.6, 70.5, 69.8, 66.1, 63.1, 62.8, 50.7, 46.2, 40.5, 38.8, 28.5, 25.4, 23.8, 21.5, 20.3, 19.5, 17.8, 15.1, 14.1, 13.7, 13.0. |
| Example 229. | Ac | 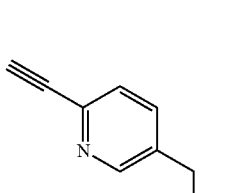 | H | 799 | 205.8, 184.7, 177.9, 167.8, 154.2, 150.0, 141.7, 136.2, 133.6, 127.2, 103.1, 83.0, 79.3, 76.7, 74.7, 73.2, 70.5, 69.8, 66.1, 63.0, 62.8, 50.7, 46.3, 40.5, 38.8, 28.5, 25.4, 23.8, 21.5, 20.2, 19.5, 17.8, 15.1, 14.1, 13.7, 13.0. |
| Example 230. | H | 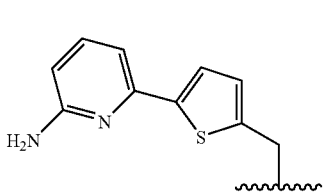 | F | 849 | N/A |

TABLE A1-continued

| Example | Q | -Ar₁-M-Ar₂ | Z | MS (ESI): m/z (M + H)⁺ | ¹³C NMR (125 MHz. CDCl₃) δ |
|---|---|---|---|---|---|
| Example 231. | H | (2-amino-pyridin-6-yl)-pyridin-5-yl- group | H | 825 | N/A |
| Example 232. | Ac | 6-amino-pyridin-2-yl- group | H | 790 | N/A |
| Example 233. | Ac | 2-(pyrimidin-2-yl)-imidazol-4-yl- group | H | 842 | N/A |
| Example 234. | Ac | 2-amino-1,3,4-thiadiazol-5-yl- group | H | 797 | 205.60, 184.52, 177.70, 169.21, 167.48, 157.86, 154.78, 102.77, 79.04, 76.44, 74.37, 70.21, 70.17, 69.36, 65.87, 62.65, 62.46, 50.47, 46.05, 40.20, 38.26, 29.66, 28.47, 25.10, 23.52, 21.20, 20.00, 19.26, 17.49, 14.81, 13.83, 13.44, 12.70 |
| Example 235. | Ac | 2-amino-1,3,4-thiadiazol-5-yl-pyridin-5-yl- group | H | 874 | 205.64, 184.49, 177.63, 167.60, 153.94, 149.06, 148.90, 136.74, 134.40, 119.56, 109.74, 102.27, 79.18, 76.50, 74.48, 72.98, 69.95, 68.88, 66.44, 62.81, 62.52, 50.45, 45.77, 40.33, 38.53, 25.13, 23.58, 21.08, 19.96, 19.20, 17.55, 14.86, 13.90, 13.28, 12.71 |
| Example 236. | Ac | 6-amino-pyridin-2-yl-alkynyl group | H | 814 | 205.8, 184.8, 178.1, 167.7, 158.4, 154.1, 140.9, 137.9, 117.9, 108.9, 103.0, 85.8, 84.4, 79.6, 79.2, 76.8, 74.5, 70.5, 69.7, 66.1, 63.0, 62.8, 62.5, 50.7, 46.1, 40.5, 38.8, 28.5, 25.4, 24.0, 21.5, 20.3, 19.5, 17.8, 15.1, 14.1, 13.6, 13.1. |
| Example 237. | Ac | 3-bromo-6-amino-pyridin-2-yl- group | H | 868 | N/A |

TABLE A1-continued

| Example | Q | -Ar₁-M-Ar₂ | Z | MS (ESI): m/z (M + H)⁺ | $^{13}$C NMR (125 MHz. CDCl₃) δ |
|---|---|---|---|---|---|
| Example 238. | Ac | | H | 872 | 205.8, 184.8, 178.0, 167.7, 156.7, 155.6, 153.8, 140.1, 138.9, 128.0, 126.1, 125.8, 113.6, 112.4, 102.9, 79.3, 79.2, 76.7, 76.5, 75.0, 70.5, 69.7, 66.1, 63.1, 50.8, 46.1, 40.5, 38.8, 28.5, 25.4, 23.8, 21.5, 20.3, 19.6, 17.7, 15.2, 14.2, 13.6, 12.8. |
| Example 239. | Ac | | H | 816 | 205.9, 184.8, 178.0, 167.7, 156.3, 155.4, 153.7, 135.6, 132.0, 117.4, 116.9, 112.9, 110.0, 102.9, 79.3, 79.2, 76.7, 76.6, 74.9, 70.5, 69.7, 66.1, 63.1, 50.8, 46.1, 40.5, 38.8, 28.5, 25.4, 23.8, 21.5, 20.3, 19.6, 17.7, 15.2, 14.2, 13.6, 12.8. |
| Example 240. | Ac | | H | 816 | N/A |
| Example 241. | Ac | | H | 814 | N/A |
| Example 242. | Ac | | H | 855 | 205.8, 184.7, 178.0, 167.8, 153.9, 151.4, 148.1, 143.2,, 139.2, 130.8, 125.8, 118.6, 11.8, 103.1, 79.3, 79.2, 77.6, 77.5, 77.3, 77.0, 76.8, 74.6, 73.2, 70.5, 69.7, 66.1, 63.1, 62.8, 50.7, 46.2, 40.5, 38.8, 28.5, 25.4, 23.8, 21.5, 20.3, 19.5, 17.8, 15.1, 14.1, 13.6, 13.0, 9.3. |
| Example 243. | Ac | | H | 818 | N/A |
| Example 244. | Ac | | H | 842 | 205.6, 184.4, 177.6, 167.6, 154.1, 148.6, 148.2, 139.2, 102.7, 79.1, 76.5, 74.4, 72.6, 70.1, 69.3, 66.0, 62.8, 62.5, 50.4, 46.0, 40.2, 38.5, 31.5, 28.6, 25.1, 23.5, 22.6, 21.2, 19.9, 19.2, 17.5, 14.8, 14.1, 13.8, 13.4, 12.7. |

TABLE A1-continued

| Example | Q | -Ar₁-M-Ar₂ | Z | MS (ESI): m/z (M + H)⁺ | ¹³C NMR (125 MHz. CDCl₃) δ |
|---|---|---|---|---|---|
| Example 245. | Ac | (5-hydroxy-1,3,4-thiadiazol-2-yl pyridine) | H | 874 | 205.60, 184.57, 177.70, 171.97, 167.62, 153.60, 153.04, 141.16, 129.92, 128.23, 125.88, 102.60, 79.15, 78.91, 76.49, 75.09, 74.55, 62.68, 50.48, 45.92, 40.21, 38.51, 28.63, 25.12, 23.55, 21.17, 20.00, 19.26, 17.52, 14.88, 13.86, 13.37, 12.65 |
| Example 246. | Ac | (1,3,4-thiadiazol-2-yl pyridine) | H | 858 | 205.58, 184.50, 177.67, 168.20, 167.57, 153.61, 151.03, 141.67, 128.46, 128.08, 102.60, 79.14, 78.90, 76.48, 75.11, 74.45, 70.14, 69.29, 66.02, 62.82, 62.65, 50.47, 40.25, 38.52, 28.60, 25.11, 23.56, 21.17, 19.99, 19.24, 17.51, 14.86, 13.85, 13.35, 12.67 |
| Example 247. | Ac | (4-iodo-pyrazolyl pyridine) | H | 967 | 205.6, 184.5, 177.7, 167.6, 153.8, 150.2, 147.9, 146.6, 139.1, 131.7, 131.6, 111.5, 102.6, 79.1, 76.5, 74.4, 72.8, 70.1, 69.2, 66.1, 62.8, 62.5, 59.6, 50.4, 45.9, 40.3, 38.5, 31.6, 28.7, 25.1, 23.5, 22.6, 21.2, 19.9, 19.2, 17.5, 14.9, 14.1, 13.8, 13.4, 12.7, |
| Example 248. | Ac | (3-methyl-pyrazolyl pyridine) | H | 855 | 205.4, 184.3, 176.7, 167.5, 153.6, 151.5, 151.0, 147.8, 138.8, 130.3, 127.6, 111.5, 107.8, 102.7, 79.0, 76.4, 74.3, 72.9, 70.1, 69.4, 65.8, 62.8, 62.4, 50.3, 45.9, 40.1, 38.4, 31.5, 28.2, 25.1, 23.5, 22.5, 21.1, 19.9, 19.2, 17.5, 14.8, 14.0, 13.8, 13.7, 13.3, 12.6, |
| Example 249. | Ac | (3-trifluoromethyl-pyrazolyl pyridine) | H | 909 | 205.6, 184.5, 177.6, 167.6, 153.9, 150.2, 147.9, 139.1, 132.5, 128.4, 112.4, 105.8, 102.6, 79.1, 78.9, 76.5, 75.4, 74.4, 72.7, 70.1, 69.2, 66.1, 62.8, 62.5, 50.4, 45.9, 40.2, 38.5, 31.6, 28.8, 25.1, 23.5, 22.6, 21.2, 20.0, 19.2, 17.5, 14.8, 14.1, 13.9, 13.3, 12.7, |
| Example 250. | Ac | (4-vinyl-pyrazolyl pyridine) | H | 867 | 205.6, 184.5, 177.7, 167.5, 153.7, 150.8, 147.9, 139.9, 139.0, 131.0, 126.4, 124.3, 122.8, 113.4, 111.8, 102.3, 79.1, 76.5, 74.4, 72.9, 69.9, 68.9, 66.3, 62.8, 62.5, 50.4, 45.8, 40.3, 38.5, 31.6, 29.3, 25.1, 23.5, 22.6, 21.1, 20.0, 19.2, 17.5, 14.8, 14.1, 13.9, 13.3, 12.7, |

TABLE A1-continued

| Example | Q | -Ar₁-M-Ar₂ | Z | MS (ESI): m/z (M + H)⁺ | ¹³C NMR (125 MHz, CDCl₃) δ |
|---|---|---|---|---|---|
| Example 251. | Ac | (4-cyano-pyrazol-1-yl)-pyridinyl | H | 866 | 205.6, 184.5, 177.6, 167.6, 154.0, 149.5, 148.2, 143.5, 139.3, 133.1, 132.1, 113.1, 112.5, 102.3, 94.4, 79.1, 76.5, 74.5, 72.6, 69.9, 68.9, 66.3, 62.8, 62.5, 50.4, 45.9, 40.3, 38.5, 31.6, 29.3, 25.1, 23.5, 22.6, 21.1, 19.9, 19.2, 17.5, 14.8, 13.9, 13.3, 12.7, |
| Example 252. | Ac | pyrazol-1-yl-pyrimidinyl | H | 842 | 205.7, 184.7, 177.9, 167.9, 159.4, 155.8, 154.6, 143.8, 129.4, 128.5, 108.8, 103.1, 79.3, 79.2, 76.8, 74.7, 70.7, 70.5, 69.7, 66.2, 63.0, 62.7, 60.6, 50.7, 46.3, 40.5, 38.7, 28.7, 25.4, 23.8, 21.5, 21.3, 20.2, 19.5, 17.8, 15.1, 14.5, 14.1, 13.7, 13.1. |
| Example 253. | Ac | (dimethylaminomethyleneamino)-triazolyl-pyridinyl | H | 912 | 205.8, 184.7, 178.0, 168.3, 167.9, 157.5, 154.1, 149.3, 148.2, 140.9, 139.6, 132.0, 112.3, 103.1, 79.3, 76.8, 74.7, 73.1, 70.5, 69.7, 66.1, 63.1, 62.8, 54.0, 50.7, 46.3, 41.0, 40.5, 38.8, 34.9, 29.5, 28.5, 25.4, 23.8, 21.5, 20.3, 19.5, 17.8, 15.1, 14.1, 13.7, 13.0. |
| Example 254. | Ac | (5-bromothien-2-yl)-pyrazolyl-pyridinyl | H | 1003 | 205.85, 184.53, 177.72, 167.64, 153.73, 150.67, 148.09, 147.87, 138.99, 138.83, 137.85, 131.16, 130.27, 128.38, 124.57, 112.18, 111.95, 104.81, 102.08, 79.16, 78.78 76.48, 76.24, 74.51, 72.90, 71.97, 67.71, 62.76, 62.48, 59.22, 52.00, 50.40, 45.82, 38.50, 34.91, 25.12, 23.55, 20.97, 20.69, 19.89, 19.15, 17.56, 14.87, 13.74, 13.71, 13.21, 12.69 |
| Example 255. | Ac | thien-2-yl-pyrazolyl-pyridinyl | H | 923 | 205.84, 184.52, 177.73, 167.64, 153.70, 150.81, 148.92, 147.86, 138.93, 136.20, 130.95, 128.25, 127.46, 125.20, 124.60, 111.98, 105.28, 102 08, 79.15, 78.77, 76.48, 76.22, 74.50, 72.93, 71.98, 67.71, 62.76, 62.47, 59.30, 51.91, 50.39, 45.81, 38.50, 34.93, 25.12, 23.54, 20.97, 19.88, 19.15, 17.56, 14.86, 13.73, 13.21, 12.68 |
| Example 256. | Ac | pyrimidinyl-(2-amino)pyridinyl | H | 868 | Selected data: 206.1, 184.9, 177.9, 167.7, 153.9, 143.5, 142.1, 141.7, 137.0, 111.3, 102.0. |

TABLE A1-continued
| Example | Q | -Ar₁-M-Ar₂ | Z | MS (ESI): m/z (M + H)⁺ | $^{13}$C NMR (125 MHz. CDCl₃) δ |
|---|---|---|---|---|---|
| Example 257. | H | 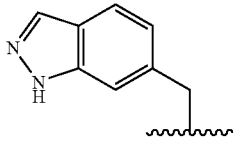 | H | 772 | 205.2, 169.5, 154.0, 140.4, 136.5, 134.3, 123.0, 121.1, 120.9, 109.9, 103.4, 80.4, 78.8, 78.3, 76.6, 75.9, 70.5, 69.7, 66.1, 64.9, 63.1, 51.6, 47.8, 41.2, 40.5, 38.3, 35.3, 28.5, 23.0, 21.4, 21.2, 19.9, 17.4, 15.7, 14.4, 14.1, 11.9. |
| Example 258. | Ac | 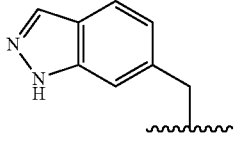 | H | 814 | 205.9, 184.8, 178.0, 167.9, 153.7, 140.4, 137.3, 134.8, 122.9, 121.5, 120.8, 109.1, 102.9, 79.4, 79.2, 76.8, 76.3, 74.9, 70.4, 69.6, 66.2, 63.1, 63.0, 50.8, 46.2, 40.5, 38.8, 28.9, 25.4, 23.8, 21.4, 20.3, 19.6, 17.9, 15.2, 14.2, 13.7, 12.9. |
| Example 259. | Ac | 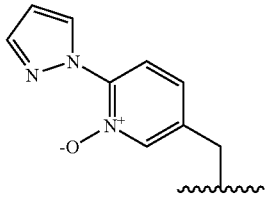 | H | 857 | 205.7, 184.7, 178.0, 167.9, 154.9, 142.4, 140.1, 133.6, 133.1, 127.2, 119.7, 107.5, 103.1, 79.3, 76.8, 74.7, 72.0, 70.5, 69.8, 66.1, 63.0, 62.7, 19.5, 17.8, 15.1, 14.0, 13.7, 13.0. |
| Example 260. | Ac | 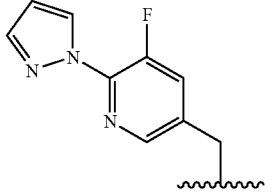 | H | 859 | N/A |
| Example 261. | —COCH₂CH₃ | 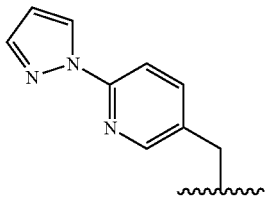 | H | 855 | 205.5, 187.7, 178.1, 167.5, 153.8, 151.1, 147.9, 141.9, 139.0, 131.1, 127.0, 111.9, 107.6, 102.9, 79.1, 76.5, 74.3, 72.9, 70.2, 69.5, 65.8, 62.8, 62.5, 50.4, 46.0, 40.2, 38.6, 31.6, 31.0, 28.2, 23.5, 22.6, 21.2, 20.1, 19.2, 17.5, 14.9, 14.1, 13.8, 13.4, 12.7, 8.6 |
| Example 262. | Ac | 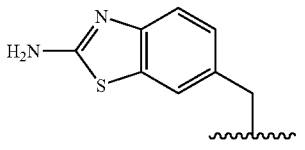 | H | 846 | N/A |
| Example 263. | Ac | 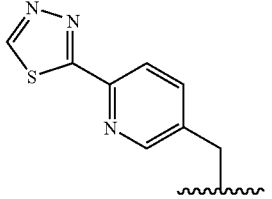 | H | 859 | 205.50, 184.42, 177.59, 170.17, 167.61, 154.15, 153.29, 149.42, 147.88, 135.95, 135.78, 120.77, 102.71, 79.07, 78.93, 76.47, 74.43, 72.79, 70.14, 69.34, 65.87, 62.73, 62.50, 50.39, 45.98, 40.17, 38.45, 29.64, 28.43, 25.08, 23.53, 21.16, 19.93, 19.21, 17.49, 14.79, 13.78, 13.37, 12.71 |

Example compounds 264–338 of formula A2:

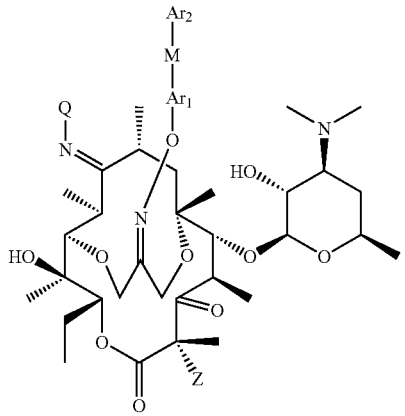

wherein $Ar_1$, $Ar_2$, M, Q, and Z are as delineated for each example in Table A2.

Example compounds 264–338, where Z=H, are made from the title compound of Example 3 and the appropriate hydroxylamine of formula $Ar_2$—M—$Ar_1$—O—$NH_2$ via the method delineated in Example 4.

Example compounds 264–338, where Z=F, are made from the title compound of Example 46 and the appropriate hydroxylamine of formula $Ar_2$—M—$Ar_1$—O—$NH_2$ via the method delineated in Example 4.

The Examples described in Table A2 are single isomers of the E designation, which are separated from the E/Z mixture via silica chromatography or HPLC.

The substituted hydroxylamines used in the following examples are either commercially available or can be made from readily-available starting materials via synthetic methods well known by one of ordinary skill in the art.

TABLE A2.

| Example | Q | —$Ar_1$—M—$Ar_2$ | Z | MS (ESI): m/z (M + H)⁺ | $^{13}C$ NMR (125 MHz, $CDCl_3$): δ |
|---|---|---|---|---|---|
| Example 264. | Ac | | H | 857 | 205.7, 184.6, 176.6, 167.7, 153.9, 152.8, 149.7, 145.2, 142.5, 136.8, 127.8, 124.4, 122.0, 118.5, 102.5, |
| Example 265. | Ac | | H | 857 | N/A |
| Example 266. | Ac | | H | 858 | N/A |
| Example 267. | Ac | | H | 780 | N/A |
| Example 268. | Ac | | H | 871 | 205.7, 184.5, 176.2, 169.5, 155.7, 153.0, 149.7, 148.6, 144.0, 136.7, 126.1, 124.4, 121.9, 118.9, 102.2, 79.7, 79.1, 78.7, 76.2, 75.8, 71.5, 70.2, 69.2, 66.7, 59.0, 50.8, 45.3, 40.6, 39.1, 29.9, 25.6, 23.4, 21.5, 20.3, 19.8, 17.1, 15.8, 14.6, 12.7, 11.9. |
| Example 269. | Ac | | H | 871 | 205.9, 184.7, 177.2, 169.0, 155.5, 153.0, 149.7, 149.0, 143.9, 136.8, 125.9, 124.4, 121.9, 118.8, 102.4, 79.4, 79.1, 77.7, 76.3, 70.3, 70.0, 69.4, 66.4, 58.0, 50.8, 45.1, 40.6, 39.0, 29.9, 25.4, 23.4, 21.9, 21.5, 20.4, 19.7, 17.3, 15.5, 14.5, 12.8, 12.1. |

TABLE A2.-continued

| Example | Q | —Ar₁—M—Ar₂ | Z | MS (ESI): m/z (M + H)⁺ | ¹³C NMR (125 MHz, CDCl₃): δ |
|---|---|---|---|---|---|
| Example 270. | Ac | thiophene-carboxamide | H | 823 | 206.1, 184.6, 176.5, 169.3, 164.0, 157.0, 146.2, 137.4, 129.9, 127.3, 102.5, 79.7, 79.0, 76.2, 75.2, 70.7, 70.5, 70.3, 69.8, 66.1, 58.4, 54.0, 50.9, 45.4, 40.5, 39.0, 36.8, 32.0, 29.5, 28.5, 25.5, 23.3, 21.6, 20.1, 19.7, 17.2, 15.7, 14.4, 12.9, 12.0 |
| Example 271. | Ac | benzyl | H | 774 | 205.9, 184.6, 176.7, 169.3, 155.9, 137.9, 128.6, 128.5, 128.0, 102.5, 79.6, 79.0, 76.6, 76.2, 75.4, 70.4, 66.2, 58.4, 50.9, 45.3, 40.5, 39.0, 28.7, 25.5, 23.4, 21.5, 20.2, 19.7, 17.2, 15.6, 14.4, 12.8, 12.0. |
| Example 272. | Ac | quinolinyl | F | 843 | 204.6, 184.0, 165.8, 157.1, 149.6, 146.2, 136.5, 136.3, 128.4, 128.2, 127.1, 126.8, 121.1, 104.0, 80.0, 79.2, 79.1, 74.4, 72.8, 70.6, 69.9, 68.2, 66.1, 57.0, 41.2, 40.5, 39.5, 28.4, 25.3, 24.4, 22.8, 21.8, 21.5, 21.0, 17.3, 15.2, 14.1, 11.8. |
| Example 273. | Ac | pyridyl-thiophene | H | 857 | 205.8, 201.1, 184.6, 176.5, 169.4, 156.4, 154.5, 150.1, 149.7, 139.8, 138.1, 136.8, 128.5, 125.3, 123.4, 121.8, 102.6, 79.7, 79.0, 77.8, 76.2, 75.4, 70.8, 70.5, 70.2, 69.7, 66.1, 58.6, 50.9, 45.4, 40.5, 39.5, 39.0, 36.8, 28.5, 25.5, 23.4, 21.6, 20.2, 19.8, 17.2, 15.7, 14.5, 12.9, 12.0. |
| Example 274. | Ac | thiophene-pyrimidine | F | 876 | Selected data: 204.4(d), 184.0, 165.6, 161.8, 157.4, 157.1, 145.1, 143.5, 128.9, 128.4, 103.7. |
| Example 275. | Ac | thiophene-pyrazine | F | 876 | (204.4, 204.2), 183.8, 176.4, (165.6, 165.4), 157.1, 148.7, 144.0, 143.9, 142.2, 141.4, 140.5, 128.3, 125.7, 103.7, (99.4, 97.8), 80.3, 79.6, 79.0, 75.9, 74.1, 70.6, 70.4, 69.6, 67.9, 65.8, 56.2, 53.8, 41.0, 40.2, 39.0, 29.7, 29.3, 28.2, 25.1, (24.1, 23.9), 22.6, 21.3, 21.2, 20.7, 17.0, 14.9, 14.0, 11.6. |
| Example 276. | Ac | thiophene-pyridyl-NHAc | H | 914 | 206.1, 184.7, 176.5, 169.3, 156.3, 151.1, 151.0, 144.8, 142.6, 139.2, 128.2, 124.6, 114.8, 111.9, 102.0, 79.6, 79.1, 76.2, 75.6, 71.1, 70.6, 70.1, 69.0, 66.9, 58.5, 50.9, 45.2, 40.6, 39.1, 29.9, 25.5, 25.1, 23.4, 21.4, 20.2, 19.7, 17.2, 15.7, 14.6, 12.8, 12.0. |

TABLE A2.-continued

| Example | Q | —Ar₁—M—Ar₂ | Z | MS (ESI): m/z (M + H)⁺ | ¹³C NMR (125 MHz, CDCl₃): δ |
|---|---|---|---|---|---|
| Example 277. | Ac | (5-substituted thiophene-2-carboxamide, N-benzyl) | H | 913 | 205.7, 184.3, 176.2, 169.1, 161.8, 156.6, 145.0, 138.1, 128.7, 128.66, 127.9, 127.6, 127.1, 102.3, 79.4, 78.8, 76.0, 75.0, 70.5, 70.2, 70.1, 69.4, 65.9, 58.1, 50.7, 45.1, 44.0, 40.2, 39.4, 38.8, 36.6, 29.7, 28.4, 25.2, 23.1, 21.3, 19.9, 19.4, 17.0, 15.4, 14.2, 12.6, 11.7 |
| Example 278. | Ac | (4-substituted benzamide) | H | 817 | N/A |
| Example 279. | Ac | (4-substituted benzamide) | F | 835 | 204.8, 184.1, 169.5, 165.8 165.7, 157.4, 142,3, 132.7, 128.4, 128.3, 127.6, 104.0, 79.3, 75.7, 70.6, 69.8, 66.1, 56.4, 41.2, 40.5, 28.5, 25.4, 22.8, 21.5, 20.9, 17.3, 15.2, 14.2, 11.9 |
| Example 280. | Ac | (5-substituted thiophene-2-carboxamide, N-2-pyridyl) | H | 900 | 205.8, 184.5, 176.4, 169.3, 160.2, 156.9, 151.6, 148.1, 147.1, 138.7, 138.6, 129.2, 127.7, 120.1, 114.1, 102.6, 79.7, 79.0, 76.2, 75.3, 70.6, 70.5, 70.4, 69.7, 66.1, 58.3, 50.9, 45.4, 41.2, 40.5, 39.6, 39.0, 36.7, 28.5, 25.5, 21.6, 20.1, 19.7, 17.2, 15.7, 14.4, 12.9, 12.0. |
| Example 281. | Ac | (5-substituted thiophene-2-carboxamide, N-phenyl) | H | 899 | N/A |
| Example 282. | Ac | (5-substituted thiophene-2-carbaldehyde) | H | 808 | 205.6, 184.3, 183.0, 176.0, 169.1, 156.9, 151.2, 143.6, 136.2, 127.5, 102.3, 79.5, 78.7, 75.9, 75.1, 70.5, 70.2, 69.5, 65.9, 58.1, 50.6, 45.2, 40.2, 38.8, 28.3, 25.3, 23.1, 21.3, 19.8, 19.4, 16.9, 15.4, 14.2, 12.7, 11.7 |
| Example 283. | Ac | (4-substituted benzamide, N-phenyl) | H | 893 | Selected data: 206.0, 184.6, 176.3, 169.4, 165.9, 156.6, 142.2, 138.3, 134.5, 129.3, 128.5, 127.3, 124.7, 120.4, 102.5, 79.7, 79.1. |

TABLE A2.-continued
| Example | Q | —Ar₁—M—Ar₂ | Z | MS (ESI): m/z (M + H)⁺ | ¹³C NMR (125 MHz, CDCl₃): δ |
|---|---|---|---|---|---|
| Example 284. | Ac | 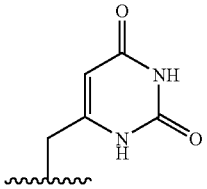 | H | 808 | Selected data: 205.9, 185.9, 174.7, 170.0, 158.7, 151.0, 145.7, 102.5, 98.8. |
| Example 285. | Ac | 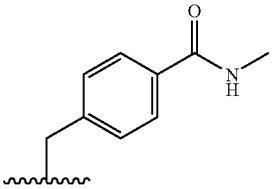 | H | 831 | 205.9, 184.6, 177.5, 169.3, 168.4, 156.5, 141.6, 134.1, 128.3, 127.0, 102.7, 79.7, 76.2, 75.8, 70.5, 69.8, 66.1, 58.4, 50.9, 45.4, 40.5, 39.7, 39.0, 28.5, 28.5, 27.1, 25.5, 23.4, 21.6, 20.2, 19.7, 17.2, 15.6, 14.4, 13.0, 12.0, |
| Example 286. | Ac | 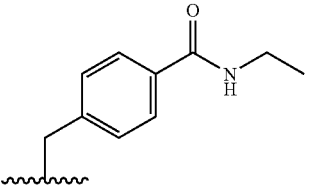 | H | 845 | 205.9, 184.6, 176.5, 169.3, 167.6, 156.4, 141.5, 134.3, 128.3, 127.0, 102.6, 79.7, 79.0, 76.2, 75.4, 70.5, 69.7, 66.1, 58.4, 50.9, 45.4, 40.5, 39.6, 39.0, 36.8, 35.1, 28.5, 25.5, 23.4, 21.6, 20.2, 19.7, 17.2, 15.6, 15.2, 14.4, 13.0, 12.0 |
| Example 287. | Ac | 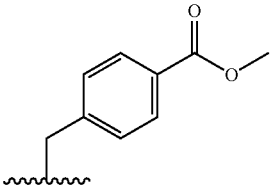 | H | 832 | 204.6, 183.5, 176.7, 166.6, 166.0, 152.6, 142.3, 128.5, 128.2, 126.4, 101.8, 78.1, 78.0, 75.5, 74.2, 73.4, 69.2, 68.5, 64.8, 61.8, 61.7, 51.0, 49.5, 45.0, 39.2, 37.5, 27.3, 24.1, 22.6, 20.2, 19.0, 18.3, 16.5, 13.9, 12.8, 12.4, 11.6, |
| Example 288. | Ac | 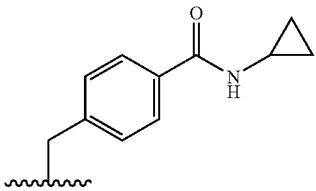 | H | 857 | 205.9, 184.6, 176.5, 169.3, 169.0, 156.5, 141.7, 133.9, 128.3, 127.0, 102.6, 79.7, 79.0, 76.2, 75.7, 75.4, 70.5, 69.7, 66.1, 58.4, 50.9, 45.4, 40.5, 39.0, 28.5, 25.5, 23.4, 21.6, 20.2, 19.7, 17.2, 15.6, 14.4, 13.0, 12.0, 7.0 |
| Example 289. | Ac | 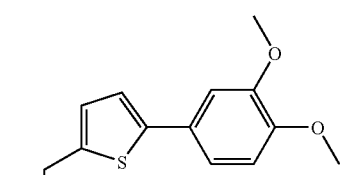 | H | 916 | 205.9, 184.8, 178.1, 167.7, 153.7, 149.3, 148.9, 145.3, 139.2, 128.03, 127.95, 122.0, 118.6, 111.7, 109.6, 102.8, 79.4, 79.1, 76.8, 74.5, 71.0, 70.3, 69.4, 66.4, 63.1, 62.9, 56.21, 56.19, 50.8, 46.1, 40.5, 38.8, 29.9, 29.2, 25.4, 23.8, 21.4, 20.3, 19.5, 17.8, 15.1, 14.2, 13.6, 13.0. |
| Example 290. | Ac | 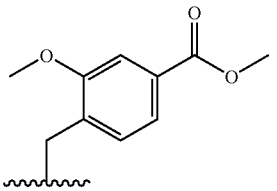 | H | 862 | 205.9, 184.5, 176.5, 169.3, 167.4, 156.3, 156.3, 132.1, 130.3, 128.8, 122.2, 110.8, 102.5, 79.6, 78.9, 77.6, 76.2, 75.3, 71.0, 70.6, 70.4, 69.7, 66.1, 58.6, 55.7, 52.3, 50.8, 45.4, 40.4, 39.6, 39.0, 29.5, 28.5, 25.4, 22.3, 21.5, 20.2, 19.7, 17.2, 15.6, 14.4, 12.9, 11.9 |

TABLE A2.-continued

| Example | Q | —Ar₁—M—Ar₂ | Z | MS (ESI): m/z (M + H)⁺ | ¹³C NMR (125 MHz, CDCl₃): δ |
|---|---|---|---|---|---|
| Example 291. | Ac | (4-acetamidophenyl-CH₂CH₂-) | H | 831 | Selected data: 205.9, 184.6, 176.6, 169.3, 168.4, 155.9, 137.7, 133.8, 129.5, 119.8, 102.4. |
| Example 292. | Ac | (5-cyanothien-2-yl-CH₂CH₂-) | H | 805 | 205.6, 184.3, 175.9, 169.1, 157.2, 148.4, 137.1, 126.7, 114.4, 109.7, 102.3, 79.5, 78.7, 75.9, 75.0, 70.2, 69.9, 69.5, 58.1, 50.6, 45.2, 40.2, 38.8, 28.2, 25.3, 23.1, 21.3, 19.8, 19.4, 16.9, 15.4, 14.1, 12.7, 11.7 |
| Example 293. | Ac | (5-(pyrazin-2-yl)thien-2-yl-CH₂CH₂-) | H | 858 | 205.8, 184.6, 176.5, 169.3, 156.5, 148.9, 144.3, 144.2, 142.5, 141.7, 140.8, 128.5, 125.9, 102.6, 79.7, 79.0, 77.6, 76.2, 75.4, 70.8, 70.6, 70.5, 69.7, 66.1, 58.4, 50.8, 45.3, 40.5, 39.6, 39.0, 36.8, 28.5, 25.5, 23.4, 21.6, 20.2, 19.7, 17.2, 15.7, 14.4, 12.9, 12.0. |
| Example 294. | Ac | (4-(methoxycarbonylamino)phenyl-CH₂CH₂-) | H | 847 | 205.8, 184.6, 176.7, 169.3, 155.9, 137.7, 133.0, 129.6, 118.7, 102.6, 79.6, 79.0, 76.2, 76.1, 75.4, 70.5(2), 69.6, 66.2, 58.4, 52.6, 50.9, 45.3, 40.5, 39.6, 39.0, 36.9, 29.9, 28.7, 25.5, 23.4, 21.6, 20.3, 19.7, 17.2, 15.6, 14.5, 12.9, 12.0. |
| Example 295. | Ac | (5-(6-aminopyridin-2-yl)thien-2-yl-CH₂CH₂-) | F | 890 | N/A |
| Example 296. | Ac | (4-(hydrazinocarbonyl)phenyl-CH₂CH₂-) | H | 832 | 205.9, 184.6, 176.4, 169.3, 168.8, 167.9, 156.6, 153.9, 142.3, 132.0, 128.4, 128.1, 127.1, 102.6, 79.7, 79.0, 76.2, 75.6, 70.5, 69.7, 66.1, 58.5, 50.9, 45.4, 40.5, 39.0, 28.5, 25.5, 23.4, 21.6, 20.1, 19.7, 17.2, 15.7, 14.4, 13.0, 12.0 |
| Example 297. | Ac | (5-(6-fluoropyridin-3-yl)thien-2-yl-CH₂CH₂-) | H | 876 | N/A |
| Example 298. | Ac | (4-formylphenyl-CH₂CH₂-) | H | 801 | N/A |

TABLE A2.-continued

| Example | Q | —Ar₁—M—Ar₂ | Z | MS (ESI): m/z (M + H)⁺ | ¹³C NMR (125 MHz, CDCl₃): δ |
|---|---|---|---|---|---|
| Example 299. | Ac | | H | 872 | N/A |
| Example 300. | H | | H | 872 | 205.6, 189.1, 170.0, 169.2, 157.5, 151.1, 151.0, 144.8, 142.8, 139.2, 127.9, 124.5, 114.7, 112.1, 102.3, 80.6, 80.3, 78.8, 76.9, 76.0, 71.9, 71.2, 70.4, 69.5, 66.1, 60.2, 50.7, 45.7, 41.6, 40.4, 39.5, 35.3, 28.9, 25.0, 23.2, 21.6, 20.0, 19.7, 16.9, 14.8, 14.6, 12.9, 11.9. |
| Example 301. | Ac | | H | 851 | N/A |
| Example 302. | Ac | | H | 887 | 205.9, 184.6, 176.6, 169.3, 163.7, 156.1, 150.3, 145.8, 141.8, 139.2, 128.4, 124.2, 111.4, 109.1, 102.3, 79.6, 79.1, 76.2, 75.5, 71.1, 70.6, 70.3, 69.3, 66.5, 58.4, 53.6, 50.9, 45.2, 40.6, 39.0, 30.0, 25.5, 23.4, 21.5, 20.3, 19.7, 17.2, 15.7, 14.5, 12.8, 12.0. |
| Example 303. | H | | H | 830 | 205.5, 188.1, 170.0, 158.3, 157.5, 151.2, 145.9, 141.7, 138.4, 127.9, 124.0, 109.4, 107.1, 102.4, 80.6, 80.3, 78.7, 77.1, 76.0, 71.9, 71.2, 70.5, 69.7, 66.1, 60.4, 50.7, 45.7, 42.0, 40.5, 39.5, 35.3, 29.9, 28.6, 23.2, 21.6, 20.1, 19.7, 16.9, 14.8, 14.6, 12.9, 11.9. |
| Example 304. | H | | F | 848 | N/A |
| Example 305. | Ac | | H | 857 | N/A |

TABLE A2.-continued

| Example | Q | —Ar₁—M—Ar₂ | Z | MS (ESI): m/z (M + H)⁺ | ¹³C NMR (125 MHz, CDCl₃): δ |
|---|---|---|---|---|---|
| Example 306. | Ac | phenyl-pyrimidine | H | 852 | 205.8, 184.6, 176.7, 169.3, 164.9, 157.4, 156.1, 140.7, 137.2, 128.6, 128.4, 119.2, 102.6, 79.6, 79.0, 76.2, 75.4, 70.5, 69.7, 66.1, 58.4, 50.9, 45.4, 40.5, 39.0, 28.5, 25.5, 25.5, 23.4, 21.6, 20.3, 19.7, 15.6, 14.5, 12.9, 12.0 |
| Example 307. | Ac | thiophene-pyridine-CN | H | 882 | 205.8, 184.7, 178.1, 167.8, 154.5, 154.2, 145.0, 142.6, 137.7, 133.8, 127.9, 126.41, 126.37, 122.1, 117.4, 103.0, 79.4, 79.2, 76.8, 74.6, 70.9, 70.5, 69.7, 66.2, 63.1, 62.9, 50.7, 46.2, 40.5, 38.8, 28.7, 25.4, 23.9, 21.5, 20.3, 19.5, 17.8, 15.1, 14.1, 13.7, 13.0. |
| Example 308. | Ac | pyridine-pyrazine | H | 853 | 205.6, 184.3, 176.1, 169.1, 156.6, 153.5, 151.2, 149.3, 144.3, 143.5, 143.4, 137.2, 134.3, 121.1, 102.4, 79.5, 79.7, 76.0, 75.2, 73.4, 70.2, 69.5, 65.9, 58.2, 50.6, 45.2, 40.2, 38.8, 28.3, 25.3, 23.1, 21.3, 19.9, 19.5, 17.0, 15.4, 14.2, 12.8, 11.7 |
| Example 309. | Ac | pyridine-pyridine | H | 852 | 205.8, 184.5, 176.5, 169.3, 156.6, 156.4, 155.9, 149.3, 137.5, 137.1, 133.5, 123.8, 121.4, 121.0, 102.7, 79.7, 79.0, 76.2, 75.4, 73.8, 70.5, 69.8, 66.1, 58.4, 50.9, 45.4, 40.5, 39.0, 28.5, 25.5, 23.4, 21.6, 20.2, 19.7, 17.2, 15.7, 14.4, 13.0, 12.0 |
| Example 310. | Ac | pyridine-thiazole | H | 858 | 205.8, 184.6, 176.4, 169.4, 156.9, 151.0, 149.4, 144.2, 137.6, 134.7, 121.5, 119.6, 102.7, 79.7, 79.0, 76.2, 75.5, 73.6, 70.5, 70.4, 69.7, 66.1, 58.4, 50.9, 45.5, 40.5, 39.0, 36.8, 30.0, 28.5, 25.6, 23.4, 21.6, 20.2, 19.7, 17.2, 15.7, 14.4, 13.0. |
| Example 311. | Ac | 2-aminopyridine | H | 790 | 205.8, 184.5, 176.6, 169.3, 158.5, 155.9, 148.8, 139.4, 123.2, 108.6, 102.7, 79.6, 79.0, 76.2, 75.4, 74.0, 70.5, 69.7, 66.1, 58.4, 50.8, 45.4, 40.5, 39.6, 39.0, 36.8, 28.5, 25.5, 23.4, 21.6, 20.3, 19.7, 17.2, 15.6, 14.4, 12.9, 12.0. |
| Example 312. | Ac | thiophene-thiazole | H | 863 | 205.6, 184.3, 176.1, 169.0, 162.0, 156.1, 143.2, 142.6, 137.6, 127.7, 126.1, 118.0, 101.8, 79.3, 78.8, 75.9, 75.4, 70.4, 70.4, 69.9, 68.8, 66.5, 58.2, 50.6, 44.9, 40.3, 38.8, 36.5, 29.6, 25.2, 23.1, 21.1, 19.9, 19.4, 16.9, 15.4, 14.3, 12.5, 11.7. |

TABLE A2.-continued
| Example | Q | —Ar₁—M—Ar₂ | Z | MS (ESI): m/z (M + H)⁺ | ¹³C NMR (125 MHz, CDCl₃): δ |
|---|---|---|---|---|---|
| Example 313. | Ac | 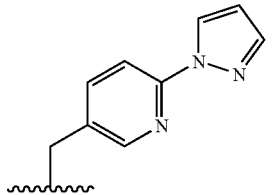 | F | 859 | 204.8, 204.5, 184.0, 176.3, 165.8, 165.6, 157.4, 151.4, 148.2, 142.1, 139.8, 131.1, 127.3, 112.3, 107.8, 104.0, 99.6, 98.0, 79.9, 79.3, 76.1, 73.9, 73.4, 70.6, 69.9, 67.9, 66.0, 56.2, 41.2, 40.5, 39.2, 37.7, 31.2, 29.9, 28.4, 25.3, 24.5, 24.4, 22.8, 21.6, 21.5, 21.0, 17.3, 15.2, 14.2, 11.9 |
| Example 314. | Ac | 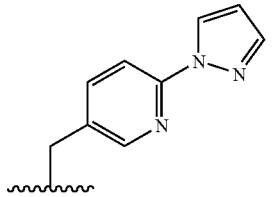 | H | 841 | 205.8, 184.5, 176.4, 169.3, 156.7, 151.4, 148.1, 142.1, 139.6, 131.3, 127.3, 112.3, 107.9, 102.6, 79.7, 79.0, 76.2, 75.4, 73.4, 70.5, 70.3, 69.7, 66.1, 58.3, 50.9, 45.4, 40.5, 39.7, 39.0, 36.8, 28.5, 25.5, 23.3, 21.6, 20.2, 19.7, 17.2, 15.6, 14.4, 13.0, 12.0. |
| Example 315. | Ac | 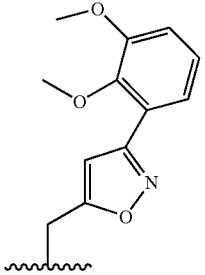 | H | 901 | N/A |
| Example 316. | Ac | 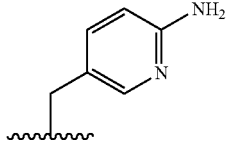 | F | 808 | 204.6, 204.4, 184.0, 176.7, 165.8, 165.6, 158.4, 156.8, 148.9, 139.5, 123.1, 108.5, 104.1, 99.6, 98.0, 79.9, 79.3, 76.1, 74.0, 70.6, 69.9, 68.0, 66.0, 56.3, 41.2, 40.5, 39.2, 37.8, 31.2, 29.9, 28.4, 25.3, 24.5, 24.3, 22.8, 21.6, 21.5, 20.9, 17.3, 15.2, 14.2, 11.9. |
| Example 317. | Ac | 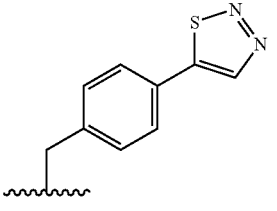 | H | 858 | 205.9, 184.6, 175.5, 169.3, 163.1, 156.3, 139.5, 130.4, 130.1, 129.2, 127.6, 102.7, 79.7, 76.2, 76.0, 70.5, 69.7, 66.1, 58.4, 50.9, 45.4, 40.5, 39.0, 28.5, 25.5, 23.4, 21.6, 20.2, 19.7, 17.2, 15.7, 14.4, 12.0 |
| Example 318. | Ac | 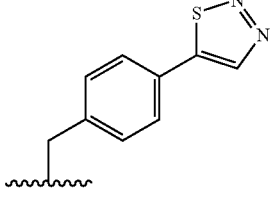 | F | 876 | 203.5, 203.3, 182.8, 164.6, 164.4, 161.9, 156.0, 138.1, 129.1, 128.7, 128.0, 126.3, 102.8, 98.4, 96.7, 78.0, 74.7, 72.8, 69.3, 68.6, 66.7, 64.8, 55.2, 39.9, 39.2, 27.1, 24.1, 23.2, 23.0, 21.5, 20.4, 20.2, 19.7, 16.0, 14.0, 12.9, 10.6 |

TABLE A2.-continued

| Example | Q | —Ar₁—M—Ar₂ | Z | MS (ESI): m/z (M + H)⁺ | ¹³C NMR (125 MHz, CDCl₃): δ |
|---|---|---|---|---|---|
| Example 319. | Ac | | H | 842 | N/A |
| Example 320. | Ac | | H | 841 | 205.9, 184.5, 176.3, 169.4, 157.0, 149.1, 148.8, 139.7, 135.2, 132.1, 130.8, 116.5, 112.2, 102.7, 79.7, 79.0, 77.4, 76.2, 75.4, 73.0, 70.4, 70.3, 69.7, 66.1, 58.4, 50.9, 45.5, 40.5, 39.7, 39.0, 36.7, 28.5, 25.5, 23.3, 21.6, 20.1, 19.7, 17.2, 15.6, 14.4, 13.0, 12.0. |
| Example 321. | Ac | | H | 873 | 205.62, 184.33, 176.23, 169.06, 167.60, 159.80, 156.14, 139.99, 130.03, 128.60, 126.92, 102.26, 79.37, 78.75, 75.93, 75.57, 75.15, 70.14, 69.34, 67.94, 65.91, 58.17, 53.40, 50.61, 45.12, 40.20, 39.39, 38.76, 36.53, 29.66, 28.47, 25.58, 25.26, 23.08, 21.27, 19.89, 19.41, 16.95, 15.40, 14.16, 12.68, 11.72 |
| Example 322. | Ac | | H | 867 | N/A |
| Example 323. | Ac | | H | 799 | N/A |
| Example 324. | Ac | | H | 874 | Partial ¹³C NMR 205.63, 184.32, 176.04 |
| Example 325. | Ac | | H | 855 | 205.8, 184.5, 176.4, 169.3, 156.6, 151.5, 148.1, 143.1, 139.5, 130.7, 125.8, 118.5, 111.9, 102.6, 79.7, 79.0, 76.2, 75.5, 73.5, 70.4, 70.3, 69.7, 66.2, 58.3, 50.9, 45.4, 40.5, 39.7, 39.0, 36.8, 29.5, 28.6, 25.5, 23.3, 21.6, 20.2, 19.7, 17.2, 15.6, 14.4, 13.0, 12.0, 9.3. |

TABLE A2.-continued

| Example | Q | —Ar₁—M—Ar₂ | Z | MS (ESI): m/z (M + H)⁺ | ¹³C NMR (125 MHz, CDCl₃): δ |
|---|---|---|---|---|---|
| Example 326. | Ac | (4-phenyl-1,3,4-thiadiazol-2-ol) | H | 874 | 205.71, 184.39, 176.16, 171.88, 169.10, 156.24, 153.13, 141.02, 129.99, 128.53, 125.93, 102.14, 79.40, 78.82, 75.92, 75.42, 75.20, 70.27, 70.09, 69.19, 66.09, 58.26, 53.41, 50.63, 45.13, 40.24, 39.37, 38.80, 36.50, 28.79, 25.31, 23.09, 21.24, 19.87, 19.41, 16.94, 21.24, 19.87, 19.41, 16.94, 15.48, 14.20, 12.68, 11.73 |
| Example 327. | Ac | (4-phenyl-1,3,4-thiadiazole) | H | 858 | 205.67, 184.31, 176.14, 169.08, 168.29, 156.29, 151.02, 141.50, 128.73, 128.13, 102.22, 79.39, 78.76, 75.93, 75.42, 75.21, 70.11, 69.27, 66.07, 58.17, 50.64, 45.11, 40.24, 39.39, 38.78, 36.55, 28.62, 25.28, 23.08, 21.26, 19.90, 19.39, 16.95, 15.40, 14.18, 12.68, 11.72 |
| Example 328. | Ac | (2-(1H-1,2,3-triazol-1-yl)pyridine) | H | 842 | 205.8, 184.4, 169.1, 156.8, 148.1, 139.6, 134.1, 121.1, 113.5, 109.7, 101.8, 79.4, 78.8, 75.9, 75.3, 72.8, 69.8, 68.7, 66.4, 58.1, 50.7, 45.1, 40.3, 38.8, 36.4, 31.6, 29.5, 25.3, 23.0, 22.6, 21.1, 19.8, 19.3, 16.9, 15.4, 14.2, 14.1, 12.7, 11.7. |
| Example 329. | Ac | (2-(4-iodo-1H-pyrazol-1-yl)pyridine) | H | 967 | 205.6, 184.3, 176.1, 169.1, 156.5, 150.3, 147.9, 146.5, 139.4, 131.7(2), 111.6, 102.2, 79.4, 78.8, 75.9, 73.0, 70.1, 69.2, 66.2, 59.6, 58.1, 50.7, 45.1, 40.3, 39.4, 38.8, 36.5, 31.6, 28.7, 25.3, 23.1, 21.3, 19.9, 19.4, 16.9, 15.4, 14.2, 14.1, 12.7, 11.7, |
| Example 330. | Ac | (2-(3-methyl-1H-pyrazol-1-yl)pyridine) | H | 855 | 205.5, 184.2, 176.2, 169.0, 156.3, 151.5, 151.1, 147.9, 139.2, 130.3, 127.7, 111.6, 107.8, 102.3, 79.4, 78.7, 75.9, 75.2, 73.2, 70.0, 69.3, 66.0, 58.0, 50.6, 45.1, 40.2, 38.7, 31.5, 28.5, 25.2, 23.1, 22.6, 21.3, 19.9, 19.4, 16.9, 15.4, 14.2, 14.0, 13.9, 12.7, 11.7, |
| Example 331. | Ac | (2-(3-(trifluoromethyl)-1H-pyrazol-1-yl)pyridine) | H | 909 | 205.6, 184.3, 176.1, 169.1, 156.7, 150.2, 147.9, 139.5, 132.4, 128.4, 112.5, 105.7, 102.3, 79.4, 78.7, 75.9, 75.2, 72.9, 70.2, 70.0, 69.4, 65.9, 58.1, 50.6, 45.2, 40.2, 39.4, 38.7, 36.5, 31.6, 28.3, 25.3, 23.0, 22.6, 21.3, 19.9, 19.4, 16.9, 15.4, 14.1, 12.8, 11.7, |

TABLE A2.-continued
| Example | Q | —Ar₁—M—Ar₂ | Z | MS (ESI): m/z (M + H)⁺ | ¹³C NMR (125 MHz, CDCl₃): δ |
|---|---|---|---|---|---|
| Example 332. | Ac | 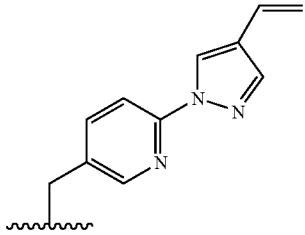 | H | 867 | N/A |
| Example 333. | Ac | 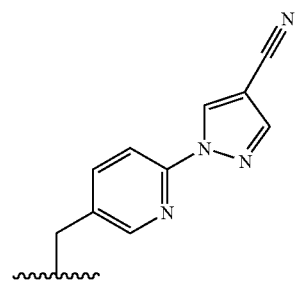 | H | 866 | N/A |
| Example 334. | Ac | 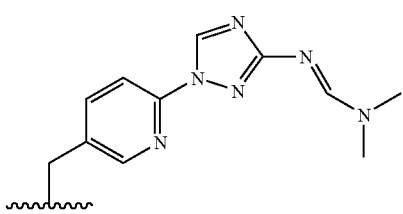 | H | 912 | N/A |
| Example 335. | Ac | 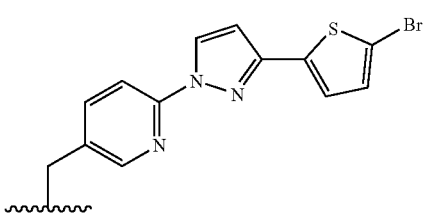 | H | 1003 | 205.76, 184.34, 176.04, 169.17, 156.45, 150.73, 148.04, 147.87, 139.38, 137.91, 131.05, 130.28, 128.41, 124.55, 112.12, 112.06, 104.75, 101.59, 79.31, 78.76, 76.26, 75.91, 75.02, 73.11, 71.95, 70.20, 67.70, 59.27, 58.12, 51.91, 58.12, 51.92, 50.57, 45.18, 58.12, 51.92, 50.57, 45.18, 39.41, 38.77, 36.45, 34.93, 25.28, 23.06, 21.06, 19.80, 19.35, 16.95, 15.43, 13.98. 12.65, 11.696 |
| Example 336. | Ac | 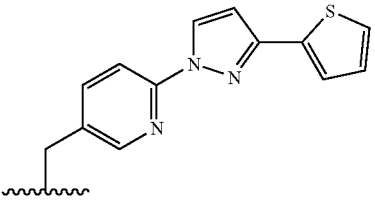 | H | 923 | 205.75, 184.34, 176.07, 169.17, 156.40, 150.90, 148.88, 147.90, 139.36, 136.28, 130.84, 128.30, 127.49, 125.17, 124.59, 112.10, 105.24, 101.61, 79.31, 78.77, 76.26, 75.92, 75.06, 73.19, 71.96, 70.21, 67.71, 59.27, 58.13, 51.94, 50.59, 45.18, 39.41, 38.78, 36.46, 34.95, 25.30, 23.08, 21.07, 19.82, 19.36, 16.96, 15.44, 14.00, 12.66, 11.70 |
| Example 337. | H | 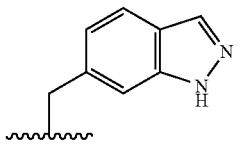 | H | 772 | 205.7, 169.9, 157.5, 140.7, 137.3, 134.5, 122.8, 120.8, 120.5, 108.7, 102.5, 80.7, 80.1, 78.9, 76.7, 76.2, 76.0, 71.9, 70.5, 69.7, 66.1, 60.2, 50.7, 45.9, 41.8, 40.5, 39.5, 35.5, 28.6, 23.2, 21.6, 20.0, 17.0, 14.8, 14.5, 13.1, 11.9. |

TABLE A2.-continued

| Example | Q | —Ar$_1$—M—Ar$_2$ | Z | MS (ESI): m/z (M + H)$^+$ | $^{13}$C NMR (125 MHz, CDCl$_3$): δ |
|---|---|---|---|---|---|
| Example 338. | Ac | 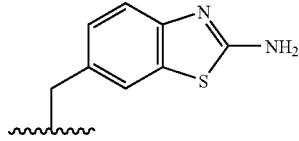 | H | 846 | N/A |

Example compounds 338–353 of formula B:

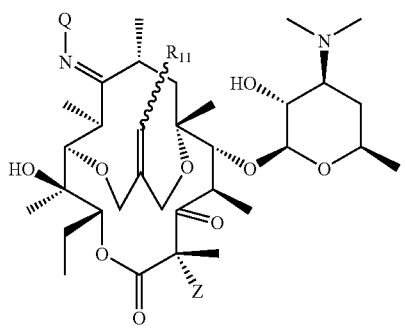

wherein R$_{11}$, Q, and Z are as delineated for each example in Table B.

Example compounds 338–353, where Z=H, are made from the title compound of formula (1-5), wherein V=N—Ac, R$_{11}$=H, and R$_2$'=H, and the appropriate bromo compound of formula Br—R$_{11}$, wherein R$_{11}$ is previously defined, via essentially the same synthetic route described in Example 35.

Example compounds 338–353, where Z=F, are made from the compound of Example 46, Step 46a and the appropriate bromo precursor via the method delineated in Example 35.

The Examples described in Table B comprise mixtures of E and Z isomers, which can be separated via silica chromatography or HPLC.

The bromo compounds used to form the following examples are commercially available or can be made from readily-available starting materials via synthetic methods well known by one of ordinary skill in the art.

TABLE B

| Examples | Q | —R$_{11}$ | Z | MS (ESI): m/z (M + H)$^+$ | $^{13}$C NMR (125 MHz, CDCl$_3$): δ |
|---|---|---|---|---|---|
| Example 339. | H | H | H | 625 | N/A |
| Example 340. | OMOM | H | H | 685 | N/A |
| Example 341. | OMOM | 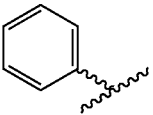 | H | 761 | N/A |
| Example 342. | Ac | 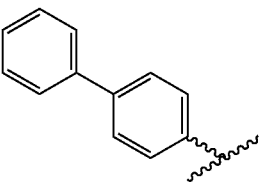 | H | 819 | N/A |
| Example 343. | Ac | 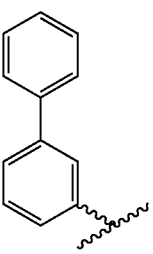 | H | 819 | N/A |

TABLE B-continued
| Examples | Q | —R₁₁ | Z | MS (ESI): m/z (M + H)⁺ | ¹³C NMR (125 MHz, CDCl₃): δ |
|---|---|---|---|---|---|
| Example 344. | Ac | 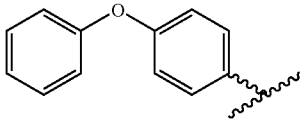 | H | 835 | N/A |
| Example 345. | Ac | 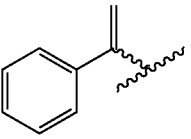 | H | 769 | N/A |
| Example 346. | Propionyl | 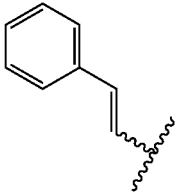 | H | 783.36 | N/A |
| Example 347. | Ac | 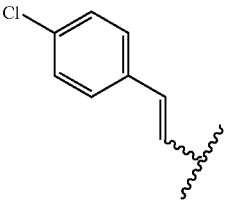 | H | 803 | N/A |
| Example 348. | C(O)OMe | 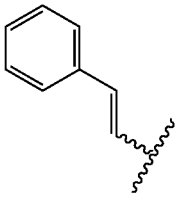 | H | 785 | N/A |
| Example 349. | C(O)NH₂ | H | H | 668 | N/A |
| Example 350. | Me | H | H | 639 | N/A |
| Example 351. | BOM | H | H | 762 | N/A |
| Example 352. | Ac | 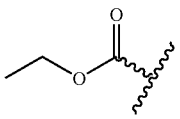 | H | 739 | N/A |
| Example 353. | Ac | 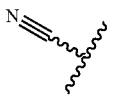 | H | 692 | N/A |

Example compounds 354–375 of formula B1:

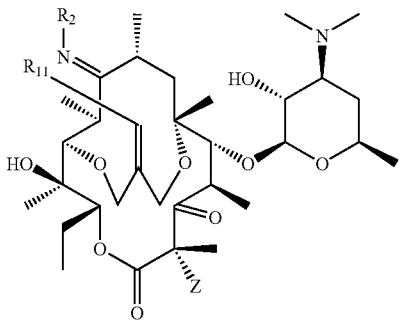

wherein $R_{11}$, Q, and Z are as delineated for each example in Table B1.

Example compounds 354–375, where Z=H, are made from the title compound of formula (1-5), wherein V=N—Ac, $R_{11}$=H, and $R_2'$=H, and the appropriate bromo compound of formula Br—$R_{11}$, wherein $R_{11}$ is as previously defined, via essentially the same synthetic route described in Example 35.

Example compounds 354–375, where Z=F, are made from the compound of Example 46, Step 46a and the appropriate bromo precursor via the method delineated in Example 35.

The Examples described in Table B1 are single isomers of the E designation, which are separated from the E/Z mixture via silica chromatography or HPLC.

The bromo compounds used to form the following examples are commercially available or can be made from readily-available starting materials via synthetic methods well known by one of ordinary skill in the art.

TABLE B1

| Examples | Q | —$R_{11}$ | Z | MS (ESI): m/z (M + H)+ | $^{13}$C NMR (125 MHz, CDCl$_3$): δ |
|---|---|---|---|---|---|
| Example 354. | Ac | 2-pyridyl-C≡C— | H | 768 | N/A |
| Example 355. | Ac | 3-pyridyl-C≡C— | H | 768 | N/A |
| Example 356. | Ac | 6-amino-3-pyridyl-C≡C— | H | 783 | 206.2, 184.4, 177.7, 167.8, 157.4, 151.5, 144.3, 140.4, 117.9, 110.1, 107.9, 103.0, 93.3, 86.9, 79.5, 78.4, 76.2, 72.7, 70.2, 69.3, 68.2, 66.1, 65.8, 50.8, 46.6, 40.3, 38.5, 25.1, 23.8, 21.2, 19.5, 17.3, 15.1, 13.8, 12.9, |
| Example 357. | Ac | 4-aminophenyl-C≡C— | H | 782 | 206.2, 184.4, 177.8, 167.7, 146.6, 143.4, 133.0, 118.4, 114.6, 112.9, 103.0, 96.8, 84.4, 79.6, 78.3, 76.2, 72.6, 70.2, 69.3, 68.3, 66.1, 65.8, 50.8, 46.6, 40.3, 38.5, 25.1, 23.7, 21.2, 19.5, 17.3, 15.1, 13.8, 12.7, |
| Example 358. | Ac | 4-methoxyphenyl-C≡C— | H | 797 | N/A |

TABLE B1-continued

| Examples | Q | —R₁₁ | Z | MS (ESI): m/z (M + H)⁺ | ¹³C NMR (125 MHz, CDCl₃): δ |
|---|---|---|---|---|---|
| Example 359. | Ac | 4-(trifluoromethyl)phenyl-C≡C- | H | 835 | N/A |
| Example 360. | Ac | styryl (PhCH=CH-CH₂-) | F | 787 | 205.36 (d), 183.93, 164.92(d), 137.25, 136.54, 136.08, 134.26, 128.52, 128.17, 126.87, 123.95, 103.95, 80.17, 79.96, 75.93, 71.71, 70.37, 69.51, 66.33, 65.99, 65.82, 40.65, 40.20, 38.90, 37.24, 28.27, 25.08, 24.68, 24.50, 23.07, 21.18, 21.06, 17.11, 15.05, 14.14, 12.57 |
| Example 361. | Ac | styryl | H | 771 | 205.72, 169.32, 169.60, 137.16, 135.90, 128.53, 128.25, 127.86, 126.71, 123.91, 103.75, 80.62, 78.92, 76.88, 70.41, 70.30, 69.30, 66.16, 65.56, 59.83, 53.76, 51.63, 48.93, 40.27, 29.23, 28.69, 23.57, 23.14, 21.45, 21.16, 16.62, 14.34, 12.61 |
| Example 362. | Ac | 2-(pyridin-2-yl)thien-5-yl- | H | 827 | 206.2, 184.4, 177.6, 167.6, 152.5, 149.5, 145.6, 140.7, 136.5, 132.2, 131.1, 129.4, 124.6, 121.8, 118.8, 103.1, 79.3, 78.6, 76.2, 75.0, 73.0, 70.3, 69.4, 67.7, 67.1, 66.2, 65.9, 50.9, 46.9, 40.2, 38.6, 29.7, 28.4: 25.1: 23.8, 21.2, 20.5, 19.7, 17.4, 14.9, 14.2, 13.8, 12.1. |
| Example 363. | Ac | 2,4-difluorostyryl | H | 805 | Selected: 206.3, 184.7, 177.9, 167.8, 163.3, 161.4, 159.6, 136.2, 135.2. 128.7, 127.7, 126.3, 111.8, 111.6, 103.4, 79.7, 78.7, 76.4, 72.5, 70.5, 69.7, 66.1, 51.1, 47.2, 40.5, 38.8, 29.5, 28.6, 25.4, 23.9, 21.5, 19.9, 17.7, 15.1, 14.1, 13.1. |
| Example 364. | 2-methoxyacetyl | styryl | H | 799 | 206.4, 183.9, 182.0, 167.8, 137.6, 136.3, 134.2, 128.7, 128.6, 128.0, 127.1, 127.0, 124.1, 103.4, 79.8, 78.7, 77.5, 76.5, 73.5, 72.7, 70.5, 69.7, 66.7, 66.1, 59.7, 51.1, 40.5, 39.0, 28.5, 23.9, 21.5, 20.9, 19.9, 17.7, 15.2, 14.2, 13.1. |
| Example 365. | 2-O-acyl-acetyl | styryl | H | 827 | N/A |

TABLE B1-continued

| Examples | Q | —R$_{11}$ | Z | MS (ESI): m/z (M + H)$^+$ | $^{13}$C NMR (125 MHz, CDCl$_3$): δ |
|---|---|---|---|---|---|
| Example 366. | 2-Fmoc-acetyl | (cinnamyl) | H | 1006 | N/A |
| Example 367. | Ac | (2-fluorocinnamyl) | H | 787 | 206.3, 184.7, 178.0, 167.8, (161.7, 159.7), 136.4, 135.1, (129.1, 129.06), 128.7, 128.0, 126.7, 126.65, (125.5, 125.4), 124.2, (116.1, 116.0), 103.5, 79.7, 78.7, 76.4, 72.5, 70.6, 69.8, 66.7, 66.5, 66.1, 51.1, 47.2, 40.5, 38.8, 31.2, 28.5, 25.4, 23.9, 21.5, 20.8, 20.0, 17.7, 15.1, 14.5, 14.1, 13.0. |
| Example 368. | Ac | (benzimidazol-2-yl) | H | 783 | N/A |
| Example 369. | 2-hydroxyacetyl | (cinnamyl) | H | 785 | N/A |
| Example 370. | 2-aminoacetyl | (cinnamyl) | H | 784 | N/A |
| Example 371. | Ac | (4-nitrocinnamyl) | H | 814 | 206.1, 184.4, 177.5, 167.7, 146.8, 143.8, 137.6, 135.0, 133.4, 130.1, 128.1, 127.0, 124.0, 123.4, 103.2, 79.4, 78.6, 76.2, 72.3, 70.3, 69.5, 66.4, 66.0, 65.8, 50.8, 47.0, 40.2, 38.5, 28.2, 25.1, 23.7, 21.2, 19.7, 17.5, 14.8, 13.8, 13.0 |
| Example 372. | Ac | (3-chloro-4-fluorocinnamyl) | H | 821 | Partial $^{13}$C NMR: 206.09, 184.41, 167.60, 158.43 |

TABLE B1-continued

| Examples | Q | —R₁₁ | Z | MS (ESI): m/z (M + H)⁺ | ¹³C NMR (125 MHz, CDCl₃): δ |
|---|---|---|---|---|---|
| Example 373. | Ac | (4-methoxyphenyl allyl) | H | 799 | 206.10, 184.38, 167.47, 159.30, 136.23, 135.69, 132.65, 130.18, 127.96, 121.79, 113.88, 103.16, 79.58, 78.31, 76.16, 72.09, 70.27, 69.46, 66.53, 66.43, 65.80, 55.19, 50.82, 46.87, 40.19, 38.57, 31.63, 28.20, 25.22, 25.08, 23.68, 22.60, 21.22, 20.51, 19.67, 17.43, 14.87, 14.08, 13.80, 12.89 |
| Example 374. | Ac | (3-chlorophenyl allyl) | H | 803 | Selected: 206.4, 184.7, 177.9, 167.8, 139.5, 135.7, 135.5, 134.8, 134.7, 129.9, 127.8, 126.8, 125.4, 125.3, 103.4, 79.8, 78.7, 76.5, 72.5, 70.5, 69.7, 66.8, 66.4, 66.1, 54.0, 51.1, 47.2, 40.5, 38.8, 31.2, 29.5, 28.5, 25.4, 23.9, 21.5, 19.9, 17.8, 15.1, 14.1, 13.2. |
| Example 375. | Ac | (benzimidazol-2-yl) | H | 800 | N/A |

Example compounds 376–384 of formula B2:

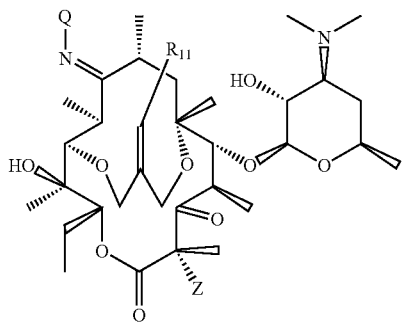

(B2)

wherein R₁₁, Q, and Z are as delineated for each example in Table B2.

Example compounds 376–384, where Z=H, are made from the title compound of formula (1-5), wherein V=N—Ac, R₁₁=H, and R₂'=H, and the appropriate bromo compound of formula Br—R₁₁, wherein R₁₁ is as previously defined, via essentially the same synthetic route described in Example 35.

Example compounds 376–384, where Z=F, are made from the compound of Example 46, Step 46a and the appropriate precursor via the method delineated in Example 35.

The Examples described in Table B2 are single isomers of the Z designation, which are separated from the E/Z mixture via silica chromatography or HPLC.

The bromo compounds used to form the following examples are commercially available or can be made from readily-available starting materials via synthetic methods well known by one of ordinary skill in the art.

TABLE B2

| Examples | Q | —R₁₁ | Z | MS (ESI): m/z (M + H)⁺ | ¹³C NMR (125 MHz, CDCl₃): δ |
|---|---|---|---|---|---|
| Example 376. | Ac | (thiophene-pyridine) | H | 827 | 205.3, 184.5, 176.0, 168.8, 152.4, 149.4, 145.1, 141.0, 136.4, 135.2, 129.5, 126.1, 124.8, 121.7, 118.7, 102.4, 79.0, 78.6, 77.6, 76.3, 76.0, 74.8, 70.2, 69.4, 65.8, 61.6, 50.3, 45.1, 40.1, 39.2, 36.4, 28.2, 25.0, 23.2, 21.2, 20.0, 19.9, 16.9, 15.5, 14.0, 12.5, 11.9. |

TABLE B2-continued

| Examples | Q | —R₁₁ | Z | MS (ESI): m/z (M + H)⁺ | ¹³C NMR (125 MHz, CDCl₃): δ |
|---|---|---|---|---|---|
| Example 377. | Ac | (phenylethynyl) | H | 767 | 205.33, 184.75, 177.42, 168.32, 146.16, 131.61, 128.18, 128.12, 123.39, 115.83, 102.24, 96.78, 85.24, 78, 87, 78.59, 76.18, 75.22, 72.63, 70.19, 69.37, 65.94, 61.88, 50.45, 44.87, 40.25, 38.71, 25.29, 23.31, 21.22, 20.00, 19.56, 17.30, 15.34, 14.13, 12.65, 12.11 |
| Example 378. | Ac | (2-pyridylethynyl) | H | 768 | 205.36, 184.66, 177.23, 168.24, 149.87, 148.14, 135.89, 127.32, 122.58, 114.98, 102.54, 95.65, 84.94, 78.86, 78.77, 76.12, 75.33, 74.94, 72.49, 70.24, 69.94, 69.49, 65.83, 63.03, 50.46, 45.13, 40.22, 38.67, 28.25, 25.29, 23.30, 21.25, 20.03, 19.59, 17.27, 15.29, 14.09, 12.82, 12.11 |
| Example 379. | Ac | (3-pyridylethynyl) | H | 768 | 205.23, 184.50, 177.45, 168.08, 152.35, 148.40, 147.32, 138.48, 122.79, 115.62, 102.36, 93.03, 88.40, 78.74, 78.57, 76.18, 74.60, 74.51, 71.82, 70.19, 69.46, 65.83, 61.75, 50.33, 44.98, 40.20, 39.90, 38.71, 28.27, 25.22, 23.32, 21.23, 19.85, 19.36, 17.38, 15.20, 13.98, 12.74, 12.20 |
| Example 380. | Ac | (4-methoxyphenylethynyl) | H | 797 | 205.33, 194.80, 177.48, 168.27, 159.56, 145.23, 133.06, 132.98, 116.10, 115.59, 113.93, 113.77, 102, 30, 96, 86, 84.07, 78.88, 78.53, 76.16, 75.16, 72.70, 70.21, 69.43, 65.84, 61.87, 55.25, 50.42, 44.84, 40.22, 38.69, 30.91, 28.33, 25.28, 23.31, 21.26, 20.00, 19.57, 17.30, 15.33, 14.13, 12.63, 12.12 |
| Example 381. | Ac | (2-amino-5-pyridylethynyl) | H | 784 | In CD₃OD 211.7, 207.1, 187.1, 180.0, 170.0, 160.1, 151.4, 147.1, 141.7, 116.6, 109.6, 103.5, 95.4, 86.6, 80.1, 77.6, 76.4, 72.5, 72.0, 70.6, 70.2, 65.9, 62.5, 56.0, 46.1, 40.8, 40.2, 32.2, 32.1, 29.5, 25.4, 24.5, 21.5, 20.3, 20.2, 18.4, 15.6, 14.5, 12.6 |
| Example 382. | Ac | (4-aminophenylethynyl) | H | 782 | 205.3, 184.9, 177.5, 168.4, 144.5, 133.0, 130.9, 128.8, 116.2, 114.6, 102.3, 97.8, 83.4, 78.9, 78.5, 76.2, 73.0, 70.2, 69.4, 65.9, 61.9, 50.4, 44.8, 40.2, 38.7, 31.6, 28.4, 25.3, 23.3, 21.3, 20.0, 19.6, 17.3, 15.4, 14.1, 12.6, 12.1 |
| Example 383. | Ac | (4-trifluoromethylphenylethynyl) | H | 835 | 205.44, 184.55, 177.45, 168.12, 147.55, 131.84, 125.02, 115.58, 102.35, 95.04, 87.57, 78.77, 78.60, 76.18, 74.59, 71.89, 70.19, 69.48, 65.85, 61.76, 50.41, 44.98, 40.21, 39.88, 38.71, 28.27, 25.24, 23.31, 21.21, 19.88, 19.39, 17.37, 15.22, 14.04, 12.74, 12.18 |
| Example 384. | Ac | (3-(2-pyridyl)isoxazol-5-ylethynyl) | H | 835 | N/A |

Example compounds 385–391 of formula C:

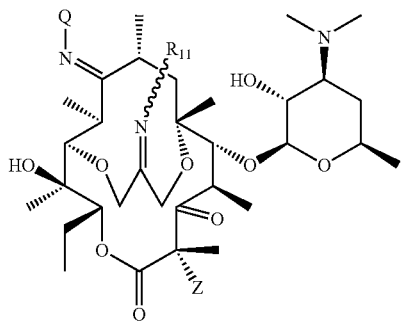

wherein $R_{11}$, Q, and Z are as delineated for each example in Table C.

Example compounds 384–390, where Z=H, are made from the title compound of formula (1-5), wherein V=N—Ac, $R_{11}$=H, and $R_2'$=H, and the appropriate compounds of formula $NH_2$—$R_{11}$, $NH_2NH_2$—$SO_2$—$R_{11}$, $NH_2NH_2$—$R_{11}$, $NH_2NH_2$—N=CH—$R_{11}$, $NH_2NH_2$—C(O)—$R_{11}$, where $R_{11}$ is as previously defined via essentially the same synthetic route described in Example 4.

Example compounds 384–390, where Z=F, are made from the compound of Example 46, Step 46a and the appropriate amino precursor via the method delineated in Example 4

The Examples described in Table C comprise mixtures of E and Z isomers, which can be separated via silica chromatography or HPLC.

The amino compounds used to form the following examples are commercially available or can be made from readily-available starting materials via synthetic methods well known by one of ordinary skill in the art.

| Examples | Q | —$R_{11}$ | Z | MS (ESI): m/z (M + H)+ | $^{13}$C NMR (125 MHz, CDCl$_3$): δ |
|---|---|---|---|---|---|
| Example 385. | Ac | benzyl | H | 758 | N/A |
| Example 386. | Ac | 2-(pyridin-2-ylamino) | H | 760 | N/A |
| Example 387. | Ac | pyridin-2-ylmethyl | H | 772 | N/A |
| Example 388. | Ac | (quinolin-3-ylmethylene)amino | H | 822 | N/A |

-continued

| Examples | Q | —R₁₁ | Z | MS (ESI): m/z (M + H)⁺ | $^{13}$C NMR (125 MHz, CDCl₃): δ |
|---|---|---|---|---|---|
| Example 389. | Ac | (phenylsulfonamide group) | H | 823 | 205.6, 185.1, 174.3, 169.8, 156.9, 138.6, 32.9, 129.0, 128.6, 102.3, 80.4, 78.9, 78.6, 76.1, 75.3, 73.9, 70.4, 69.8, 66.1, 59.9, 50.8, 45.6, 40.5, 38.9, 36.0, 29.9, 28.5, 25.5, 23.1, 21.6, 21.5, 19.9, 19.7, 17.1, 15.3, 14.3, 12.9, 11.8. |
| Example 390. | Ac | (benzamide group) | H | 788 | N/A |
| Example 391. | Ac | (vinylbenzyl amine group) | H | 799 | N/A |

Although the invention has been described with respect to various preferred embodiments, it is not intended to be limited thereto, but rather those skilled in the art will recognize that variations and modifications may be made therein which are within the spirit of the invention and the scope of the appended claims.

What is claimed is:

1. A compound represented by formula:

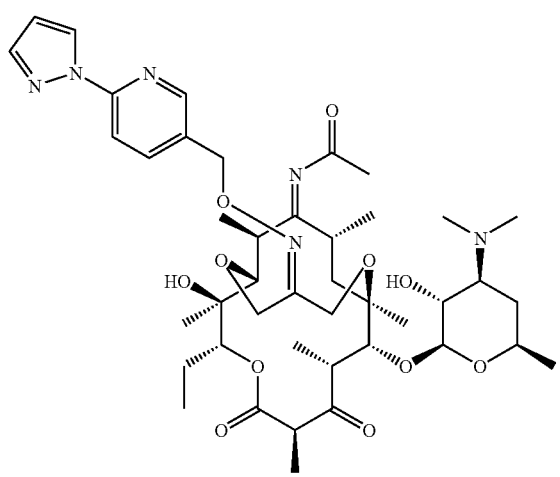

or a pharmaceutically acceptable salt, ester, prodrug, racemic mixture or stereoisomer thereof.

2. A compound according to claim 1 wherein the compound is a pharmaceutically acceptable salt.

3. A compound according to claim 1 wherein the compound is a free base.

4. A compound according to claim 1 wherein the compound is an ester or prodrug.

5. A compound according to claim 1 wherein the compound is an E oxime isomer.

6. A compound according to claim 1 wherein the compound is a Z oxime isomer.

7. A method for treating a protozoa infection or bacterial infection or disorders related to such infections in a subject in need of such treatment, comprising administering to said subject a therapeutically effective amount of a compound according to the formula:

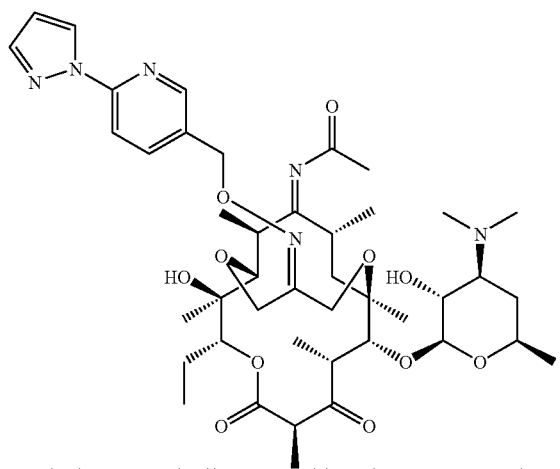

and pharmaceutically acceptable salts, esters, prodrugs, racemic mixtures and stereoisomers thereof.

8. A method according to claim 7 wherein the compound is pharmaceutically acceptable salt.

9. A method according to claim 7 wherein the compound is a free base.

10. A method according to claim 7 wherein the compound is an ester or prodrug.

11. A method according to claim 7 wherein the compound is an E oxime isomer.

12. A method according to claim 7 wherein the compound is a Z oxime isomer.

13. The method according to claim 7 wherein the compound is administered orally, parenterally, by inhalation spray, topically, rectally, nasally, buccally, vaginally or via an implanted reservoir.

14. The method according to claim 7 wherein the compound is administered orally or by injection.

15. The method according to claim 7 wherein the subject is a human.

16. The method according to claim 7 wherein the compound is administered in combination with one or more antibiotics.

17. The method according to claim 16 wherein the antibiotic is selected from the group consisting of penicillin, amoxicillin, azithromycin, erythromycin, ciproflaxin, telithromycin, and cethromycin or a pharmaceutically acceptable salt ester, or prodrug thereof.

18. The method according to claim 7 wherein the infection or disorder is selected from the group consisting of pneumonia, otitis media, sinusitus, bronchitis, tonsillitis, and mastoiditis related to infection by *Streptococcus pneumoniae*, *Haemophilus influenzae*, *Moraxella catarrhalis*, *Staphylococcus aureus*, or *Peptostreptococcus* spp. *Pseudomonas* spp.; pharynigitis, rheumatic fever, and glomerulonephritis related to infection by *Streptococcus pyogenes*, Groups C and G streptococci, *Clostridium diptheriae*, or *Actinobacillus haemolyticum*; respiratory tract infections related to infection by *Mycoplasma pneumoniae*, *Legionella pneumophila*, *Streptococcus pneumoniae*, *Haemophilus influenzae*, or *Chlamydia pneumoniae*; uncomplicated skin and soft tissue infections, abscesses and osteomyelitis, and puerperal fever related to infection by *Staphylococcus aureus*, coagulase-positive staphylococci, *S. pyogenes*, *S. agalactiae*, *Streptococcal* groups C–F. viridans streptococci, *Corynebacterium* spp., *Clostridium* spp., or *Bartonella henselae*; uncomplicated acute urinary tract infections related to infection by *S. saprophyticus* or *Enterococcus* spp.; urethritis and cervicitis; and sexually transmitted diseases related to infection by *Chlamydia trachomatis*, *Haemophilus ducreyi*, *Treponema pallidum*, *Ureaplasma urealyticum*, or *Nesseria gonorrheae*; toxin diseases related to infection by *S. aureus*, or Groups A, S, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *C. trachomatis*, *N. gonorrhoeae*, *S. aureus*, *S. pneumoniae*, *S. pyogenes*, *H. influenzae*, or *Listeria* spp.; disseminated *Mycobacterium avium* complex (MAC) disease related to infection by *Mycobacterium avium*, or *Mycobacterium intracellulare*; gastroenteritis related to infection by *Campylobacter jejuni*; intestinal protozoa related to infection by *Cryptosporidium* spp. odontogenic infection related to infection by viridans streptococci; persistent cough related to infection by *Bordetella pertussis*; gas gangrene related to infection by *Clostridium perfringens* or *Bacteroides* spp.; Skin infection by *S. aureus*, *Propionibacterium acne*; atherosclerosis related to infection by *Helicobacter pylori* and *Chlamydia pneumoniae*.

19. The method according to claim 18 wherein the infection is selected from the group consisting of pneumonia, otitis-media, sinusitus, bronchitis, tonsillitis, *Propionibacterium acne* and skin and soft tissue infection.

20. The method according to claim 7 wherein the infection or disorder is selected from the group consisting of bovine respiratory disease related to infection by *P. haemolytica.*, *P. multocida*, *Mycoplasma bovis*, or *Bordetella* spp.; cow enteric disease related to infection by *E. coli* or protozoa, dairy cow mastitis related to infection by *S. aureus*, *S. uberis*, *S. agalactiae*, *S. dysgalactiae*, *Klebsiella* spp., *Corynebacterium*, or *Enterococcus* spp.; swine respiratory disease related to infection by *A. pleuropneumoniae.*, *P. multocida*, or *Mycoplasma* spp.; swine enteric disease related to infection by *E. coli*, *Lawsonia intracellularis*, *Salmonella* spp., or *Serpulina hyodyisinteriae*; cow footrot related to infection by *Fusobacterium* spp.; cow metritis related to infection by *E. coli*; cow hairy warts related to Infection by *Fusobacterium necrophorum* or *Bacteroides nodosus*; cow pink-eye related to infection by *Moraxella bovis*, cow premature abortion related to infection by protozoa; urinary tract infection in dogs and cats related to infection by *E. coli*; skin and soft tissue infections in dogs and cats related to infection by *S. epidermidis*, *S. intermedius*, coagulase neg. *Staphylococcus* or *P. multocida*; and dental or mouth infections in dogs and cats related to infection by *Alcaligenes* spp., *Bacteroides* spp., *Clostridium* spp., *Enterobacter* spp., *Eubacterium* spp., *Peptostreptococcus* spp., *Porphfyromonas* spp., *Campylobacter* spp., *Actinomyces* spp., *Erysipelothrix* spp., *Rhodococcus* spp., *Trypanosoma* spp., *Plasmodium* spp., *Babesia* spp., *Toxoplasma* spp., *Pneumocystis* spp., *Leishmania* spp., and *Trichomonas* spp, and *Prevotella* spp.

21. A pharmaceutical composition comprising a therapeutically effective amount of a compound of the formula:

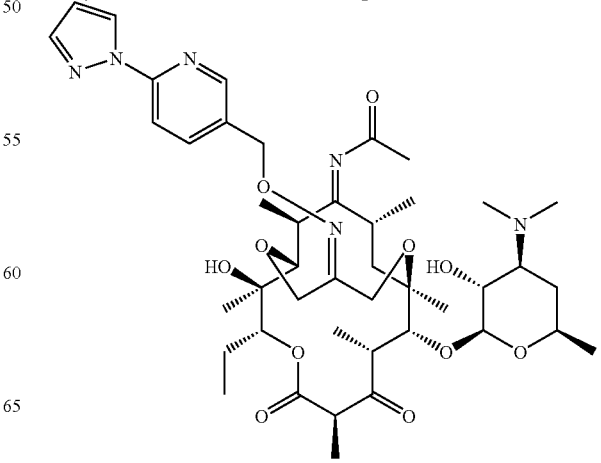

and pharmaceutically acceptable salts, esters, prodrugs, racemic mixtures and stereoisomers thereof, in combination with a pharmaceutically acceptable carrier.

22. A method for controlling a bacterial infection in a subject, comprising administering to said subject a therapeutically effective amount of a pharmaceutical composition according to claim 21.

* * * * *

UNITED STATES PATENT AND TRADEMARK OFFICE
CERTIFICATE OF CORRECTION

PATENT NO. : 7,064,110 B2
APPLICATION NO. : 10/717290
DATED : June 20, 2006
INVENTOR(S) : Yat Sun Or et al.

It is certified that error appears in the above-identified patent and that said Letters Patent is hereby corrected as shown below:

Title Page:

In the Title section (54):
Delete "BIcycle" before "Ketolide..." and replace with --Bicyclic--.

In the Inventors section (75):
Delete "Yat Sun Or, Wang Guoqiang, Ly Tam Phan, Deqiang Niu, Nha Huu Vo, Yao-Ling Qiu, Yanchun Wang, Marina Busuyek, Ying Hou, Yulin Peng, Heejin Kim, Tongzhu Liu, Jay Judson Farmer and Guoyou Xu" and replace with --Guoqiang Wang, Yat Sun Or and Ly Tam Phan--.

Signed and Sealed this

Eighteenth Day of September, 2007

JON W. DUDAS
*Director of the United States Patent and Trademark Office*